(12) United States Patent
Kishi et al.

(10) Patent No.: US 11,155,562 B2
(45) Date of Patent: Oct. 26, 2021

(54) SYNTHESIS OF HALICHONDRIN ANALOGS AND USES THEREOF

(71) Applicant: President and Fellows of Harvard College, Cambridge, MA (US)

(72) Inventors: Yoshito Kishi, Cambridge, MA (US); Atsushi Ueda, Nagasaki (JP); Akihiko Yamamoto, Tsukuba (JP); Daisuke Kato, Arlington, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/746,233

(22) Filed: Jan. 17, 2020

(65) Prior Publication Data

US 2020/0223863 A1    Jul. 16, 2020

Related U.S. Application Data

(63) Continuation of application No. 15/322,756, filed as application No. PCT/US2015/038439 on Jun. 30, 2015, now Pat. No. 10,556,910.

(60) Provisional application No. 62/019,224, filed on Jun. 30, 2014.

(51) Int. Cl.
| | | |
|---|---|---|
| *A61P 35/00* | (2006.01) | |
| *C07D 493/22* | (2006.01) | |
| *C07D 493/04* | (2006.01) | |
| *C07D 493/14* | (2006.01) | |

(52) U.S. Cl.
CPC ......... *C07D 493/22* (2013.01); *C07D 493/04* (2013.01); *C07D 493/14* (2013.01)

(58) Field of Classification Search
CPC .................................................... A61P 35/00
See application file for complete search history.

(56) References Cited

U.S. PATENT DOCUMENTS

| | | |
|---|---|---|
| 5,338,865 A | 8/1994 | Kishi et al. |
| 5,436,238 A | 7/1995 | Kishi et al. |
| 5,786,492 A | 7/1998 | Gravalos et al. |
| 6,214,865 B1 | 4/2001 | Littlefield et al. |
| 6,469,182 B1 | 10/2002 | Littlefield et al. |
| 6,653,341 B1 | 11/2003 | Littlefield et al. |
| 7,470,720 B2 | 12/2008 | Littlefield et al. |
| 7,982,060 B2 | 7/2011 | Austad et al. |
| 8,093,410 B2 | 1/2012 | Chase et al. |
| 8,097,648 B2 | 1/2012 | Littlefield et al. |
| 8,203,010 B2 | 6/2012 | Endo et al. |
| 8,350,067 B2 | 1/2013 | Endo et al. |
| 8,445,701 B2 | 5/2013 | Austad et al. |
| 8,598,373 B2 | 12/2013 | Hu |
| 8,618,313 B2 | 12/2013 | Benayoud et al. |
| 8,884,031 B2 | 11/2014 | Chase et al. |
| RE45,324 E | 1/2015 | Austad et al. |
| 8,927,597 B2 | 1/2015 | Endo et al. |
| 8,975,422 B2 | 3/2015 | Fang et al. |
| 8,987,479 B2 | 3/2015 | Chase et al. |
| 9,206,194 B2 | 12/2015 | Hu |
| 9,278,979 B2 | 3/2016 | Souza et al. |
| 9,303,039 B2 | 4/2016 | Zhang et al. |

(Continued)

FOREIGN PATENT DOCUMENTS

| | | |
|---|---|---|
| JP | 6-122687 | 5/1994 |
| JP | 6-279450 | 10/1994 |

(Continued)

OTHER PUBLICATIONS

US 9,029,573 B2, 05/2015, Hu (withdrawn)
Jackson, K.L., et al. "The Halichondrins and E7389." Chem. Rev. (2009), vol. 109, pp. 3044-3079. (Year: 2009).*
Berge, S. "Pharmaceutical Salts." J. Pharmaceutical Sciences. (Jan. 1977), vol. 66, No. 1, pp. 1-19. (Year: 1977).*
U.S. Appl. No. 15/322,756, filed Dec. 29, 2016, Kishi et al.
U.S. Appl. No. 15/570,593, filed Oct. 30, 2017, Kishi et al.
U.S. Appl. No. 16/441,843, filed Jun. 14, 2019, Kishi et al.

(Continued)

*Primary Examiner* — John S Kenyon
(74) *Attorney, Agent, or Firm* — Wolf, Greenfield & Sacks, P.C.

(57) ABSTRACT

The present invention provides halichondrin analogs, such as compounds of Formula (I). The compounds may bind to microtubule sites, thereby inhibiting microtubule dynamics. Also provided are methods of synthesis, pharmaceutical compositions, kits, methods of treatment, and uses that involve the compounds for treatment of a proliferative disease (e.g., cancer). Compounds of the present invention are particularly useful for the treatment of metastatic breast cancer, non-small cell lung cancer, prostate cancer, and sarcoma. The included methods of synthesis are useful for the preparation of compounds of Formula (I)-(III) along with naturally occurring halicondrins (e.g., halichondrin B & C, norhalichondrin A, B, & C, and homohalichondrin A, B, & C). Also included are methods for interconverting between the halichondrins, norhalichondrins, and homohalichondrins and their unnatural epimers at the C38 ketal stereocenter through the use of an acid-mediated equilibration.

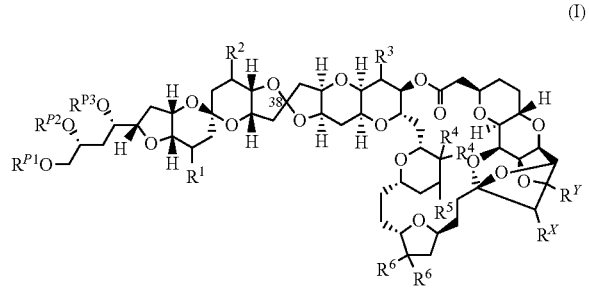

(I)

21 Claims, 7 Drawing Sheets

(56) References Cited

U.S. PATENT DOCUMENTS

| | | |
|---|---|---|
| 9,303,050 B2 | 4/2016 | Benayoud et al. |
| 9,382,262 B2 | 7/2016 | Endo et al. |
| 9,469,651 B2 | 10/2016 | Hu |
| 9,938,288 B1 | 4/2018 | Kishi et al. |
| 10,344,038 B2 | 7/2019 | Kishi et al. |
| 10,556,910 B2 | 2/2020 | Kishi et al. |
| 10,633,392 B2 | 4/2020 | Kishi et al. |
| 10,844,073 B2 | 11/2020 | Lee et al. |
| 2004/0198806 A1 | 10/2004 | Eisai et al. |
| 2006/0104984 A1 | 5/2006 | Littlefield et al. |
| 2006/0154312 A1 | 7/2006 | Agoulnik et al. |
| 2007/0244187 A1 | 10/2007 | Austad et al. |
| 2009/0198074 A1 | 8/2009 | Chase et al. |
| 2009/0203771 A1 | 8/2009 | Inanaga et al. |
| 2010/0254996 A1 | 10/2010 | Brantley-Sieders et al. |
| 2011/0054194 A1 | 3/2011 | Hu et al. |
| 2011/0184190 A1 | 7/2011 | Endo et al. |
| 2013/0336974 A1 | 12/2013 | Collier et al. |
| 2014/0198806 A1 | 7/2014 | Pani et al. |
| 2017/0137437 A1 | 5/2017 | Kishi et al. |
| 2018/0155361 A1 | 6/2018 | Lee et al. |
| 2018/0230164 A1 | 8/2018 | Kishi et al. |
| 2020/0002352 A1 | 1/2020 | Lee et al. |
| 2020/0148698 A1 | 3/2020 | Kishi et al. |
| 2020/0165183 A1 | 5/2020 | Kishi et al. |
| 2020/0325152 A1 | 10/2020 | Kishi et al. |
| 2021/0009605 A1 | 1/2021 | Kishi et al. |

FOREIGN PATENT DOCUMENTS

| | | |
|---|---|---|
| JP | 6-279451 A | 10/1994 |
| JP | 2001-305734 A | 11/2001 |
| JP | 2003-261447 A | 9/2003 |
| WO | WO 1993/017690 A1 | 9/1993 |
| WO | WO 1999/065894 A1 | 12/1999 |
| WO | WO 2005/118565 A1 | 12/2005 |
| WO | WO 2006/076100 A2 | 7/2006 |
| WO | WO 2007/139149 A1 | 12/2007 |
| WO | WO 2009/046308 A1 | 4/2009 |
| WO | WO 2009/064029 A1 | 5/2009 |
| WO | WO 2009/124237 A1 | 10/2009 |
| WO | WO 2011/094339 A1 | 8/2011 |
| WO | WO 2012/147900 A1 | 11/2012 |
| WO | WO 2013/086634 A1 | 6/2013 |
| WO | WO 2013/097042 A1 | 7/2013 |
| WO | WO 2013/142999 A1 | 10/2013 |
| WO | WO 2015/000070 A1 | 1/2015 |
| WO | WO 2015/066729 A1 | 5/2015 |
| WO | WO 2015/085193 A1 | 6/2015 |
| WO | WO 2016/003975 A1 | 1/2016 |
| WO | WO 2016/038624 A1 | 3/2016 |
| WO | WO 2016/176560 A1 | 11/2016 |
| WO | WO 2016/179607 A1 | 11/2016 |
| WO | WO 2018/187331 A1 | 10/2018 |
| WO | WO 2019/009956 A1 | 1/2019 |
| WO | WO 2019/010363 A1 | 1/2019 |

OTHER PUBLICATIONS

U.S. Appl. No. 15/814,105, filed Nov. 15, 2017, Kishi et al.
U.S. Appl. No. 16/500,924, filed Oct. 4, 2019, Kishi et al.
U.S. Appl. No. 16/628,504, filed Jan. 3, 2020, Kishi et al.
U.S. Appl. No. 15/809,845, filed Nov. 10, 2017, Lee et al.
U.S. Appl. No. 16/459,120, filed Jul. 1, 2019, Lee et al.
U.S. Appl. No. 16/628,419, filed Jan. 3, 2020, Kishi et al.
EP 15814059.0, Nov. 24, 2017, Extended European Search Report.
PCT/US2015/038439, Sep. 29, 2015, International Search Report and Written Opinion.
PCT/US2015/038439, Jan. 12, 2017, International Preliminary Report on Patentability.
PCT/US2016/030064, Aug. 8, 2016, International Search Report and Written Opinion.
PCT/US2016/030064, Nov. 9, 2017, International Preliminary Report on Patentability.
PCT/US2016/57661, Jan. 19, 2017, Invitation to Pay Additional Fees.
PCT/US2018/025887, Jun. 21, 2018, International Search Report and Written Opinion.
PCT/US2018/025887, Oct. 17, 2019, International Preliminary Report on Patentability.
PCT/US2018/041005, Sep. 14, 2018, Invitation to Pay Additional Fees.
PCT/US2018/041005, Jan. 16, 2020, International Preliminary Report on Patentability.
PCT/US2018/061250, Feb. 26, 2019, Invitation to Pay Additional Fees.
PCT/US2018/061250, Apr. 16, 2019, International Search Report and Written Opinion.
PCT/US2018/031765, Jul. 2, 2018, International Search Report and Written Opinion.
PCT/US2018/031765, Jan. 16, 2020, International Preliminary Report on Patentability.
U.S. Appl. No. 16/859,018, filed Apr. 27, 2020, Kishi et al.
U.S. Appl. No. 16/764,245, filed May 14, 2020, Kishi et al.
PCT/US2018/061250, May 28, 2020, International Preliminary Report on Patentability.
Extended European Search Report for EP 15814059.0, dated Nov. 24, 2017.
International Search Report and Written Opinion for PCT/US2015/038439, dated Sep. 29, 2015.
International Preliminary Report on Patentability for PCT/US2015/038439, dated Jan. 12, 2017.
International Search Report and Written Opinion for PCT/US2016/030064, dated Aug. 8, 2016.
International Preliminary Report on Patentability for PCT/US2016/030064, dated Nov. 9, 2017.
Invitation to Pay Additional Fees for PCT/US2016/57661, dated Jan. 19, 2017.
International Search Report and Written Opinion for PCT/US2018/025887, dated Jun. 21, 2018.
International Preliminary Report on Patentability for Application No. PCT/US2018/025887 dated Oct. 17, 2019.
Invitation to Pay Additional Fees for PCT/US2018/041005, dated Sep. 14, 2018.
International Preliminary Report on Patentability for PCT/US2018/041005, dated Jan. 16, 2020.
Invitation to Pay Additional Fees for PCT/US2018/061250, dated Feb. 26, 2019.
International Search Report and Written Opinion for PCT/US2018/061250, dated Apr. 16, 2019.
International Search Report and Written Opinion for PCT/US2018/031765, dated Jul. 2, 2018.
International Preliminary Report on Patentability for PCT/US2018/031765, dated Jan. 16, 2020.
[No Author Listed] American Chemical Society. STN Database. Apr. 11, 2014. RN # 1583253-64-8.
[No Author Listed] Application for Product Designation Under the SAKIGAKE Designation System. Generic name E7130. Eisai Co., Ltd. Nov. 22, 2017.
[No Author Listed] Evidentiary Document for Applicability of E7130 to Designation Requirements. Eisai Co., Ltd. Nov. 22, 2017.
[No Author Listed] Overview Relating to the Suitability for Designation Requirements Under the SAKIGAKE Designation System. Generic name E7130. Eisai Co., Ltd.
Aicher et al., Synthetic studies towards halichondrins. Tetrahedron Lett. 1987;28(30):3463-66.
Aicher et al., Synthetic Studies towards Halichondrins: Synthesis of the C.27-C.38 Segment. Tetrahedron Lett. 1992;33(12):1549-52.
Aicher et al., Total synthesis of halichondrin B and norhalichondrin B. J. Am. Chem. Soc., 1992, 114(8), pp. 3162-3164.
Austed et al., Commercial Manufacture of Halaven®: Chemoselective Transformations En Route to Structurally Complex Macrocyclic Ketones. Synlett 2013; 24(3): 333-337. doi: 10.1055/s-0032-1318026.
Berge et al., Pharmaceutical Salts. J. Pharmaceutical Sciences 1977;66(1):1-19.

(56) References Cited

OTHER PUBLICATIONS

Bringans, Studies on natural product derivatives: HIV therapies incorporating marine natural products. Dissertation. University of Canterbury, 2001.

Buszek et al., Synthetic Studies Towards Halichondrins: Synthesis of the Left Half of Halichondrins. Tetrahedron Lett. 1992;33:1553.

Chen et al., Ni(II)/Cr(II)-mediated coupling reaction: an asymmetric process. J. Org. Chem., 1995, 60(17), pp. 5386-5387.

Choi et al., Asymmetric Ni(II)/Cr(II)-Mediated Coupling Reaction: Catalytic Process. Org. Lett., 2002, 4 (25), pp. 4435-4438. doi: 10.1021/ol026981x.

Choi et al., Synthetic studies on the marine natural product halichondrins. Pure Appl. Chem., 2003, vol. 75, No. 1, pp. 1-17.

Dong et al., New syntheses of E7389 C14-C35 and halichondrin C14-C38 building blocks: reductive cyclization and oxy-Michael cyclization approaches. J Am Chem Soc. Nov. 4, 2009;131(43):15642-6. doi: 10.1021/ja9058487.

Fang et al., Synthetic Studies Towards Halichondrins: Synthesis of the Left Halves of Norhalichondrins and Homohalichondrins. Tetrahedron Lett. 1992;33(12):1557-60.

Fukuyama et al., Application of a Rotor-Stator High-Shear System for Cr/Mn-Mediated Reactions in Eribulin Mesylate Synthesis. Org. Process Res. Dev., 2016, 20 (1), pp. 100-104. doi: 10.1021/acs.oprd.5b00383.

Fukuyama et al., Application of Continuous Flow for DIBAL-H Reduction and n-BuLi Mediated Coupling Reaction in the Synthesis of Eribulin Mesylate. Org. Process Res. Dev., 2016, 20 (2), pp. 503-509. doi: 10.1021/acs.oprd.5b00353.

Gould et al., Salt selection for basic drugs. International Journal of Pharmaceutics Nov. 1986;33(1-3):201-217. https://doi.org/10.1016/0378-5173(86)90055-4.

Guo et al., Toolbox approach to the search for effective ligands for catalytic asymmetric Cr-mediated coupling reactions. J Am Chem Soc. Oct. 28, 2009;131(42):15387-93. doi: 10.1021/ja905843e.

Hickford et al., Antitumour polyether macrolides: four new halichondrins from the New Zealand deep-water marine sponge *Lissodendoryx* sp. Bioorg Med Chem. Mar. 15, 2009;17(6):2199-203. doi: 10.1016/j.bmc.2008.10.093. Epub Nov. 19, 2008.

Hirata et al., Halichondrins—antitumor polyether macrolides from a marine sponge. Pure Appl. Chem., 1986, vol. 58, No. 5, pp. 701-710.

Jackson et al., A total synthesis of norhalichondrin B. Angew Chem Int Ed Engl. 2009;48(13):2346-50. doi: 10.1002/anie.200806111.

Kaburagi et al., Effective procedure for selective ammonolysis of monosubstituted oxiranes: application to E7389 synthesis. Tetrahedron Lett. 2007;48(51):8967-71.

Kim et al., New syntheses of E7389 C14-C35 and halichondrin C14-C38 building blocks: double-inversion approach. J Am Chem Soc. Nov. 4, 2009;131(43):15636-41. doi: 10.1021/ja9058475.

Kress et al., Investigations of the intramolecular Ni(II)/Cr(II)-mediated coupling reaction: Application to the taxane ring system. Tetrahedron Letters 1993;34(38);6003-6.

Kumar et al., Fe/Cu-Mediated One-Pot Ketone Synthesis. Org Lett. May 19, 2017;19(10):2766-2769. doi: 10.1021/acs.orglett.7b01128. Epub May 10, 2017.

Li et al., Unified Synthesis of C1-C19 Building Blocks of Halichondrins via Selective Activation/Coupling of Polyhalogenated Nucleophiles in (Ni)/Cr-Mediated Reactions. J Am Chem Soc. May 20, 2015;137(19):6226-31. doi: 10.1021/jacs.5b03499. Epub May 11, 2015.

Lill, Studies on New Zealand marine natural products. Dissertation. University of Canterbury, 1999.

Liu et al., Catalytic enantioselective Cr-mediated propargylation: application to halichondrin synthesis. Org Lett. Oct. 15, 2009;11(20):4520-3. doi: 10.1021/ol9016595.

Liu et al., Dramatic improvement in catalyst loadings and molar ratios of coupling partners for Ni/Cr-mediated coupling reactions: heterobimetallic catalysts. J Am Chem Soc. Nov. 25, 2009;131(46):16678-80. doi: 10.1021/ja9079308.

Liu et al., Synthesis of Alcohols from m-Fluorophenylsulfones and Dialkylboranes: Application to the C14-C35 Building Block of E7389. Org. Lett., 2012, 14 (9), pp. 2262-2265. doi: 10.1021/ol300672q.

Namba et al., New catalytic cycle for couplings of aldehydes with organochromium reagents. Org Lett. Dec. 23, 2004;6(26):5031-3.

Narayan et al., Novel second generation analogs of eribulin. Part I: Compounds containing a lipophilic C32 side chain overcome P-glycoprotein susceptibility. Bioorg Med Chem Lett, Mar. 15, 2011;21(6):1630-3.

Narayan et al., Novel second generation analogs of eribulin. Part II: Orally available and active against resistant tumors in vivo. Bioorg Med Chem Lett, Mar. 15, 2011;21(6):1634-8.

Narayan et al., Novel second generation analogs of eribulin. Part III: Blood-brain barrier permeability and in vivo activity in a brain tumor model. Bioorg Med Chem Lett, Mar. 15, 2011;21(6):1639-43.

Ortega et al., Potential clinical applications of halichondrins in breast cancer and other neoplasms. Breast Cancer (Dove Med Press). Feb. 8, 2012;4:9-19. doi: 10.2147/BCTT.S12423.

Seletsky et al., Structurally simplified macrolactone analogues of halichondrin B. Bioorg Med Chem Lett, Nov. 15, 2004;14(22):5547-50.

Shan et al., Concise and Highly Stereoselective Synthesis of the C20-C26 Building Block of Halichondrins and Eribulin. Org. Lett., 2012, 14 (2), pp. 660-663. doi: 10.1021/ol203373d.

Stamos et al., Ni(II)/Cr(II)-Mediated Coupling Reaction: Beneficial Effects of 4-tert-Butylpyridine as an Additive and Development of New and Improved Workup Procedures. Tetrahedron Lett. 1997;38(36):6355-8.

Stamos et al., Synthetic studies on halichondrins: A practical synthesis of the C.1 C.13 segment. Tetrahedron Letters Nov. 25, 1996;37(48):8643-8646.

Ueda et al., Total synthesis of halichondrin A, the missing member in the halichondrin class of natural products. J Am Chem Soc. Apr. 2, 2014;136(13):5171-6. doi: 10.1021/ja5013307. Epub Mar. 19, 2014.

Uemura et al., Norhalichondrin A: an antitumor polyether macrolide from a marine sponge. J. Am. Chem. Soc., 1985, 107 (16), pp. 4796-4798. doi: 10.1021/ja00302a042.

Uemura, Exploratory research on bioactive natural products with a focus on biological phenomena. Proc Jpn Acad Ser B Phys Biol Sci. 2010;86(3):190-201.

Wan et al., Asymmetric Ni(II)/Cr(II)-mediated coupling reaction: stoichiometric process. Org Lett. Dec. 12, 2002;4(25):4431-4.

Wang et al., Structure-activity relationships of Halichondrin B analogues: modifications at C.30-C.38. Bioorg Med Chem Lett, May 15, 2000; 10(10):1029-32.

Xie et al., Synthesis of the C20-C26 Building Block of Halichondrins via a Regiospecific and Stereoselective SN2' Reaction. Org. Lett., 2002;4(25):4427-1429.DOI: 10.1021/ol026982p.

Yahata et al., Unified, Efficient, and Scalable Synthesis of Halichondrins: Zirconium/Nickel-Mediated One-Pot Ketone Synthesis as the Final Coupling Reaction. Angew Chem Int Ed Engl. Aug. 28, 2017;56(36):10796-10800. doi: 10.1002/anie.201705523. Epub Jul. 28, 2017.

Yamamoto et al., Total synthesis of halichondrin C. J Am Chem Soc. Jan. 18, 2012;134(2):893-6. doi: 10.1021/ja2108307. Epub Dec. 23, 2011.

Yan et al., Selective Activation/Coupling of Polyhalogenated Nucleophiles in Ni/Cr-Mediated Reactions: Synthesis of C1-C19 Building Block of Halichondrin Bs. J. Am. Chem. Soc., 2015, 137 (19), pp. 6219-6225.

Zheng et al., Macrocyclic ketone analogues of halichondrin B. Bioorg Med Chem Lett. Nov. 15, 2004;14(22):5551-4.

International Preliminary Report on Patentability for PCT/US2018/061250, dated May 28, 2020.

U.S. Appl. No. 17/167,480, filed Feb. 4, 2021, Kishi et al.

PCT/US2020/043501, Dec. 3, 2020, International Search Report and Written Opinion.

International Search Report and Written Opinion for PCT/US2020/043501, dated Dec. 3, 2020.

(56) References Cited

OTHER PUBLICATIONS

Araki et al., A Convenient Method for the Preparation of Ketones by the Reaction of Grignard Reagents with Carboxylic Acid Derivatives. Chem. Soc. Jpn. 1974;47:1777-80.

Bockus et al., Form and Function in Cyclic Peptide Natural Products: A Pharmacokinetic Perspective. Curr Top Med Chem. 2013;13(7):821-36. doi: 10.2174/1568026611313070005.

Britovsek et al., Synthesis of iron(ii), manganese(ii) cobalt(ii) and ruthenium(ii) complexes containing tridentate nitrogenligands and their application in the catalytic oxidation of alkanes. Dalton Trans. 2005, 945-55.

Buchwald et al., Synthesis, structure, and reactions of (1-ethoxyethyl)zirconocene chloride, a stable acyclic secondary zirconocene alkyl. Organometallics. 1988;7(11):2324-2328.

Cardellicchio et al., A highly efficient synthetic route to ketones through sequential coupling reactions of grignard reagents with s-phenyl carbonochloridothioate in the presence of nickel or iron catalysts. Tetrahedron Lett. 1985;26(30):3595-98.

Chen et al., Attempts to Improve the Overall Stereoselectivity of the Ireland-Claisen Rearrangement. Org. Lett. Jan. 15, 2009; 11(2):409-12.

Corey et al., Synthesis of 1,n-Dicarbonyl Derivates Using Carbanions from 1,3-Dithianes. Angew. Chem. Int. Ed. 1965;4(12):1077-78.

Dieter, Reaction of acyl chlorides with organometallic reagents: A banquet table of metals for ketone synthesis. Tetrahedron. 1999;55:4177-4236.

Dybdal-Hargreaves et al., Eribulin Mesylate: Mechanism of Action of a Unique Microtubule-Targeting Agent. Clin Cancer Res. Jun. 1, 2015;21(11):2445-52. doi: 10.1158/1078-0432.CCR-14-3252. Epub Apr. 2, 2015.

Eliel et al., Conformational analysis. 42. Monosubstituted tetrahydropyrans. J. Am. Chem. Soc. 1982; 104(13):3635-43.

Fiandanese et al., One-step synthesis of ketones from carylic acids and grignard reagents in the presence of a nickel(II)-phosphine catalyst. Tetrahedron Lett. 1983;24(34):3677-80.

Fleming et al., Grignard Reagents: Alkoxide-Directed Iodine-Magnesium Exchange at sp3 Centers. Org. Lett. 2007; 9(22):4507-09.

Gerlach et al., Bildung von Estern und Lactonen durch Silberionen-Katalyse. Helv. Chim. Acta. 1974; 57(8): 2661-63.

Hayashi et al., Diarylprolinol in an Asymmetric, Direct Cross-Aldol Reaction with Alkynyl Aldehydes. ChemCatChem. 2013; 5:2887-92.

Hayashi et al., A diarylprolinol in an asymmetric, catalytic, and direct crossed-aldol reaction of acetaldehyde. Angew Chem Int Ed Engl. 2008;47(11):2082-4. doi: 10.1002/anie.200704870.

Hoveyda et al., The remarkable metal-catalysed olefin metathesis reaction. Nature. 2007;450:243-51.

Johannes et al., Biomimetic macrocycle-forming Diels-Alder reaction of an iminium dienophile: synthetic studies directed toward gymnodimine. Org Lett. Sep. 1, 2005;7(18):3997-4000. doi: 10.1021/ol051553n.

Jung et al., Synthesis of 1,4-, 2,4-, and 3,4-dimethylphenanthrenes: a novel deoxygenation of arene 1,4-endoxides with trimethylsilyl iodide. J. Org. Chem. 1989; 54:5667-75.

Kaburagi, Operationally Simple and Efficient Workup Procedure for TBAF-Mediated Desilylation: Application to Halichondrin Synthesis. Org. Lett. 2007; 9(4):723-26.

Katsuki et al., The first practical method for asymmetric epoxidation. J. Am. Chem. Soc. 1980, 102(18) 5974-76.

Kim et al., Copper ion promoted esterification of (S)-2-pyridyl thioates and 2-pyridyl esters. Efficient methods for the preparation of hindered esters. J. Org. Chem. 1984;49(10):1712-16.

Knochel et al., Modern Organocopper Chemistry. 2002. Wiley-VCH, Eds.

Kobayashi et al., Complete Stereochemistry of Tetrafibricin. Org. Lett. 2003; 5(1):93-96.

Lee et al., Extension of Pd-Mediated One-Pot Ketone Synthesis to Macrocyclization: Application to a New Convergent Synthesis of Eribulinv. J. Am. Chem. Soc. 2016; 138(50):16248-51.

Lewis et al., Hishly stereoselective approaches to .alpha.- and .beta.-C-glycopyranosides. J. Am. Chem. Soc. 1982;104(18):4976-78.

Li et al., Stereocontrolled Synthesis of α-Amino-α'-alkoxy Ketones by a Copper-Catalyzed Cross-Coupling of Peptidic Thiol Esters and α-Alkoxyalkylstannanes. Org. Lett. 2011; 13(14):3682-85.

Liebeskind et al., Thiol Ester-Boronic Acid Coupling. A Mechanistically Unprecedented and General Ketone Synthesis. J. Am. Chem. Soc. 2000;122(45):11260-61.

Lipschutz, Applications of Higher-Order Mixed Organocuprates to Organic Synthesis. Synthesis. Apr. 1987:325-41.

Loots et al., Nickel-catalyzed conjugate addition of zirconium alkenyls to .alpha.,.beta.-unsaturated ketones. J. Am. Chem. Soc. 1977;99(24):8045-46.

Lu et al., Alkyl-Alkyl Suzuki Cross-Coupling of Unactivated Secondary Alkyl Chlorides. C. Angew. Chem. Int. Ed. 2010;49(37):6676-78.

Masashi et al., A Convenient Method for the Preparation of Ketones by the Reaction of Grignard Reagents with Carboxylic Acid Derivatives. Chem. Soc. Jpn. 1974;47:1777-80.

McGee et al., Synthesis and Isolation of Organogold Complexes through a Controlled 1,2-Silyl Migration. Chem. Eur. J. 2015;21(27): 9662-9665.

Miyajima et al., Electric-field-responsive handle for large-area orientation of discotic liquid-crystalline molecules in millimeter-thick films. Angew. Chem., Int. Ed. 2011;123:8011-15.

Mori et al., Pd(OH)2/C (Pearlman's catalyst): a highly active catalyst for Fukuyama, Sonogashira, and Suzuki coupling reactions. J Org Chem. Feb. 21, 2003;68(4):1571-4. doi: 10.1021/jo0265277.

Mori et al., A novel procedure for the synthesis of multifunctional ketones through the Fukuyama coupling reaction employing dialkylzincs. Tetrahedron Letters. Sep. 20, 2004; 45(39):7343-45.

Mori et al., Synthesis of Multi-Functionalized Ketones Through The Fukuyama Coupling Reaction Catalyzed by Pearlman's Catalyst: Preparation of Ethyl 6-Oxotridecanoate (Tridecanoic Acid, 6-Oxo-, Ethyl Ester).Organic Syntheses. 2007;84: 285-294.

Movassaghi et al., Enantioselective total synthesis of (−)-acylfulvene and (−)-irofulven. Angew Chem Int Ed Engl. Sep. 4, 2006;45(35):5859-63. doi: 10.1002/anie.200602011.

Nahm et al., N-methoxy-n-methylamides as effective acylating agents. Tetrahedron Lett. 1981;22(39):3815-18.

Negishi et al., Palladium-catalyzed acylation of organozincs and other organometallics as a convenient route to ketones. Tetrahedron Lett. 1983;24(47): 5181-4.

Negri et al., A total synthesis of polyether antibiotic (−)-A23187 (calcimycin). Tetrahedron Lett. 1987; 28(10):1063-66.

Normant, Organocopper(I) Compounds and Organocuprates in Synthesis. Synthesis. Feb. 1972; 1972(2):63-80.

Onaka et al., A Convenient Method For The Direct Preparation Of Ketones From 2-(6-(2-Methoxyethyl)Pyridyl)Carboxylates And Alkyl Iodides By Use Of Zinc Dust And A Catalytic Amount Of Nickel Dichloride. Chem. Lett. 1981;10(4):531-34.

Ruscoe et al., Copper-Catalyzed Double Additions and Radical Cyclization Cascades in the Re-Engineering of the Antibacterial Pleuromutilin. J. Chem. Eur. J. 2016; 22:116-119.

Schrock, Multiple Metal-Carbon Bonds for Catalytic Metathesis Reactions. Adv. Synth Catal. 2007;349: 41-53.

Scriven et al., Azides: their preparation and synthetic uses. Chem Rev. 1988;88(2):297-368.

Seebach, Methods of Reactivity Umpolung. Angew. Chem. Int. Ed. 1979;18(4):239-58.

Seebach et al., Generation and synthetic applications of 2-lithio-1,3-dithianes. J. Org. Chem. 1975;40(2): 231-37.

Serrano et al., Nickel-Catalyzed Reductive Amidation of Unactivated Alkyl Bromides. Angew. Chem. Int. Ed. 2016;55(37):11207-11.

Sharpless et al., High stereo- and regioselectivities in the transition metal catalyzed epoxidations of olefinic alcohols by tert-butyl hydroperoxide. J. Am. Chem. Soc. 1973;95(18):6136-37.

Shiina, An Adventurous Synthetic Journey with MNBA from Its Reaction Chemistry to the Total Synthesis of Natural Products. Bull Chem. Soc. Jpn. 2014; 87(2):196-233.

(56) References Cited

OTHER PUBLICATIONS

Shiina et al., A novel and efficient macrolactonization of ω-hydroxycarboxylic acids using 2-methyl-6-nitrobenzoic anhydride (MNBA). Tetrahedron Lett. Oct. 14, 2002;43(42):7535-39.

Shiina et al., A Novel Method for the Preparation of Macrolides from ω-Hydroxycarboxylic Acids. Chem. Lett. 1994;23(4):677-80.

Smith III et al., Evolution of Dithiane-Based Strategies for the Construction of Architecturally Complex Natural Products. Acc. Chem. Rev. 2004; 37(6): 365-77.

Takai et al., A practical transformation of aldehydes into (E)-iodoalkenes with geminal di chromium reagents. Synlett. 1999;8:1268-70.

Takai et al., Simple and selective method for aldehydes (RCHO) → (E)-haloalkenes (RCH:CHX) conversion by means of a haloform-chromous chloride system. J. Am. Chem. Soc. 1986;108(23):7408-10.

Takaya et al., Investigation of Organoiron Catalysis in Kumada-Tamao-Corriu-Type Cross-Coupling Reaction Assisted by Solution-Phase X-ray Absorption Spectroscopy. Bull. Chem. Soc. Jpn. 2015;88(3):410-418.

Takuji et al., Kumada-Tamao-Corriu Coupling of Alkyl Halides Catalyzed by an Iron-Bisphosphine Complex. Chem. Lett. 2011, 40(9):1030-32.

Thornton et al., π-Nucleophile Traps for Metallonitrene/Alkyne Cascade Reactions: A Versatile Process for the Synthesis of α-Aminocyclopropanes and β-Aminostyrenes. J. Am. Chem. Soc. 2009;131(7): 2434-2435.

Trnka et al., The Development of L2X2RuCHR Olefin Metathesis Catalysts: An Organometallic Success Story. Acc. Chem. Res. 2001;34(1):18-29.

Turhanen et al., A powerful tool for acid catalyzed organic addition and substitution reactions. RSC Adv. 2015; 5:26218-26222.

Ueda et al., Total synthesis of (+)-haplophytine. Angew Chem Int Ed Engl. 2009;48(41):7600-3. doi: 10.1002/anie.200902192.

Umehara et al., Further Studies on Ni/Zr-mediated One-pot Ketone Synthesis: Use of a 1-6 Mixture of NiI- and NiII-catalysts Greatly Improves the Molar Ratio of Coupling Partners. Chem.Lett. 2019;48:947-950.

Velder et al., Modular Synthesis of Chiral Phosphine-Phosphite-Ligands from Phenolic Precursors: A New Approach to Bidentate Chelate Ligands Exploiting a P O to P C Migration Rearrangement. Adv Synth Catal. 2008; 350(9):1309-15.

Weix et al., Nickel-Catalyzed Cross-Electrophile Coupling with Organic Reductants in Non-Amide Solvents. Chem. Eur. J. 2016; 22(33):11564-11567.

Williams et al., Competitive oxidation processes in the reaction between (dicyclopentadienyl)zirconium bis(phosphine) complexes and alkyl halides. J. Am. Chem. Soc. 1980; 102(10):3660-62.

Williams et al., Direct observation of metal-centered radicals in an oxidative-addition reaction. J. Am. Chem. Soc. 1982; 104(4):1122-24.

Wipf et al., Transmetalation reactions of alkylzirconocenes: copper-catalyzed conjugate addition to enones. J. Org. Chem. 1991;56(23): 6494-96.

Wittenberg et al., Ketone synthesis under neutral conditions. Cu(I) diphenylphosphinate-mediated, palladium-catalyzed coupling of thiol esters and organostannanes. Org Lett. Aug. 21, 2003;5(17):3033-5. doi: 10.1021/ol034962x.

Wu et al., Ketone Formation via Mild Nickel-Catalyzed Reductive Coupling of Alkyl Halides with Aryl Acid Chlorides. Org. Lett. 2012; 14(12):3044-47.

Yoneda et al., Asymmetric Synthesis of Spiroketals with Aminothiourea Catalysts. Angew Chem Int Ed Engl. Dec. 14, 2015;54(51):15497-500. doi: 10.1002/anie.201508405.

Yus et al., The role of 1,3-dithianes in natural product synthesis. Tetrahedron. Aug. 11, 2003; 59(33):6147-6212.

Zhang et al., Alcohols as Latent Coupling Fragments for Metal-laphotoredox Catalysis: sp3-sp2 Cross-Coupling of Oxalates with Aryl Halides. J. Am. Chem. Soc. 2016; 138(42):13862-65.

Zhang et al., A Unique Catalyst Effects the Rapid Room-Temperature Cross-Coupling of Organozinc Reagents with Carboxylic Acid Fluorides, Chlorides, Anhydrides, and Thioesters. J. Am. Chem. Soc. 2004; 126(49):15964-65.

Zhao et al., Ni-Catalyzed Reductive Coupling of Alkyl Acids with Unactivated Tertiary Alkyl and Glycosyl Halides. J. Am. Chem. Soc. 2014;136(50):17645-51.

\* cited by examiner

*Table 1.* $^1$H NMR chemical shifts of halichondrins (in $CD_3OD$)

|  | Natural Hali B | Natural Hali C | Synthetic Hali A | Natural Nor A | Natural Homo A |
|---|---|---|---|---|---|
| H2 | 2.44 | 2.44 | 2.45 | 2.44 | 2.44 |
| H2 | 2.57 | 2.56 | 2.57 | 2.58 | 2.56 |
| H3 | 3.88 | 3.88 | 3.87[a] | 3.89 | 3.88 |
| H6 | 4.33 | 4.30 | 4.31[a] | 4.32 | 4.31 |
| H7 | 2.98 | 2.98 | 2.93 | 2.93 | 2.93 |
| H8 | 4.31 | 4.30 | 4.37 | 4.37 | 4.37 |
| H9 | 4.13 | 4.10 | 4.31[a] | 4.31 | 4.31 |
| H10 | 4.18 | 4.18 | 4.20 | 4.21 | 4.21 |
| H11 | 4.60 | 4.40 | 4.31[a] | 4.31 | 4.31 |
| H12 | 4.71 | ----- | ----- | ----- | ----- |
| H13 | 1.98 | 2.27 | 3.53[a] | 3.53 | 3.53 |
| H13 | 2.09 | 2.27 | ----- | ----- | ----- |
| H17 | 4.08 | 4.10 | 4.10[a] | 4.09 | 4.10 |
| H18 | 2.32 | 2.32 | 2.34 | 2.32 | 2.32 |
| H18 | 2.80 | 2.80 | 2.82 | 2.82 | 2.82 |
| C19=$CH_2$ | 5.02 | 5.02 | 5.03 | 5.02 | 5.02 |
| C19=$CH_2$ | 5.07 | 5.06 | 5.08 | 5.06 | 5.07 |
| H20 | 4.46 | 4.43 | 4.45 | 4.44 | 4.44 |
| H23 | 3.71 | 3.70 | 3.73 | 3.72 | 3.72 |
| C25–Me | 1.10 | 1.09 | 1.10 | 1.09 | 1.09 |
| C26=$CH_2$ | 4.82 | 4.82 | 4.81 | 4.81 | 4.80 |
| C26=$CH_2$ | 4.88 | 4.87 | 4.88 | 4.86 | 4.85 |
| H27 | 3.62 | 3.59 | 3.63 | 3.61 | 3.61 |
| H29 | 4.25 | 4.25 | 4.25 | 4.24 | 4.24 |
| H30 | 4.63 | 4.63 | 4.62 | 4.61 | 4.62 |
| C31–Me | 1.07 | 1.05 | 1.06 | 1.06 | 1.04 |
| H32 | 3.22 | 3.22 | 3.22 | 3.22 | 3.22 |
| H33 | 3.87 | 3.88 | 3.87[a] | 3.87 | 3.88 |
| H35 | 4.12 | 4.10 | 4.10[a] | 4.11 | 4.10 |
| H36 | 4.10 | 4.10 | 4.10[a] | 4.09 | 4.10 |
| H40 | 4.05 | 4.05 | 4.05 | 3.98 | 3.96 |
| H41 | 3.69 | 3.68 | 3.70 | 3.69 | 3.66 |
| C42–Me | 0.94 | 0.96 | 0.97 | 0.97 | 0.94 |
| C46–Me | 1.01 | 1.00 | 1.02 | 0.96 | 0.93 |
| H47 | 3.56 | 3.56 | 3.56 | 3.30 | 3.12 |
| H48 | 4.10 | 4.10 | 4.10[a] | 3.77 | 3.58 |
| H49 | 1.83 |  | 1.84 | 1.94 | 1.91 |
| H49 | 2.27 |  | 2.28 | 2.09 | 2.16 |
| H50 | 4.00 | 3.99 | 3.99 | 3.61 | 3.90 |
| H51 | 3.78 | 3.78 | 3.78 | 3.78 | 4.02 |
| H52 | 1.61 | 1.61 | 1.60 | 2.47 | 2.00 |
| H52 | 1.75 | 1.75 | 1.75 | 2.47 | 2.00 |
| H53 | 3.87 | 3.88 | 3.87[a] | — | 4.23 |
| H54 | 3.46 | 3.47 | 3.47 | — | 3.50 |
| H54 | 3.53 | 3.53 | 3.53[a] | — | — |
| H55 | ----- | ----- | ----- | — | 3.58 |
| H55 | ----- | ----- | ----- | — | 3.59 |

[a] overlap with other protons

Figure 6

*Table 2.* $^{13}$C NMR chemical shifts of halichondrins (in CD$_3$OD)

|  | Natural Hali B | Natural Hali C | Synthetic Hali A | Natural Nor A | Natural Homo A |
|---|---|---|---|---|---|
| C1 | 172.8 | 172.8 | 172.8 | 172.8 | 172.8 |
| C2 | 41.2 | 41.2 | 41.1 | 41.1 | 41.1 |
| C3 | 74.9 | 74.7 | 75.1 | 75.1 | 75.1 |
| C6 | 69.6 | 69.5 | 69.6 | 69.6 | 69.6 |
| C7 | 79.1 | 79.0 | 79.0 | 79.0 | 79.0 |
| C8 | 75.8 | 76.1 | 75.8 | 75.8 | 75.9 |
| C9 | 73.3 | 73.3 | 73.7 | 73.8 | 73.8 |
| C10 | 78.0 | 73.0 | 85.5 | 85.5 | 85.5 |
| C11 | 83.8 | 86.2 | 75.5 | 75.5 | 75.5 |
| C12 | 82.5 | 114.2 | 113.3 | 113.4 | 113.3 |
| C13 | 49.4 | 49.3 | 82.3 | 82.4 | 82.3 |
| C14 | 111.3 | 110.4 | 112.9 | 112.9 | 112.8 |
| C17 | 76.3 | 76.3 | 76.3 | 76.3 | 76.3 |
| C18 | 39.7 | 39.7 | 39.8 | 39.8 | 39.8 |
| C19 | 153.2 | 153.2 | 153.1 | 153.2 | 153.0 |
| C19=CH$_2$ | 105.8 | 105.8 | 105.7 | 105.8 | 105.8 |
| C20 | 76.1 | 76.3 | 76.0 | 76.0 | 75.9 |
| C23 | 75.3 | 75.3 | 75.2 | 75.3 | 75.2 |
| C25 | 37.5 | 37.5 | 37.2 | 37.2 | 37.2 |
| C25-Me | 18.4 | 18.4 | 18.4 | 18.4 | 18.4 |
| C26 | 153.2 | 153.2 | 153.3 | 153.2 | 153.2 |
| C26=CH$_2$ | 104.8 | 104.8 | 104.8 | 104.8 | 104.8 |
| C27 | 75.1 | 74.8 | 75.1 | 75.1 | 75.0 |
| C29 | 73.8 | 73.8 | 73.8 | 73.8 | 73.8 |
| C30 | 77.3 | 77.3 | 77.4 | 77.3 | 77.3 |
| C31 | 37.5 | 37.5 | 37.5 | 37.5 | 37.4 |
| C31-Me | 15.9 | 15.9 | 15.9 | 15.9 | 15.8 |
| C32 | 78.0 | 78.0 | 78.0 | 77.9 | 77.9 |
| C33 | 65.5 | 65.5 | 65.6 | 65.6 | 65.6 |
| C35 | 77.3 | 77.3 | 77.6 | 77.6 | 77.6 |
| C36 | 78.0 | 78.0 | 78.0 | 78.0 | 78.0 |
| C37 | 45.6 | 45.5 | 45.6 | 45.6 | 45.6 |
| C38 | 114.8 | 114.9 | 114.8 | 114.9 | 114.8 |
| C39 | 45.0 | 45.0 | 45.0 | 44.9 | 44.9 |
| C40 | 73.0 | 73.0 | 73.0 | 72.7 | 72.3 |
| C41 | 80.8 | 80.8 | 80.7 | 80.7 | 81.0 |
| C42 | 27.1 | 27.1 | 27.1 | 27.3 | 27.1 |
| C42-Me | 18.2 | 18.1 | 18.1 | 18.1 | 18.2 |
| C44 | 98.4 | 98.4 | 98.4 | 98.5 | 98.1 |
| C46 | 27.1 | 27.1 | 27.1 | 30.1 | 30.1 |
| C46-Me | 18.3 | 18.3 | 18.3 | 17.5 | 17.6 |
| C47 | 81.3 | 81.3 | 81.3 | 77.2 | 74.5 |
| C48 | 75.1 | 74.8 | 73.3 | 68.2 | 65.2 |
| C50 | 81.3 | 81.3 | 81.2 | 68.1 | 75.4 |
| C51 | 73.1 | 73.2 | 73.1 | 79.1 | 78.4 |
| C53 | 71.6 | 71.6 | 71.6 | 172.8 | 79.8 |
| C54 | 67.1 | 67.1 | 67.2 | -- | 75.0 |
| C55 | -- | -- | -- | -- | 65.1 |

Figure 7

SYNTHESIS OF HALICHONDRIN ANALOGS AND USES THEREOF

RELATED APPLICATIONS

The present application is a continuation of and claims priority under 35 U.S.C. § 120 to U.S. patent application U.S. Ser. No. 15/322,756, filed Dec. 29, 2016, which is a national stage filing under 35 U.S.C. § 371 of international PCT application, PCT/US2015/038439, filed Jun. 30, 2015, which claims priority under 35 U.S.C. § 119(e) to U.S. provisional patent application, U.S. Ser. No. 62/019,224, filed Jun. 30, 2014, each of which is incorporated herein by reference.

BACKGROUND OF THE INVENTION

The halichondrins are polyether macrolides, originally isolated from the marine sponge *Halichondria okadai* by Uemura, Hirata, and coworkers. Several additional members, including halistatin, were also isolated from marine sponges. This class of natural products displays interesting structural diversity at two main sites, one being the oxidation state at C10, C12, and C13 of the C8-C14 polycycle, and the other being the length of the carbon backbone. Based on the elements providing structural diversity, this class of natural products has been grouped into the norhalichondrin, halichondrin, and homohalichondrin series with several representative sub-groups (see FIG. 1). While norhalichondrins A-C, homohalichondrins A-C, and halichondrins B & C have all been isolated from the natural sources, halichondrin A has never been isolated from natural sources.

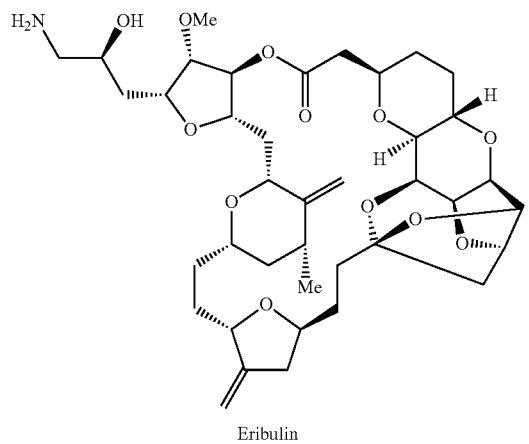

Eribulin

Due to their intriguing structural architecture and extraordinary in vitro and in vivo anti-proliferative activity, the halichondrins have received much attention from the scientific community. Indeed, Eisai recently received FDA approval for the halichondrin derivative eribulin (HALAVEN®) for treatment of metastatic breast cancer, further highlighting the importance these natural products derivatives. Thus, further research focused on the discovery of novel agents within this structural class is likely to provide new anti-proliferative agents with improved efficacy or safety. Furthermore, new synthetic methods that streamline the preparation of these natural products or related derivatives are important given the structural complexity of the halichondrin backbone.

SUMMARY OF THE INVENTION

The present invention provides the synthesis of halichondrin A and analogs of Formula (I);

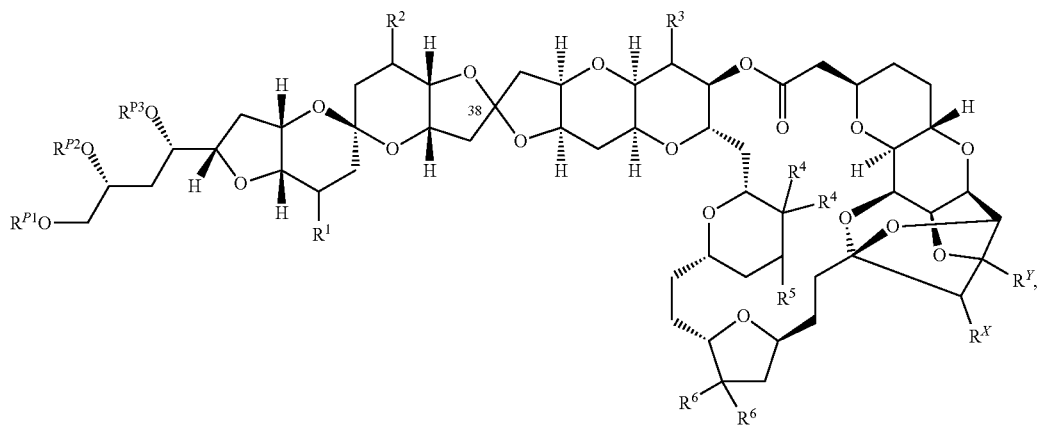

and pharmaceutically acceptable salts thereof, wherein $R^{P1}$, $R^{P2}$, $R^{P3}$, $R^1$, $R^2$, $R^3$, $R^4$, $R^5$, $R^6$, $R^X$, and $R^Y$ are described herein.

In another aspect, the present invention provides the synthesis of analogs of norhalichondrin A and homohalichondrin A of Formula (II) and (III), respectively:

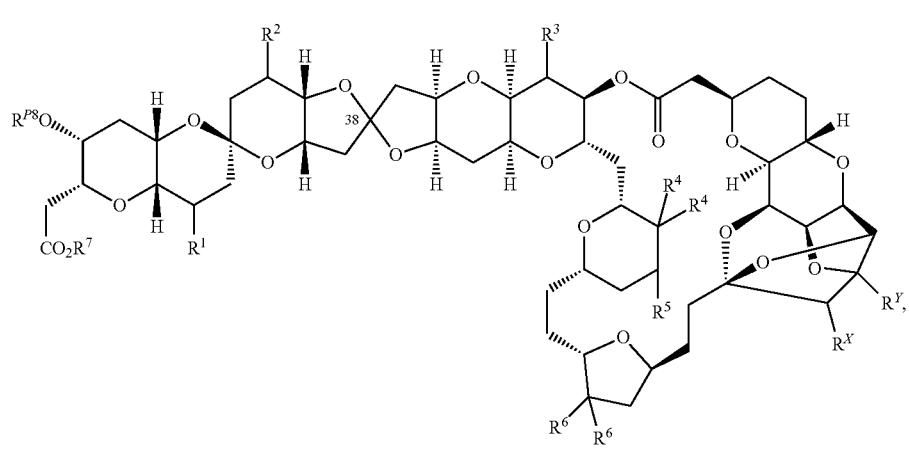

(II)

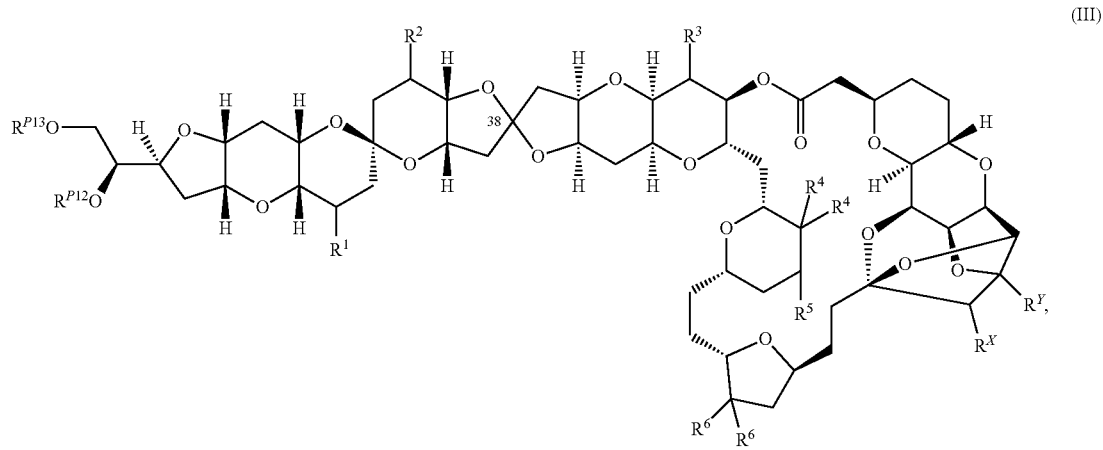

(III)

and pharmaceutically acceptable salts thereof, wherein $R^{P8}$, $R^{P12}$, $R^{P13}$, $R^1$, $R^2$, $R^3$, $R^4$, $R^5$, $R^6$, $R^7$, $R^X$, and $R^Y$ are described herein.

In another aspect, the present invention provides methods of preparing compounds of Formula (I)-(III) and intermediates thereto, including compounds of Formula (A-1)-(L-1) as described herein.

In another aspect, the present invention provides methods for interconverting between the halichondrins, norhalichondrins, and homohalichondrins, and their unnatural epimers at the C38 ketal stereocenter through the use of an acid-mediated equilibration (see FIG. 2).

In another aspect, the present invention provides the following compounds and methods for their preparation:
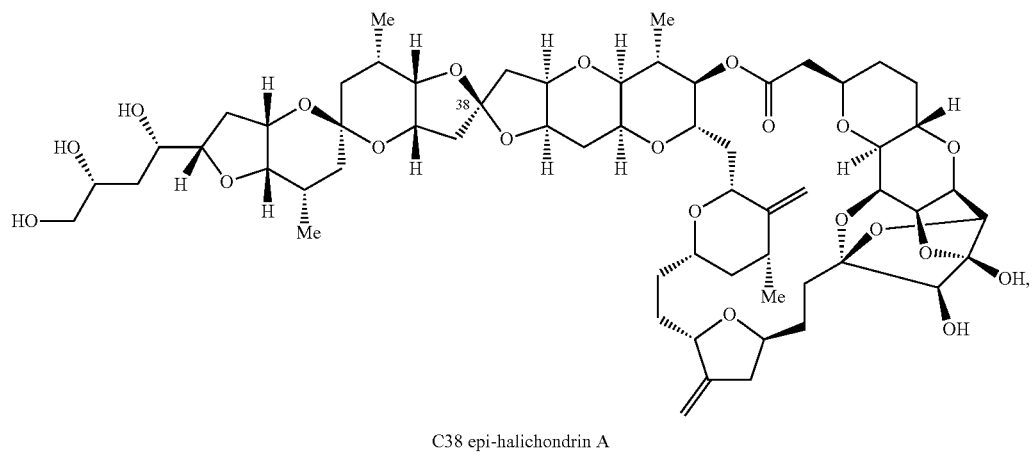
C38 epi-halichondrin A
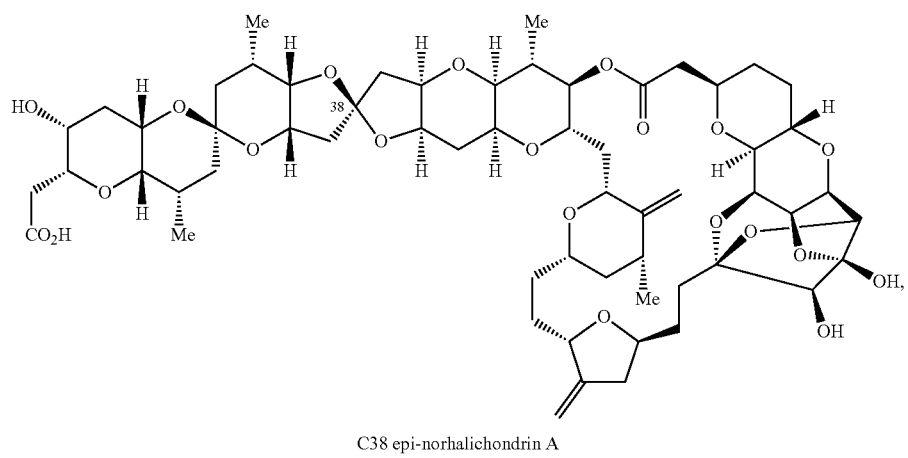
C38 epi-norhalichondrin A
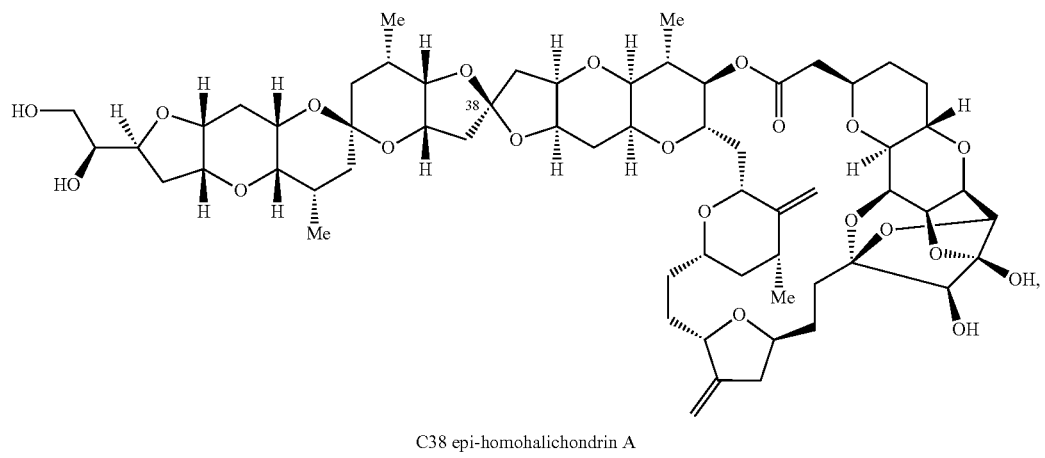
C38 epi-homohalichondrin A

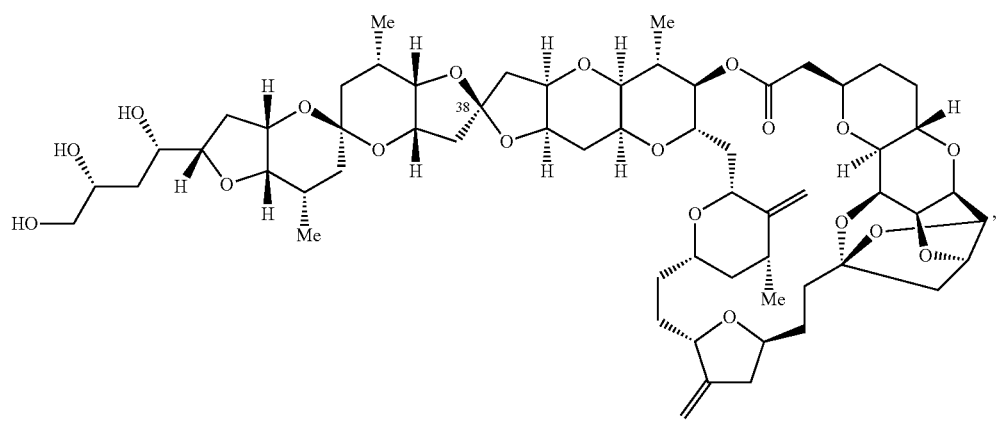
C38 epi-halichondrin B
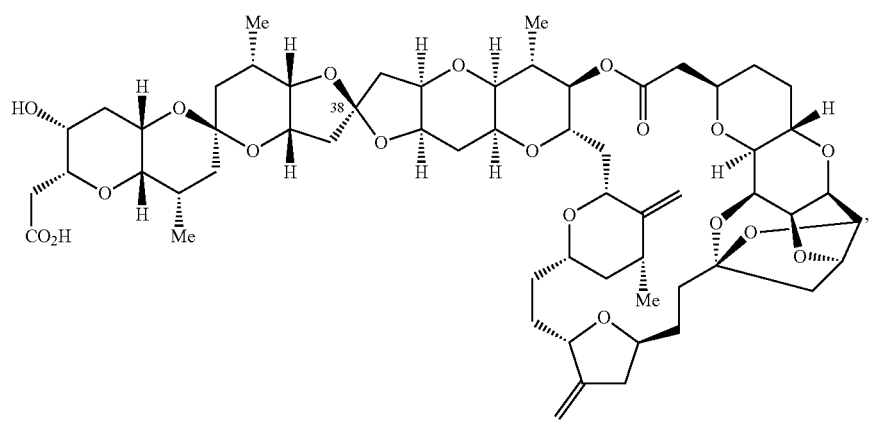
C38 epi-norhalichondrin B
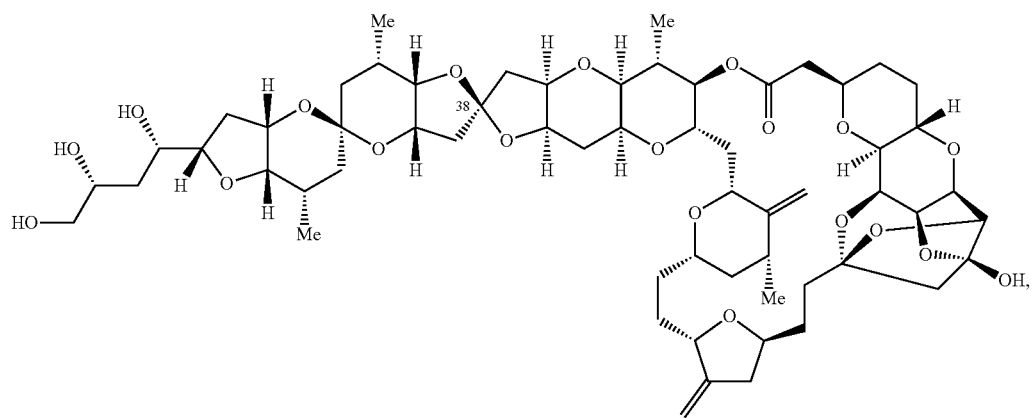
C38 epi-halichondrin C -continued
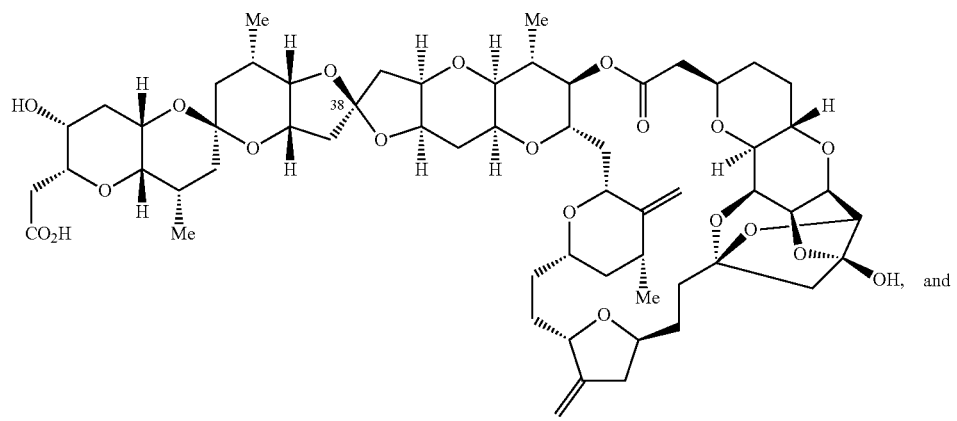
C38 epi-norhalichondrin C
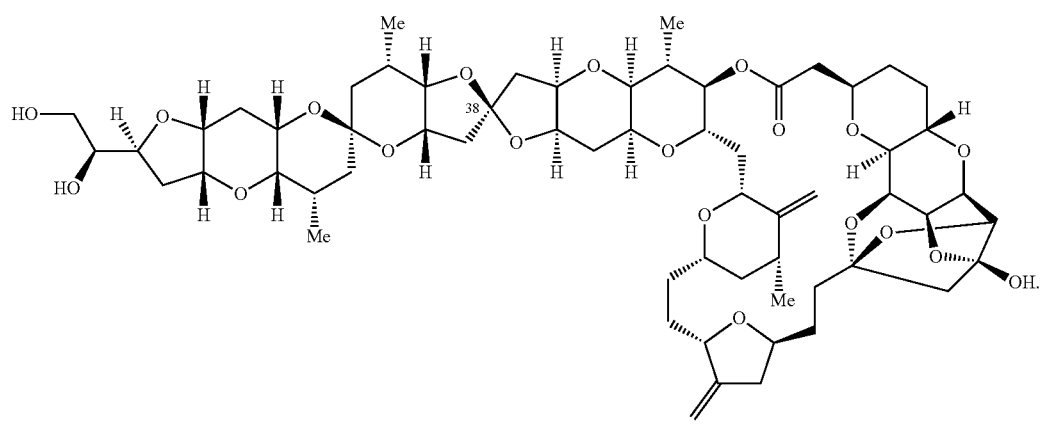
C38 epi-homohalichondrin C
In another aspect, the present invention provides methods of preparing any one of the following compounds:
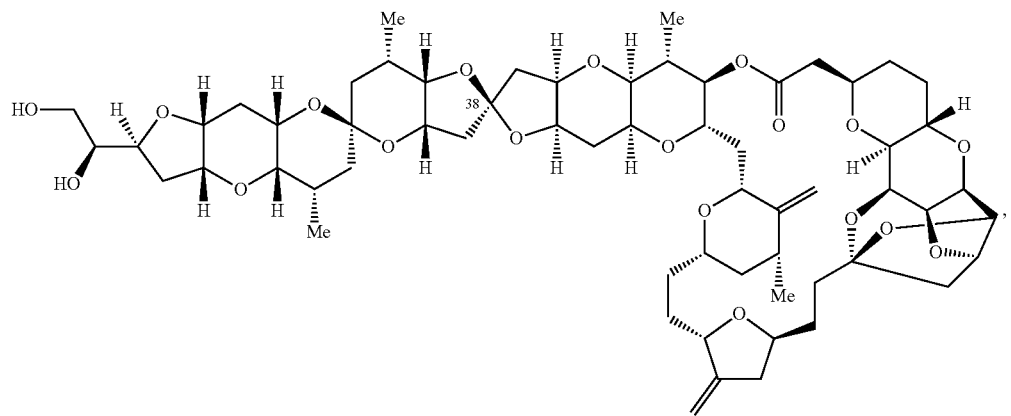
C38 epi-homohalichondrin B

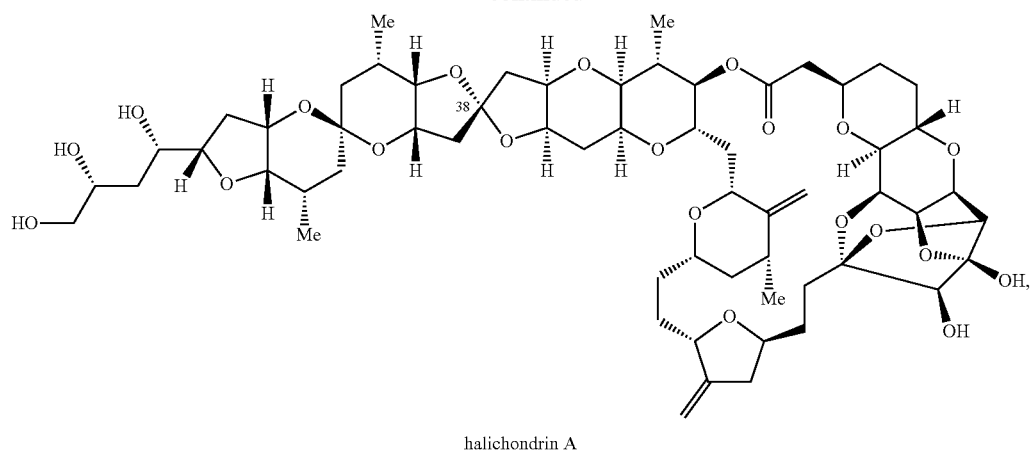
halichondrin A
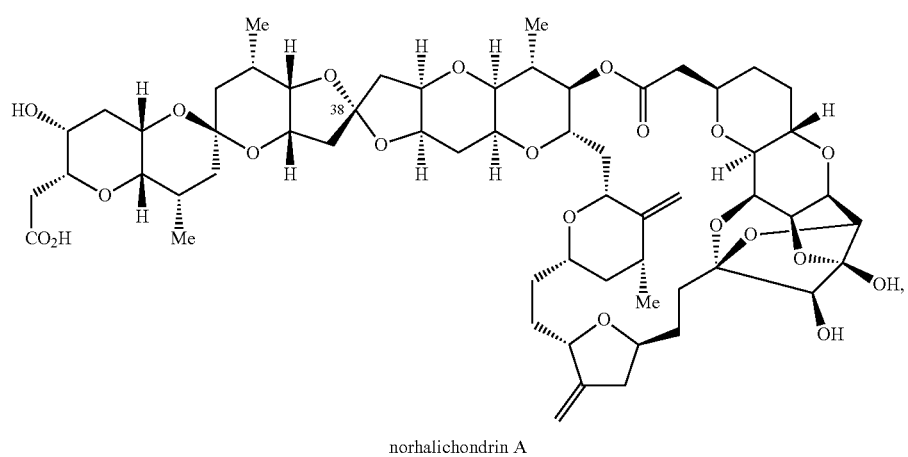
norhalichondrin A
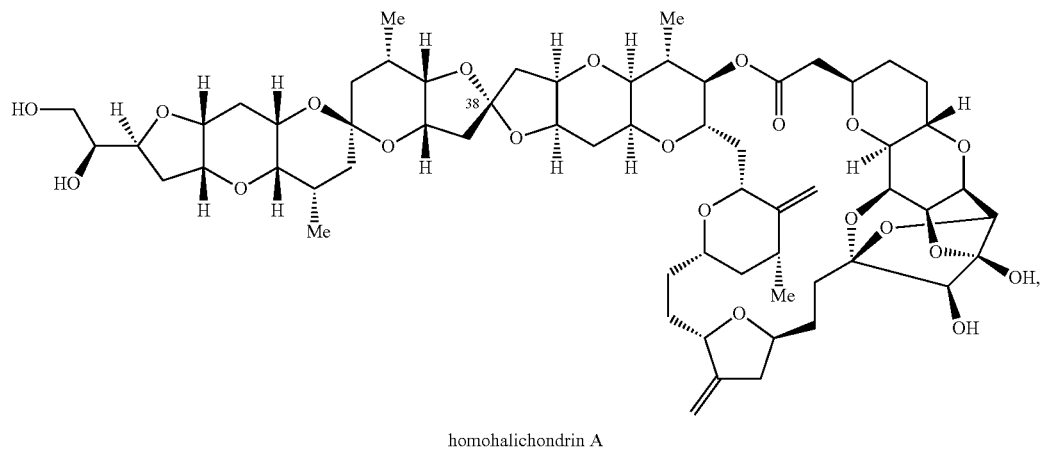
homohalichondrin A

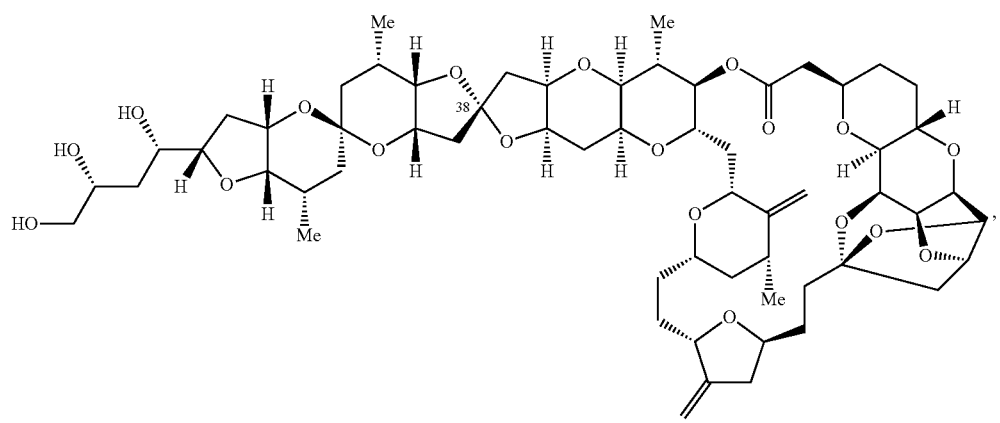
halichondrin B
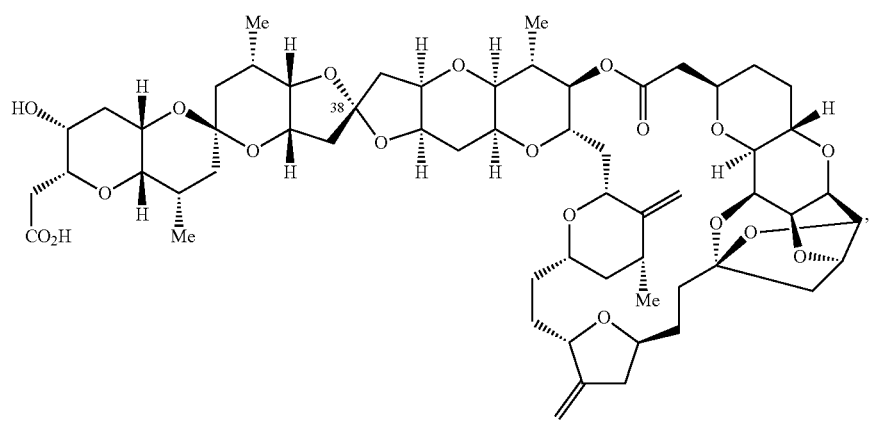
norhalichondrin B
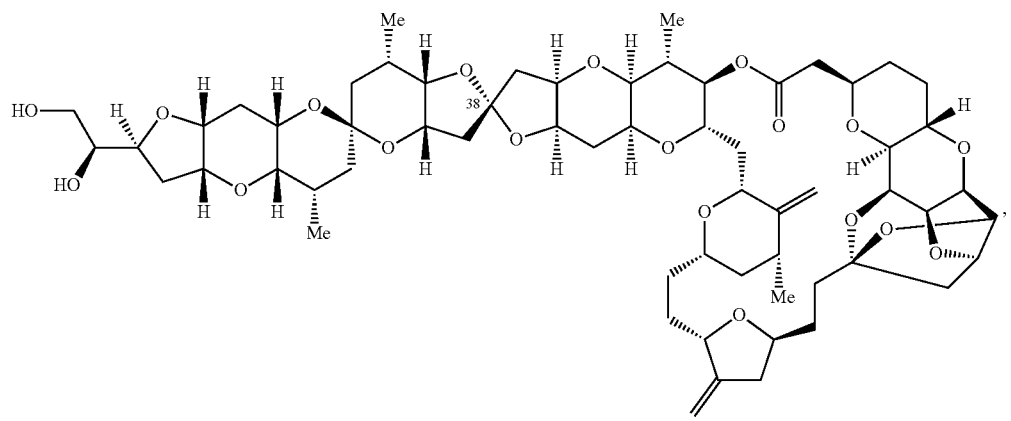
homohalichondrin B -continued

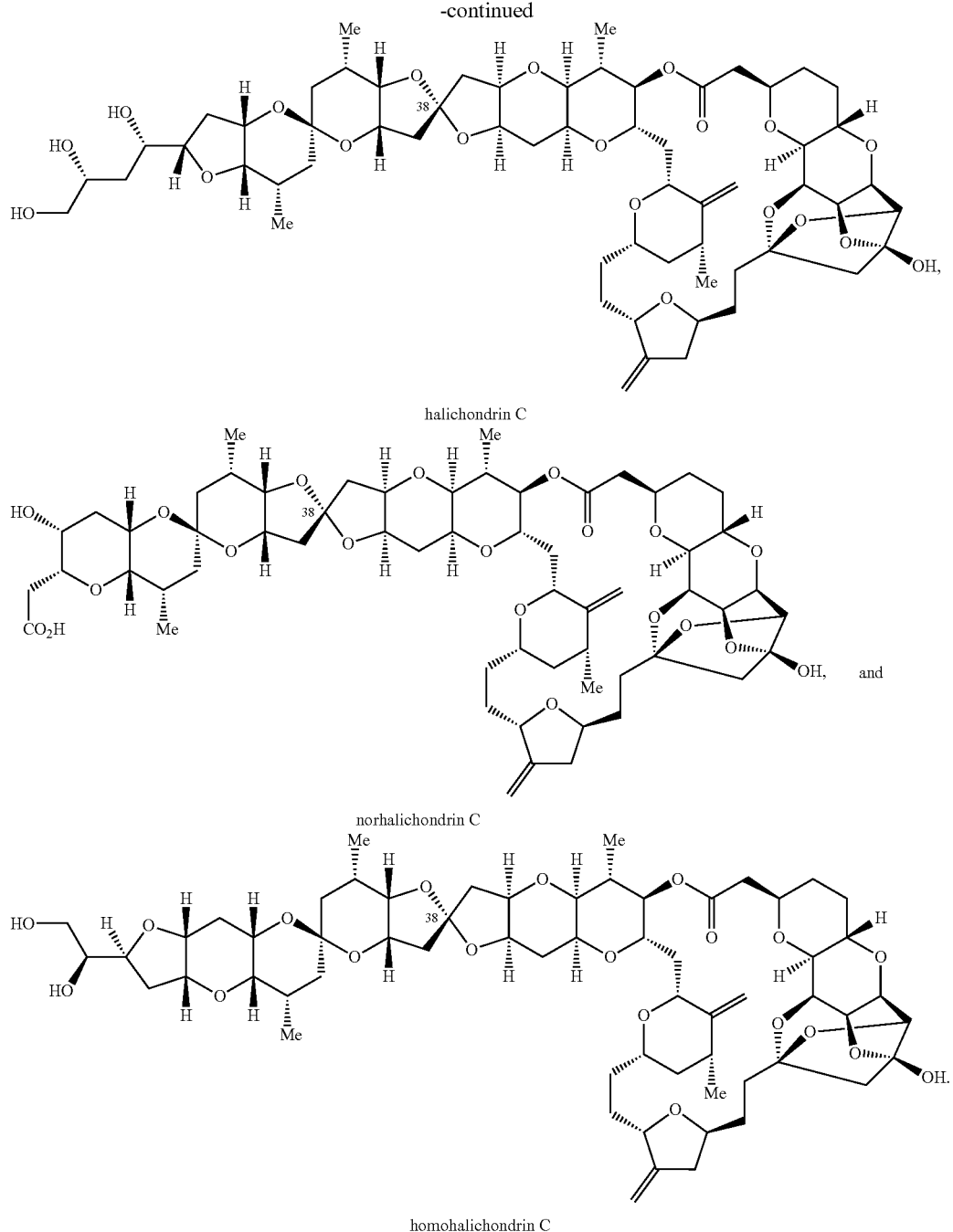

halichondrin C norhalichondrin C homohalichondrin C

In another aspect, provided are pharmaceutical compositions comprising a compound of Formula (I)-(III) and optionally a pharmaceutically acceptable excipient. In certain embodiments, the pharmaceutical composition is useful for treating and/or preventing a proliferative disease (e.g., cancer) in a subject in need thereof. In certain embodiments, the method includes administering to the subject a compound described herein, or a pharmaceutical composition thereof, in an amount sufficient to treat and/or prevent a proliferative disease.

In another aspect, provided are kits comprising a container with a compound described herein, or a pharmaceutical composition thereof. The kits may include a single dose or multiple doses of a compound described herein or a pharmaceutical composition thereof. The kits may also be useful for treating and/or preventing a proliferative disease (e.g., cancer) in a subject in need thereof. In certain embodiments, the kits further include instructions for using the kit (e.g., for administering a compound described herein, or a pharmaceutical composition thereof).

The details of certain embodiments of the invention are set forth in the Detailed Description of Certain Embodiments of the Invention, as described below. Other features, objects, and advantages of the invention will be apparent from the Claims.

BRIEF DESCRIPTION OF THE DRAWINGS

FIG. 6 shows $^1$H NMR chemical shifts of halichondrins (in CD$_3$OD).

FIG. 7 shows $^{13}$C NMR chemical shifts of halichondrins (in CD$_3$OD).

DEFINITIONS

Chemical Definitions

Figure 1:
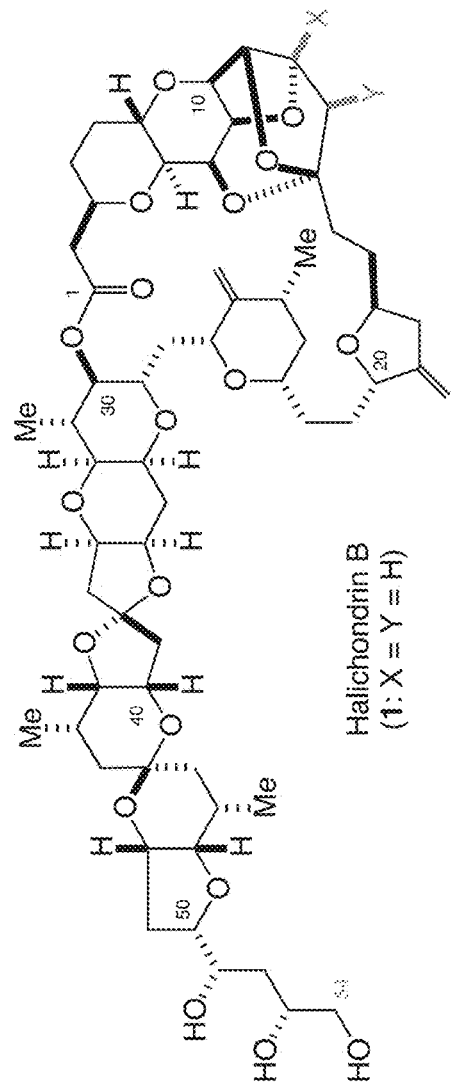
FIG. 1 shows the various sub-classes of halichondrins, norhalichondrins, and homohalichondrins. Norhalichondrins A-C, homohalichondrins A-C, and halichondrins B & C are known natural products, while halichondrin A has never been isolated from a natural source.
Figure 1:
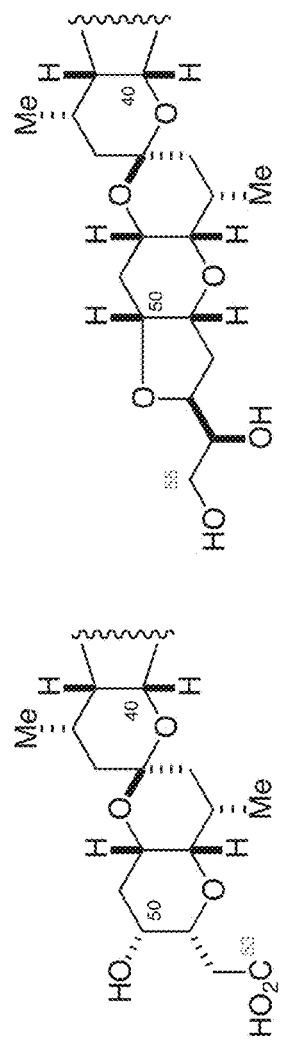

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The disclosure additionally encompasses compounds as individual isomers substantially free of other isomers, and alternatively, as mixtures of various isomers.

The term "heteroatom" refers to an atom that is not hydrogen or carbon. In certain embodiments, the heteroatom is nitrogen. In certain embodiments, the heteroatom is oxygen. In certain embodiments, the heteroatom is sulfur.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —CH$_3$). In certain embodiments, the alkyl group is a substituted $C_{1-10}$ alkyl.

The term "haloalkyl" is a substituted alkyl group, wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —CF$_3$, —CF$_2$CF$_3$, —CF$_2$CF$_2$CF$_3$, —CCl$_3$, —CFCl$_2$, —CF$_2$Cl, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("heteroC$_{1-10}$ alkyl"). In some embodiments, a heteroalkyl group is a saturated group having 1 to 9 carbon atoms and 1 or more heteroatoms within the parent chain ("heteroC$_{1-9}$ alkyl"). In some embodiments, a heteroalkyl group is a saturated group having 1 to 8 carbon atoms and 1 or more heteroatoms within the parent chain ("heteroC$_{1-8}$ alkyl"). In some embodiments, a heteroalkyl group is a saturated group having 1 to 7 carbon atoms and 1 or more heteroatoms within the parent chain ("heteroC$_{1-7}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and 1 or 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_{1-3}$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl. In an alkenyl group, a C=C double bond for which the stereochemistry is unspecified (e.g., —CH=CHCH$_3$ or

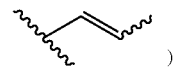
)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C$2-7 alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and 1 or 2 heteroatoms within the parent chain ("hetero$C$2-4 alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_4$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each hetermatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group substituted by a heteroaryl group, wherein the point of attachment is on the alkyl moiety.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C (=S)N(R$^{bb}$)$_2$, —C(=O)SR$^{aa}$, —C(=S)SR$^{aa}$, —SC(=S) SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCOR$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl) (C$_{1-6}$ alkyl), —N(OH)(C$_{1-6}$ alkyl), —NH (OH), —SH, —SC$_{1-6}$ alkyl, —SS(C$_{1-6}$ alkyl), —C(=O) (C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH) NH(C$_{1-6}$ alkyl), —OC(NH)NH$_2$, —NHC(NH) N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S) SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O) SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein.

The term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(NR$^{bb}$)$_2$, wherein R$^{aa}$, R$^{bb}$ and R$^{cc}$ are as defined herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(NR$^{bb}$)$_2$, wherein R$^{aa}$, R$^{bb}$, and R$^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3^+$X$^-$, wherein R$^{bb}$ and X$^-$ are as defined herein.

The term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

The term "sulfinyl" refers to the group —S(=O)R$^{aa}$, wherein R$^{aa}$ is as defined herein.

The term "carbonyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N(R$^{bb}$)$_2$, —C(=O)NR$^{bb}$SO$_2$R$^{aa}$, —C(=S)N(R$^{bb}$)$_2$), and imines (—C(=NR$^{bb}$)R$^{aa}$, —C(=NR$^{bb}$)OR$^{aa}$, —C(=NR$^{bb}$)N(R$^{bb}$)$_2$), wherein R$^{aa}$ and R$^{bb}$ are as defined herein.

The term "silyl" refers to the group —Si(R$^{aa}$)$_3$, wherein R$^{aa}$ is as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonicethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., $-S(=O)_2R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-rimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})$, —$C(=NR^{bb})$ $R^{aa}$, —$C(=NR^{bb})OR^{aa}$, —$C(=NR^{bb})N(R^{bb})_2$, —$S(=O)$ $R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{cc})_2$, —$P(=O)(OR^{bb})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

The term "leaving group" is given its ordinary meaning in the art of synthetic organic chemistry and refers to an atom or a group capable of being displaced by a nucleophile. Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

A "hydrocarbon chain" refers to a substituted or unsubstituted divalent alkyl, alkenyl, or alkynyl group. A hydrocarbon chain. includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms") and does not include hydrogen atoms or heteroatoms. However, a non-chain substituent of a hydrocarbon chain may include any atoms, including hydrogen atoms, carbon atoms, and heteroatoms. For example, hydrocarbon chain —$C^AH(C^BH_2C^CH_3)$— includes one chain atom $C^A$, one hydrogen atom on $C^A$, and non-chain substituent —$(C^BH_2C^CH_3)$. The term "$C_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —$CH(C_2H_5)$— is a $C_1$ hydrocarbon chain, and

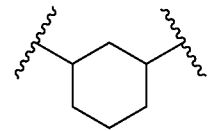 [SMILES: *C1CCCC(*)C1]

is a $C_3$ hydrocarbon chain. When a range of values is used, the meaning of the range is as described herein. For example, a $C_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —$(CH_2)_4$—). A hydrocarbon chain may also be unsaturated and include one or more C=C and/or C≡C bonds anywhere in the hydrocarbon chain. For instance, —CH=CH—$(CH_2)_2$—, —$CH_2$—C≡C—$CH_2$—, and —C≡C—CH=CH— are all examples of a unsubstituted and unsaturated hydrocarbon chain. In certain embodiments, the hydrocarbon chain is unsubstituted (e.g., —C≡C— or —$(CH_2)_4$—). In certain embodiments, the hydrocarbon chain is substituted (e.g., —$CH(C_2H_5)$— and —$CF_2$—). Any two substituents on the hydrocarbon chain may be joined to form an optionally substituted carbocyclyl, optionally substituted heterocyclyl, optionally substituted aryl, or optionally substituted heteroaryl ring. For instance,

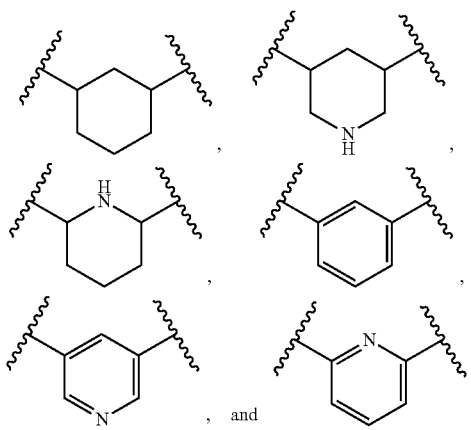

are all examples of a hydrocarbon chain. In contrast, in certain embodiments,

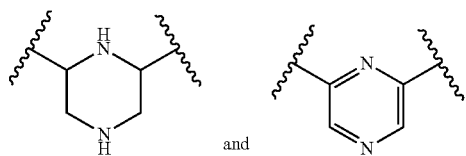 [SMILES: *C1CNCC(*)N1 ; *c1cncc(*)n1]

are not within the scope of the hydrocarbon chains described herein. When a chain atom of a $C_x$ hydrocarbon chain is replaced with a heteroatom, the resulting group is referred to as a $C_x$ hydrocarbon chain wherein a chain atom is replaced with a heteroatom, as opposed to a $C_{x-1}$ hydrocarbon chain. For example,

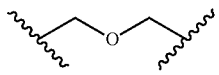

is a $C_3$ hydrocarbon chain wherein one chain atom is replaced with an oxygen atom.

The term "acyl" refers a group wherein the carbon directly attached to the parent molecule is $sp^2$ hybridized, and is substituted with an oxygen, nitrogen, or sulfur atom, e.g., a group selected from ketones (—C(=O)$R^{aa}$), carboxylic acids (—CO$_2$H), aldehydes (—CHO), esters (—CO$_2R^{aa}$, —C(=O)S$R^{aa}$, —C(=S)S$R^{aa}$), amides (—C(=O)N($R^{bb}$)$_2$, —C(=O)N$R^{bb}$SO$_2R^{aa}$, —C(=S)N($R^{bb}$)$_2$), and imines (—C(=N$R^{bb}$)$R^{aa}$, —C(=NR)O$R^{aa}$, —C(=N$R^{bb}$)N($R^{bb}$)), wherein $R^{aa}$ and $R^{bb}$ are as defined herein.

The term "Lewis acid" refers to a species as defined by IUPAC, that is "a molecular entity (and the corresponding chemical species) that is an electron-pair acceptor and therefore able to react with a Lewis base to form a Lewis adduct, by sharing the electron pair furnished by the Lewis base." Exemplary Lewis acids include, without limitation, boron trifluoride, aluminum trichloride, tin tetrachloride, titanium tetrachloride, and iron tribromide.

The term "Brønsted acid" refers to a protic or proton-donating species. Exemplary Brønsted acids include, without limitation, acetic acid, triflic acid, hydrochloric acid, and barbituric acid.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$ (C$_{1-4}$ alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.x H$_2$O, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5H$_2$O)), and polyhydrates (x is a number greater than 1, e.g., dihydrates (R.2H$_2$O) and hexahydrates (R.6H$_2$O)).

The term "tautomers" or "tautomeric" refers to two or more interconvertable compounds resulting from at least one formal migration of a hydrogen atom and at least one change in valency (e.g., a single bond to a double bond, a triple-bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refer to compounds which have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The terms "composition" and "formulation" are used interchangeably.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female at any stage of development. The animal may be a transgenic animal or genetically engineered animal. In certain embodiments, the subject is a non-human animal. In certain embodiments, the animal is a fish or reptile. A "patient" refers to a human subject in need of treatment of a disease.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The term "prevent" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population.

The terms "condition," "disease," and "disorder" are used interchangeably.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "inhibition", "inhibiting", "inhibit," or "inhibitor" refer to the ability of a compound to reduce, slow, halt, or prevent activity of a particular biological process (e.g., kinase activity) in a cell relative to vehicle.

When a compound, pharmaceutical composition, method, use, or kit is referred to as "selectively" or "specifically" modulating (e.g., increasing or inhibiting) the activity of a first protein kinase, the compound, pharmaceutical composition, method, use, or kit modulates the activity of the first protein kinase to a greater extent (e.g., not less than about 2-fold, not less than about 5-fold, not less than about 10-fold, not less than about 30-fold, not less than about 100-fold, not less than about 1,000-fold, or not less than about 10,000-fold) than the activity of at least a second protein kinase that is different from the first protein kinase.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, acoustic neuroma; adenocarcinoma; adrenal gland cancer, anal cancer, angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer, breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor, cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer, gastric cancer (e.g., stomach adenocarcinoma); gastrointestinal stromal tumor (GIST); germ cell cancer, head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angio-immunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer, myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer, sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer, vaginal cancer, and vulvar cancer (e.g., Paget's disease of the vulva).

DETAILED DESCRIPTION OF CERTAIN EMBODIMENTS OF THE INVENTION

The present invention provides the first synthesis of halichondrin A, and analogs thereof, and analogs of norhalichondrin A and homohalichondrin A. The present invention provides methods of preparing these compounds and their analogs along with various intermediates used in these syntheses. The synthetic routes presented herein include: (1) synthesis of a C1-C19 building block via a catalytic asymmetric chromium-mediated coupling; (2) synthesis of the macrocyclic core via an asymmetric nickel/chromium-mediated coupling, followed by base-induced furan formation, and macrolactonization; (3) synthesis of an unsaturated ketone intermediate via nickel/chromium-mediated coupling, followed by Dess-Martin oxidation; and (4) a newly discovered, highly selective acid-mediated equilibration of C38-epi-halichondrin A to halichondrin A. In addition, the structure of these compounds including halichondrin A has been determined unambiguously. The present invention also provides pharmaceutical compositions comprising any of the halichondrin A, norhalichondrin A, or homohalichondrin A analogs described herein, and optionally a pharmaceutically acceptable excipient. These pharmaceutical compositions may be useful for treating and/or preventing a proliferative disease (e.g., cancer) in a subject in need thereof. The present invention also provides kits comprising a container with a compound described herein, or a pharmaceutical composition thereof.

As generally described herein, provided are halichondrin A and analogs thereof of Formula (I):

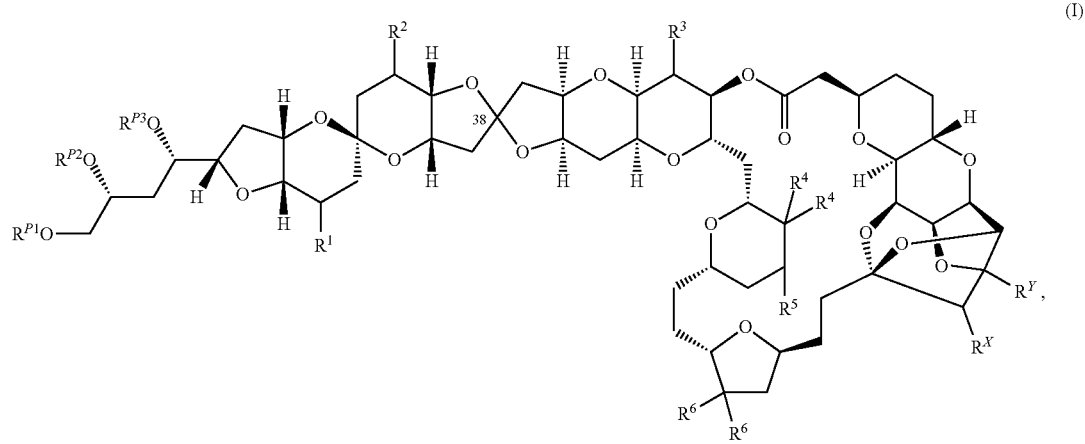

and pharmaceutically acceptable salts thereof,
wherein
$R^{P1}$, $R^{P2}$, and $R^{P3}$ are each independently hydrogen, substituted or unsubstituted alkyl, or an oxygen protecting group;
$R^1$, $R^2$, $R^3$, and $R^5$ are each independently hydrogen, halogen, or substituted or unsubstituted alkyl;
each instance of $R^4$ is independently hydrogen, halogen, substituted or unsubstituted alkyl, or two $R^4$ groups can be taken together to form a

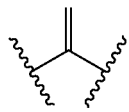 [SMILES: *C(*)=C]

group;
each instance of $R^6$ is independently hydrogen, halogen, substituted or unsubstituted alkyl, or two $R^6$ groups can be taken together to form a

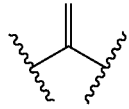 [SMILES: *C(*)=C]

group;
$R^X$ is —$OR^{X1}$, wherein $R^{X1}$ is hydrogen, substituted or unsubstituted alkyl, or an oxygen protecting group;
$R^Y$ is —$OR^{Y1}$, wherein $R^{Y1}$ is hydrogen, substituted or unsubstituted alkyl, or an oxygen protecting group; and
$R^X$ and $R^Y$ can be taken with their intervening atoms to form a substituted or unsubstituted heterocyclic ring.

In another aspect, provided are norhalichondrin A analogs of Formula (II):

and pharmaceutically acceptable salts thereof,
wherein
$R^{P8}$ is hydrogen, substituted or unsubstituted alkyl, or an oxygen protecting group;
$R^1$, $R^2$, $R^3$, and $R^5$ are each independently hydrogen, halogen, or substituted or unsubstituted alkyl;
each instance of $R^4$ is independently hydrogen, halogen, substituted or unsubstituted alkyl, or two $R^4$ groups can be taken together to form a

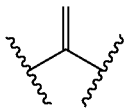

group;
each instance of $R^6$ is independently hydrogen, halogen, substituted or unsubstituted alkyl, or two $R^6$ groups can be taken together to form a

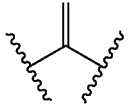

group;
$R^7$ is hydrogen, substituted or unsubstituted alkyl, or an oxygen protecting group;
$R^X$ is —$OR^{X1}$, wherein $R^{X1}$ is hydrogen, substituted or unsubstituted alkyl, or an oxygen protecting group;
$R^Y$ is —$OR^{Y1}$, wherein $R^{Y1}$ is hydrogen, substituted or unsubstituted alkyl, or an oxygen protecting group; and
$R^X$ and $R^Y$ can be taken with their intervening atoms to form a substituted or unsubstituted heterocyclic ring;

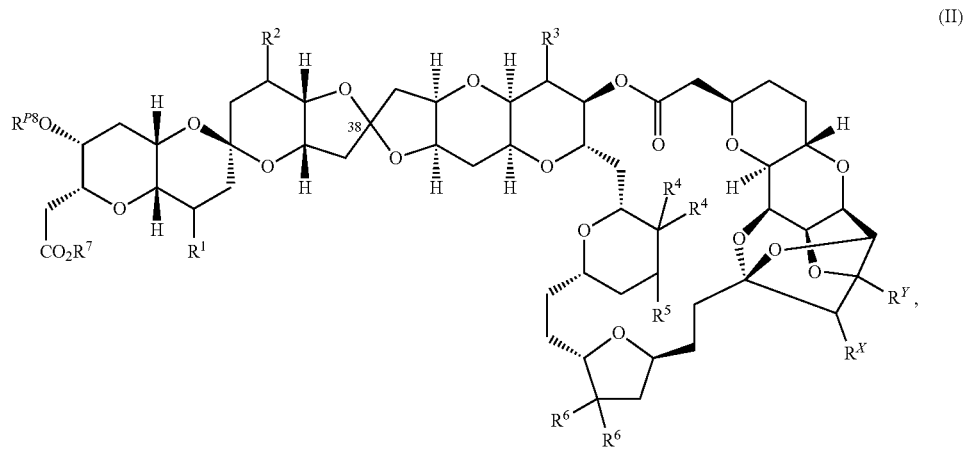

(II)

provided that a compound of Formula (II) is not norhalichondrin A:

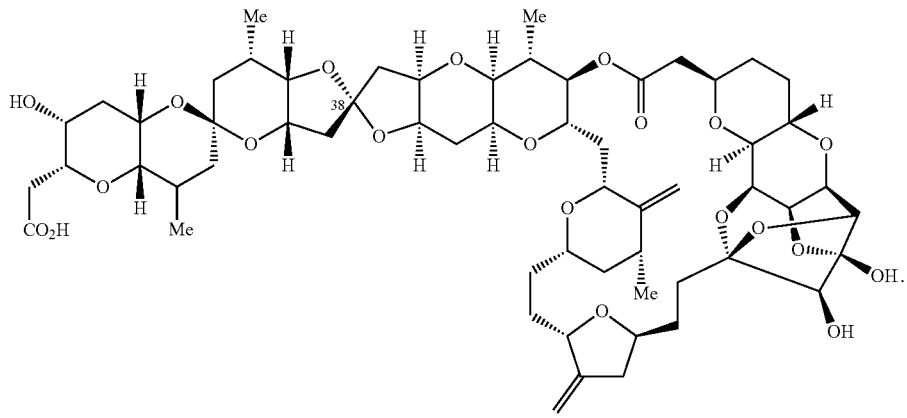

In another aspect, provided are homohalichondrin A analogs of Formula (IM):

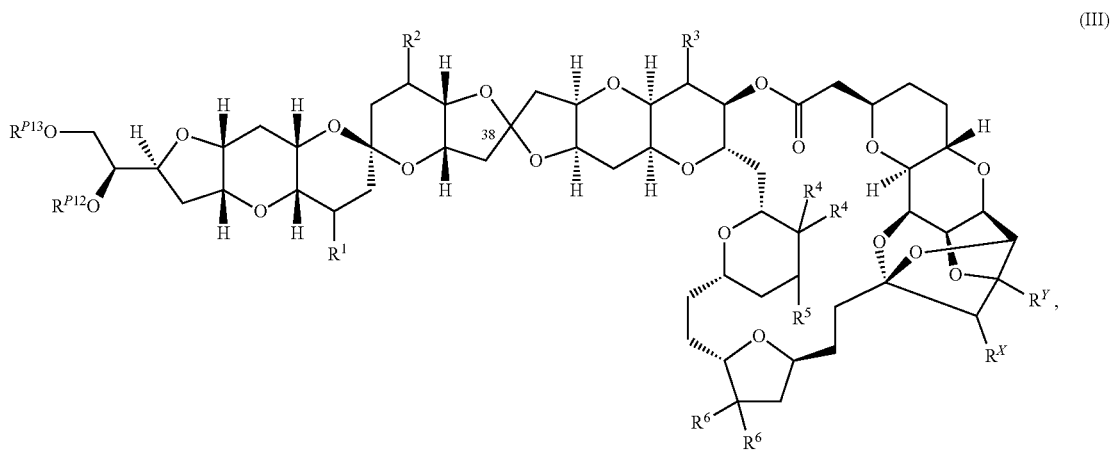

and pharmaceutically acceptable salts thereof,
wherein $R^{P12}$ and $R^{P13}$ are each independently hydrogen, substituted or unsubstituted alkyl, or an oxygen protecting group;

$R^1$, $R^2$, $R^3$, and $R^5$ are each independently hydrogen, halogen, or substituted or unsubstituted alkyl;

each instance of $R^4$ is independently hydrogen, halogen, substituted or unsubstituted alkyl, or two $R^4$ groups can be taken together to form a

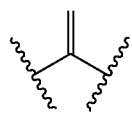

group;

each instance of $R^6$ is independently hydrogen, halogen, substituted or unsubstituted alkyl, or two $R^6$ groups can be taken together to form

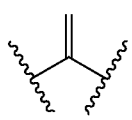 [SMILES: *C(*)=C]

group;

$R^X$ is —$OR^{X1}$, wherein $R^{X1}$ is hydrogen, substituted or unsubstituted alkyl, or an oxygen protecting group;

$R^Y$ is —$OR^{Y1}$, wherein $R^{Y1}$ is hydrogen, substituted or unsubstituted alkyl, or an oxygen protecting group; and $R^X$ and $R^Y$ can be taken with their intervening atoms to form a substituted or unsubstituted heterocyclic ring;

provided that a compound of Formula (III) is not homohalichondrin A:

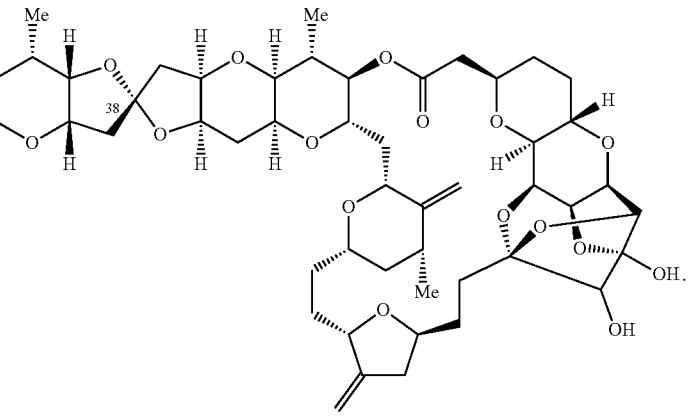

Groups $R^{P1}$, $R^{P2}$, $R^{P3}$, $R^{P4}$, $R^{P5}$, $R^{P6}$, $R^{P7}$, $R^{P8}$, $R^{P9}$, $R^{P10}$, $R^{P11}$, $R^{P12}$, $R^{P13}$, $R^{P14}$, $R^{P15}$, $R^{P16}$, $R^{P17}$, $R^{P18}$, and $R^{P19}$ As generally described herein, $R^{P1}$, $R^{P2}$, $R^{P3}$, $R^{P4}$, $R^{P5}$, $R^{P6}$, $R^{P7}$, $R^{P8}$, $R^{P9}$, $R^{P10}$, $R^{P11}$, $R^{P12}$, $R^{P13}$, $R^{P14}$, $R^{P15}$, $R^{P16}$, $R^{P17}$, $R^{P18}$, and $R^{P19}$ are each independently hydrogen, substituted or unsubstituted alkyl; or an oxygen protecting group.

In certain embodiments, $R^{P1}$ is hydrogen. In certain embodiments, $R^{P1}$ is substituted or unsubstituted alkyl. In certain embodiments, $R^{P1}$ is substituted or unsubstituted $C_{1-6}$ alkyl. In certain embodiments, $R^{P1}$ is substituted or unsubstituted, branched $C_{1-6}$ alkyl. In certain embodiments, $R^{P1}$ is unsubstituted $C_{1-6}$ alkyl. In certain embodiments, $R^{P1}$ is methyl. In certain embodiments, $R^{P1}$ is ethyl. In certain embodiments, $R^{P1}$ is propyl. In certain embodiments, $R^{P1}$ is iso-propyl. In certain embodiments, $R^{P1}$ is t-butyl. In certain embodiments, $R^{P1}$ is an oxygen protecting group. In certain embodiments, $R^{P1}$ is a silyl protecting group. In certain embodiments, $R^{P1}$ is a trialkyl silyl protecting group. In certain embodiments, $R^{P1}$ is a t-butyldimethylsilyl protecting group. In certain embodiments, $R^{P1}$ is a trimethylsilyl protecting group. In certain embodiments, $R^{P1}$ is a triethylsilyl protecting group. In certain embodiments, $R^{P1}$ is a t-butyldiphenylsilyl protecting group. In certain embodiments, $R^{P1}$ is a triisopropylsilyl protecting group. In certain embodiments, $R^{P1}$ is a benzylic protecting group. In certain embodiments, $R^{P1}$ is a p-methoxybenzyl protecting group. In certain embodiments, $R^{P1}$ is an acyl protecting group. In certain embodiments, $R^{P1}$ is an acetyl protecting group. In certain embodiments, $R^{P1}$ is a benzoyl protecting group. In certain embodiments, $R^{P1}$ is ap-nitro benzoyl protecting group. In certain embodiments, $R^{P1}$ is a pivaloyl protecting group. In certain embodiments, $R^{P1}$ is a t-butyl carbonate (BOC) protecting group. In certain embodiments, $R^{P1}$ is an acetal protecting group. In certain embodiments, $R^{P1}$ is a tetrahydropyranyl protecting group. In certain embodiments, $R^{P1}$ is an alkoxyalkyl protecting group. In certain embodiments, $R^{P1}$ is an ethoxyethyl protecting group.

In certain embodiments, $R^{P2}$ is hydrogen. In certain embodiments, $R^{P2}$ is substituted or unsubstituted alkyl. In certain embodiments, $R^{P2}$ is substituted or unsubstituted $C_{1-6}$ alkyl. In certain embodiments, $R^{P2}$ is substituted or unsubstituted, branched $C_{1-6}$ alkyl. In certain embodiments, $R^{P2}$ is unsubstituted $C_{1-6}$ alkyl. In certain embodiments, $R^{P2}$ is methyl. In certain embodiments, $R^{P2}$ is ethyl. In certain embodiments, $R^{P2}$ is propyl. In certain embodiments, $R^{P2}$ is iso-propyl. In certain embodiments, $R^{P2}$ is t-butyl. In certain embodiments, $R^{P2}$ is an oxygen protecting group. In certain embodiments, $R^{P2}$ is a silyl protecting group. In certain embodiments, $R^{P2}$ is a trialkyl silyl protecting group. In certain embodiments, $R^{P2}$ is a t-butyldimethylsilyl protecting group. In certain embodiments, $R^{P2}$ is a trimethylsilyl protecting group. In certain embodiments, $R^{P2}$ is a triethylsilyl protecting group. In certain embodiments, $R^{P2}$ is a t-butyldiphenylsilyl protecting group. In certain embodiments, $R^{P2}$ is a triisopropylsilyl protecting group. In certain embodiments, $R^{P2}$ is a benzylic protecting group. In certain embodiments, $R^{P2}$ is a p-methoxybenzyl protecting group. In certain embodiments, $R^{P2}$ is an acyl protecting group. In certain embodiments, $R^{P2}$ is an acetyl protecting group. In certain embodiments, $R^{P2}$ is a benzoyl protecting group. In certain embodiments, $R^{P2}$ is ap-nitro benzoyl protecting group. In certain embodiments, $R^{P2}$ is a pivaloyl protecting group. In certain embodiments, $R^{P2}$ is a t-butyl carbonate (BOC) protecting group. In certain embodiments, $R^{P2}$ is an acetal protecting group. In certain embodiments, $R^{P2}$ is a tetrahydropyranyl protecting group. In certain embodiments, $R^{P2}$ is an alkoxyalkyl protecting group. In certain embodiments, $R^{P2}$ is an ethoxyethyl protecting group.

In certain embodiments, $R^{P3}$ is hydrogen. In certain embodiments, $R^{P3}$ is substituted or unsubstituted alkyl. In certain embodiments, $R^{P3}$ is substituted or unsubstituted $C_{1-6}$ alkyl. In certain embodiments, $R^{P3}$ is substituted or unsubstituted, branched $C_{1-6}$ alkyl. In certain embodiments, $R^{P3}$ is unsubstituted $C_{1-6}$ alkyl. In certain embodiments, $R^{P3}$ is methyl. In certain embodiments, $R^{P3}$ is ethyl. In certain embodiments, $R^{P3}$ is propyl. In certain embodiments, $R^{P3}$ is iso-propyl. In certain embodiments, $R^{P3}$ is t-butyl. In certain embodiments, $R^{P3}$ is an oxygen protecting group. In certain embodiments, $R^{P3}$ is a silyl protecting group. In certain embodiments, $R^{P3}$ is a trialkyl silyl protecting group. In certain embodiments, $R^{P3}$ is a t-butyldimethylsilyl protecting group. In certain embodiments, $R^{P3}$ is a trimethylsilyl protecting group. In certain embodiments, $R^{P3}$ is a triethylsilyl protecting group. In certain embodiments, $R^{P3}$ is a t-butyldiphenylsilyl protecting group. In certain embodiments, $R^{P3}$ is a triisopropylsilyl protecting group. In certain embodiments, $R^{P3}$ is a benzylic protecting group. In certain embodiments, $R^{P3}$ is a p-methoxybenzyl protecting group. In certain embodiments, $R^{P3}$ is an acyl protecting group. In certain embodiments, $R^{P3}$ is an acetyl protecting group. In certain embodiments, $R^{P3}$ is a benzoyl protecting group. In certain embodiments, $R^{P3}$ is ap-nitro benzoyl protecting group. In certain embodiments, $R^{P3}$ is a pivaloyl protecting group. In certain embodiments, $R^{P3}$ is a t-butyl carbonate (BOC) protecting group. In certain embodiments, $R^{P3}$ is an acetal protecting group. In certain embodiments, $R^{P3}$ is a tetrahydropyranyl protecting group. In certain embodiments, $R^{P3}$ is an alkoxyalkyl protecting group. In certain embodiments, $R^{P3}$ is an ethoxyethyl protecting group.

In certain embodiments, $R^{P4}$ is hydrogen. In certain embodiments, $R^{P4}$ is substituted or unsubstituted alkyl. In certain embodiments, $R^{P4}$ is substituted or unsubstituted $C_{1-6}$ alkyl. In certain embodiments, $R^{P4}$ is substituted or unsubstituted, branched $C_{1-6}$ alkyl. In certain embodiments, $R^{P4}$ is unsubstituted $C_{1-6}$ alkyl. In certain embodiments, $R^4$ is methyl. In certain embodiments, $R^{P4}$ is ethyl. In certain embodiments, $R^{P4}$ is propyl. In certain embodiments, $R^{P4}$ is iso-propyl. In certain embodiments, $R^{P4}$ is t-butyl. In certain embodiments, $R^{P4}$ is an oxygen protecting group. In certain embodiments, $R^{P4}$ is a silyl protecting group. In certain embodiments, $R^{P4}$ is a trialkyl silyl protecting group. In certain embodiments, $R^{P4}$ is a t-butyldimethylsilyl protecting group. In certain embodiments, $R^{P4}$ is a trimethylsilyl protecting group. In certain embodiments. $R^{P4}$ is a triethylsilyl protecting group. In certain embodiments, $R^{P4}$ is a t-butyldiphenylsilyl protecting group. In certain embodiments, $R^{P4}$ is a triisopropylsilyl protecting group. In certain embodiments, $R^{P4}$ is a benzylic protecting group. In certain embodiments, $R^{P4}$ is ap-methoxybenzyl protecting group. In certain embodiments, $R^{P4}$ is an acyl protecting group. In certain embodiments, $R^1$ is an acetyl protecting group. In certain embodiments, $R^{P4}$ is a benzoyl protecting group. In certain embodiments, $R^{P4}$ is a p-nitro benzoyl protecting group. In certain embodiments, $R^{P4}$ is a pivaloyl protecting group. In certain. embodiments, $R^{P4}$ is a t-butyl carbonate (BOC) protecting group. In certain embodiments, $R^{P4}$ is an acetal protecting group. In certain embodiments, $R^{P4}$ is a tetrahydropyranyl protecting group. In certain embodiments, $R^{P4}$ is an alkoxyalkyl protecting group. In certain embodiments, $R^{P4}$ is an ethoxyethyl protecting group.

In certain embodiments, $R^{P5}$ is hydrogen. In certain embodiments, $R^{P5}$ is substituted or unsubstituted alkyl. In certain embodiments, $R^{P5}$ is substituted or unsubstituted $C_{1-6}$ alkyl. In certain embodiments, $R^{P5}$ is substituted or unsubstituted, branched $C_{1-6}$ alkyl. In certain embodiments, $R^{P5}$ is unsubstituted $C_{1-6}$ alkyl. In certain embodiments, $R^{P5}$ is methyl. In certain embodiments, $R^{P5}$ is ethyl. In certain embodiments, $R^{P5}$ is propyl. In certain embodiments, $R^{P5}$ is iso-propyl. In certain embodiments, $R^{P5}$ is t-butyl. In certain embodiments, $R^{P5}$ is an oxygen protecting group. In certain embodiments, $R^{P5}$ is a silyl protecting group. In certain embodiments, $R^{P5}$ is a trialkyl silyl protecting group. In certain embodiments, $R^{P5}$ is a t-butyldimethylsilyl protecting group. In certain embodiments, $R^{P5}$ is a trimethylsilyl protecting group. In certain embodiments, $R^{P5}$ is a triethylsilyl protecting group. In certain embodiments, $R^{P5}$ is a t-butyldiphenylsilyl protecting group. In certain embodiments, $R^{P5}$ is a triisopropylsilyl protecting group. In certain embodiments, $R^{P5}$ is a benzylic protecting group. In certain embodiments, $R^{P5}$ is a p-methoxybenzyl protecting group. In certain embodiments, $R^{P5}$ is an acyl protecting group. In certain embodiments, $R^{P5}$ is an acetyl protecting group. In certain embodiments, $R^{P5}$ is a benzoyl protecting group. In certain embodiments, $R^{P5}$ is ap-nitro benzoyl protecting group. In certain embodiments, $R^{P5}$ is a pivaloyl protecting group. In certain embodiments, $R^{P5}$ is a t-butyl carbonate (BOC) protecting group. In certain embodiments, $R^{P5}$ is an acetal protecting group. In certain embodiments, $R^{P5}$ is a tetrahydropyranyl protecting group. In certain embodiments, $R^{P5}$ is an alkoxyalkyl protecting group. In certain embodiments, $R^{P5}$ is an ethoxyethyl protecting group.

In certain embodiments, $R^{P6}$ is hydrogen. In certain embodiments, $R^{P6}$ is substituted or unsubstituted alkyl. In certain embodiments, $R^{P6}$ is substituted or unsubstituted $C_{1-6}$ alkyl. In certain embodiments, $R^{P6}$ is substituted or unsubstituted, branched $C_{1-6}$ alkyl. In certain embodiments, $R^{P6}$ is unsubstituted $C_{1-6}$ alkyl. In certain embodiments, $R^{P6}$ is methyl. In certain embodiments, $R^{P6}$ is ethyl. In certain embodiments, $R^{P6}$ is propyl. In certain embodiments, $R^{P6}$ is iso-propyl. In certain embodiments, $R^{P6}$ is t-butyl. In certain embodiments, $R^{P6}$ is an oxygen protecting group. In certain embodiments, $R^{P6}$ is a silyl protecting group. In certain embodiments, $R^{P6}$ is a trialkyl silyl protecting group. In certain embodiments, $R^{P6}$ is a t-butyldimethylsilyl protecting group. In certain embodiments, $R^{P6}$ is a trimethylsilyl protecting group. In certain embodiments, $R^{P6}$ is a triethylsilyl protecting group. In certain embodiments, $R^{P6}$ is a t-butyldiphenylsilyl protecting group. In certain embodiments, $R^{P6}$ is a triisopropylsilyl protecting group. In certain embodiments, $R^{P6}$ is a benzylic protecting group. In certain embodiments, $R^6$ is a p-methoxybenzyl protecting group. In certain embodiments, $R^{P6}$ is an acyl protecting group. In certain embodiments, $R^{P6}$ is an acetyl protecting group. In certain embodiments, $R^{P6}$ is a benzoyl protecting group. In certain embodiments, $R^{P6}$ is a p-nitro benzoyl protecting group. In certain embodiments, $R^{P6}$ is a pivaloyl protecting group. In certain embodiments, $R^{P6}$ is a t-butyl carbonate (BOC) protecting group. In certain embodiments, $R^{P6}$ is an acetal protecting group. In certain embodiments, $R^{P6}$ is a tetrahydropyranyl protecting group. In certain embodiments, $R^{P6}$ is an alkoxyalkyl protecting group. In certain embodiments, $R^{P6}$ is an ethoxyethyl protecting group.

In certain embodiments, $R^{P7}$ is hydrogen. In certain embodiments, $R^{P7}$ is substituted or unsubstituted alkyl. In certain embodiments, $R^{P7}$ is substituted or unsubstituted $C_{1-6}$ alkyl. In certain embodiments, $R^{P7}$ is substituted or unsubstituted, branched $C_{1-6}$ alkyl. In certain embodiments, $R^{P7}$ is unsubstituted $C_{1-6}$ alkyl. In certain embodiments, $R^{P7}$ is methyl. In certain embodiments, $R^{P7}$ is ethyl. In certain embodiments, $R^{P7}$ is propyl. In certain embodiments, $R^{P7}$ is iso-propyl. In certain embodiments, $R^{P7}$ is t-butyl. In certain embodiments, $R^{P7}$ is an oxygen protecting group. In certain embodiments, $R^{P7}$ is a silyl protecting group. In certain embodiments, $R^{P7}$ is a trialkyl silyl protecting group. In certain embodiments, $R^{P7}$ is a t-butyldimethylsilyl protecting group. In certain embodiments, $R^{P7}$ is a trimethylsilyl protecting group. In certain embodiments, $R^{P7}$ is a triethylsilyl protecting group. In certain embodiments, $R^{P7}$ is a t-butyldiphenylsilyl protecting group. In certain embodiments, $R^{P7}$ is a triisopropylsilyl protecting group. In certain embodiments, $R^{P7}$ is a benzylic protecting group. In certain embodiments, $R^{P7}$ is a p-methoxybenzyl protecting group. In certain embodiments, $R^{P7}$ is an acyl protecting group. In certain embodiments, $R^{P7}$ is an acetyl protecting group. In certain embodiments, $R^{P7}$ is a benzoyl protecting group. In certain embodiments, $R^{P7}$ is ap-nitro benzoyl protecting group. In certain embodiments, $R^{P7}$ is a pivaloyl protecting group. In certain embodiments, $R^{P7}$ is a t-butyl carbonate (BOC) protecting group. In certain embodiments, $R^{P7}$ is an acetal protecting group. In certain embodiments, $R^{P7}$ is a tetrahydropyranyl protecting group. In certain embodiments, $R^{P7}$ is an alkoxyalkyl protecting group. In certain embodiments, $R^{P7}$ is an ethoxyethyl protecting group.

In certain embodiments, $R^{P8}$ is hydrogen. In certain embodiments, $R^{P8}$ is substituted or unsubstituted alkyl. In certain embodiments, $R^{P8}$ is substituted or unsubstituted $C_{1-6}$ alkyl. In certain embodiments, $R^{P8}$ is substituted or unsubstituted, branched $C_{1-6}$ alkyl. In certain embodiments, $R^{P8}$ is unsubstituted $C_{1-6}$ alkyl. In certain embodiments, $R^{P8}$ is methyl. In certain embodiments, $R^{P8}$ is ethyl. In certain embodiments, $R^{P8}$ is propyl. In certain embodiments, $R^{P8}$ is iso-propyl. In certain embodiments, $R^{P8}$ is t-butyl. In certain embodiments, $R^{P8}$ is an oxygen protecting group. In certain embodiments, $R^{P8}$ is a silyl protecting group. In certain embodiments, $R^{P8}$ is a trialkyl silyl protecting group. In certain embodiments, $R^{P8}$ is a t-butyldimethylsilyl protecting group. In certain embodiments, $R^{P8}$ is a trimethylsilyl protecting group. In certain embodiments, $R^{P8}$ is a triethylsilyl protecting group. In certain embodiments, $R^{P8}$ is a t-butyldiphenylsilyl protecting group. In certain embodiments, $R^{P8}$ is a triisopropylsilyl protecting group. In certain embodiments, $R^{P8}$ is a benzylic protecting group. In certain embodiments, $R^{P8}$ is a p-methoxybenzyl protecting group. In certain embodiments, $R^{P8}$ is an acyl protecting group. In certain embodiments, $R^{P8}$ is an acetyl protecting group. In certain embodiments, $R^{P8}$ is a benzoyl protecting group. In certain embodiments, $R^{P8}$ is a p-nitro benzoyl protecting group. In certain embodiments, $R^{P8}$ is a pivaloyl protecting group. In certain embodiments, $R^{P8}$ is a t-butyl carbonate (BOC) protecting group. In certain embodiments, $R^{P8}$ is an acetal protecting group. In certain embodiments, $R^{P8}$ is a tetrahydropyranyl protecting group. In certain embodiments, $R^{P8}$ is an alkoxyalkyl protecting group. In certain embodiments, $R^{P8}$ is an ethoxyethyl protecting group.

In certain embodiments, $R^{P9}$ is hydrogen. In certain embodiments, $R^{P9}$ is substituted or unsubstituted alkyl. In certain embodiments, $R^{P9}$ is substituted or unsubstituted $C_{1-6}$ alkyl. In certain embodiments, $R^{P9}$ is substituted or unsubstituted, branched $C_{1-6}$ alkyl. In certain embodiments, $R^{P9}$ is unsubstituted $C_{1-6}$ alkyl. In certain embodiments, $R^{P9}$ is methyl. In certain embodiments, $R^{P9}$ is ethyl. In certain embodiments, $R^{P9}$ is propyl. In certain embodiments, $R^{P9}$ is iso-propyl. In certain embodiments, $R^{P9}$ is t-butyl. In certain embodiments, $R^{P9}$ is an oxygen protecting group. In certain embodiments, $R^{P9}$ is a silyl protecting group. In certain embodiments, $R^{P9}$ is a trialkyl silyl protecting group. In certain embodiments, $R^{P9}$ is a t-butyldimethylsilyl protecting group. In certain embodiments, $R^{P9}$ is a trimethylsilyl protecting group. In certain embodiments, $R^{P9}$ is a triethylsilyl protecting group. In certain embodiments, $R^{P9}$ is a t-butyldiphenylsilyl protecting group. In certain embodiments, $R^{P9}$ is a triisopropylsilyl protecting group. In certain embodiments, $R^{P9}$ is a benzylic protecting group. In certain embodiments, $R^{P9}$ is a p-methoxybenzyl protecting group. In certain embodiments, $R^{P9}$ is an acyl protecting group. In certain embodiments, $R^{P9}$ is an acetyl protecting group. In certain embodiments, $R^{P9}$ is a benzoyl protecting group. In certain embodiments, $R^{P9}$ is a p-nitro benzoyl protecting group. In certain embodiments, $R^{P9}$ is a pivaloyl protecting group. In certain embodiments, $R^{P9}$ is a t-butyl carbonate (BOC) protecting group. In certain embodiments, $R^{P9}$ is an acetal protecting group. In certain embodiments, $R^{P9}$ is a tetrahydropyranyl protecting group. In certain embodiments, $R^{P9}$ is an alkoxyalkyl protecting group. In certain embodiments, $R^{P9}$ is an ethoxyethyl protecting group.

In certain embodiments, $R^{P10}$ is hydrogen. In certain embodiments, $R^{P10}$ is substituted or unsubstituted alkyl. In certain embodiments, $R^{P10}$ is substituted or unsubstituted $C_{1-6}$ alkyl. In certain embodiments, $R^{P10}$ is substituted or unsubstituted, branched $C_{1-6}$ alkyl. In certain embodiments, $R^{P10}$ is unsubstituted $C_{1-6}$ alkyl. In certain embodiments, $R^{P10}$ is methyl. In certain embodiments, $R^{P10}$ is ethyl. In certain embodiments, $R^{P10}$ is propyl. In certain embodiments, $R^{P10}$ is iso-propyl. In certain embodiments, $R^{P10}$ is t-butyl. In certain embodiments, $R^{P10}$ is an oxygen protecting group. In certain embodiments, $R^{P10}$ is a silyl protecting group. In certain embodiments, $R^{P10}$ is a trialkyl silyl protecting group. In certain embodiments, $R^{P10}$ is a t-butyldimethylsilyl protecting group. In certain embodiments, $R^{P10}$ is a trimethylsilyl protecting group. In certain embodiments, $R^{P10}$ is a triethylsilyl protecting group. In certain embodiments, $R^{P10}$ is a t-butyldiphenylsilyl protecting group. In certain embodiments, $R^{P10}$ is a triisopropylsilyl protecting group. In certain embodiments, $R^{P10}$ is a benzylic protecting group. In certain embodiments, $R^{P10}$ is a p-methoxybenzyl protecting group. In certain embodiments, $R^{P10}$ is an acyl protecting group. In certain embodiments, $R^{P10}$ is an acetyl protecting group. In certain embodiments, $R^{P10}$ is a benzoyl protecting group. In certain embodiments, $R^{P10}$ is a p-nitro benzoyl protecting group. In certain embodiments, $R^{P10}$ is a pivaloyl protecting group. In certain embodiments, $R^{P10}$ is a t-butyl carbonate (BOC) protecting group. In certain embodiments, $R^{P10}$ is an acetal protecting group. In certain embodiments, $R^{P10}$ is a tetrahydropyranyl protecting group. In certain embodiments, $R^{P10}$ is an alkoxyalkyl protecting group. In certain embodiments, $R^{P10}$ is an ethoxyethyl protecting group.

In certain embodiments, $R^{P11}$ is hydrogen. In certain embodiments, $R^{P11}$ is substituted or unsubstituted alkyl. In certain embodiments, $R^{P11}$ is substituted or unsubstituted $C_{1-6}$ alkyl. In certain embodiments, $R^{P11}$ is substituted or unsubstituted, branched $C_{1-6}$ alkyl. In certain embodiments, $R^{P11}$ is unsubstituted $C_{1-6}$ alkyl. In certain embodiments, $R^{P11}$ is methyl. In certain embodiments, $R^{P11}$ is ethyl. In certain embodiments, $R^{P11}$ is propyl. In certain embodiments, $R^{P11}$ is iso-propyl. In certain embodiments, $R^{P11}$ is t-butyl. In certain embodiments, $R^{P11}$ is an oxygen protecting group. In certain embodiments, $R^{P11}$ is a silyl protecting group. In certain embodiments, $R^{P11}$ is a trialkyl silyl protecting group. In certain embodiments, $R^{P11}$ is a t-butyldimethylsilyl protecting group. In certain embodiments, $R^{P11}$ is a trimethylsilyl protecting group. In certain embodiments, $R^{P11}$ is a triethylsilyl protecting group. In certain embodiments, $R^{P11}$ is a t-butyldiphenylsilyl protecting group. In certain embodiments, $R^{P11}$ is a triisopropylsilyl protecting group. In certain embodiments, $R^{P11}$ is a benzylic protecting group. In certain embodiments, $R^{P11}$ is a p-methoxybenzyl protecting group. In certain embodiments, $R^{P11}$ is an acyl protecting group. In certain embodiments, $R^{P11}$ is an acetyl protecting group. In certain embodiments, $R^{P11}$ is a benzoyl protecting group. In certain embodiments, $R^{P11}$ is a p-nitro benzoyl protecting group. In certain embodiments, $R^{P11}$ is a pivaloyl protecting group. In certain embodiments, $R^{P11}$ is a t-butyl carbonate (BOC) protecting group. In certain embodiments, $R^{P11}$ is an acetal protecting group. In certain embodiments, $R^{P11}$ is a tetrahydropyranyl protecting group. In certain embodiments, $R^{P11}$ is an alkoxyalkyl protecting group. In certain embodiments, $R^{P11}$ is an ethoxyethyl protecting group.

In certain embodiments, $R^{P12}$ is hydrogen. In certain embodiments, $R^{P12}$ is substituted or unsubstituted alkyl. In certain embodiments, $R^{P12}$ is substituted or unsubstituted $C_{1-6}$ alkyl. In certain embodiments, $R^{P12}$ is substituted or unsubstituted, branched $C_{1-6}$ alkyl. In certain embodiments, $R^{P12}$ is unsubstituted $C_{1-6}$ alkyl. In certain embodiments, $R^{P12}$ is methyl. In certain embodiments, $R^{P12}$ is ethyl. In certain embodiments, $R^{P12}$ is propyl. In certain embodiments, $R^{P12}$ is iso-propyl. In certain embodiments, $R^{P12}$ is t-butyl. In certain embodiments, $R^{P12}$ is an oxygen protecting group. In certain embodiments, $R^{P12}$ is a silyl protecting group. In certain embodiments, $R^{P12}$ is a trialkyl silyl protecting group. In certain embodiments, $R^{P12}$ is a t-butyldimethylsilyl protecting group. In certain embodiments, $R^{P12}$ is a trimethylsilyl protecting group. In certain embodiments, $R^{P12}$ is a triethylsilyl protecting group. In certain embodiments, $R^{P12}$ is a t-butyldiphenylsilyl protecting group. In certain embodiments, $R^{P12}$ is a triisopropylsilyl protecting group. In certain embodiments, $R^{P12}$ is a benzylic protecting group. In certain embodiments, $R^{P12}$ is a p-methoxybenzyl protecting group. In certain embodiments, $R^{P12}$ is an acyl protecting group. In certain embodiments, $R^{P12}$ is an acetyl protecting group. In certain embodiments, $R^{P12}$ is a benzoyl protecting group. In certain embodiments, $R^{P12}$ is ap-nitro benzoyl protecting group. In certain embodiments, $R^{P12}$ is a pivaloyl protecting group. In certain embodiments, $R^{P12}$ is a t-butyl carbonate (BOC) protecting group. In certain embodiments, $R^{P12}$ is an acetal protecting group. In certain embodiments, $R^{P12}$ is a tetrahydropyranyl protecting group. In certain embodiments, $R^{P12}$ is an alkoxyalkyl protecting group. In certain embodiments, $R^{P12}$ is an ethoxyethyl protecting group.

In certain embodiments, $R^{P13}$ is hydrogen. In certain embodiments, $R^{P13}$ is substituted or unsubstituted alkyl. In certain embodiments, $R^{P13}$ is substituted or unsubstituted $C_{1-6}$ alkyl. In certain embodiments, $R^{P13}$ is substituted or unsubstituted, branched $C_{1-6}$ alkyl. In certain embodiments, $R^{P13}$ is unsubstituted $C_{1-6}$ alkyl. In certain embodiments, $R^{P13}$ is methyl. In certain embodiments, $R^{P13}$ is ethyl. In certain embodiments, $R^{P13}$ is propyl. In certain embodiments, $R^{P13}$ is iso-propyl. In certain embodiments, $R^{P13}$ is t-butyl. In certain embodiments, $R^{P13}$ is an oxygen protecting group. In certain embodiments, $R^{P13}$ is a silyl protecting group. In certain embodiments, $R^{P13}$ is a trialkyl silyl protecting group. In certain embodiments, $R^{P13}$ is a t-butyldimethylsilyl protecting group. In certain embodiments, $R^{P13}$ is a trimethylsilyl protecting group. In certain embodiments, $R^{P13}$ is a triethylsilyl protecting group. In certain embodiments, $R^{P13}$ is a t-butyldiphenylsilyl protecting group. In certain embodiments, $R^{P13}$ is a triisopropylsilyl protecting group. In certain embodiments, $R^{13}$ is a benzylic protecting group. In certain embodiments, $R^{P13}$ is a p-methoxybenzyl protecting group. In certain embodiments, $R^{P13}$ is an acyl protecting group. In certain embodiments, $R^{P13}$ is an acetyl protecting group. In certain embodiments, $R^{P13}$ is a benzoyl protecting group. In certain embodiments, $R^{P13}$ is a p-nitro benzoyl protecting group. In certain embodiments, $R^{13}$ is a pivaloyl protecting group. In certain embodiments, $R^{P13}$ is a t-butyl carbonate (BOC) protecting group. In certain embodiments, $R^{P13}$ is an acetal protecting group. In certain embodiments, $R^{P13}$ is a tetrahydropyranyl protecting group. In certain embodiments, $R^{P13}$ is an alkoxyalkyl protecting group. In certain embodiments, $R^{P13}$ is an ethoxyethyl protecting group.

In certain embodiments, $R^{P14}$ is hydrogen. In certain embodiments, $R^{P14}$ is substituted or unsubstituted alkyl. In certain embodiments, $R^{P14}$ is substituted or unsubstituted $C_{1-6}$ alkyl. In certain embodiments, $R^{P14}$ is substituted or unsubstituted, branched $C_{1-6}$ alkyl. In certain embodiments, $R^{P14}$ is unsubstituted $C_{1-6}$ alkyl. In certain embodiments, $R^{P14}$ is methyl. In certain embodiments, $R^{P14}$ is ethyl. In certain embodiments, $R^{P14}$ is propyl. In certain embodiments, $R^{P14}$ is iso-propyl. In certain embodiments, $R^{P14}$ is t-butyl. In certain embodiments, $R^{P14}$ is an oxygen protecting group. In certain embodiments, $R^{P14}$ is a silyl protecting group. In certain embodiments, $R^{P14}$ is a trialkyl silyl protecting group. In certain embodiments, $R^{P14}$ is a t-butyldimethylsilyl protecting group. In certain embodiments, $R^{P14}$ is a trimethylsilyl protecting group. In certain embodiments, $R^{P14}$ is a triethylsilyl protecting group. In certain embodiments, $R^{P14}$ is a t-butyldiphenylsilyl protecting group. In certain embodiments, $R^{P14}$ is a triisopropylsilyl protecting group. In certain embodiments, $R^{P14}$ is a benzylic protecting group. In certain embodiments, $R^{P14}$ is a p-methoxybenzyl protecting group. In certain embodiments, $R^{P14}$ is an acyl protecting group. In certain embodiments, $R^{P14}$ is an acetyl protecting group. In certain embodiments, $R^{P14}$ is a benzoyl protecting group. In certain embodiments, $R^{P14}$ is ap-nitro benzoyl protecting group. In certain embodiments, $R^{P14}$ is a pivaloyl protecting group. In certain embodiments, $R^{P14}$ is a t-butyl carbonate (BOC) protecting group. In certain embodiments, $R^{P14}$ is an acetal protecting group. In certain embodiments, $R^{P14}$ is a tetrahydropyranyl protecting group. In certain embodiments, $R^{P14}$ is an alkoxyalkyl protecting group. In certain embodiments, $R^{P14}$ is an ethoxyethyl protecting group.

In certain embodiments, $R^{P15}$ is hydrogen. In certain embodiments, $R^{P15}$ is substituted or unsubstituted alkyl. In certain embodiments, $R^{P15}$ is substituted or unsubstituted $C_{1-6}$ alkyl. In certain embodiments, $R^{P15}$ is substituted or unsubstituted, branched $C_{1-6}$ alkyl. In certain embodiments, $R^{P15}$ is unsubstituted $C_{1-6}$ alkyl. In certain embodiments, $R^{P15}$ is methyl. In certain embodiments, $R^{P15}$ is ethyl. In certain embodiments, $R^{P15}$ is propyl. In certain embodiments, $R^{P15}$ is iso-propyl. In certain embodiments, $R^{P15}$ is t-butyl. In certain embodiments, $R^{P15}$ is an oxygen protecting group. In certain embodiments, $R^{P15}$ is a silyl protecting group. In certain embodiments, $R^{P15}$ is a trialkyl silyl protecting group. In certain embodiments, $R^{P15}$ is a t-butyldimethylsilyl protecting group. In certain embodiments, $R^{P15}$ is a trimethylsilyl protecting group. In certain embodiments, $R^{P15}$ is a triethylsilyl protecting group. In certain embodiments, $R^{P15}$ is a t-butyldiphenylsilyl protecting group. In certain embodiments, $R^{P15}$ is a triisopropylsilyl protecting group. In certain embodiments, $R^{P15}$ is a benzylic protecting group. In certain embodiments, $R^{P15}$ is a p-methoxybenzyl protecting group. In certain embodiments, $R^{P15}$ is an acyl protecting group. In certain embodiments, $R^{P15}$ is an acetyl protecting group. In certain embodiments, $R^{P15}$ is a benzoyl protecting group. In certain embodiments, $R^{P15}$ is ap-nitro benzoyl protecting group. In certain embodiments, $R^{P15}$ is a pivaloyl protecting group. In certain embodiments, $R^{P15}$ is a t-butyl carbonate (BOC) protecting group. In certain embodiments, $R^{P15}$ is an acetal protecting group. In certain embodiments, $R^{P15}$ is a tetrahydropyranyl protecting group. In certain embodiments, $R^{P15}$ is an alkoxyalkyl protecting group. In certain embodiments, $R^{P15}$ is an ethoxyethyl protecting group.

In certain embodiments, $R^{P16}$ is hydrogen. In certain embodiments, $R^{P16}$ is substituted or unsubstituted alkyl. In certain embodiments, $R^{P16}$ is substituted or unsubstituted $C_{1-6}$ alkyl. In certain embodiments, $R^{P16}$ is substituted or unsubstituted, branched $C_{1-6}$ alkyl. In certain embodiments, $R^{P16}$ is unsubstituted $C_{1-6}$ alkyl. In certain embodiments, $R^{P16}$ is methyl. In certain embodiments, $R^{P16}$ is ethyl. In certain embodiments, $R^{P16}$ is propyl. In certain embodiments, $R^{P16}$ is iso-propyl. In certain embodiments, $R^{P16}$ is t-butyl. In certain embodiments, $R^{P16}$ is an oxygen protecting group. In certain embodiments, $R^{P16}$ is a silyl protecting group. In certain embodiments, $R^{P16}$ is a trialkyl silyl protecting group. In certain embodiments, $R^{P16}$ is a t-butyldimethylsilyl protecting group. In certain embodiments, $R^{P16}$ is a trimethylsilyl protecting group. In certain embodiments, $R^{P16}$ is a triethylsilyl protecting group. In certain embodiments, $R^{P16}$ is a t-butyldiphenylsilyl protecting group. In certain embodiments, $R^{P16}$ is a triisopropylsilyl protecting group. In certain embodiments, $R^{P16}$ is a benzylic protecting group. In certain embodiments, $R^{P16}$ is a p-methoxybenzyl protecting group. In certain embodiments, $R^{P16}$ is an acyl protecting group. In certain embodiments, $R^{P16}$ is an acetyl protecting group. In certain embodiments, $R^{P16}$ is a benzoyl protecting group. In certain embodiments, $R^{P16}$ is ap-nitro benzoyl protecting group. In certain embodiments, $R^{P16}$ is a pivaloyl protecting group. In certain embodiments, $R^{P16}$ is a t-butyl carbonate (BOC) protecting group. In certain embodiments, $R^{P16}$ is an acetal protecting group. In certain-embodiments, $R^{P16}$ is a tetrahydropyranyl protecting group. In certain embodiments, $R^{P16}$ is an alkoxyalkyl protecting group. In certain embodiments, $R^{P16}$ is an ethoxyethyl protecting group.

In certain embodiments, $R^{P17}$ is hydrogen. In certain embodiments, $R^{P17}$ is substituted or unsubstituted alkyl. In certain embodiments, $R^{P17}$ is substituted or unsubstituted $C_{1-6}$ alkyl. In certain embodiments, $R^{P17}$ is substituted or unsubstituted, branched $C_{1-6}$ alkyl. In certain embodiments, $R^{P17}$ is unsubstituted $C_{1-6}$ alkyl. In certain embodiments, $R^{P17}$ is methyl. In certain embodiments, $R^{P17}$ is ethyl. In certain embodiments, $R^{P17}$ is propyl. In certain embodiments, $R^{P17}$ is iso-propyl. In certain embodiments, $R^{P17}$ is t-butyl. In certain embodiments, $R^{P17}$ is an oxygen protecting group. In certain embodiments, $R^{P17}$ is a silyl protecting group. In certain embodiments, $R^{P17}$ is a trialkyl silyl protecting group. In certain embodiments, $R^{P17}$ is a t-butyldimethylsilyl protecting group. In certain embodiments, $R^{P17}$ is a trimethylsilyl protecting group. In certain embodiments, $R^{P17}$ is a triethylsilyl protecting group. In certain embodiments, $R^{P17}$ is a t-butyldiphenylsilyl protecting group. In certain embodiments, $R^{P17}$ is a triisopropylsilyl protecting group. In certain embodiments, $R^{P17}$ is a benzylic protecting group. In certain embodiments, $R^{P17}$ is ap-methoxybenzyl protecting group. In certain embodiments, $R^{P17}$ is an acyl protecting group. In certain embodiments, $R^{P17}$ is an acetyl protecting group. In certain embodiments, $R^{P17}$ is a benzoyl protecting group. In certain embodiments, $R^{P17}$ is ap-nitro benzoyl protecting group. In certain embodiments, $R^{P17}$ is a pivaloyl protecting group. In certain embodiments, $R^{P17}$ is a t-butyl carbonate (BOC) protecting group. In certain embodiments, $R^{P17}$ is an acetal protecting group. In certain embodiments, $R^{P17}$ is a tetrahydropyranyl protecting group. In certain embodiments, $R^{P17}$ is an alkoxyalkyl protecting group. In certain embodiments, $R^{P17}$ is an ethoxyethyl protecting group.

In certain embodiments, $R^{P18}$ is hydrogen. In certain embodiments, $R^{P18}$ is substituted or unsubstituted alkyl. In certain embodiments, $R^{P18}$ is substituted or unsubstituted $C_{1-6}$ alkyl. In certain embodiments, $R^{P18}$ is substituted or unsubstituted, branched $C_{1-6}$ alkyl. In certain embodiments, $R^{P18}$ is unsubstituted $C_{1-6}$ alkyl. In certain embodiments, $R^{P18}$ is methyl. In certain embodiments, $R^{P18}$ is ethyl. In certain embodiments, $R^{P18}$ is propyl. In certain embodiments, $R^{P18}$ is iso-propyl. In certain embodiments, $R^{P18}$ is t-butyl. In certain embodiments, $R^{P18}$ is an oxygen protecting group. In certain embodiments, $R^{P18}$ is a silyl protecting group. In certain embodiments, $R^{P18}$ is a trialkyl silyl protecting group. In certain embodiments, $R^{P18}$ is a t-butyldimethylsilyl protecting group. In certain embodiments, $R^{P18}$ is a trimethylsilyl protecting group. In certain embodiments, $R^{P18}$ is a triethylsilyl protecting group. In certain embodiments, $R^{P18}$ is a t-butyldiphenylsilyl protecting group. In certain embodiments, $R^{P18}$ is a triisopropylsilyl protecting group. In certain embodiments, $R^{P18}$ is a benzylic protecting group. In certain embodiments, $R^{P18}$ is ap-methoxybenzyl protecting group. In certain embodiments, $R^{P18}$ is an acyl protecting group. In certain embodiments, $R^{P18}$ is an acetyl protecting group. In certain embodiments, $R^{P18}$ is a benzoyl protecting group. In certain embodiments, $R^{P18}$ is ap-nitro benzoyl protecting group. In certain embodiments, $R^{P18}$ is a pivaloyl protecting group. In certain embodiments, $R^{P18}$ is a t-butyl carbonate (BOC) protecting group. In certain embodiments, $R^{P18}$ is an acetal protecting group. In certain embodiments, $R^{P18}$ is a tetrahydropyranyl protecting group. In certain embodiments, $R^{P18}$ is an alkoxyalkyl protecting group. In certain embodiments, $R^{P18}$ is an ethoxyethyl protecting group.

In certain embodiments, $R^{P19}$ is hydrogen. In certain embodiments, $R^{P19}$ is substituted or unsubstituted alkyl. In certain embodiments, $R^{P19}$ is substituted or unsubstituted $C_{1-6}$ alkyl. In certain embodiments, $R^{P19}$ is substituted or unsubstituted, branched $C_{1-6}$ alkyl. In certain embodiments, $R^{P19}$ is unsubstituted $C_{1-6}$ alkyl. In certain embodiments, $R^{P19}$ is methyl. In certain embodiments, $R^{P19}$ is ethyl. In certain embodiments, $R^{P19}$ is propyl. In certain embodiments, $R^{P19}$ is iso-propyl. In certain embodiments, $R^{P19}$ is t-butyl. In certain embodiments, $R^{P19}$ is an oxygen protecting group. In certain embodiments, $R^{P19}$ is a silyl protecting group. In certain embodiments, $R^{P19}$ is a trialkyl silyl protecting group. In certain embodiments, $R^{P19}$ is a t-butyldimethylsilyl protecting group. In certain embodiments, $R^{P19}$ is a trimethylsilyl protecting group. In certain embodiments, $R^{P19}$ is a triethylsilyl protecting group. In certain embodiments, $R^{P19}$ is a t-butyldiphenylsilyl protecting group. In certain embodiments, $R^{P19}$ is a triisopropylsilyl protecting group. In certain embodiments, $R^{P19}$ is a benzylic protecting group. In certain embodiments, $R^{P19}$ is a p-methoxybenzyl protecting group. In certain embodiments, $R^{P19}$ is an acyl protecting group. In certain embodiments, $R^{P19}$ is an acetyl protecting group. In certain embodiments, $R^{P19}$ is a benzoyl protecting group. In certain embodiments, $R^{P19}$ is ap-nitro benzoyl protecting group. In certain embodiments, $R^{P19}$ is a pivaloyl protecting group. In certain embodiments, $R^{P19}$ is a t-butyl carbonate (BOC) protecting group. In certain embodiments, $R^{P19}$ is an acetal protecting group. In certain embodiments, $R^{P19}$ is a tetrahydropyranyl protecting group. In certain embodiments, $R^{P19}$ is an alkoxyalkyl protecting group. In certain embodiments, $R^{P19}$ is an ethoxyethyl protecting group.

In certain embodiments, all of $R^{P17}$, $R^{P18}$, and $R^{P19}$ are independently a silyl protecting group. In certain embodiments, all of $R^{P17}$, $R^{P18}$, and $R^{P19}$ are a t-butyldimethylsilyl protecting group. In certain embodiments, $R^{P4}$ is a silyl protecting group; and $R^{P5}$ is an acyl protecting group. In certain embodiments, $R^{P4}$ is a t-butyldimethylsilyl protecting group; and $R^{P5}$ is an acyl protecting group. In certain embodiments, $R^{P4}$ is a silyl protecting group; and $R^{P5}$ is an acetyl protecting group. In certain embodiments, $R^{P4}$ is a t-butyldimethylsilyl protecting group; and $R^{P5}$ is an acetyl protecting group. In certain embodiments, all of $R^{P1}$, $R^{P2}$, $R^{P3}$, $R^{P4}$, and $R^{P7}$ are independently a silyl protecting group; and $R^{P6}$ is a benzylic protecting group. In certain embodiments, all of $R^{P1}$, $R^{P2}$, $R^{P3}$, $R^{P4}$, and $R^{P7}$ are a t-butyldimethylsilyl protecting group; and $R^{P6}$ is a benzylic protecting group. In certain embodiments, all of $R^{P1}$, $R^{P2}$, $R^{P3}$, $R^{P4}$, and $R^{P7}$ are independently a silyl protecting group; and $R^{P6}$ is a p-methoxybenzyl protecting group. In certain embodiments, all of $R^{P1}$, $R^{P2}$, $R^{P3}$, $R^{P4}$, and $R^{P7}$ are a t-butyldimethylsilyl protecting group; and $R^{P6}$ is a p-methoxybenzyl protecting group. In certain embodiments, all of $R^{P8}$, $R^{P9}$, and $R^{P11}$ are each independently a silyl protecting group; and $R^{P10}$ is a benzylic protecting group. In certain embodiments, all of $R^{P8}$, $R^{P9}$, and $R^{P11}$ are a t-butyldimethylsilyl protecting group; and $R^{P10}$ is a benzylic protecting group. In certain embodiments, all of $R^{P8}$, $R^{P9}$, and $R^{P11}$ are independently a silyl protecting group; and $R^{P10}$ is ap-methoxybenzyl protecting group. In certain embodiments, all of $R^{P8}$, $R^{P9}$, and $R^{P11}$ are a t-butyldimethylsilyl protecting group; and $R^{P10}$ is a p-methoxybenzyl protecting group. In certain embodiments, all of $R^{P12}$, $R^{P13}$, $R^{P14}$, and $R^{P15}$ are independently a silyl protecting group; and $R^{P16}$ is a benzylic protecting group. In certain embodiments, all of $R^{P12}$, $R^{P13}$, $R^{P14}$, and $R^{P15}$ are a t-butyldimethylsilyl protecting group; and $R^{P16}$ is a benzylic protecting group. In certain embodiments, all of $R^{P12}$, $R^{P13}$, $R^{P14}$, and $R^{P15}$ are independently a silyl protecting group; and $R^{P16}$ is ap-methoxybenzyl protecting group. In certain embodiments, all of $R^{P12}$, $R^{P13}$, $R^{P14}$, and $R^{P15}$ are a t-butyldimethylsilyl protecting group; and $R^{16}$ is ap-methoxybenzyl protecting group.

Groups $R^1$, $R^2$, $R^3$, and $R^5$

As generally described herein, $R^1$, $R^2$, $R^3$, and $R^5$ are each independently hydrogen, halogen, or substituted or unsubstituted alkyl.

In certain embodiments, $R^1$ is hydrogen. In certain embodiments, $R^1$ is halogen (e.g., —F, —Cl, —Br, or —I). In certain embodiments, $R^1$ is fluorine. In certain embodiments, $R^1$ is chlorine.

In certain embodiments, $R^1$ is substituted or unsubstituted alkyl. In certain embodiments, $R^1$ is substituted or unsubstituted $C_{1-6}$ alkyl. In certain embodiments, $R^1$ is substituted or unsubstituted, branched $C_{1-6}$ alkyl. In certain embodiments, $R^1$ is unsubstituted C1-6 alkyl. In certain embodiments, $R^1$ is methyl. In certain embodiments, $R^1$ is methyl; and the carbon to which the methyl group is attached is in the (S)-configuration. In certain embodiments, $R^1$ is methyl; and the carbon to which the methyl group is attached is in the (R)-configuration. In certain embodiments, $R^1$ is ethyl. In certain embodiments, $R^1$ is propyl. In certain embodiments, $R^1$ is iso-propyl. In certain embodiments, $R^1$ is butyl. In certain embodiments, $R^1$ is t-butyl.

In certain embodiments, the stereochemical configuration of the carbon atom to which $R^1$ is attached is (S). In certain embodiments, the stereochemical configuration of the carbon atom to which $R^1$ is attached is (R).

In certain embodiments, $R^2$ is hydrogen. In certain embodiments, $R^2$ is halogen (e.g., —F, —Cl, —Br, or —I). In certain embodiments, $R^2$ is fluorine. In certain embodiments, $R^2$ is chlorine. In certain embodiments, $R^2$ is substituted or unsubstituted alkyl. In certain embodiments, $R^2$ is substituted or unsubstituted $C_{1-6}$ alkyl. In certain embodiments, $R^2$ is substituted or unsubstituted, branched $C_{1-6}$ alkyl. In certain embodiments, $R^2$ is unsubstituted $C_{1-6}$ alkyl. In certain embodiments, $R^2$ is methyl. In certain embodiments, $R^2$ is methyl; and the carbon to which the methyl group is attached is in the (S)-configuration. In certain embodiments, $R^2$ is methyl; and the carbon to which the methyl group is attached is in the (R)-configuration. In certain embodiments, $R^2$ is ethyl. In certain embodiments, $R^2$ is propyl. In certain embodiments, $R^2$ is iso-propyl. In certain embodiments, $R^2$ is butyl. In certain embodiments, $R^2$ is t-butyl.

In certain embodiments, the stereochemical configuration of the carbon atom to which $R^2$ is attached is (S). In certain embodiments, the stereochemical configuration of the carbon atom to which $R^2$ is attached is (R).

In certain embodiments, $R^3$ is hydrogen. In certain embodiments, $R^3$ is halogen (e.g., —F, —Cl, —Br, or —I). In certain embodiments, $R^3$ is fluorine. In certain embodiments, $R^3$ is chlorine. In certain embodiments, $R^3$ is substituted or unsubstituted alkyl. In certain embodiments, $R^3$ is substituted or unsubstituted C1-6 alkyl. In certain embodiments, $R^3$ is substituted or unsubstituted, branched $C_{1-6}$ alkyl. In certain embodiments, $R^3$ is unsubstituted $C_{1-6}$ alkyl. In certain embodiments, $R^3$ is methyl. In certain embodiments, $R^3$ is methyl; and the carbon to which the methyl group is attached is in the (S)-configuration. In certain embodiments, $R^3$ is methyl; and the carbon to which the methyl group is attached is in the (R)-configuration. In certain embodiments, $R^3$ is ethyl. In certain embodiments, $R^3$ is propyl. In certain embodiments, $R^3$ is iso-propyl. In certain embodiments, $R^3$ is butyl. In certain embodiments, $R^3$ is t-butyl.

In certain embodiments, the stereochemical configuration of the carbon atom to which $R^3$ is attached is (S). In certain embodiments, the stereochemical configuration of the carbon atom to which $R^3$ is attached is (R).

In certain embodiments, $R^5$ is hydrogen. In certain embodiments, $R^5$ is halogen (e.g., —F, —Cl, —Br, or —I). In certain embodiments, $R^5$ is fluorine. In certain embodiments, $R^5$ is chlorine.

In certain embodiments, $R^5$ is substituted or unsubstituted alkyl. In certain embodiments, $R^5$ is substituted or unsubstituted $C_{1-6}$ alkyl. In certain embodiments, $R^5$ is substituted or unsubstituted, branched $C_{1-6}$ alkyl. In certain embodiments, $R^5$ is unsubstituted $C_{1-6}$ alkyl. In certain embodiments, $R^5$ is methyl. In certain embodiments, $R^5$ is methyl; and the carbon to which the methyl group is attached is in the (S)-configuration. In certain embodiments, $R^5$ is methyl; and the carbon to which the methyl group is attached is in the (R)-configuration. In certain embodiments, $R^5$ is ethyl. In certain embodiments, $R^5$ is propyl. In certain embodiments, $R^5$ is iso-propyl. In certain embodiments, $R^5$ is butyl. In certain embodiments, $R^5$ is t-butyl.

In certain embodiments, the stereochemical configuration of the carbon atom to which $R^5$ is attached is (S). In certain embodiments, the stereochemical configuration of the carbon atom to which $R^5$ is attached is (R).

In certain embodiments, all of $R^1$, $R^2$, $R^3$, and $R^5$ are independently substituted or unsubstituted alkyl. In certain embodiments, all of $R^1$, $R^2$, $R^3$, and $R^5$ are independently substituted or unsubstituted $C_{1-6}$ alkyl. In certain embodiments, all of $R^1$, $R^2$, $R^3$, and $R^5$ are independently substituted or unsubstituted, branched $C_{1-6}$ alkyl. In certain embodiments, all of $R^1$, $R^2$, $R^3$, and $R^5$ are independently unsubstituted $C_{1-6}$ alkyl. In certain embodiments, all of $R^1$, $R^2$, $R^3$, and $R^5$ are methyl. In certain embodiments, the stereochemical configuration of the carbon atom to which each of $R^1$, $R^2$, and $R^3$ is attached is (S); and the stereochemical configuration of the carbon atom to which $R^5$ is attached is (R). In certain embodiments, the stereochemical configuration of the carbon atom to which each of $R^1$, $R^2$, and $R^3$ is attached is (S); the stereochemical configuration of the carbon atom to which $R^5$ is attached is (R); and all of $R^1$, $R^2$, $R^3$, and $R^3$ are methyl.

Groups $R^4$ and $R^6$

As generally described herein, $R^4$ and $R^6$ are each independently hydrogen, halogen, or substituted or unsubstituted alkyl, or two $R^4$ groups can be taken together to form a

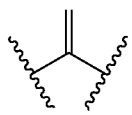

group. In certain embodiments, at least one $R^4$ is hydrogen.

In certain embodiments, both of $R^4$ are hydrogen. In certain embodiments, at least one $R^4$ is halogen (e.g., —F, —Cl, —Br, or —I). In certain embodiments, at least one $R^4$ is fluorine. In certain embodiments, at least one $R^4$ is chlorine. In certain embodiments, at least one $R^4$ is substituted or unsubstituted alkyl. In certain embodiments, at least one $R^4$ is substituted or unsubstituted C1-6 alkyl. In certain embodiments, at least one $R^4$ is substituted or unsubstituted, branched $C_{1-6}$ alkyl. In certain embodiments, at least one $R^4$ is unsubstituted $C_{1-6}$ alkyl. In certain embodiments, at least one $R^4$ is methyl. In certain embodiments, at least one $R^4$ is methyl; and the carbon to which the methyl group is attached is in the (S)-configuration. In certain embodiments, at least one $R^4$ is methyl; and the carbon to which the methyl group is attached is in the (R)-configuration. In certain embodiments, both of $R^4$ are methyl. In certain embodiments, at least one $R^4$ is ethyl. In certain embodiments, at least one $R^4$ is propyl. In certain embodiments, at least one $R^4$ is butyl. In certain embodiments, at least one $R^4$ is t-butyl. In certain embodiments, the stereochemical configuration of the carbon atom to which $R^4$ is attached is (S). In certain embodiments, the stereochemical configuration of the carbon atom to which $R^4$ is attached is (R). In certain embodiments, two $R^4$ groups are taken together to form

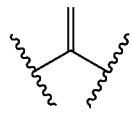 [SMILES: *C(*)=C]

group.

In certain embodiments, at least one $R^6$ is hydrogen. In certain embodiments, both of $R^6$ are hydrogen. In certain embodiments, at least one $R^6$ is halogen (e.g., —F, —Cl, —Br, or —I). In certain embodiments, at least one $R^6$ is fluorine. In certain embodiments, at least one $R^6$ is chlorine. In certain embodiments, at least one $R^6$ is substituted or unsubstituted alkyl. In certain embodiments, at least one $R^6$ is substituted or unsubstituted $C_{1-6}$ alkyl. In certain embodiments, at least one $R^6$ is substituted or unsubstituted, branched $C_{1-6}$ alkyl. In certain embodiments, at least one $R^6$ is unsubstituted $C_{1-6}$ alkyl. In certain embodiments, at least one $R^6$ is methyl. In certain embodiments, at least one $R^6$ is methyl; and the carbon to which the methyl group is attached is in the (S)-configuration. In certain embodiments, at least one $R^6$ is methyl; and the carbon to which the methyl group is attached is in the (R)-configuration. In certain embodiments, both of $R^6$ are methyl. In certain embodiments, at least one $R^6$ is ethyl. In certain embodiments, at least one $R^6$ is propyl. In certain embodiments, at least one $R^6$ is butyl. In certain embodiments, at least one $R^6$ is t-butyl. In certain embodiments, the stereochemical configuration of the carbon atom to which $R^6$ is attached is (S). In certain embodiments, the stereochemical configuration of the carbon atom to which $R^6$ is attached is (R). In certain embodiments, two $R^6$ groups are taken together to form a

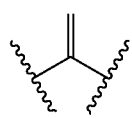

group.

In certain embodiments, two $R^4$ groups are taken together to form a

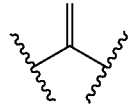

group; and two $R^6$ groups are taken together to form a

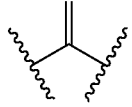 [SMILES: *C(*)=C]

group.

Groups $R^X$, $R^Y$, $R^X$, $R^{Y1}$, and $R^{XY}$

As generally described herein, $R^X$ is —$OR^{X1}$, wherein $R^{X1}$ is hydrogen, substituted or unsubstituted alkyl, or an oxygen protecting group; $R^Y$ is —$OR^{Y1}$, wherein $R^{Y1}$ is hydrogen, substituted or unsubstituted alkyl, or an oxygen protecting group; and $R^X$ and $R^Y$ can be taken with their intervening atoms to form a substituted or unsubstituted heterocyclic ring.

In certain embodiments, the stereochemical configuration of the carbon atom to which $R^X$ is attached is (S). In certain embodiments, the stereochemical configuration of the carbon atom to which $R^X$ is attached is (R).

In certain embodiments, the stereochemical configuration of $R^Y$ is (S). In certain embodiments, the stereochemical configuration of $R^Y$ is (R).

In certain embodiments, $R^{X1}$ is hydrogen. In certain embodiments, $R^{X1}$ is substituted or unsubstituted alkyl. In certain embodiments, $R^{X1}$ is substituted or unsubstituted $C_{1-6}$ alkyl. In certain embodiments, $R^{X1}$ is substituted or unsubstituted, branched $C_{1-6}$ alkyl. In certain embodiments, $R^{X1}$ is unsubstituted $C_{1-6}$ alkyl. In certain embodiments, $R^{X1}$ is methyl. In certain embodiments, $R^{X1}$ is ethyl. In certain embodiments, $R^{X1}$ is propyl. In certain embodiments, $R^{X1}$ is iso-propyl. In certain embodiments, $R^{X1}$ is t-butyl. In certain embodiments, $R^{X1}$ is an oxygen protecting group. In certain embodiments, $R^{X1}$ is a silyl protecting group. In certain embodiments, $R^{X1}$ is a trialkyl silyl protecting group. In certain embodiments, $R^{X1}$ is a t-butyldimethylsilyl protecting group. In certain embodiments, $R^{X1}$ is a trimethylsilyl protecting group. In certain embodiments, $R^{X1}$ is a triethylsilyl protecting group. In certain embodiments, $R^{X1}$ is a t-butyldiphenylsilyl protecting group. In certain embodiments, $R^{X1}$ is a triisopropylsilyl protecting group. In certain embodiments, $R^{X1}$ is a benzylic protecting group. In certain, embodiments, $R^{X1}$ is a p-methoxybenzyl protecting group. In certain embodiments, $R^{X1}$ is an acyl protecting group. In certain embodiments, $R^{X1}$ is an acetyl protecting group. In certain embodiments, $R^{X1}$ is a benzoyl protecting group. In certain embodiments, $R^{X1}$ is ap-nitro benzoyl protecting group. In certain embodiments, $R^{X1}$ is a pivaloyl protecting group. In certain embodiments, $R^{X1}$ is a t-butyl carbonate (BOC) protecting group. In certain embodiments, $R^{X1}$ is an acetal protecting group. In certain embodiments, $R^{X1}$ is a tetrahydropyranyl protecting group. In certain embodiments, $R^{X1}$ is an alkoxyalkyl protecting group. In certain embodiments, $R^{X1}$ is an ethoxyethyl protecting group.

In certain embodiments, $R^{Y1}$ is hydrogen. In certain embodiments, $R^{Y1}$ is substituted or unsubstituted alkyl. In certain embodiments, $R^{Y1}$ is substituted or unsubstituted $C_{1-6}$ alkyl. In certain embodiments, $R^{Y1}$ is substituted or unsubstituted, branched $C_{1-6}$ alkyl. In certain embodiments, $R^{Y1}$ is unsubstituted $C_{1-6}$ alkyl. In certain embodiments, $R^{Y1}$ is methyl. In certain embodiments, $R^{Y1}$ is ethyl. In certain embodiments, $R^{Y1}$ is propyl. In certain embodiments, $R^{Y1}$ is iso-propyl. In certain embodiments, $R^{Y1}$ is t-butyl. In certain embodiments, $R^{Y1}$ is an oxygen protecting group. In certain embodiments, $R^{Y1}$ is a silyl protecting group. In certain embodiments, $R^{Y1}$ is a trialkyl silyl protecting group. In certain embodiments, $R^{Y1}$ is a t-butyldimethylsilyl protecting group. In certain embodiments, $R^{Y1}$ is a trimethylsilyl protecting group. In certain embodiments, $R^{Y1}$ is a triethylsilyl protecting group. In certain embodiments, $R^{Y1}$ is a t-butyldiphenylsilyl protecting group. In certain embodiments, $R^{Y1}$ is a triisopropylsilyl protecting group. In certain embodiments, $R^{Y1}$ is a benzylic protecting group. In certain embodiments, $R^{Y1}$ is a p-methoxybenzyl protecting group. In certain embodiments, $R^{Y1}$ is an acyl protecting group. In certain embodiments, $R^{Y1}$ is an acetyl protecting group. In certain embodiments, $R^{Y1}$ is a benzoyl protecting group. In certain embodiments, $R^{Y1}$ is ap-nitro benzoyl protecting group. In certain embodiments, $R^{Y1}$ is a pivaloyl protecting group. In certain embodiments, $R^{Y1}$ is a t-butyl carbonate (BOC) protecting group. In certain embodiments, $R^{Y1}$ is an acetal protecting group. In certain embodiments, $R^{Y1}$ is a tetrahydropyranyl protecting group. In certain embodiments, $R^{Y1}$ is an alkoxyalkyl protecting group. In certain embodiments, $R^{Y1}$ is an ethoxyethyl protecting group.

In certain embodiments, both $R^{X1}$ and $R^{Y1}$ are hydrogen.

In certain embodiments, the stereochemical configuration of the carbon atom to which $R^X$ is attached is (S). In certain embodiments, the stereochemical configuration of the carbon atom to which $R^X$ is attached is (R). In certain embodiments, the stereochemical configuration of the carbon atom to which $R^Y$ is attached is (S). In certain embodiments, the stereochemical configuration of the carbon atom to which $R^Y$ is attached is (R).

In certain embodiments, the stereochemical configuration of the carbon atom to which $R^X$ is attached is (S); and the stereochemical configuration of the carbon atom to which $R^Y$ is attached is (S). In certain embodiments, the stereochemical configuration of the carbon atom to which $R^X$ is attached is (R); and the stereochemical configuration of the carbon atom to which $R^Y$ is attached is (R). In certain embodiments, the stereochemical configuration of the carbon atom to which $R^X$ is attached is (S); and the stereochemical configuration of the carbon atom to which $R^Y$ is attached is (R). In certain embodiments, the stereochemical configuration of the carbon atom to which $R^X$ is attached is (R); and the stereochemical configuration of the carbon atom to which $R^Y$ is attached is (S).

In certain embodiments, $R^X$ and $R^Y$ are taken with their intervening atoms to form a substituted or unsubstituted heterocyclic ring. In certain embodiments, $R^X$ and $R^Y$ form a substituted or unsubstituted, 5-membered heterocyclic ring. In certain embodiments, $R^X$ and $R^Y$ form a substituted or unsubstituted, 6-membered heterocyclic ring. In certain embodiments, $R^X$ and $R^Y$ form a substituted or unsubstituted dioxolane. In certain embodiments, $R^X$ and $R^Y$ form a mono-substituted dioxolane. In certain embodiments, $R^X$ and $R^Y$ form a dioxolane substituted with one instance of a substituted or unsubstituted phenyl ring. In certain embodiments, $R^X$ and $R^Y$ form a dioxolane substituted with one instance of a mono-substituted phenyl ring. In certain embodiments, $R^X$ and $R^Y$ form a substituted or unsubstituted dioxane.

In certain embodiments, $R^X$ and $R^Y$ form a dioxolane ring substituted with one instance of $R^X$ of formula. For example, in a compound of Formula (I), when $R^X$ and $R^Y$ form a dioxolane ring substituted with one instance of $R^X$, provided is a compound of Formula (I-a):

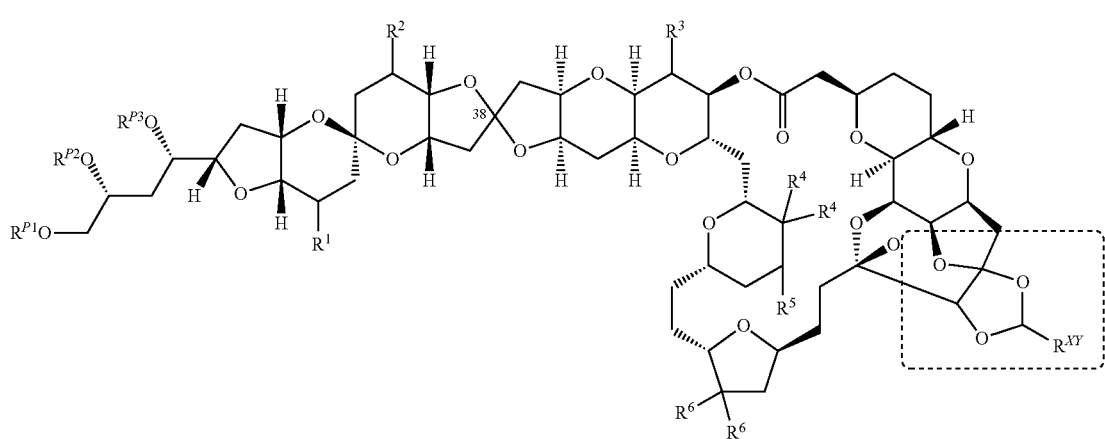

(I-a)

In certain embodiments, $R^X$ and $R^Y$ form

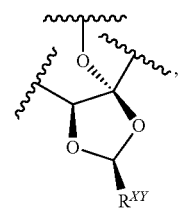

wherein $R^{XY}$ is a substituted or unsubstituted aryl ring. In certain embodiments, $R^X$ and $R^Y$ form

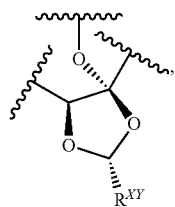

wherein $R^{XY}$ is a substituted or unsubstituted aryl ring. In certain embodiments, $R^X$ and $R^Y$ form

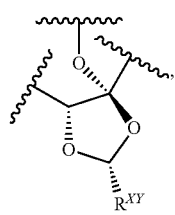

wherein $R^{XY}$ is a substituted or unsubstituted aryl ring. In certain embodiments, $R^X$ and $R^Y$ form

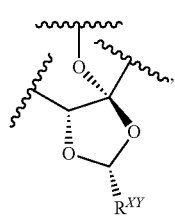

wherein $R^{XY}$ is a substituted or unsubstituted aryl ring. In certain embodiments, $R^X$ and $R^Y$ form

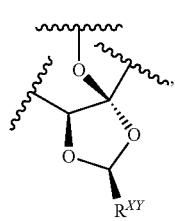

wherein $R^{XY}$ is a substituted or unsubstituted aryl ring. In certain embodiments, $R^X$ and $R^Y$ form

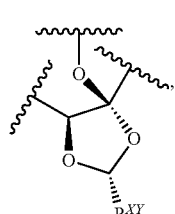

wherein $R^{XY}$ is a substituted or unsubstituted aryl ring. In certain embodiments, $R^X$ and $R^Y$ form

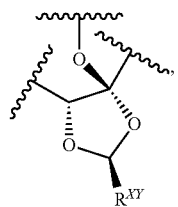

wherein $R^{XY}$ is a substituted or unsubstituted aryl ring. In certain embodiments, $R^X$ and $R^Y$ form

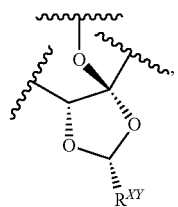

wherein $R^{XY}$ is a substituted or unsubstituted aryl ring. In certain embodiments, $R^{XY}$ is monosubstituted phenyl. In certain embodiments, $R^{XY}$ is p-methoxyphenyl. In certain embodiments, $R^{XY}$ is disubstituted phenyl.

Group $R^7$

In certain embodiments, $R^7$ is hydrogen. In certain embodiments, $R^7$ is substituted or unsubstituted alkyl. In certain embodiments, $R^7$ is substituted or unsubstituted $C_{1-6}$ alkyl. In certain embodiments, $R^7$ is substituted or unsubstituted, branched $C_{1-6}$ alkyl. In certain embodiments, $R^7$ is unsubstituted $C_{1-6}$ alkyl. In certain embodiments, $R^7$ is methyl. In certain embodiments, $R^7$ is ethyl. In certain embodiments, $R^7$ is propyl. In certain embodiments, $R^7$ is iso-propyl. In certain embodiments, $R^7$ is t-butyl. In certain embodiments, $R^7$ is an oxygen protecting group. In certain embodiments, $R^7$ is a silyl protecting group. In certain embodiments, $R^7$ is a trialkyl silyl protecting group. In certain embodiments, $R^7$ is a t-butyldimethylsilyl protecting group. In certain embodiments, $R^7$ is a trimethylsilyl protecting group. In certain embodiments, $R^7$ is a triethylsilyl protecting group. In certain embodiments, $R^7$ is a t-butyldiphenylsilyl protecting group. In certain embodiments, $R^7$ is a triisopropylsilyl protecting group. In certain embodiments, $R^7$ is a benzylic protecting group. In certain embodiments, $R^7$ is a p-methoxybenzyl protecting group. In certain embodiments, $R^7$ is an acyl protecting group. In certain embodiments, $R^7$ is an acetyl protecting group. In certain embodiments, $R^7$ is a benzoyl protecting group. In certain embodiments, $R^7$ is a p-nitro benzoyl protecting group. In certain embodiments, $R^7$ is a pivaloyl protecting group. In certain embodiments, $R^7$ is a t-butyl carbonate (BOC) protecting group. In certain embodiments, $R^7$ is an acetal protecting group. In certain embodiments, $R^7$ is a tetrahydropyranyl protecting group. In certain embodiments, $R^7$ is an alkoxyalkyl protecting group. In certain embodiments, $R^7$ is an ethoxyethyl protecting group.

Pharmaceutical Compositions and Administration

The present invention provides pharmaceutical compositions comprising a halichondrin A, norhalichondrin A, or homohalichondrin A analog of the present invention, or a pharmaceutically acceptable salt thereof, as described herein, and optionally a pharmaceutically acceptable excipient.

The present disclosure provides pharmaceutical compositions comprising a halichondrin A, norhalichondrin A, or homohalichondrin A analog described herein, e.g., a compound of Formula (I)-(III), or a pharmaceutically acceptable salt thereof, as described herein, and optionally a pharmaceutically acceptable excipient. It will be understood by one of ordinary skill in the art that the halichondrin A, norhalichondrin A, or homohalichondrin A analogs described herein, or salts thereof, may be present in various forms, such as amorphous forms, hydrates, solvates, or polymorphic forms. In certain embodiments, a provided composition comprises two or more compounds described herein. In certain embodiments, a halichondrin A, norhalichondrin A, or homohalichondrin A analog described herein, or a pharmaceutically acceptable salt thereof, is provided in an effective amount in the pharmaceutical composition. In certain embodiments, the effective amount is a therapeutically effective amount. In certain embodiments, the effective amount is an amount effective for treating or preventing a condition associated with aberrant cell proliferation. In certain embodiments, the effective amount is an amount effective for treating or preventing cancer. In certain embodiments, the effective amount is an amount effective for treating or preventing metastatic breast cancer. In certain embodiments, the effective amount is an amount effective for treating or preventing non-small cell lung cancer. In certain embodiments, the effective amount is an amount effective for treating or preventing prostate cancer. In certain embodiments, the effective amount is an amount effective for treating or preventing a sarcoma. In certain embodiments, the effective amount is an amount effective for inhibiting mitosis in a cancer cell in a subject. In certain embodiments, the effective amount is an amount effective for inducing apoptosis in a cancer cell in a subject. In certain embodiments, the effective amount is an amount effective for binding to microtubules in a cancer cell in a subject. In certain embodiments, the effective amount is an amount effective for inhibiting microtubule dynamics in a cancer cell in a subject.

Pharmaceutically acceptable excipients include any and all solvents, diluents, or other liquid vehicles, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Pharmaceutical compositions described herein can be prepared by any method known in the art of pharmacology. In general, such preparatory methods include the steps of bringing the halichondrin A, norhalichondrin A, or homohalichondrin A analog of the present invention into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the halichondrin A, norhalichondrin A, or homohalichondrin A analog of the present invention. The amount of the halichondrin A, norhalichondrin A, or homohalichondrin A analog is generally equal to the dosage of the halichondrin A, norhalichondrin A, or homohalichondrin A analog which would be administered to a subject and/or a convenient fraction of such a dosage, such as, for example, one-half or one-third of such a dosage.

Relative amounts of the halichondrin A, norhalichondrin A, or homohalichondrin A analog, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) of the halichondrin A, norhalichondrin A, or homohalichondrin A analog.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor), polyoxyethylene ethers, (e.g., polyoxyethylene lauryl ether (Brij 30), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F68, Poloxamer 188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluene (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughly, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the halichondrin A, norhalichondrin A, or homohalichondrin A analogs, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the compounds of the invention with suitable non-irritating excipients or carriers such as cocoa butter, polyethylene glycol, or a suppository wax which are solid at ambient temperature but liquid at body temperature and therefore melt in the rectum or vaginal cavity and release the halichondrin A, norhalichondrin A, or homohalichondrin A analog.

Solid dosage forms for oral administration include capsules, tablets, pills, powders, and granules. In such solid dosage forms, the halichondrin A, norhalichondrin A, or homohalichondrin A analog is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical Formulating art. They may optionally comprise opacifying agents and can be of a composition that they release the halichondrin A, norhalichondrin A, or homohalichondrin A analog (s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight poletheylene glycols and the like.

The halichondrin A, norhalichondrin A, or homohalichondrin A analog can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the halichondrin A, norhalichondrin A, or homohalichondrin A analog can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the halichondrin A, norhalichondrin A, or homohalichondrin A analog (s) only, or preferentially, in a certain part of the intestinal tract, optionally, in a delayed manner. Examples of embedding compositions which can be used include polymeric substances and waxes.

Dosage forms for topical and/or transdermal administration of a halichondrin A, norhalichondrin A, or homohalichondrin A analog of this invention may include ointments, pastes, creams, lotions, gels, powders, solutions, sprays, inhalants and/or patches. Generally, the halichondrin A, norhalichondrin A, or homohalichondrin A analog is admixed under sterile conditions with a pharmaceutically acceptable carrier and/or any needed preservatives and/or buffers as can be required. Additionally, the present invention contemplates the use of transdermal patches, which often have the added advantage of providing controlled delivery of a halichondrin A, norhalichondrin A, or homohalichondrin A analog to the body. Such dosage forms can be prepared, for example, by dissolving and/or dispensing the halichondrin A, norhalichondrin A, or homohalichondrin A analog in the proper medium. Alternatively or additionally, the rate can be controlled by either providing a rate controlling membrane and/or by dispersing the halichondrin A, norhalichondrin A; or homohalichondrin A analog in a polymer matrix and/or gel.

Suitable devices for use in delivering intradermal pharmaceutical compositions described herein include short needle devices. Intradermal compositions can be administered by devices which limit the effective penetration length of a needle into the skin. Jet injection devices which deliver liquid vaccines to the dermis via a liquid jet injector and/or via a needle which pierces the stratum corneum and produces a jet which reaches the dermis are suitable. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) halichondrin A, norhalichondrin A, or homohalichondrin A analog, although the concentration of the halichondrin A, norhalichondrin A, or homohalichondrin A analog can be as high as the solubility limit of the halichondrin A, norhalichondrin A, or homohalichondrin A analog in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the halichondrin A, norhalichondrin A, or homohalichondrin A analog and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the halichondrin A, norhalichondrin A, or homohalichondrin A analog dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the halichondrin A, norhalichondrin A, or homohalichondrin A analog may constitute 0.1 to 20% (w/w) of the composition. The propellant may further comprise additional ingredients such as a liquid non-ionic and/or solid anionic surfactant and/or a solid diluent (which may have a particle size of the same order as particles comprising the halichondrin A, norhalichondrin A, or homohalichondrin A analog).

Pharmaceutical compositions of the invention formulated for pulmonary delivery may provide the halichondrin A, norhalichondrin A, or homohalichondrin A analog in the form of droplets of a solution and/or suspension. Such formulations can be prepared, packaged, and/or sold as aqueous and/or dilute alcoholic solutions and/or suspensions, optionally sterile, comprising the halichondrin A, norhalichondrin A, or homohalichondrin A analog, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the halichondrin A, norhalichondrin A, or homohalichondrin A analog and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the halichondrin A, norhalichondrin A, or homohalichondrin A analog, and may comprise one or more of the additional ingredients described herein. A pharmaceutical composition can be prepared, packaged, and/or sold in a formulation for buccal administration. Such formulations may, for example, be in the form of tablets and/or lozenges made using conventional methods, and may contain, for example, 0.1 to 20% (w/w) of the halichondrin A, norhalichondrin A, or homohalichondrin A analog, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the halichondrin A, norhalichondrin A, or homohalichondrin A analog. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition can be prepared, packaged, and/or sold in a formulation for ophthalmic administration. Such formulations may, for example, be in the form of eye drops including, for example, a 0.1/1.0% (w/w) solution and/or suspension of the halichondrin A, norhalichondrin A, or homohalichondrin A analog in an aqueous or oily liquid carrier. Such drops may further comprise buffering agents, salts, and/or one or more other of the additional ingredients described herein. Other opthalmically-administrable formulations which are useful include those which comprise the halichondrin A, norhalichondrin A, or homohalichondrin A analog in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Halichondrin A, norhalichondrin A, or homohalichondrin A analogs provided herein are typically formulated in dosage unit form for ease of administration and uniformity of dosage. It will be understood, however, that the total daily amount of the halichondrin A, norhalichondrin A, or homohalichondrin A analog will be decided by the attending physician within the scope of sound medical judgment. The specific therapeutically effective dose level for any particular subject will depend upon a variety of factors including the disease, disorder, or condition being treated and the severity of the disorder; the activity of the specific halichondrin A, norhalichondrin A, or homohalichondrin A analog employed; the specific composition employed; the age, body weight, general health, sex and diet of the subject; the time of administration, route of administration, and rate of excretion of the specific halichondrin A, norhalichondrin A, or homohalichondrin A analog employed; the duration of the treatment; drugs used in combination or coincidental with the specific halichondrin A, norhalichondrin A, or homohalichondrin A analog employed; and like factors well known in the medical arts.

The halichondrin A, norhalichondrin A, or homohalichondrin A analogs and compositions provided herein can be administered by any route, including enteral (e.g., oral), parenteral, intravenous, intramuscular, intra-arterial, intramedullary, intrathecal, subcutaneous, intraventricular, transdermal, intradermal, rectal, intravaginal, intraperitoneal, topical (as by powders, ointments, creams, and/or drops), mucosal, nasal, buccal, sublingual; by intratracheal instillation, bronchial instillation, and/or inhalation; and/or as an oral spray, nasal spray, and/or aerosol. In general the most appropriate route of administration will depend upon a variety of factors including the nature of the agent, the therapeutic regimen, and/or the condition of the subject. Oral administration is the preferred mode of administration. However, in certain embodiments, the subject may not be in a condition to tolerate oral administration, and thus intravenous, intramuscular, and/or rectal administration are also preferred alternative modes of administration.

The exact amount of a halichondrin A, norhalichondrin A, or homohalichondrin A analog required to achieve an effective amount will vary from subject to subject, depending, for example, on species, age, and general condition of a subject, severity of the side effects or disorder, identity of the particular halichondrin A, norhalichondrin A, or homohalichondrin A analog(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a halichondrin A, norhalichondrin A, or homohalichondrin A analog for administration one or more times a day to a 70 kg adult human may comprise about 0.1 mg to about 3000 mg, about 0.1 mg to about 2000 mg, about 0.1 mg to about 1000 mg, about 0.1 mg to about 100 mg, about 1 mg to about 100 mg, or about 10 mg to about 100 mg, of a halichondrin A, norhalichondrin A, or homohalichondrin A analog per unit dosage form.

In certain embodiments, the halichondrin A, norhalichondrin A, or homohalichondrin A analogs of the present invention may be administered at dosage levels sufficient to deliver from about 0.001 mg/kg to about 100 mg/kg, from about 0.01 mg/kg to about 100 mg/kg, from about 0.1 mg/kg to about 100 mg/kg, from about 0.5 mg/kg to about 100 mg/kg, from about 10 mg/kg to about 100 mg/kg, from about 20 mg/kg to about 100 mg/kg, and from about 25 mg/kg to about 100 mg/kg, of subject body weight per day, one or more times a day, to obtain the desired therapeutic effect.

It will be also appreciated that a halichondrin A, norhalichondrin A, or homohalichondrin A analog or composition, as described herein, can be administered in combination with one or more additional therapeutically active agents. The halichondrin A, norhalichondrin A, or homohalichondrin A analog or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive halichondrin A, norhalichondrin A, or homohalichondrin A analog with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

In any of the above described methods, one or more additional therapeutic agents (also referred to as the "agent") may be administered concurrently with, prior to, or subsequent to, the halichondrin A, norhalichondrin A, or homohalichondrin A analog of the present invention, as described herein. The agent may be added at the same time as the halichondrin A, norhalichondrin A, or homohalichondrin A analog of the present invention (simultaneous administration), before or after administration of the halichondrin A, norhalichondrin A, or homohalichondrin A analog of the present invention (sequential administration), or any combination thereof. For example, in certain embodiments, the agent is administered first, followed by simultaneous administration of the agent and the halichondrin A, norhalichondrin A, or homohalichondrin A analog of the present invention. In certain embodiments, the halichondrin A, norhalichondrin A, or homohalichondrin A analog of the present invention is administered first, followed by simultaneous administration of the agent and the halichondrin A, norhalichondrin A, or homohalichondrin A analog of the present invention. In any of the above embodiments, either the agent or the halichondrin A, norhalichondrin A, or homohalichondrin A analog of the present invention may be further administered alone after the simultaneous administration.

Exemplary additional therapeutically active agents include, but are not limited to, antibiotics, anti-viral agents, anesthetics, anti-coagulants, inhibitors of an enzyme, steroidal agents, steroidal or non-steroidal anti-inflammatory agents, antihistamine, immunosuppressant agents, antigens, vaccines, antibodies, decongestant, sedatives, opioids, pain-relieving agents, analgesics, anti-pyretics, hormones, and prostaglandins. Therapeutically active agents include small organic molecules such as drug compounds (e.g., compounds approved by the US Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

In certain embodiments, the additional therapeutically agent is another anti-cancer agent. Anti-cancer agents encompass biotherapeutic anti-cancer agents as well as chemotherapeutic agents.

Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g., HERCEPTIN (trastuzumab), T-DM1, AVAS- TIN (bevacizumab), ERBITUX (cetuximab), VECTIBIX (panitumumab), RITUXAN (rituximab), BEXXAR (tositumomab)).

Exemplary chemotherapeutic agents include, but are not limited to, anti-estrogens (e.g., tamoxifen, raloxifene, and megestrol), LHRH agonists (e.g., goscrelin and leuprolide), anti-androgens (e.g., flutamide and bicalutamide), photodynamic therapies (e.g., vertoporfin (BPD-MA), phthalocyanine, photosensitizer Pc4, and demethoxy-hypocrellin A (2BA-2-DMHA)), nitrogen mustards (e.g., cyclophosphamide, ifosfamide, trofosfamide, chlorambucil, estramustine, and melphalan), nitrosoureas (e.g., carmustine (BCNU) and lomustine (CCNU)), alkylsulphonates (e.g., busulfan and treosulfan), triazenes (e.g., dacarbazine, temozolomide), platinum containing compounds (e.g., cisplatin, carboplatin, oxaliplatin), *vinca* alkaloids (e.g., vincristine, vinblastine, vindesine, and vinorelbine), taxoids (e.g., paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound, to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g., etoposide, etoposide phosphate, teniposide, topotecan, 9-aminocamptothecin, camptoirinotecan, irinotecan, crisnatol, mytomycin C), anti-metabolites, DHFR inhibitors (e.g., methotrexate, dichloromethotrexate, trimetrexate, edatrexate), IMP dehydrogenase inhibitors (e.g., mycophenolic acid, tiazofurin, ribavirin, and EICAR), ribonucleotide reductase inhibitors (e.g., hydroxyurea and desferrioxamine), uracil analogs (e.g., 5-fluorouracil (5-FU), floxuridine, doxifluridine, raltitrexed, tegafur-uracil, capecitabine), cytosine analogs (e.g., cytarabine (ara C), cytosine arabinoside, and fludarabine), purine analogs (e.g., mercaptopurine and Thioguanine), Vitamin D3 analogs (e.g., EB 1089, CB 1093, and KH 1060), isoprenylation inhibitors (e.g., lovastatin), dopaminergic neurotoxins (e.g., 1-methyl-4-phenylpyridinium ion), cell cycle inhibitors (e.g., staurosporine), actinomycin (e.g., actinomycin D, dactinomycin), bleomycin (e.g., bleomycin A2, bleomycin B2, peplomycin), anthracycline (e.g., daunorubicin, doxorubicin, pegylated liposomal doxorubicin, idarubicin, epirubicin, pirarubicin, zorubicin, mitoxantrone), MDR inhibitors (e.g., verapamil), Ca2+ ATPase inhibitors (e.g., thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SJ5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647; and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

Also encompassed by the invention are kits (e.g., pharmaceutical packs). The kits provided may comprise an inventive pharmaceutical composition or halichondrin A, norhalichondrin A, or homohalichondrin A analog and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or halichondrin A, norhalichondrin A, or homohalichondrin A analog. In some embodiments, the inventive pharmaceutical composition or halichondrin A, norhalichondrin A, or homohalichondrin A analog provided in the container and the second container are combined to form one unit dosage form.

Methods of Treatment

The present invention also provides methods of using a compound of Formula (I)-(III) or pharmaceutically acceptable salt thereof, e.g., by treating or preventing a condition associated with aberrant cell proliferation in a subject in need thereof, or by inhibiting mitosis or inducing cell apoptosis in a subject in need thereof, comprising administering to the subject a compound of Formula (I)-(III), or a pharmaceutically acceptable salt thereof, or a pharmaceutical composition thereof, in an amount sufficient to treat the condition. In certain embodiments, a compound of Formula (I)-(III), or a pharmaceutically acceptable salt thereof, binds to microtubules and inhibits mitosis or induces cell apoptosis through inhibition of microtubule dynamics in a subject in need thereof. In certain embodiments, a compound of Formula (I)-(III), or a pharmaceutically acceptable salt thereof, binds to high affinity sites at the plus end of existing microtubules.

In certain embodiments, compounds of Formula (I)-(III) are useful for treatment of a proliferative disease. Exemplary proliferative diseases include, but are not limited to, tumors, begin neoplasms, pre-malignant neoplasms (carcinoma in situ), and malignant neoplasms (cancers). Exemplary cancers include, but are not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarcinoma), Ewing's sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematological malignancy (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenström's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described herein; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendocrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva). In certain embodiments, the cancer is a hematological malignancy. In certain embodiments, the cancer is lymphoma. In certain embodiments, the cancer is leukemia.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), reptiles, amphibians, and fish. In certain embodiments, the non-human animal is a mammal. The non-human animal may be a male or female and at any stage of development. A non-human animal may be a transgenic animal.

As used herein, and unless otherwise specified, the terms "treat," "treating," and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder, or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

As used herein "inhibition", "inhibiting", "inhibit" and "inhibitor", and the like, refer to the ability of a compound to reduce, slow, halt or prevent activity of a particular biological process (e.g., microtubule dynamics or growth) in a cell relative to vehicle.

Methods of Synthesis and Intermediates

The synthesis of halichondrin A was planned from 4c and 5. The right half 4c was disconnected retrosynthetically into the C1-C19 and C20-C38 building blocks 6 and 7 (see Scheme 1). Such a synthetic scheme enables the proposed synthesis of 4c from 6 and 7 to be achieved by recently developed asymmetric Ni/Cr-mediated coupling, followed by base-induced cyclization.[1,2] The specified route also leads to certain additional advantages. For example, two known building blocks 5 and 7 can also be utilized.[3] The current synthetic scheme for halichondrin A also possesses a higher degree of convergency than in the previous routes.[4] Furthermore, the specified synthetic approach can be extended to the synthesis of halichondrins B and C (see building blocks 6-B and 6-C).

Scheme 1.

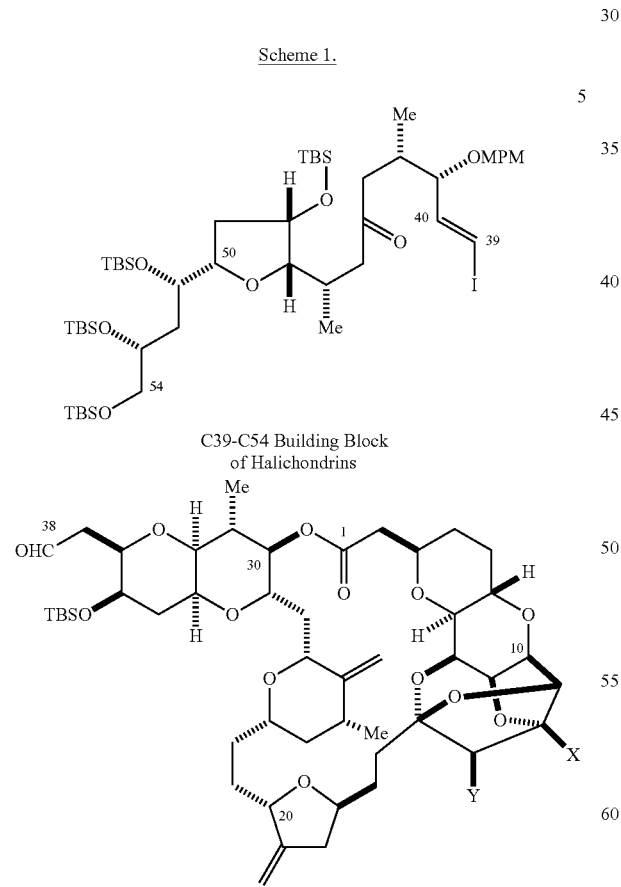

4a (Halichondrin B series): X = Y = H
4b (Halichondrin C series): X = OCH₂CH=CH₂; Y = H
4c (Halichondrin A series): X = Y = protected OH

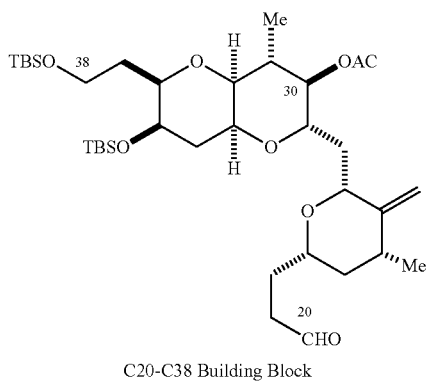

C20-C38 Building Block

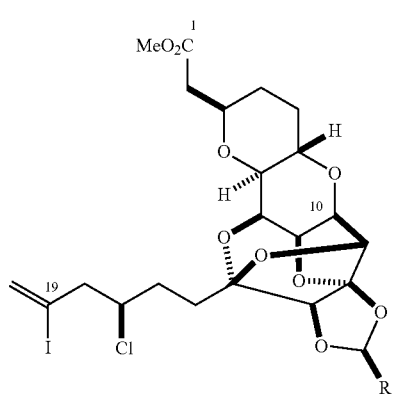

(R = C₆H₄OMe-p)
C1-C19 Building Block
of Halichondrin As

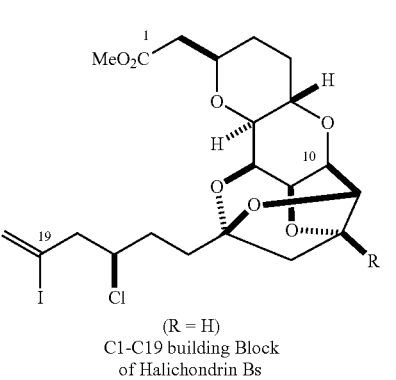

(R = H)
C1-C19 building Block
of Halichondrin Bs

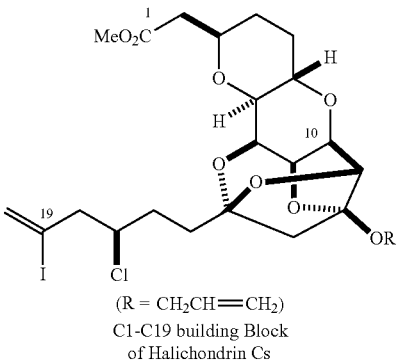

(R = CH₂CH=CH₂)
C1-C19 building Block
of Halichondrin Cs

The central question for the synthesis of building block 6 was how to construct the C8-C14 polycycle of halichondrin A. Through the model studies conducted in connection with the synthesis of halichondrin C, valuable information was gained to address this question.[5] Scheme 2 summarizes a transformation of 8 into β-10 possessing the C8-C14 polycycle of halichondrin A. This transformation involves: (1) selective TBS-deprotection of both C9-OTBS (equatorial) and C11-OTBS (acyclic) over C8-OTBS (axial), (2) oxy-Michael addition of the resultant C9-alcohol to ynone 8, to form preferentially E-isomer with assistance of hydrogen-bonding stabilization, (3) stereoselective DMDO-epoxidation from convex face, and (4) acid-promoted ketalization to form β-10. Interestingly, DMDO-epoxidation of the corresponding Z-isomer Z-9, followed by acid-treatment, gave α-10 non-contaminated from β-10, thereby demonstrating the high stereoselectivity of DMDO oxidation. On treatment with p-anisaldehyde dimethyl acetal in the presence of camphorsulfonic acid (CSA), β-10 gave single p-methoxybenzylidene acetal 11.[6]

are far more reactive than iodoolefins in the Cr-mediated coupling.[7] This suggested the possibility that the (12+13a) coupling can be achieved without interference from the C19-iodoolefin present in 6a. Indeed, it was found that the coupling was effectively achieved with a trace amount of Ni-catalyst or without added Ni-catalyst. At present, however, it is not clear whether a trace amount of Ni-catalyst is required for this coupling.[7] As the resultant allylic alcohol is oxidized to the ketone, the C14 stereochemistry outcome is not an issue for this coupling. However, the Cr-catalyst derived from a sulfonamide ligand such as sulfonamide-I (Scheme 4) significantly accelerates the coupling. Interestingly, (R)-ligand was found to be more effective than (S)-ligand. The coupling was conducted routinely with 15-20 mol % Cr-catalyst, however, the catalyst loading was improved up to 5 mol % with the iodoacetylene with TES, i.e., R=TES in 12, without a loss of the coupling efficiency.

In ligands of Scheme 4, $R^{L1}$ is substituted or unsubstituted $C_{1-6}$ alkyl. In certain embodiments, $R^{L1}$ is isopropyl. In certain embodiments, $R^{L1}$ is t-butyl. In certain embodiments, Scheme 2.

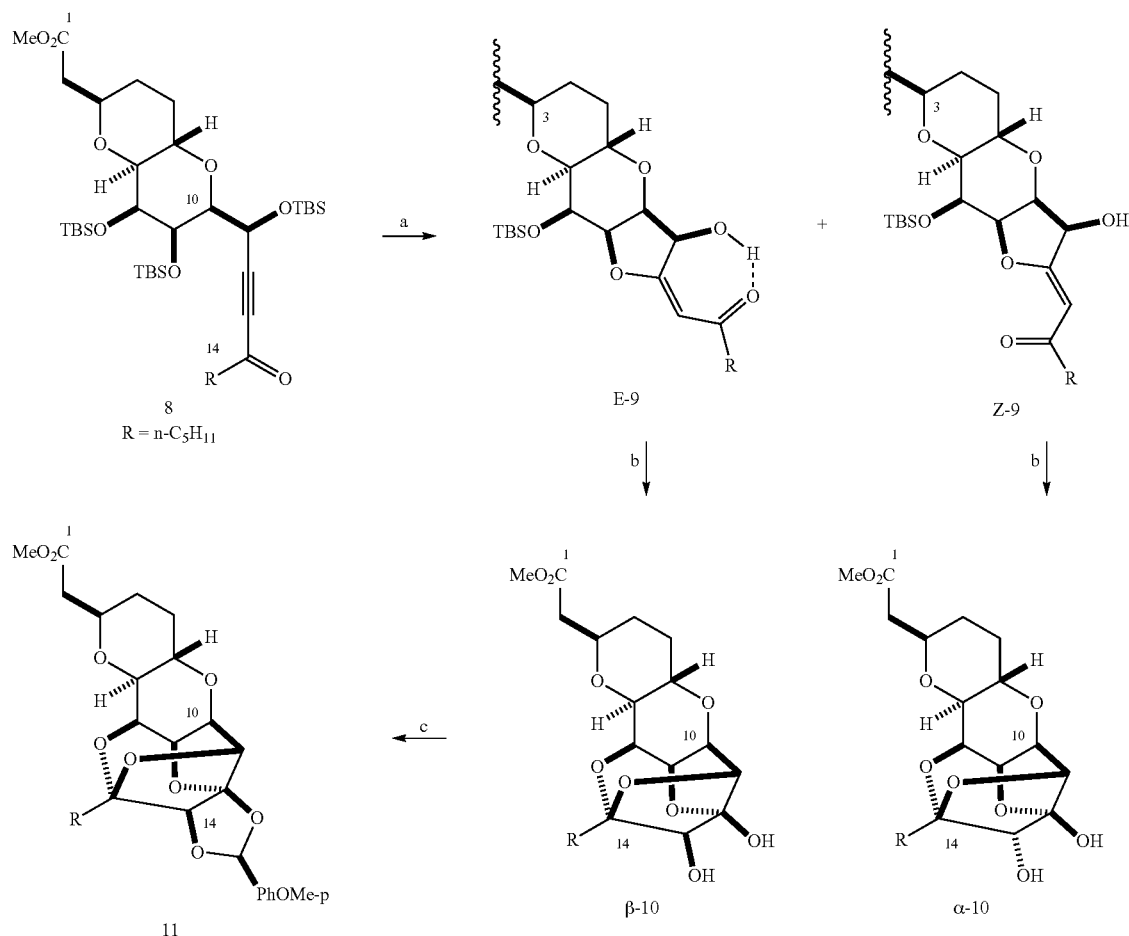

Reagents and Conditions. (a) HF·py, py, MeCN, rt; E-9: 69% and Z-9: 7%. (b) 1. DMDO, acetone, 0° C. 2. CSA, CH$_2$Cl$_2$ (wet), rt. 3. HF·py, MeCN, rt; 74% for E-9→β-10 and 50% for Z-9→α-10. (c) CSA (cat), p-MeOC$_6$H$_4$CH(OMe)$_2$, DMF, 100° C.; 67%.

Guided by the model study, the C1-C19 building block 6a was prepared (Scheme 3). The coupling of aldehyde 13a with iodoacetylene 12 was effectively achieved with catalytic asymmetric Ni/Cr-mediated coupling. Iodoacetylenes the carbon to which $R^{L1}$ is attached is in the (R)-configuration. In certain embodiments, the carbon to which $R^{L1}$ is attached is in the (S)-configuration. In ligands of Scheme 4, $R^{L2}$ is substituted or unsubstituted $C_{1-6}$ alkyl or substituted or unsubstituted aryl. In certain embodiments, $R^{L2}$ is methyl. In certain embodiments, $R^{L2}$ is substituted or unsubstituted phenyl. In certain embodiments, $R^{L2}$ is phenyl substituted with at least one halogen. In certain embodiments, $R^{L2}$ is phenyl substituted with at least two halogens. In ligands of Scheme 4, each $R^{L3}$ is independently substituted or unsubstituted alkoxy or substituted or unsubstituted carbocyclyl and p is 1, 2, 3, or 4. In certain embodiments, at least one $R^{L3}$ is methoxy; and p is 1 or 2. In certain embodiments, at least one $R^{L3}$ is substituted or unsubstituted 5-6 membered carbocyclyl. In certain embodiments, at least one $R^{L3}$ is substituted or unsubstituted cyclohexyl. In certain embodiments, at least one $R^{L2}$ is cyclohexyl substituted with at least one methyl. In certain embodiments, at least one $R^{L3}$ is cyclohexyl substituted with at least two methyls. In ligands of Scheme 4, each $R^{L4}$ is independently substituted or unsubstituted $C_{1-6}$ alkyl or substituted or unsubstituted aryl. In ligands of Scheme 4, each $R^{L5}$ is independently hydrogen or substituted or unsubstituted alkoxy. In certain embodiments, both of $R^{L5}$ are hydrogen. In certain embodiments, at least one $R^{L5}$ is methoxy. In certain embodiments, both of $R^{L5}$ are methoxy.

After oxidation of the propargyl alcohol, 14a was subjected to selective TBS-deprotection conditions to give enone 15 (E-isomer: 62%; Z-isomer: 6%). DMDO-oxidation, followed by acid-treatment and then p-anisaldehyde dimethyl acetal, furnished the desired C1-C19 building block 6a in 45% overall yield. However, the product thus obtained was a 2:1 mixture of desired 6a and acetylene 16. An NMR analysis showed that this by-product formation took place during the DMDO-step.

Scheme 3.

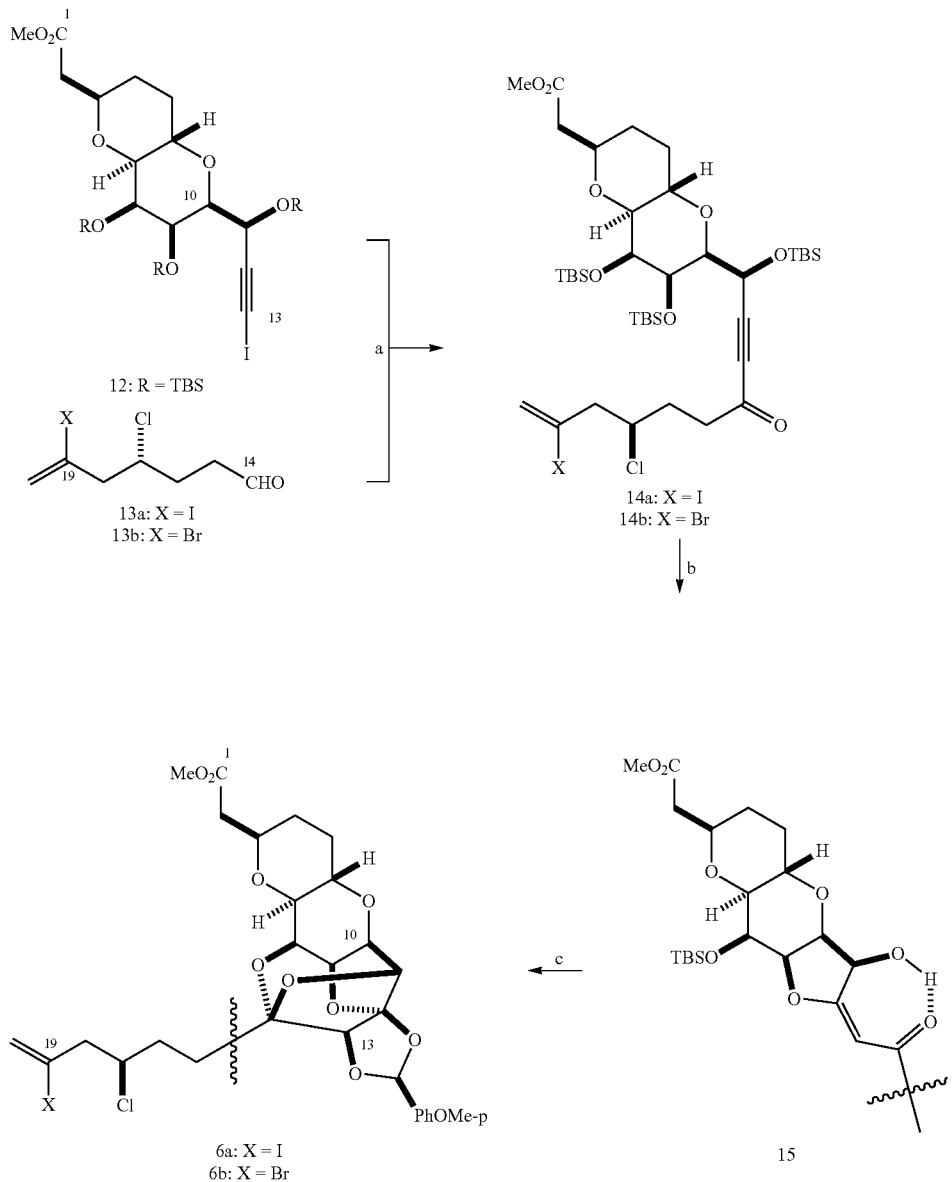

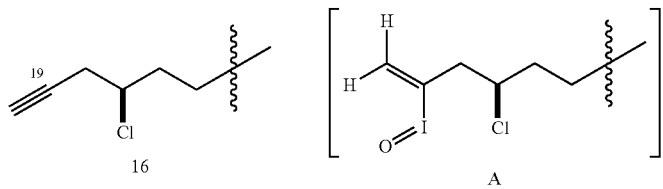

Reagents and Conditions. (a) Ni/Cr-mediated coupling with Cr-catalyst (20 mol %) derived from (R)-sulfonamide-I and NiCl₂•DEP (0.03 mol %) (12 + 13b) → 14b; 91%. 2. Dess Martin oxidation, CH₂Cl₂, rt; 96%. (b) HF•py, py, MeCN, rt; 59% of 15 and 6% of its Z-isomer. (c) 1. DMDO, acetone, rt. 2. CSA, CH₂Cl₂ (wet), rt. 3. HF•py, MeCN, rt; 92% yield over 3-steps. 4. p-TsOH (cat), p-MeOC₆H₄CH(OMe)₂, CH₂Cl₂, rt; 76% of 6b and 12% of rsm.

Scheme 4.

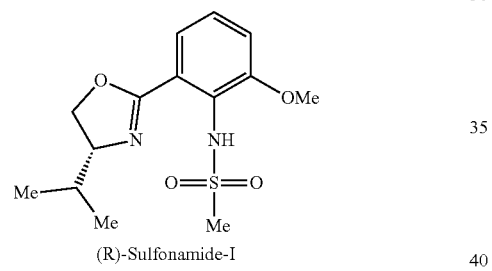

(R)-Sulfonamide-I

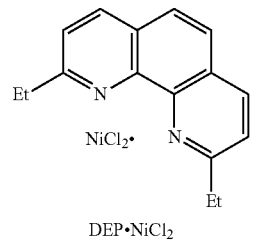

DEP•NiCl₂

General Ligand and Metal Complex Structures:

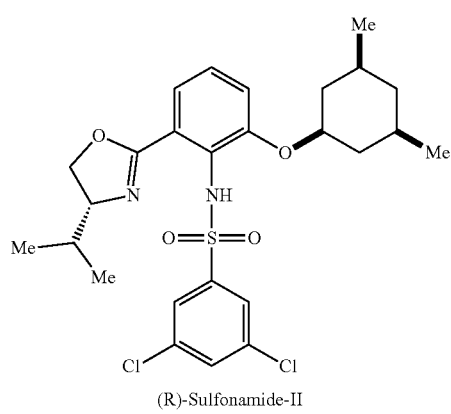

(R)-Sulfonamide-II

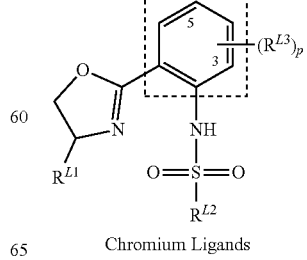

Chromium Ligands

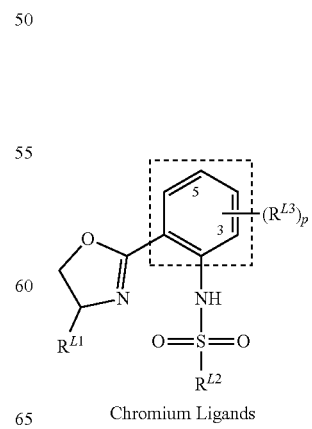

Nickel Ligands

A literature search revealed no example known for DMDO-mediated transformation of iodoolefins to acetylenes.[8] Nevertheless, formation of 16 is likely caused by the DMDO-oxidation of the iodine to iodoso intermediate A, followed by syn-elimination reported by Reich.[9] Alternatively, the synthesis was carried out using bromoolefin aldehyde 13b. The synthesis of this series proceeded in the parallel way with the 13a series, except for: (1) as anticipated, there was no acetylene by-product 16 formed and (2) the efficiency of Ni/Cr-mediated (12+13b)-coupling was slightly higher in this series (70% overall yield from 15). Coupling of the C1-C19 building block 6b with the C20-C38 building block 7 was realized by Ni/Cr-mediated reaction in the presence of the Cr-catalyst derived from (R)-sulfonamide II (Scheme 5).[2] However, to overcome the poorer reactivity of the bromoolefin of 6b, this coupling was carried out with 40 mol % Cr-reagent. The induced cyclization of the resultant allylic alcohol with AgOTf-Ag$_2$O gave desired product 17 in 70% overall yield from 7, with 20:1 stereoselectivity.[10] On treatment with aq. LiOH, both acetate and methyl ester of 17 were hydrolyzed to yield the expected seco-acid, macrolactonization of which was effected with Shiina's reagent to furnish 18 in 77% overall yield.[11] Selective deprotection of the 1°-TBS at C38 over the 2°-TBS at C35 was effected with HF•py and imidazole in MeCN at 4° C., to furnish the halichondrin-A right-half 19 in 85% yield. After Dess-Martin oxidation, 19 was subjected to Ni/Cr-mediated coupling with the halichondrin left-half 5, followed by oxidation, to furnish the trans-enone 20 in 85% yield (Scheme 6). Once again, (S)-sulfonamide-I was used to accelerate the coupling rate.

Scheme 5.

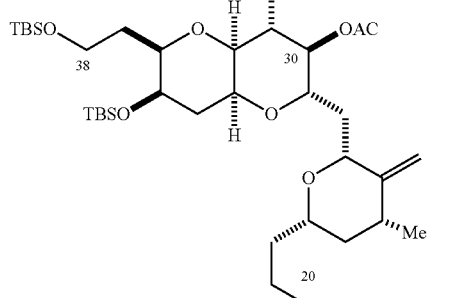

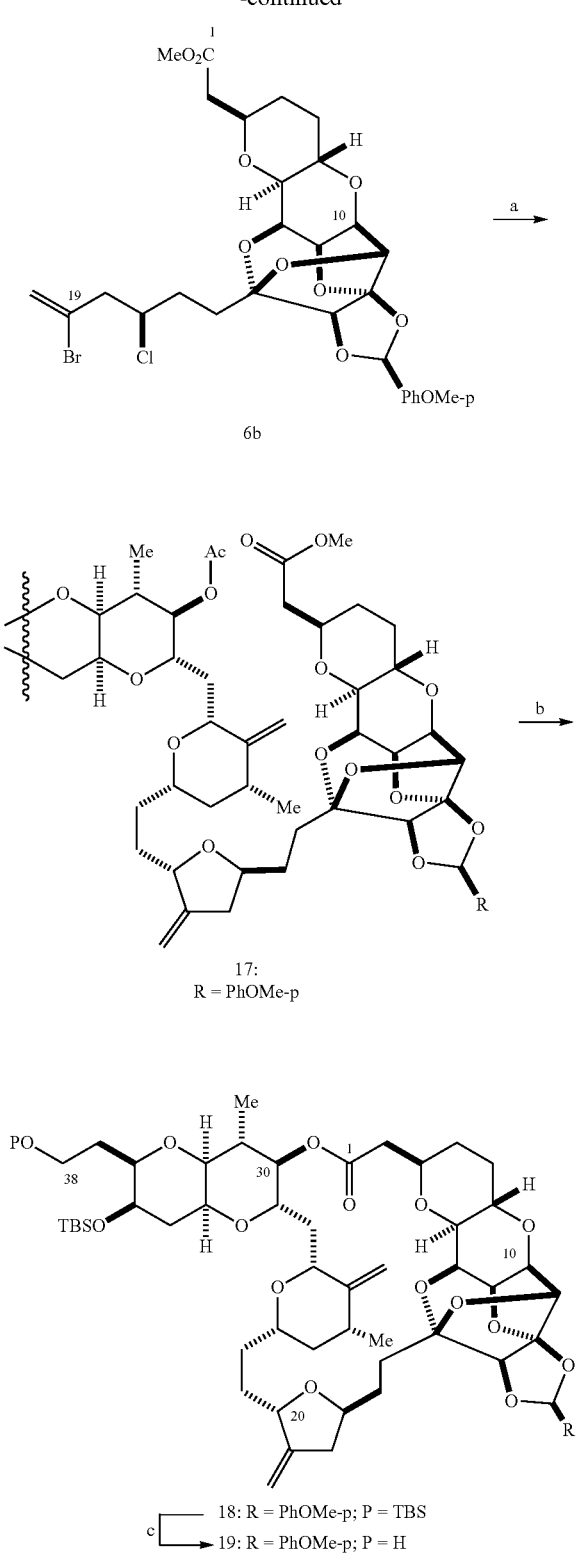

Reagents and Conditions. (a) 1. Ni/Cr-mediated coupling with Cr-catalyst (40 mol %) derived from (R)-sulfonamide-II and NiCl$_2$•DEP (10 mol %); 91% yield (dr = 20:1) 2. AgOTf, Ag$_2$O, THF, rt; 78% yield. (b) 1. LiOH, aq. MeOH, rt. 2. 2-methyl-6-nitrobenzoic anhydride, i-Pr$_2$NEt, DMAP, toluene, 70° C.; 77% over 2-steps. (c) HF•py, imidazole, MeCN,4° C.; 85% yield.

Scheme 6.

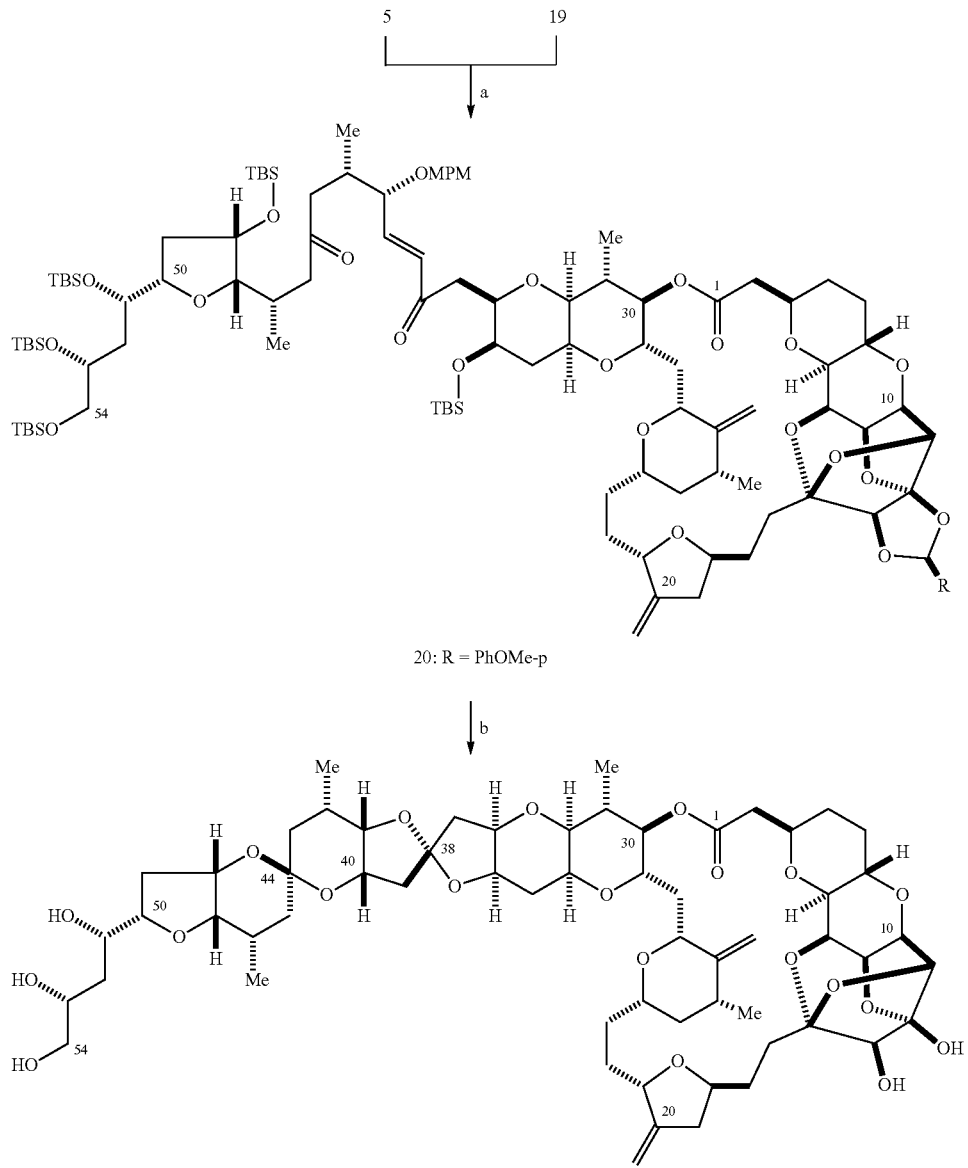

20: R = PhOMe-p

21: Halichondrin A

Reagents and Conditions. (a) 1. Dess-Martin oxidation of 19, CH$_2$Cl$_2$, rt; 96% yield. 2. Ni/Cr-mediated coupling with Cr-catalyst (5 eq) derived from (S)-sulfonamide-I and NiCl$_2$•DEP (2 mol %). 3. Dess-Martin oxidation; 85% yield over 2-steps. (b) 1. TBAF, imidazole•HCl, DMF, rt. 2. DDQ, t-BuOH, CH$_2$Cl$_2$, phosphate buffer (pH = 7.0), rt. 3. PPTS, i-PrOH, rt. 4. TMSOTf, CH$_2$Cl$_2$, -78° C.; 39% isolated yield of 21 and ~ 3% of 22 over 4-steps.

The following chemical transformations were required to convert 20 to halichondrin A: (1) deprotection of the five TBS groups, (2) hemiketal formation at C44, (3) oxy-Michael addition of the resultant hemiketal hydroxyl group to the α,β-unsaturated ketone to form the [6,6]-spiroketal at C44, (4) deprotection of the C41-MPM group, (5) formation of [5,5]-spiroketal at C38, and (6) deprotection of the anisylidene group at C12/C13. The anisylidene group could be removed by PPTS in protic solvent and therefore the transformation of 20 into halichondrin A could be achieved with use of a 3-step protocol. Compound 20 was subjected to TBAF, DDQ, and then PPTS treatments. In the third step (PPTS in isopropanol at RT), the anisylidene group was indeed removed, but two major products (ca. 3:2 ratio) were formed. Mass spectral (MS) and $^1$H NMR analysis suggested that the major and minor products were likely to correspond to C38-epi-halichondrin A and halichondrin A, respectively.

Figure 2:
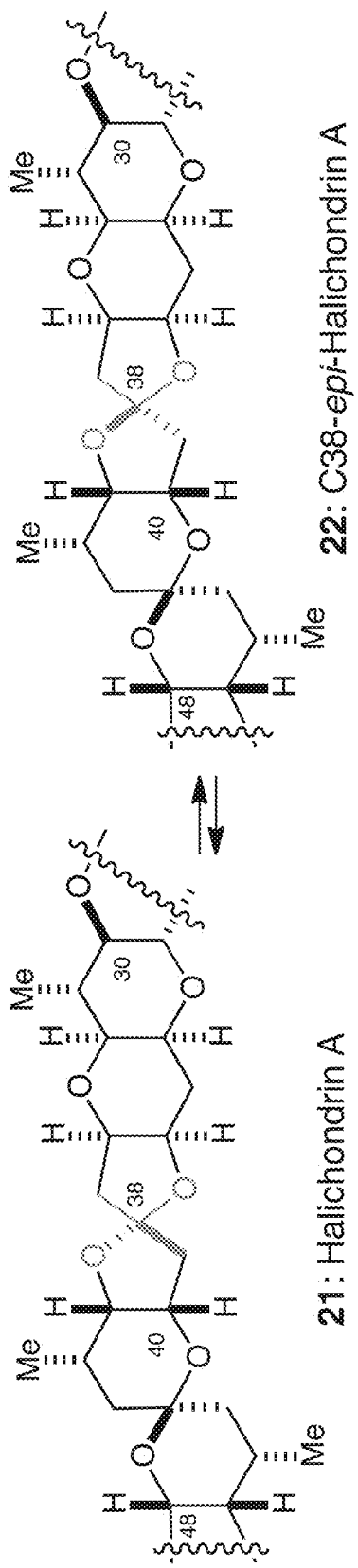
FIG. 2 shows the interconversion of halichondrin A and its C38 epimer. Conditions have been developed that favor formation of either of the epimers.
Figure 3:
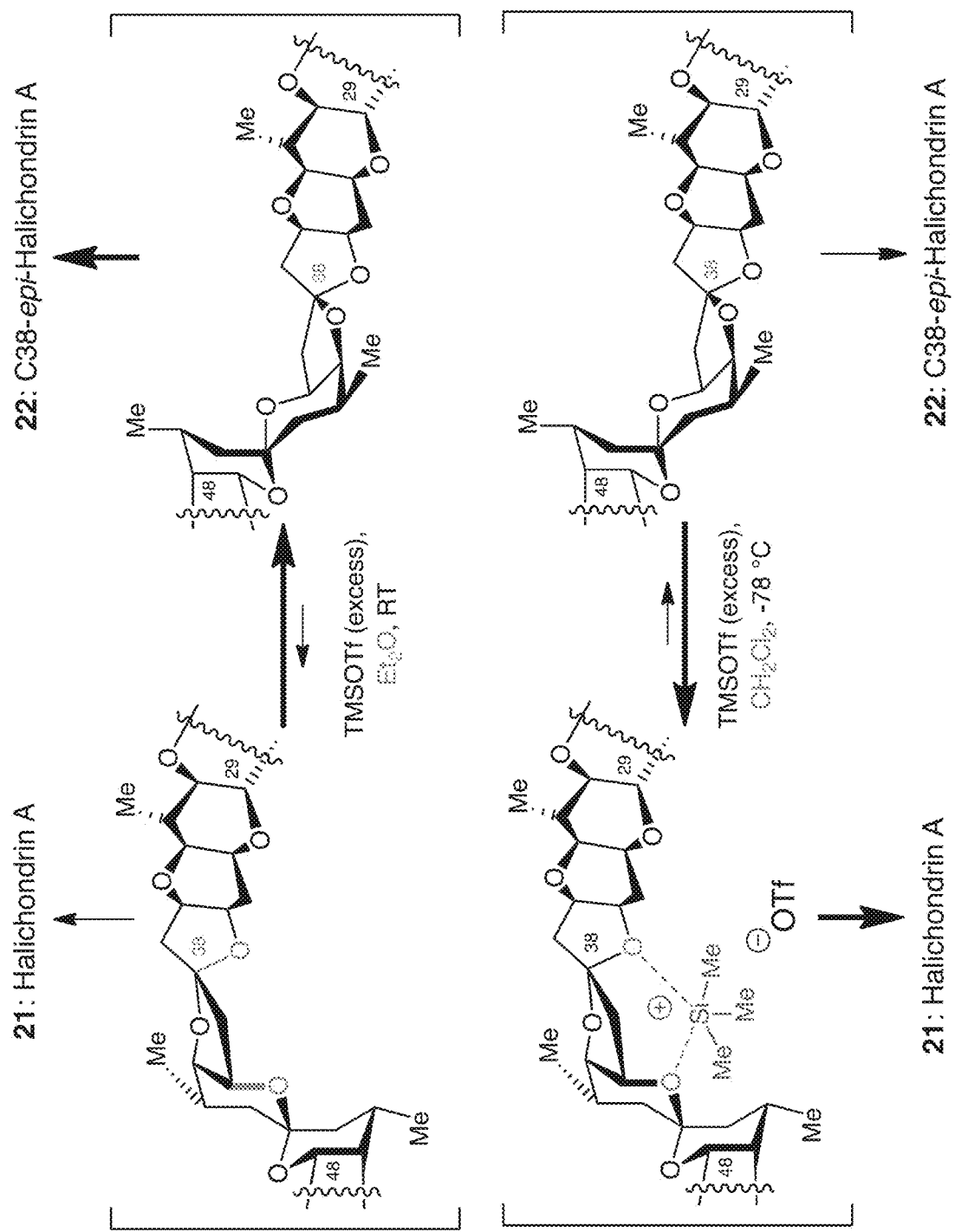
FIG. 3 shows a possible mechanism for the observed solvent-dependent [5,5]-spiroketal equilibration at C38.

For this reason, the acid-catalyzed equilibration of the [5,5]-spiroketal at C38 was studied (see FIG. 2). Compared with [6,6]-spiroketals, the stereochemical behaviors of [5,5]-spiroketals are complex,[12] and it is not straightforward to suggest a chemical means to favor halichondrin A over C38-epi-halichondrin A or vice versa. After numerous attempts, a simple, but remarkably effective method was discovered to favor either halichondrin A (21) or C38-epihalichondrin A (22) in the equilibrium; 21 and 22 were formed as the major stereoisomer on treatment with TMSOTf in CH$_2$Cl$_2$ or Et$_2$O, respectively.[13] It is worthwhile noting: (1) no furan formation was observed under the conditions employed and (2) both halichondrins B and C exhibited the identical reactivity.

Without wishing to be limited to any particular theory, but realizing that solvents play a key role,[14] a speculative mechanistic explanation is proposed; the C35-C44 moiety of halichondrins provides a polyether-type cavity for cations such as Me$_3$Si$^+$ in non-oxygen-containing solvents, which shifts the equilibrium in favor to halichondrin A (Scheme 5). In oxygen-containing solvents, the cavity effect is cancelled out with solvents and an unfavorable dipole-dipole interaction between the C38-O and C40-O bonds in halichondrin A shifts the equilibrium towards C38-epi-halichondrin A.

Based on the insight on the [5,5]-spiroketal behavior, a total synthesis of halichondrin A was completed in a stereoselective manner. Namely, the product mixture obtained in the PPTS step was subjected to the TMSOTf-promoted equilibration, followed by chromatographic separation, to furnish synthetic halichondrin A (21) in 39% overall yield from 20, along with C38-epi-halichondrin A (22; ca. 3%).

Norhalichondrin A (24) was synthesized with coupling 19 and 23 (Scheme 7).[15] It should be noted that 23 was the left half used for the synthesis of norhalichondrin B.[16] Synthetic norhalichondrin A (24) thus obtained was confirmed to be identical with natural norhalichondrin A ($^1$H- and $^{13}$C-NMR, HR-MS, TLC), thereby establishing the structure of the halichondrin right-half 19. Note worthily, norhalichondrin A (24) played the central role in structure elucidation of this class of natural products, i.e., the X-ray structure analysis of its p-bromophenacyl ester. Taken together, the stereochemistry of the two building blocks 5 and 19 used for the current halichondrin A synthesis were unambiguously established.

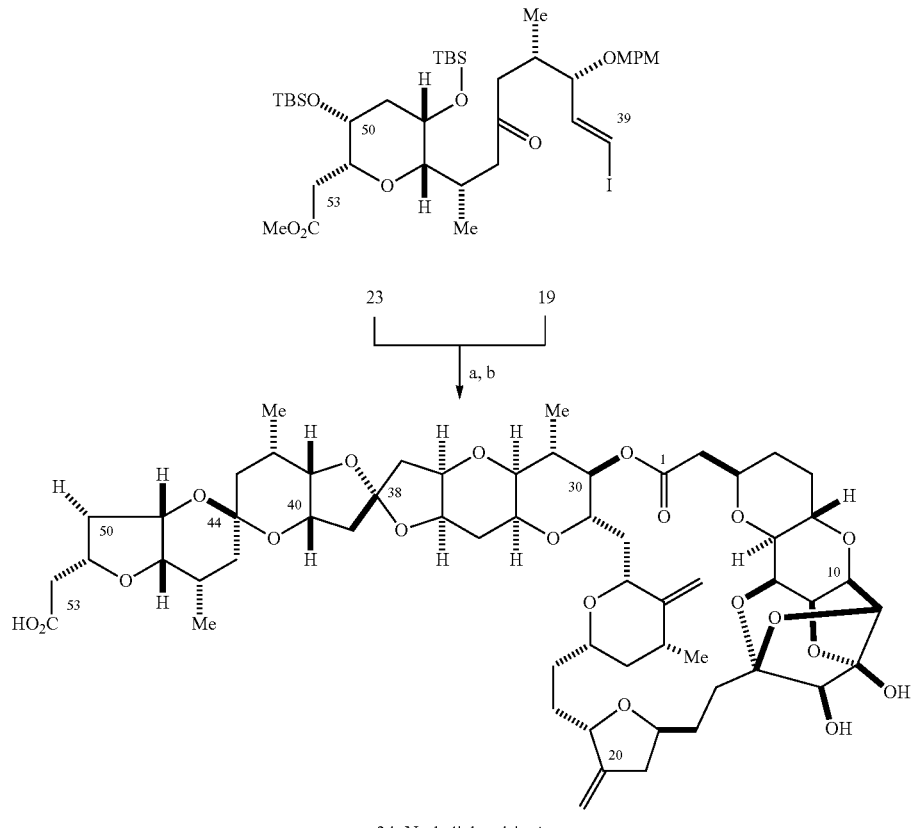

Scheme 7.

24: Norhalichondrin A

Reagents and Conditions. (a) same as step a in Scheme 6. 83% overall yield. (b) 1-4. same as step b in Scheme 6. 5. LiOH, aq. THF, rt; 30% isolated yield of 24 over 5 steps.

Figure 4:
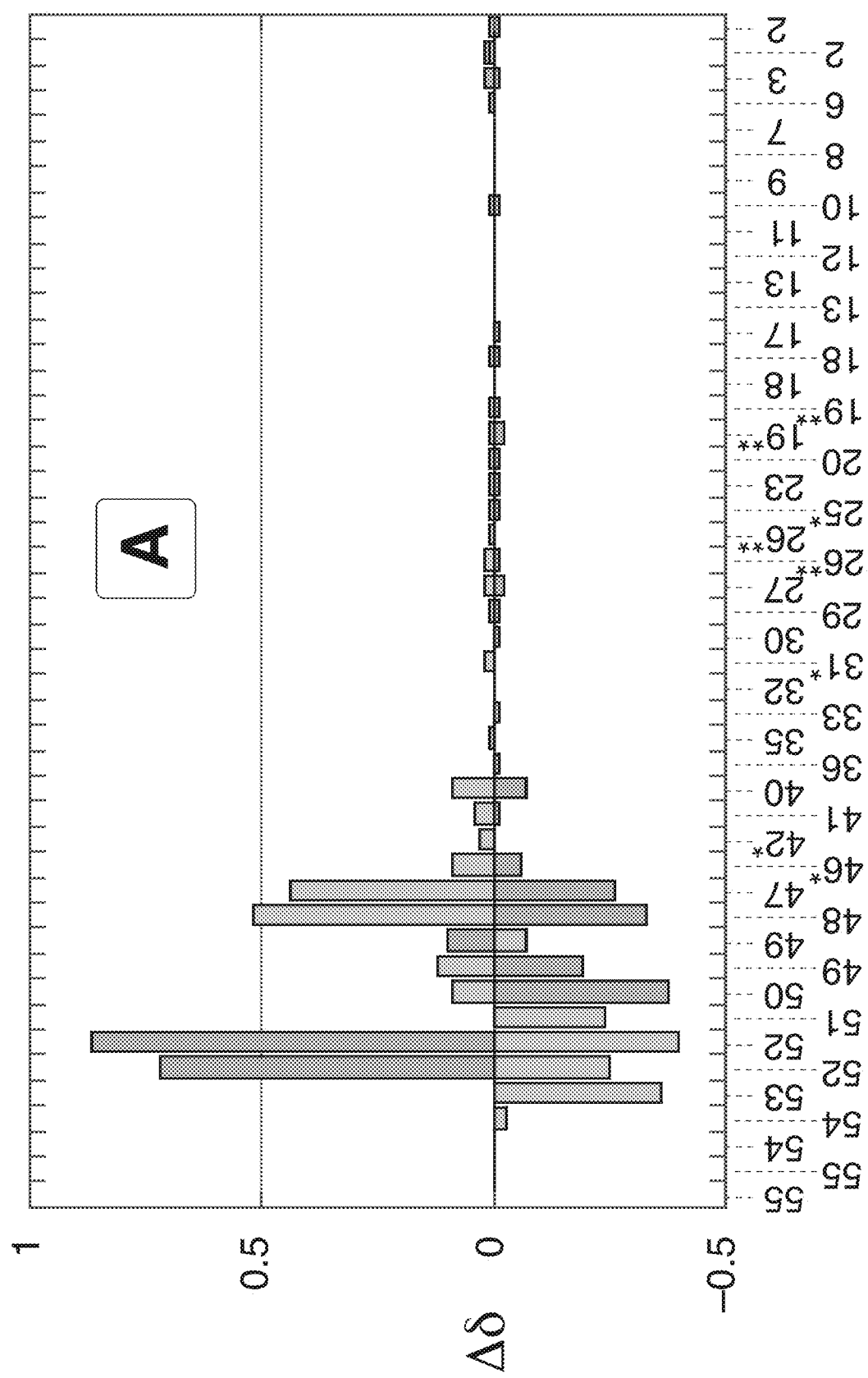
FIG. 4 shows proton chemical shift differences between halichondrin A, norhalichondrin A, and homohalichondrin A. The x-axis represents carbon number at which protons in question are attached. The y-axis shows proton chemical shift differences in ppm: dark gray: Δδ=(norhalichondrin A)−(synthetic halichondrin A); light gray: Δδ=(synthetic halichondrin A)−(homohalichondrin A). *methyl group attached at the indicated carbon; **exo-methylene group attached at the indicated carbon.
Figure 5:
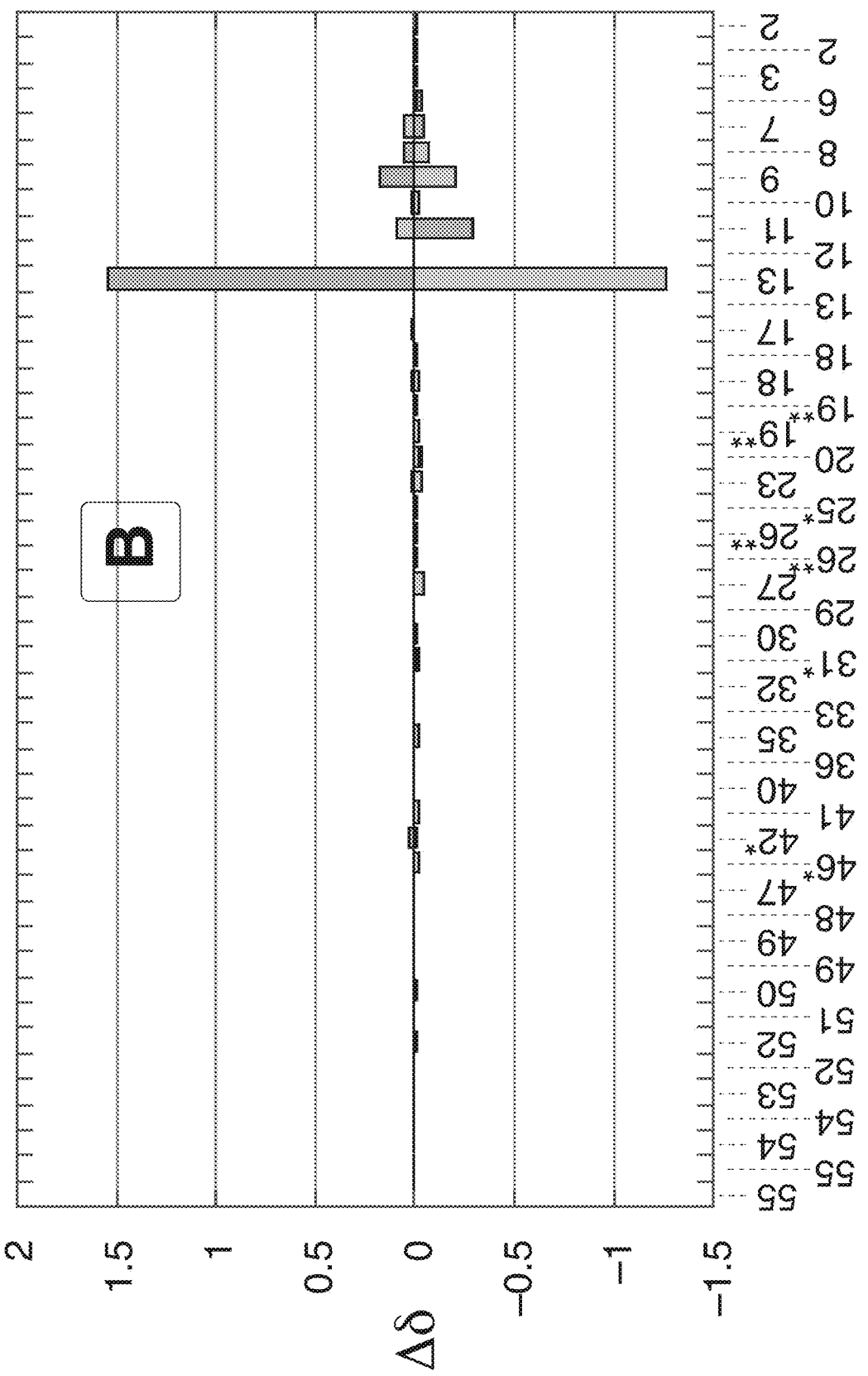
FIG. 5 shows proton chemical shift differences between halichondrin A, halichondrin B, and halichondrin C. The x-axis represents carbon number at which protons in question are attached. The y-axis shows proton chemical shift differences in ppm: dark gray: Δδ=(synthetic halichondrin A)−(halichondrin B); light gray: Δδ=(halichondrin C)−(synthetic halichondrin A). *methyl group attached at the indicated carbon; **exo-methylene group attached at the indicated carbon.

Three chiral centers at C38, C40, and C44 were introduced at the transformation from the enone 20 to the final product. The fact that norhalichondrin A (24) was successfully obtained by using the virtually same procedure strongly suggests that the newly introduced three chiral centers match with those present in the halichondrin class natural products. Detailed NMR analysis provided further evidence. The panel in FIG. 4 summarizes the proton chemical shift differences between norhalichondrin A and synthetic halichondrin A (dark gray) and synthetic halichondrin A and homohalichondrin A (light gray). This comparison demonstrates that these three halichondrins share the same right-half structure. Similarly, the panel in FIG. 5 shows the proton chemical shift differences between synthetic halichondrin A and halichondrin B (dark gray) and halichondrin C and synthetic halichondrin A (light gray), thereby demonstrating that these three halichondrins share the same left-half structure. The two NMR comparisons once again proved that halichondrin A obtained through the total synthesis is a unique compound.

Provided herein are synthetic intermediates for the synthesis of halichondrin A, homohalichondrin A, and norhalichondrin A and analogs thereof. In one aspect, provided are compounds of Formula (A-1):

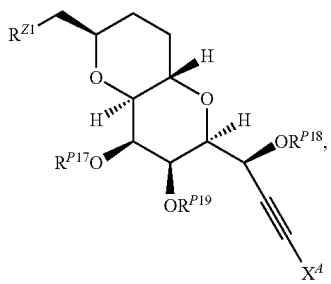

(A-1)

and pharmaceutically acceptable salts thereof, wherein:

$R^{P17}$, $R^{P18}$, and $R^{P19}$ are each independently hydrogen, substituted or unsubstituted alkyl, or an oxygen protecting group;

$R^{Z1}$ is —$CO_2R^{Z1a}$, wherein $R^{Z1a}$ is hydrogen, substituted or unsubstituted alkyl, or an oxygen protecting group; and $X^A$ is hydrogen or a halogen.

In another aspect, provided are compounds of Formula (B-1):

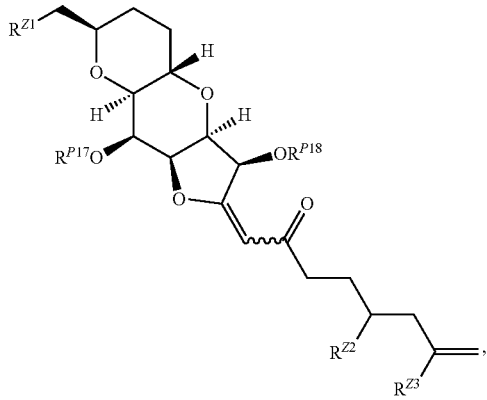

(B-1)

and pharmaceutically acceptable salts thereof, wherein:

$R^{P17}$ and $R^{P18}$ are each independently hydrogen, substituted or unsubstituted alkyl, or an oxygen protecting group;

$R^{Z1}$ is —$CO_2R^{Z1a}$, wherein $R^{Z1a}$ is hydrogen, substituted or unsubstituted alkyl, or an oxygen protecting group;

$R^{Z2}$ is a halogen or a leaving group; and $R^{Z3}$ is a halogen.

In another aspect, provided are compounds of Formula (C-1):

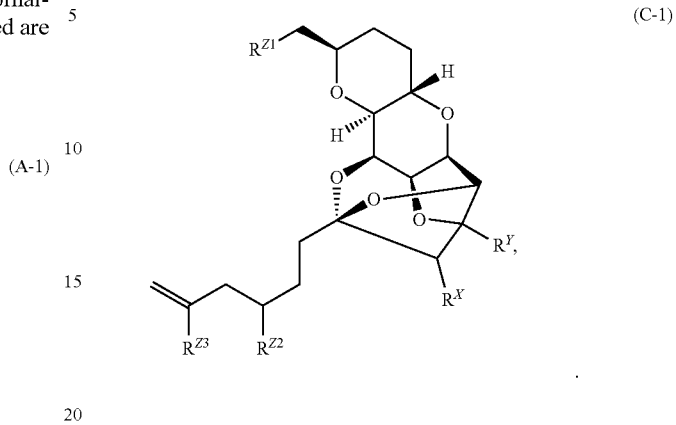

(C-1)

and pharmaceutically acceptable salts thereof, wherein:

$R^{Z1}$ is —$CO_2R^{Z1a}$, wherein $R^{Z1a}$ is hydrogen, substituted or unsubstituted alkyl, or an oxygen protecting group;

$R^{Z2}$ is a halogen or a leaving group;

$R^{Z3}$ is a halogen;

$R^X$ is —$OR^{X1}$, wherein $R^{X1}$ is hydrogen, substituted or unsubstituted alkyl, or an oxygen protecting group;

$R^Y$ is —$OR^{Y1}$, wherein $R^{Y1}$ is hydrogen, substituted or unsubstituted alkyl, or an oxygen protecting group; and $R^X$ and $R^Y$ can be taken with their intervening atoms to form a substituted or unsubstituted heterocyclic ring.

In another aspect, provided are compounds of Formula (D-1):

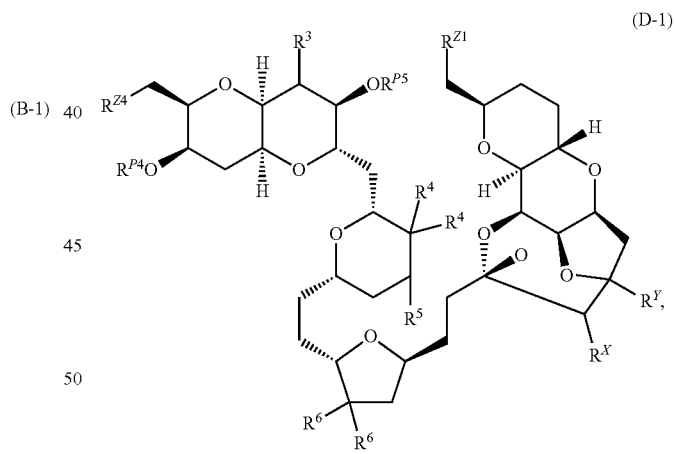

(D-1)

and pharmaceutically acceptable salts thereof, wherein:

$R^{Z1}$ is —$CO_2R^{Z1a}$, wherein $R^{Z1a}$ is hydrogen, substituted or unsubstituted alkyl, or an oxygen protecting group;

$R^{Z4}$ is —$CH_2OR^{Z4a}$ or —CHO, wherein $R^{Z4a}$ is hydrogen, substituted or unsubstituted alkyl, or an oxygen protecting group;

$R^{P4}$ and $R^{P5}$ are each independently hydrogen, substituted or unsubstituted alkyl, or an oxygen protecting group;

$R^3$ and $R^5$ are each independently hydrogen, halogen, or substituted or unsubstituted alkyl;

each instance of $R^4$ is independently hydrogen, halogen, substituted or unsubstituted alkyl, or two $R^4$ groups can be taken together to form a

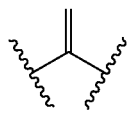 [SMILES: *C(*)=C]

group;
each instance of $R^6$ is independently hydrogen, halogen, substituted or unsubstituted alkyl, or two $R^6$ groups can be taken together to form a

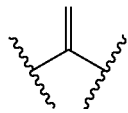 [SMILES: *C(*)=C]

group;
$R^X$ is $-OR^{X1}$, wherein $R^{X1}$ is hydrogen, substituted or unsubstituted alkyl, or an oxygen protecting group;
$R^Y$ is $-OR^{Y1}$, wherein $R^{Y1}$ is hydrogen, substituted or unsubstituted alkyl, or an oxygen protecting group; and
$R^X$ and $R^Y$ can be taken with their intervening atoms to form a substituted or unsubstituted heterocyclic ring.
In another aspect, provided are compounds of Formula (E-1):

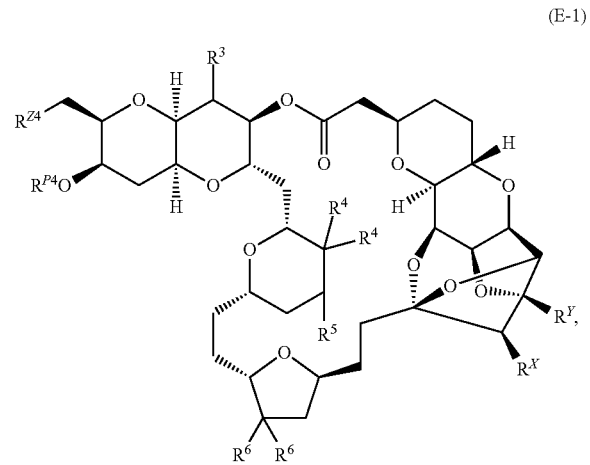

(E-1)

and pharmaceutically acceptable salts thereof, wherein:
$R^{Z4}$ is $-CH_2OR^{Z4a}$ or $-CHO$, wherein $R^{Z4a}$ is hydrogen, substituted or unsubstituted alkyl, or an oxygen protecting group;
$R^{P4}$ is hydrogen, substituted or unsubstituted alkyl, or an oxygen protecting group;
$R^3$ and $R^5$ are each independently hydrogen, halogen, or substituted or unsubstituted alkyl;
each instance of $R^4$ is independently hydrogen, halogen, substituted or unsubstituted alkyl, or two $R^4$ groups can be taken together to form a

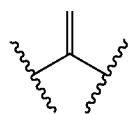

group;
each instance of $R^6$ is independently hydrogen, halogen, substituted or unsubstituted alkyl, or two $R^6$ groups can be taken together to form a

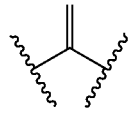 [SMILES: *C(*)=C]

group;
$R^X$ is $-OR^{X1}$, wherein $R^{X1}$ is hydrogen, substituted or unsubstituted alkyl, or an oxygen protecting group;
$R^Y$ is $-OR^{Y1}$, wherein $R^{Y1}$ is hydrogen, substituted or unsubstituted alkyl, or an oxygen protecting group; and
$R^X$ and $R^Y$ can be taken with their intervening atoms to form a substituted or unsubstituted heterocyclic ring.
In another aspect, provided are compounds of Formula (F-1):

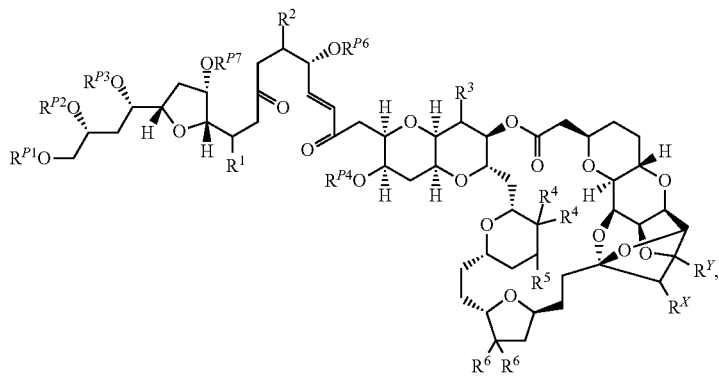

(F-1)

and pharmaceutically acceptable salts thereof, wherein:

$R^{P1}$, $R^{P2}$, $R^{P3}$, $R^{P4}$, $R^{P6}$, and $R^{P7}$ are each independently hydrogen, substituted or unsubstituted alkyl, or an oxygen protecting group;

$R^1$, $R^2$, $R^3$, and $R^5$ are each independently hydrogen, halogen, or substituted or unsubstituted alkyl;

each instance of $R^4$ is independently hydrogen, halogen, substituted or unsubstituted alkyl, or two $R^4$ groups can be taken together to form a

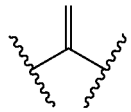

group;

each instance of $R^6$ is independently hydrogen, halogen, substituted or unsubstituted alkyl, or two $R^6$ groups can be taken together to form a

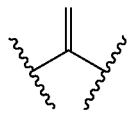 [SMILES: *C(*)=C]

group;

$R^X$ is —$OR^{X1}$, wherein $R^{X1}$ is hydrogen, substituted or unsubstituted alkyl, or an oxygen protecting group;

$R^Y$ is —$OR^{Y1}$, wherein $R^{Y1}$ is hydrogen, substituted or unsubstituted alkyl, or an oxygen protecting group; and $R^X$ and $R^Y$ can be taken with their intervening atoms to form a substituted or unsubstituted heterocyclic ring.

In another aspect, provided are compounds of Formula (G-1):

and pharmaceutically acceptable salts thereof, wherein:

$R^{P8}$, $R^{P9}$, $R^{P10}$, and $R^{P11}$ are each independently hydrogen, substituted or unsubstituted alkyl, or an oxygen protecting group;

$R^1$, $R^2$, $R^3$, and $R^5$ are each independently hydrogen, halogen, or substituted or unsubstituted alkyl;

each instance of $R^4$ is independently hydrogen, halogen, substituted or unsubstituted alkyl, or two $R^4$ groups can be taken together to form a

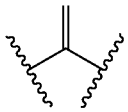 [SMILES: *C(*)=C]

group;

each instance of $R^6$ is independently is hydrogen, halogen, substituted or unsubstituted alkyl, or two $R^6$ groups can be taken together to form a

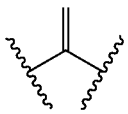 [SMILES: *C(*)=C]

group;

$R^7$ is hydrogen, substituted or unsubstituted alkyl, or an oxygen protecting group;

$R^X$ is —$OR^{X1}$, wherein $R^{X1}$ is hydrogen, substituted or unsubstituted alkyl, or an oxygen protecting group;

$R^Y$ is —$OR^{Y1}$, wherein $R^{Y1}$ is hydrogen, substituted or unsubstituted alkyl, or an oxygen protecting group; and $R^X$ and $R^Y$ can be taken with their intervening atoms to form a substituted or unsubstituted heterocyclic ring.

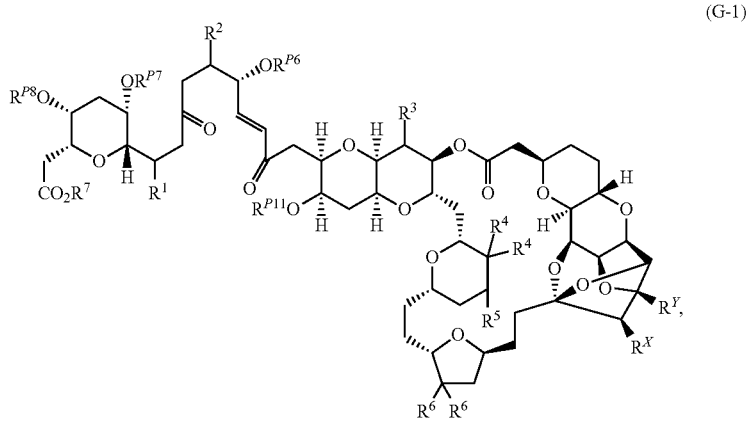

(G-1)

In another aspect, provided are compounds of Formula (H-1):

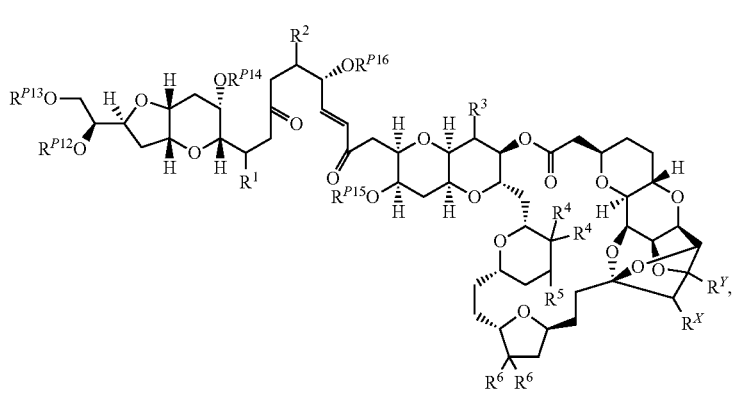

(H-1)

and pharmaceutically acceptable salts thereof, wherein:

$R^{P12}$, $R^{P13}$, $R^{P14}$, $R^{P15}$ and $R^{16}$ are each independently hydrogen, substituted or unsubstituted alkyl, or an oxygen protecting group;

$R^1$, $R^2$; $R^3$, and $R^5$ are each independently hydrogen, halogen, or substituted or unsubstituted alkyl;

each instance of $R^4$ is independently hydrogen, halogen, substituted or unsubstituted alkyl, or two $R^4$ groups can be taken together to form a

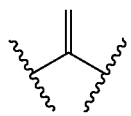

group;

each instance of $R^6$ is independently hydrogen, halogen, substituted or unsubstituted alkyl, or two $R^6$ groups can be taken together to form a

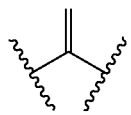 [SMILES: *C(*)=C]

group;

$R^X$ is —$OR^{X1}$, wherein $R^{X1}$ is hydrogen, substituted or unsubstituted alkyl, or an oxygen protecting group;

$R^Y$ is —$OR^{Y1}$, wherein $R^{Y1}$ is hydrogen, substituted or unsubstituted alkyl, or an oxygen protecting group; and $R^X$ and $R^Y$ can be taken with their intervening atoms to form a substituted or unsubstituted heterocyclic ring.

In another aspect, provided are compounds of Formula (I-1):

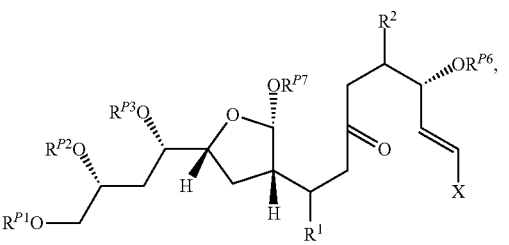

(I-1)

and pharmaceutically acceptable salts thereof, wherein:

$R^{P1}$, $R^{P2}$, $R^{P3}$, $R^{P6}$, and $R^{P7}$ are each independently hydrogen, substituted or unsubstituted alkyl, or an oxygen protecting group;

$R^1$ and $R^2$ are each independently hydrogen, halogen, or substituted or unsubstituted alkyl; and X is a halogen.

In another aspect, provided are compounds of Formula (J-1):

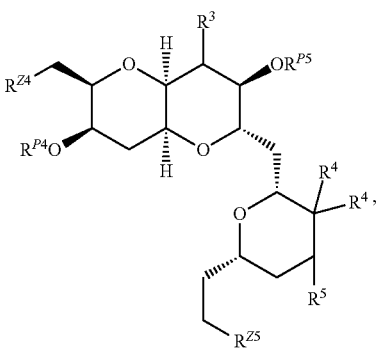

(J-1)

and pharmaceutically acceptable salts thereof, wherein:

$R^{Z5}$ is —$CH_2OR^{Z5a}$ or —CHO, wherein $R^{Z5a}$ is hydrogen, substituted or unsubstituted alkyl, or an oxygen protecting group;

$R^{Z4}$ is —CH$_2$OR$^{Z4a}$ or —CHO, wherein R$^{Z4a}$ is hydrogen, substituted or unsubstituted alkyl, or an oxygen protecting group;

R$^{P4}$ and R$^{P5}$ are each independently hydrogen, substituted or unsubstituted alkyl, or an oxygen protecting group;

R$^3$ and R$^5$ are each independently hydrogen, halogen, or substituted or unsubstituted alkyl; and each instance of R$^4$ is independently is hydrogen, halogen, substituted or unsubstituted alkyl, or two R$^4$ groups can be taken together to form a

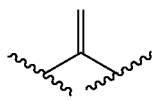 [SMILES: *C(*)=C]

group.

In another aspect, provided are compounds of Formula (K-1):

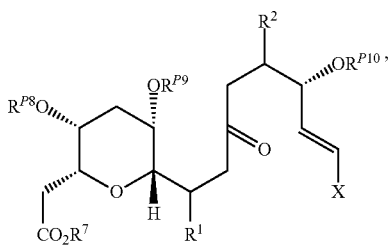

(K-1)

and pharmaceutically acceptable salts thereof, wherein:

R$^{P8}$, R$^{P9}$, and R$^{P10}$ are each independently hydrogen, substituted or unsubstituted alkyl, or an oxygen protecting group;

R$^1$ and R$^2$ are each independently hydrogen, halogen, or substituted or unsubstituted alkyl;

R$^7$ is hydrogen, substituted or unsubstituted alkyl, or an oxygen protecting group; and X is a halogen.

In another aspect, provided are compounds of Formula (L-1):

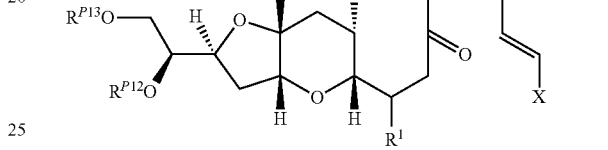

(L-1)

and pharmaceutically acceptable salts thereof, wherein:

R$^{P12}$, R$^{P13}$, R$^{P14}$, and R$^{P16}$ are each independently hydrogen, substituted or unsubstituted alkyl, or an oxygen protecting group;

R$^1$ and R$^2$ are each independently hydrogen, halogen, or substituted or unsubstituted alkyl; and X is a halogen.

In another aspect, provided are any one of the following compounds:

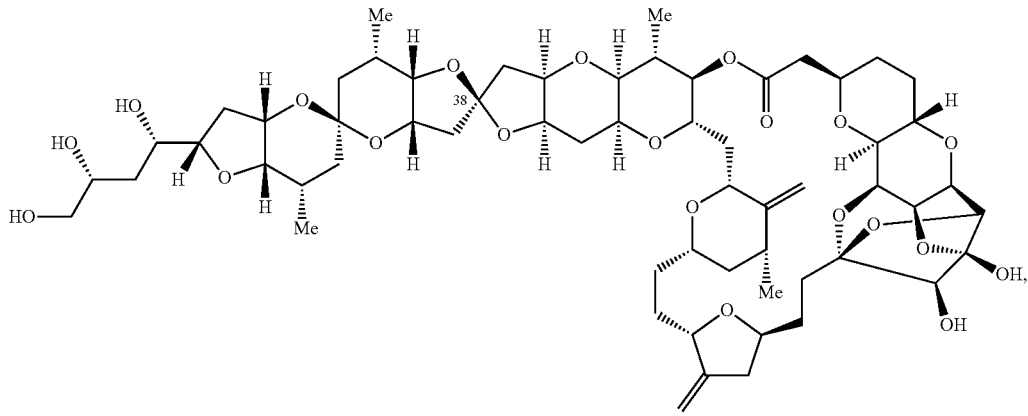

C38 epi-halichondrin A

-continued
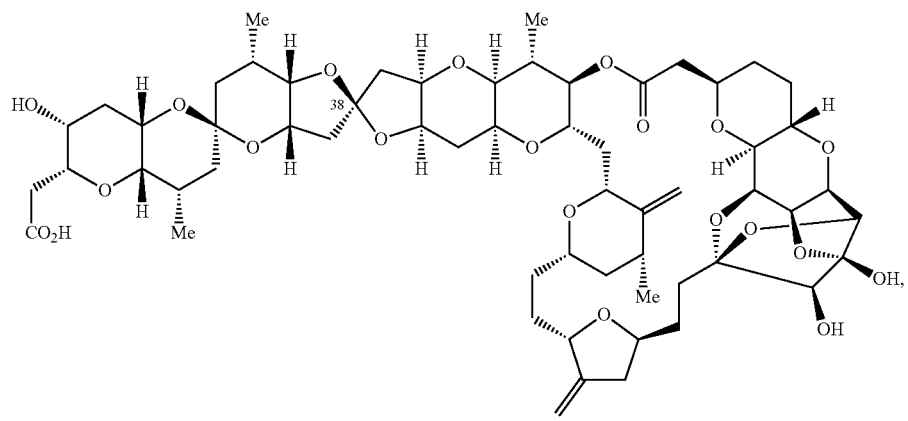
C38 epi-norhalichondrin A
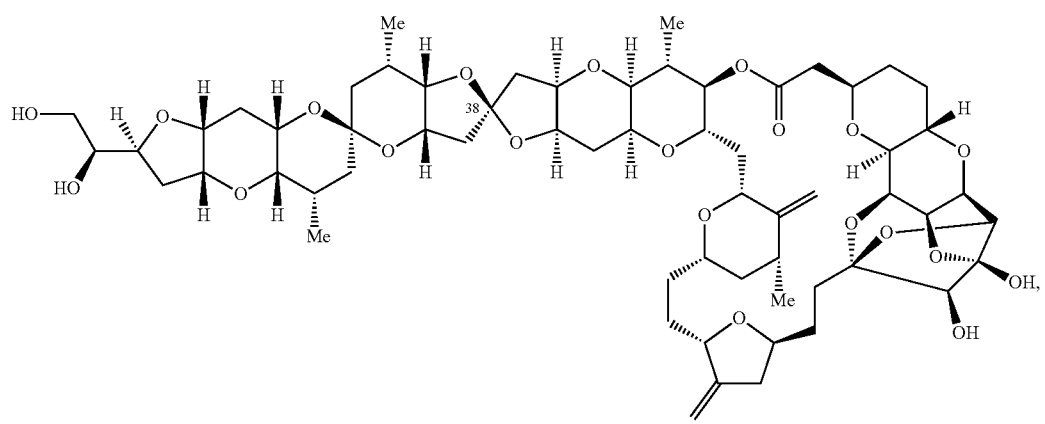
C38 epi-homohalichondrin A
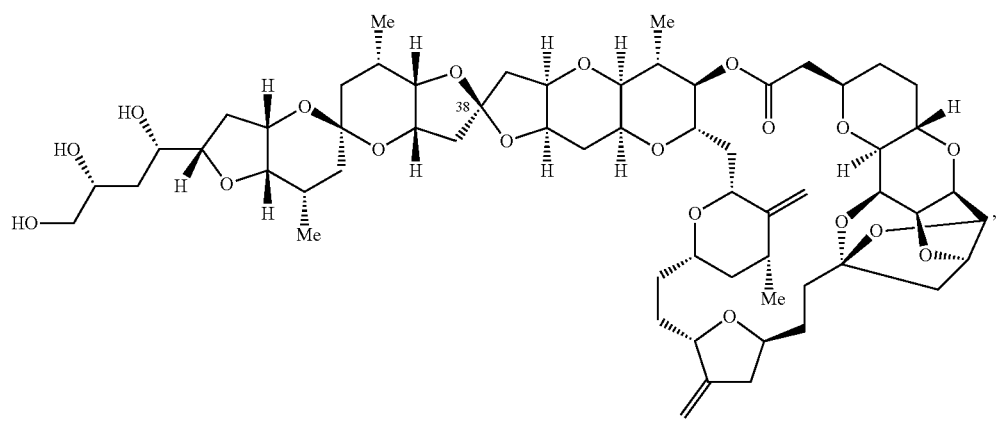
C38 epi-halichondrin B

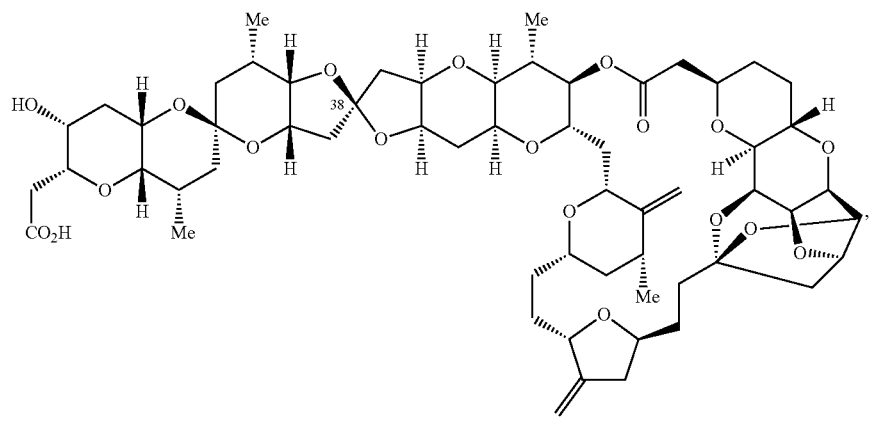
C38 epi-norhalichondrin B
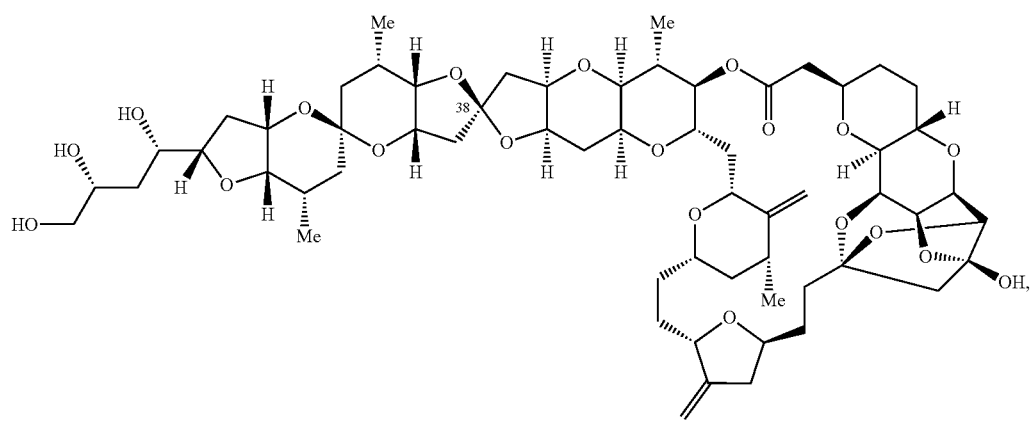
C38 epi-halichondrin C
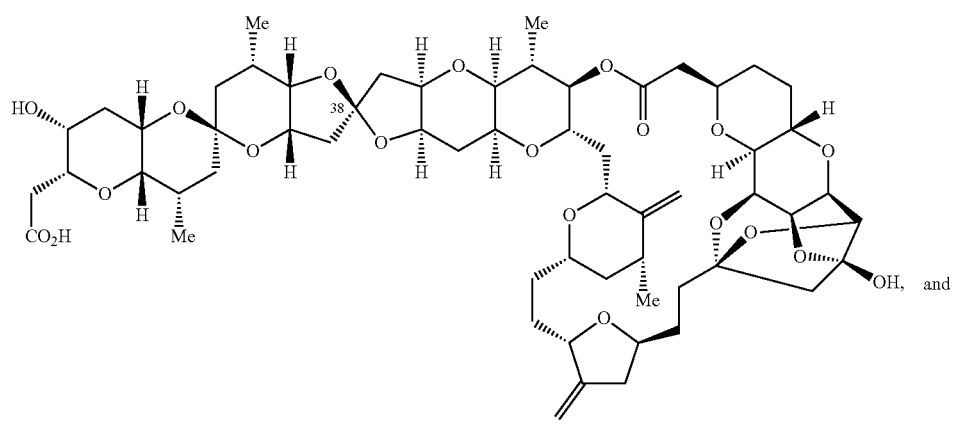
C38 epi-norhalichondrin C -continued

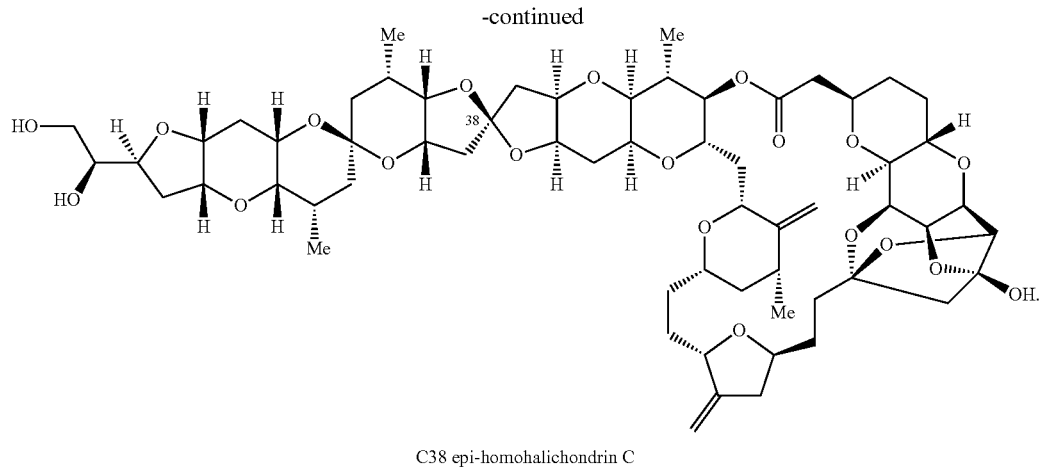

C38 epi-homohalichondrin C

Groups X and $X^A$

As generally described herein, X is halogen (e.g., —F, —Cl, —Br, or —I). In certain embodiments, X is bromine. In certain embodiments, X is iodine.

As generally described herein, $X^A$ is hydrogen or halogen (e.g., —F, —Cl, —Br, or —I). In certain embodiments, $X^A$ is bromine. In certain embodiments, $X^A$ is iodine.

Groups $R^{Z1}$, $R^{Z4}$, $R^{Z5}$, $R^{Z1a}$, $R^{Z4a}$, and $R^{Z5a}$

As generally described herein, $R^{Z1}$ is —$CO_2R^{Z1a}$, wherein $R^{Z1a}$ is hydrogen, substituted or unsubstituted alkyl, or an oxygen protecting group. In certain embodiments, $R^{Z1a}$ is hydrogen. In certain embodiments, $R^{Z1a}$ is substituted or unsubstituted alkyl. In certain embodiments, $R^{Z1a}$ is substituted or unsubstituted $C_{1-6}$ alkyl. In certain embodiments, $R^{Z1a}$ is substituted or unsubstituted, branched $C_{1-6}$ alkyl. In certain embodiments, $R^{Z1a}$ is unsubstituted $C_{1-6}$ alkyl. In certain embodiments, $R^{Z1a}$ is methyl. In certain embodiments, $R^{Z1a}$ is ethyl. In certain embodiments, $R^{Z1a}$ is propyl. In certain embodiments, $R^{Z1a}$ is iso-propyl. In certain embodiments, $R^{Z1a}$ is t-butyl. In certain embodiments, $R^{Z1a}$ is an oxygen protecting group. In certain embodiments, $R^{Z1a}$ is a silyl protecting group. In certain embodiments, $R^{Z1a}$ is a trialkyl silyl protecting group. In certain embodiments, $R^{Z1a}$ is a t-butyldimethylsilyl protecting group. In certain embodiments, $R^{Z1a}$ is a trimethylsilyl protecting group. In certain embodiments, $R^{Z1a}$ is a triethylsilyl protecting group. In certain embodiments, $R^{Z1a}$ is a t-butyldiphenylsilyl protecting group. In certain embodiments, $R^{Z1a}$ is a triisopropylsilyl protecting group. In certain embodiments, $R^{Z1a}$ is a benzylic protecting group. In certain embodiments, $R^{Z1a}$ is a p-methoxybenzyl protecting group. In certain embodiments, $R^{Z1a}$ is an acyl protecting group. In certain embodiments, $R^{Z1a}$ is an acetyl protecting group. In certain embodiments, $R^{Z1a}$ is a benzoyl protecting group. In certain embodiments, $R^{Z1a}$ is a p-nitro benzoyl protecting group. In certain embodiments, $R^{Z1a}$ is a pivaloyl protecting group. In certain embodiments, $R^{Z1a}$ is a t-butyl carbonate (BOC) protecting group. In certain embodiments, $R^{Z1a}$ is an acetal protecting group. In certain embodiments, $R^{Z1a}$ is a tetrahydropyranyl protecting group. In certain embodiments, $R^{Z1a}$ is an alkoxyalkyl protecting group. In certain embodiments, $R^{Z1a}$ is an ethoxyethyl protecting group.

As generally described herein, $R^{Z4}$ is —$CH_2OR^{Z4a}$ or —CHO, wherein $R^{Z4a}$ is hydrogen, substituted or unsubstituted alkyl, or an oxygen protecting group. In certain embodiments, $R^{Z4a}$ is hydrogen. In certain embodiments, $R^{Z4a}$ is substituted or unsubstituted alkyl. In certain embodiments, $R^{Z4a}$ is substituted or unsubstituted $C_{1-6}$ alkyl. In certain embodiments, $R^{Z4a}$ is substituted or unsubstituted, branched $C_{1-6}$ alkyl. In certain embodiments, $R^{Z4a}$ is unsubstituted $C_{1-6}$ alkyl. In certain embodiments, $R^{Z4a}$ is methyl. In certain embodiments, $R^{Z4a}$ is ethyl. In certain embodiments, $R^{Z4a}$ is propyl. In certain embodiments, $R^{Z4a}$ is iso-propyl. In certain embodiments, $R^{Z4a}$ is t-butyl. In certain embodiments, $R^{Z4a}$ is an oxygen protecting group. In certain embodiments, $R^{Z4a}$ is a silyl protecting group. In certain embodiments, $R^{Z4a}$ is a trialkyl silyl protecting group. In certain embodiments, $R^{Z4a}$ is a t-butyldimethylsilyl protecting group. In certain embodiments, $R^{Z4a}$ is a trimethylsilyl protecting group. In certain embodiments, $R^{Z4a}$ is a triethylsilyl protecting group. In certain embodiments, $R^{Z4a}$ is a t-butyldiphenylsilyl protecting group. In certain embodiments, $R^{Z4a}$ is a triisopropylsilyl protecting group. In certain embodiments, $R^{Z4a}$ is a benzylic protecting group. In certain embodiments, $R^{Z4a}$ is a p-methoxybenzyl protecting group. In certain embodiments, $R^{Z4a}$ is an acyl protecting group. In certain embodiments, $R^{Z4a}$ is an acetyl protecting group. In certain embodiments, $R^{Z4a}$ is a benzoyl protecting group. In certain embodiments, $R^{Z4a}$ is a p-nitro benzoyl protecting group. In certain embodiments, $R^{Z4a}$ is a pivaloyl protecting group. In certain embodiments, $R^{Z4a}$ is a t-butyl carbonate (BOC) protecting group. In certain embodiments, $R^{Z4a}$ is an acetal protecting group. In certain embodiments, $R^{Z4a}$ is a tetrahydropyranyl protecting group. In certain embodiments, $R^{Z4a}$ is an alkoxyalkyl protecting group. In certain embodiments, $R^{Z4a}$ is an ethoxyethyl protecting group.

As generally described herein, $R^{Z5}$ is —$CH_2OR^{Z5a}$ or —CHO, wherein $R^{Z5a}$ is hydrogen, substituted or unsubstituted alkyl, or an oxygen protecting group. In certain embodiments, $R^{Z5a}$ is hydrogen. In certain embodiments, $R^{Z5a}$ is substituted or unsubstituted alkyl. In certain embodiments, $R^{Z5a}$ is substituted or unsubstituted $C_{1-6}$ alkyl. In certain embodiments, $R^{Z5a}$ is substituted or unsubstituted, branched $C_{1-6}$ alkyl. In certain embodiments, $R^{Z5a}$ is unsubstituted $C_{1-6}$ alkyl. In certain embodiments, $R^{Z5a}$ is methyl. In certain embodiments, $R^{Z5a}$ is ethyl. In certain embodiments, $R^{Z5a}$ is propyl. In certain embodiments, $R^{Z5a}$ is iso-propyl. In certain embodiments, $R^{Z5a}$ is t-butyl. In certain embodiments, $R^{Z5a}$ is an oxygen protecting group. In certain embodiments, $R^{Z5a}$ is a silyl protecting group. In certain embodiments, $R^{Z5a}$ is a trialkyl silyl protecting group. In certain embodiments, $R^{Z5a}$ is a t-butyldimethylsilyl protecting group. In certain embodiments, $R^{Z5a}$ is a trimethylsilyl protecting group. In certain embodiments, $R^{Z5a}$ is a triethylsilyl protecting group. In certain embodiments, $R^{Z5a}$ is a t-butyldiphenylsilyl protecting group. In certain embodiments, $R^{Z5a}$ is a triisopropylsilyl protecting group. In certain embodiments, $R^{Z5a}$ is a benzylic protecting group. In certain embodiments, $R^{Z5a}$ is a p-methoxybenzyl protecting group. In certain embodiments, $R^{Z5a}$ is an acyl protecting group. In certain embodiments, $R^{Z5a}$ is an acetyl protecting group. In certain embodiments, $R^{Z5a}$ is a benzoyl protecting group. In certain embodiments, $R^{Z5a}$ is ap-nitro benzoyl protecting group. In certain embodiments, $R^{Z5a}$ is a pivaloyl protecting group. In certain embodiments, $R^{Z5a}$ is a t-butyl carbonate (BOC) protecting group. In certain embodiments, $R^{Z5a}$ is an acetal protecting group. In certain embodiments, $R^{Z5a}$ is a tetrahydropyranyl protecting group. In certain embodiments, $R^{Z5a}$ is an alkoxyalkyl protecting group. In certain embodiments, $R^{Z5a}$ is an ethoxyethyl protecting group.

Groups $R^{Z2}$ and $R^{Z3}$

As generally described herein, $R^{Z2}$ is halogen (e.g., —F, —Cl, —Br, or —I) or a leaving group. In certain embodiments, $R^{Z2}$ is chlorine. In certain embodiments, $R^{Z2}$ is bromine. In certain embodiments, $R^{Z2}$ is iodine.

As generally described herein, $R^{Z3}$ is halogen (e.g., —F, —Cl, —Br, or —I). In certain embodiments, $R^{Z3}$ is bromine. In certain embodiments, $R^{Z3}$ is iodine.

General Description of Synthesis

Preparation of halichondrin A, norhalichondrin A, and homohalichondrin A and analogs of the present invention is further described herein. However, the below description of synthesizing these compounds is one of many methods of their preparation and should not limit the invention as a whole.

In certain embodiments, preparation of compounds of Formula (I) or pharmaceutically acceptable salts thereof comprises cyclizing an intermediate compound of Formula (F-1) or salt thereof (see Scheme S1). In certain embodiments, when a compound of Formula (F-1) is protected (e.g., with silyl or benzylic protecting groups), the synthetic route comprises a deprotection step prior to cyclization. In certain embodiments, deprotection of a compound of Formula (F-1) comprises a source of fluoride (e.g., TBAF, HF•pyridine). In certain embodiments, deprotection of a compound of Formula (F-1) comprises a hydrogenolysis (e.g., a palladium or nickel catalyst and $H_2$) or oxidation (e.g., DDQ) step. In certain embodiments, the cyclization conditions comprise an acid. In certain embodiments, the cyclization conditions comprise a Brønsted acid (i.e., a source of $H^+$). In certain embodiments, the cyclization conditions comprise an organic acid (e.g., PPTS). In certain embodiments, the cyclization conditions provide a compound of Formula (I) as a single diastereomer. In certain embodiments, the cyclization conditions provide a diastereomeric mixture that is enriched in one of two epimeric C38 ketals. In certain embodiments, the synthetic route comprises an equilibration step to enrich a compound of Formula (I) in one of two epimeric C38 ketals. In certain embodiments, the equilibration step enriches a compound of Formula (I) in the (R)-epimer. In certain embodiments, the equilibration step enriches a compound of Formula (I) in the (R)-epimer in a range of 2:1, 3:1, 4:1, 5:1, or >5:1. In certain embodiments, the equilibration step enriches a compound of Formula (I) in the (S)-epimer. In certain embodiments, the equilibration step enriches a compound of Formula (I) in the (S)-epimer in a range of 2:1, 3:1, 4:1, 5:1, 10:1, or >10:1. In certain embodiments, the equilibration step comprises a Lewis acid. In certain embodiments, the equilibration step comprises a silyl Lewis acid (e.g., a silicon tetrahalide or and organosilicon halide or triflate). In certain embodiments, the equilibration step comprises trimethylsilyl triflate. In certain embodiments, the equilibration step comprises a solvent. In certain embodiments, the equilibration step comprises a halogenated (e.g., dichloromethane) or ethereal (e.g., diethylether) solvent.

Scheme S1.

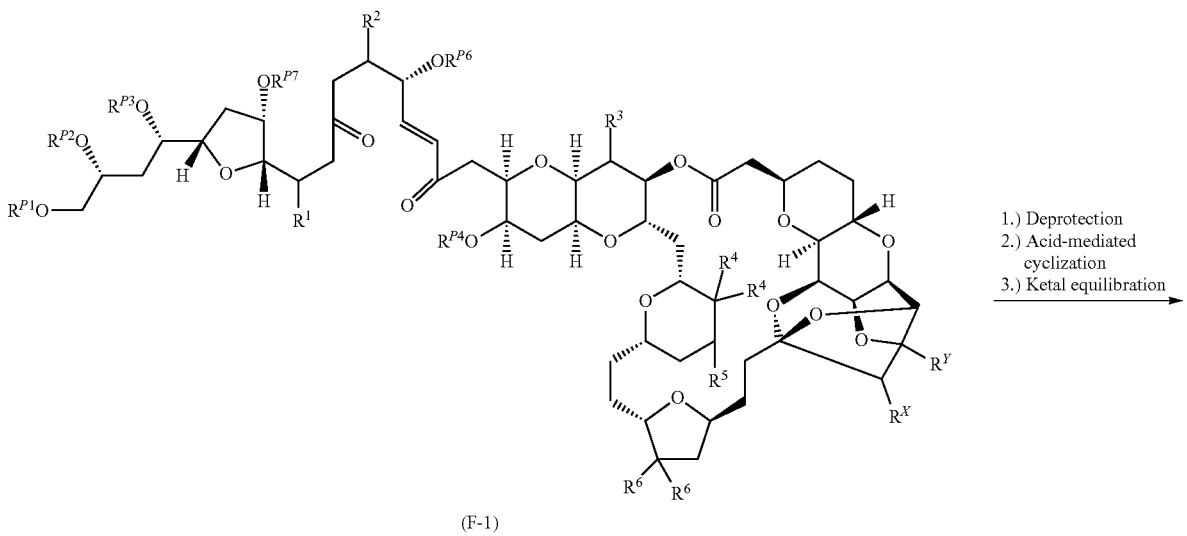

1.) Deprotection
2.) Acid-mediated cyclization
3.) Ketal equilibration (F-1)

-continued

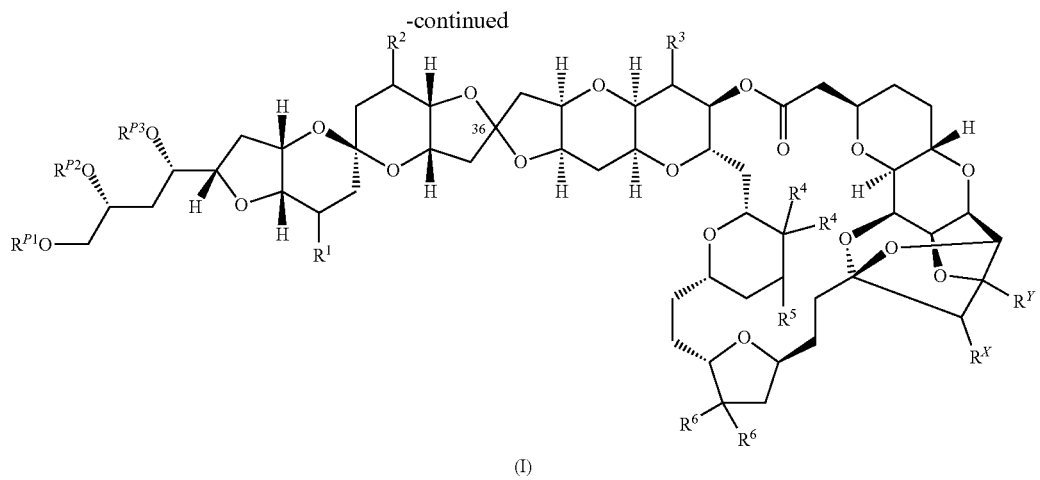

(I)

In certain embodiments, preparation of C38 epi-halichondrin A comprises an acid-mediated equilibration of the C38 ketal stereocenter of halichondrin A. In certain embodiments, preparation of halichondrin A comprises an acid-mediated equilibration of the C38 ketal stereocenter of C38 epi-halichondrin A (see Scheme S1a).

Scheme S1a.

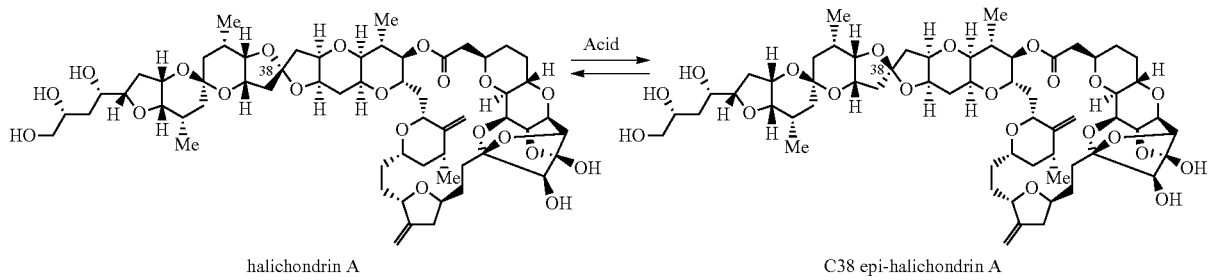

halichondrin A             C38 epi-halichondrin A

In certain embodiments, preparation of C38 epi-norhalichondrin A comprises an acid-mediated equilibration of the C38 ketal stereocenter of norhalichondrin A. In certain embodiments, preparation of norhalichondrin A comprises an acid-mediated equilibration of the C38 ketal stereocenter of C38 epi-norhalichondrin A (see Scheme S1b).

Scheme S1b.

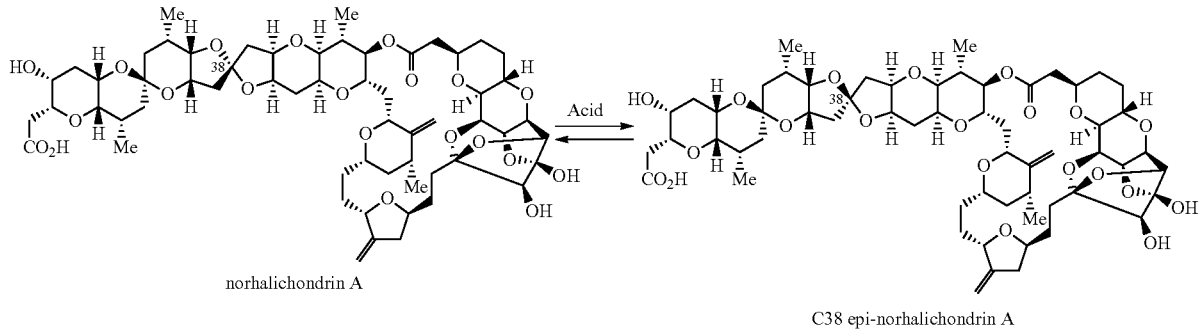

norhalichondrin A             C38 epi-norhalichondrin A

In certain embodiments, preparation of C38 epi-homohalichondrin A comprises an acid-mediated equilibration of the C38 ketal stereocenter of homohalichondrin A. In certain embodiments, preparation of homohalichondrin A comprises an acid-mediated equilibration of the C38 ketal stereocenter of C38 epi-homohalichondrin A (see Scheme S1c).

Scheme S1c.

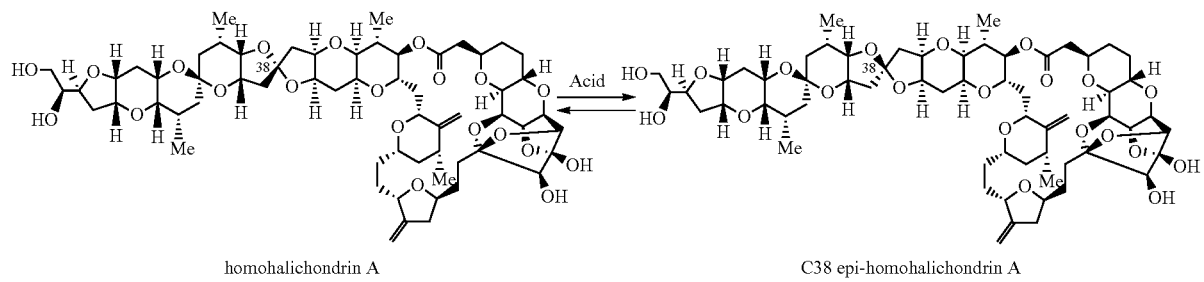

homohalichondrin A          C38 epi-homohalichondrin A

In certain embodiments, preparation of C38 epi-halichondrin B comprises an acid-mediated equilibration of the C38 ketal stereocenter of halichondrin B. In certain embodiments, preparation of halichondrin B comprises an acid-mediated equilibration of the C38 ketal stereocenter of C38 epi-halichondrin B (see Scheme S1d).

Scheme S1d.

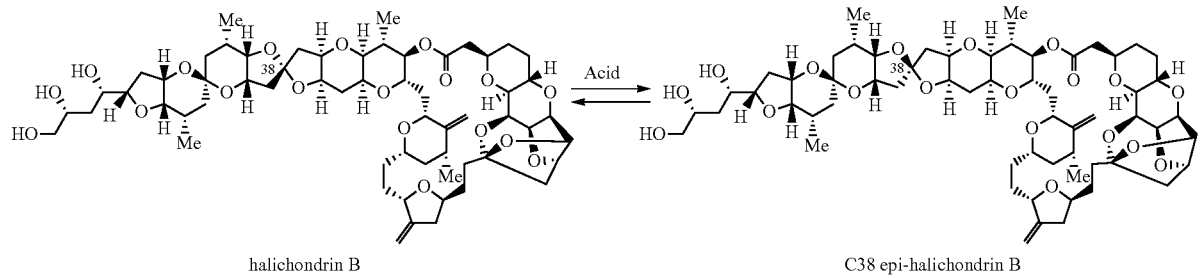

halichondrin B          C38 epi-halichondrin B

In certain embodiments, preparation of C38 epi-norhalichondrin B comprises an acid-mediated equilibration of the C38 ketal stereocenter of norhalichondrin B. In certain embodiments, preparation of norhalichondrin B comprises an acid-mediated equilibration of the C38 ketal stereocenter of C38 epi-norhalichondrin B (see Scheme S1e).

Scheme S1e.
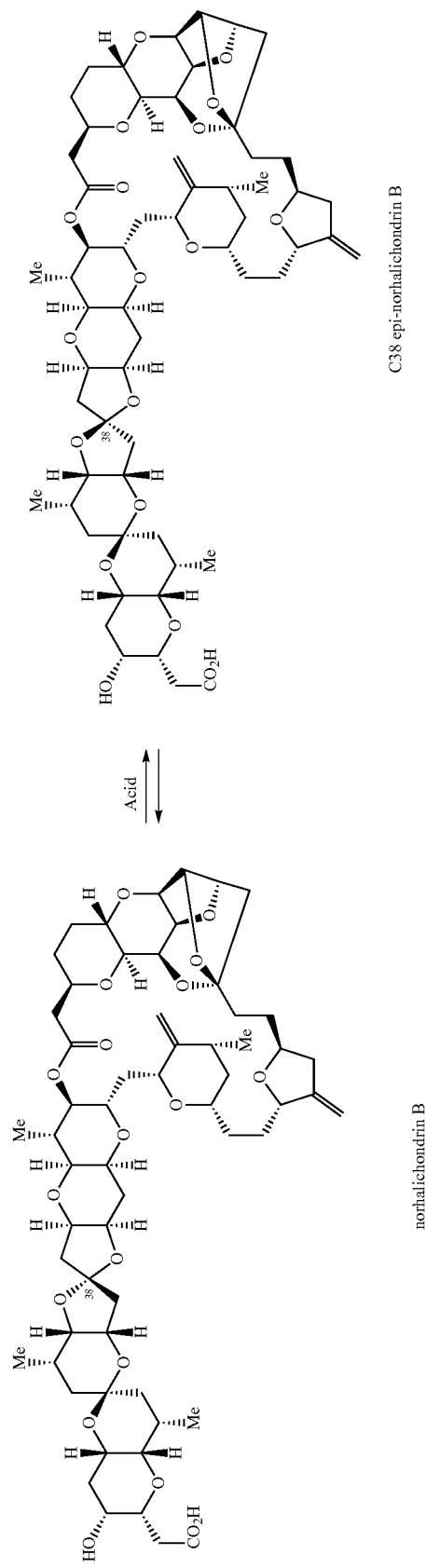

In certain embodiments, preparation of C38 epi-homohalichondrin B comprises an acid-mediated equilibration of the C38 ketal stereocenter of homohalichondrin B. In certain embodiments, preparation of homohalichondrin B comprises an acid-mediated equilibration of the C38 ketal stereocenter of C38 epi-homohalichondrin B (see Scheme S1f).

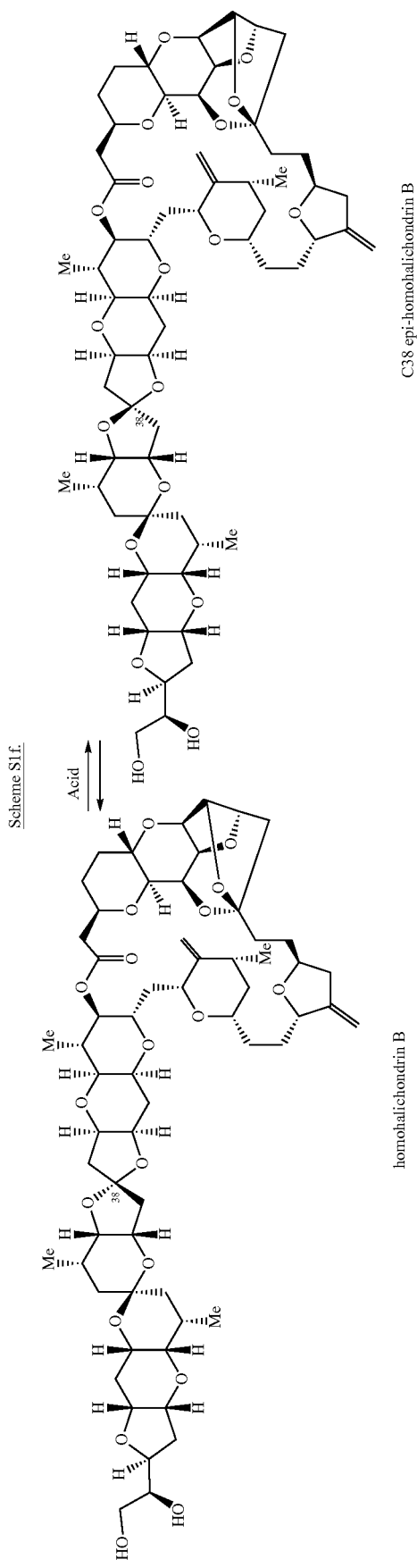

In certain embodiments, preparation of C38 epi-halichondrin C comprises an acid-mediated equilibration of the C38 ketal stereocenter of halichondrin C. In certain embodiments, preparation of halichondrin C comprises an acid-mediated equilibration of the C38 ketal stereocenter of C38 epi-halichondrin C (see Scheme S1g).

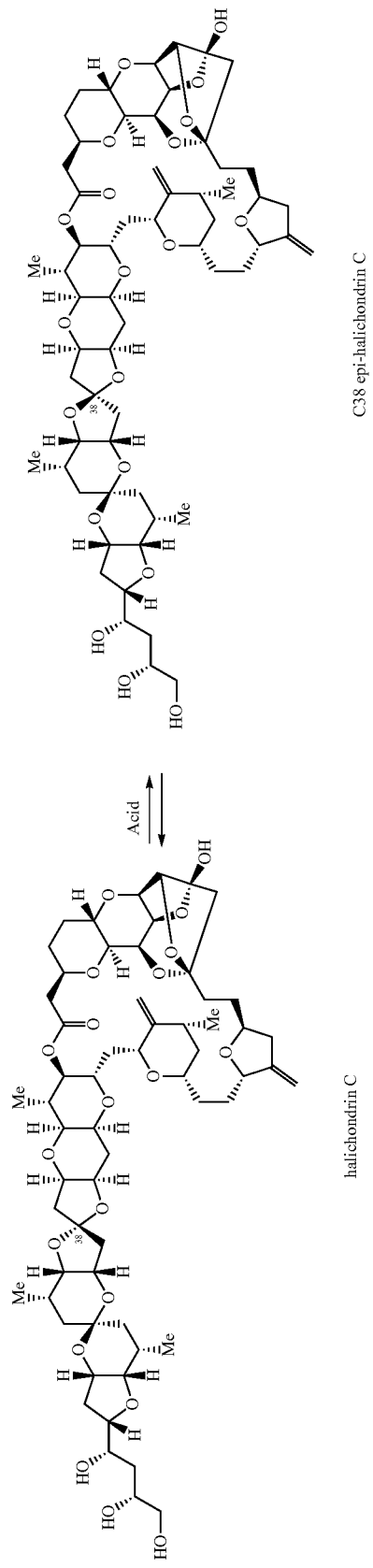

In certain embodiments, preparation of C38 epi-norhalichondrin C comprises an acid-mediated equilibration of the C38 ketal stereocenter of norhalichondrin C. In certain embodiments, preparation of norhalichondrin C comprises an acid-mediated equilibration of the C38 ketal stereocenter of C38 epi-norhalichondrin C (see Scheme S1h).

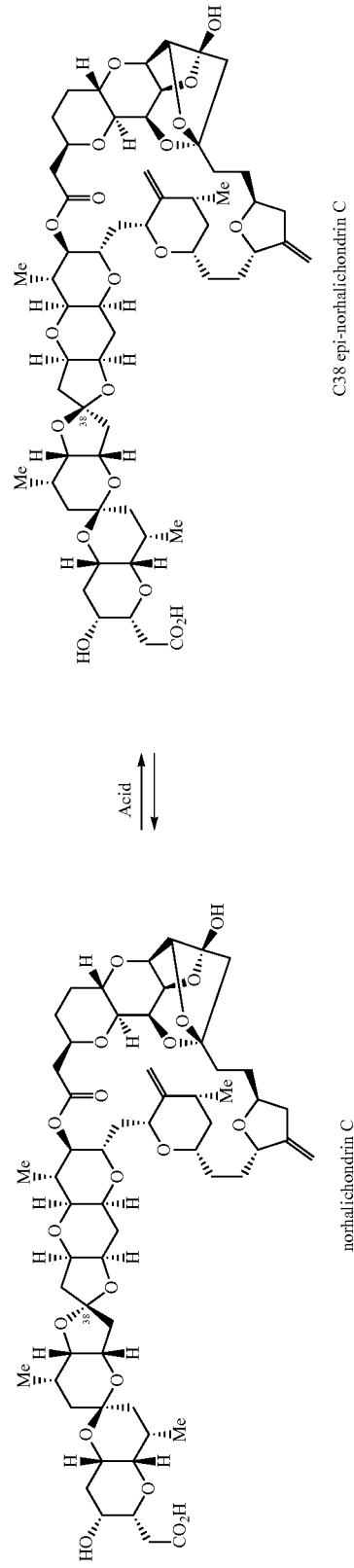
Scheme S1h.

In certain embodiments, preparation of C38 epi-homohalichondrin C comprises an acid-mediated equilibration of the C38 ketal stereocenter of homohalichondrin C. In certain embodiments, preparation of homohalichondrin C comprises an acid-mediated equilibration of the C38 ketal stereocenter of C38 epi-homohalichondrin C (see Scheme S1i).

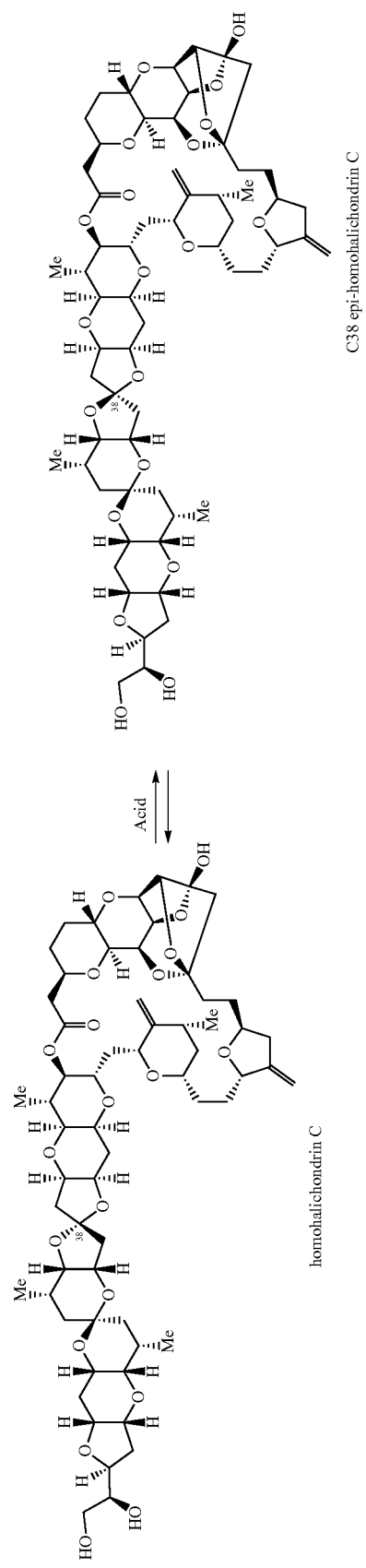
Scheme S1i.

In certain embodiments, preparation of a compound of Formula (F-1) or salt thereof comprises joining an intermediate compound of Formula (E-1) or salt thereof and an intermediate of Formula (I-1) or salt thereof (see Scheme S2). In certain embodiments, when $R^{Z4}$ is —CH$_2$OR$^{Z4a}$ and $R^{Z4a}$ is a protecting group, the synthetic route comprises a deprotection step. In certain embodiments, when $R^{Z4a}$ is a silyl protecting group (e.g., t-butyldimethylsilyl), selective deprotection of $R^{Z4a}$ comprises a mild source of fluoride (e.g., TBAF, HF•pyridine). In certain embodiments, when $R^{Z4}$ is —CH$_2$OH, the synthetic route comprises an oxidation step. In certain embodiments, $R^{Z4}$ is oxidized into an aldehyde (—CHO) under mild and selective conditions (e.g., Dess-Martin periodinane, SO$_3$•pyridine, or Swern oxidation). Compounds of Formula (E-1) are joined with a compound of Formula (I-1) under reductive coupling conditions. In certain embodiments, the conditions used to join a compound of Formula (E-1) with a compound of Formula (I-1) comprise a transition metal (e.g., nickel or chromium). In certain embodiments, the coupling reaction is catalytic in transition metal (e.g., 2-40 mol %). In certain embodiments, the coupling reaction is stoichiometric in transition metal (e.g., 1-3 equivalents). In certain embodiments, the coupling comprises a ligand or ligated transition metal complex (e.g., see Scheme 4). The reaction used to join a compound of Formula (E-1) and Formula (I-1) provides an intermediate hydroxy group that must be oxidized to provide a compound of Formula (F-1). In certain embodiments, the oxidation is carried out under mild and selective conditions (e.g., Dess-Martin periodinane, SO$_3$•pyridine, or Swern oxidation).

Scheme S2.

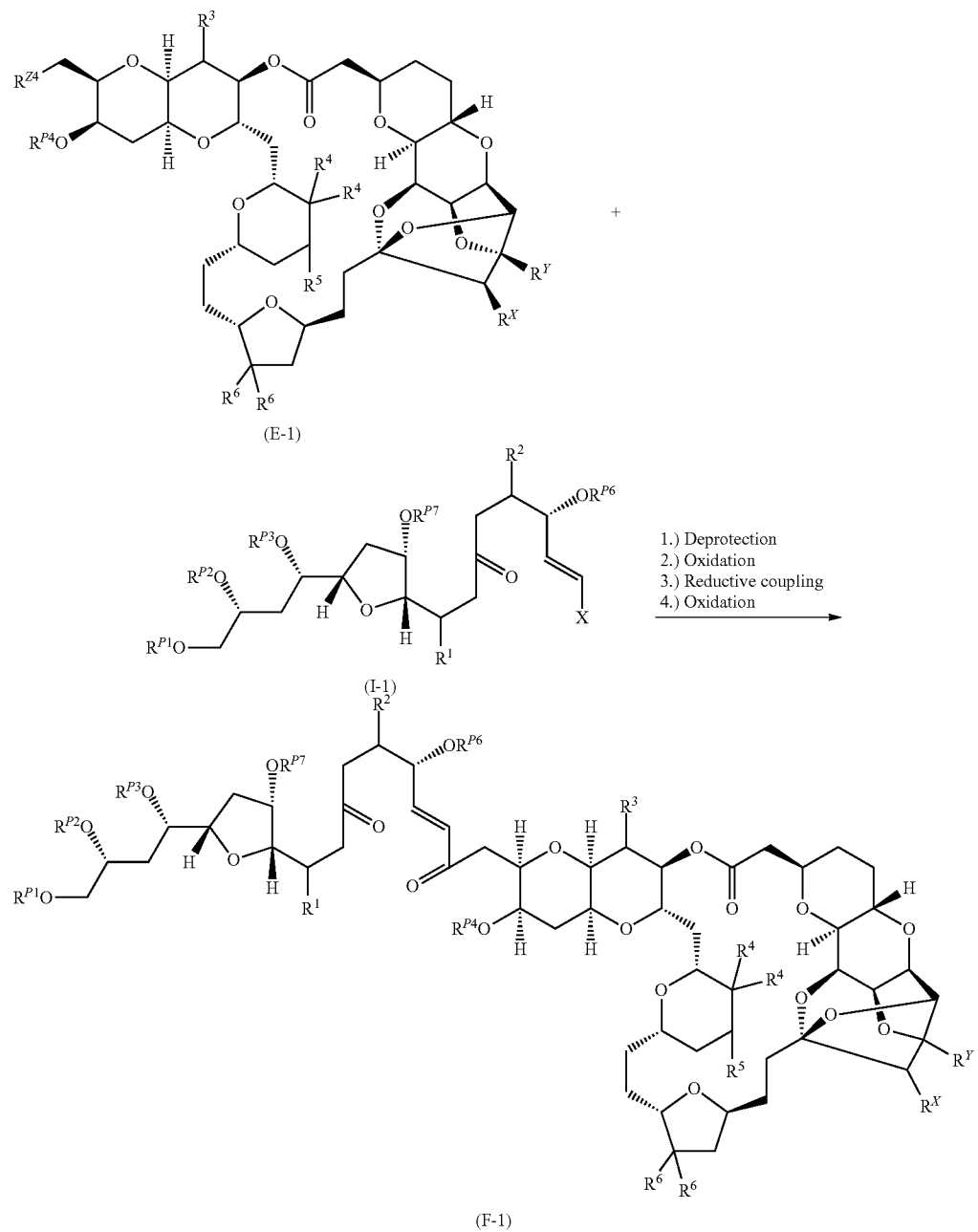

In certain embodiments, preparation of a compound of Formula (E-1) or a salt thereof comprises cyclizing an intermediate compound of Formula (D-1) or salt thereof (see Scheme S3). In certain embodiments, wherein $R^{Z1}$ is —$CO_2R^{Z1a}$ and $R^{Z1a}$ is not hydrogen, and/or $R^{P5}$ is an acyl protecting group, the synthetic route comprises a deprotection step prior to cyclization. In certain embodiments, the deprotection conditions comprise a hydrolysis reaction. In certain embodiments, the deprotection conditions comprise a base (e.g., lithium, sodium, or potassium hydroxide). In certain embodiments, the cyclization reaction comprises a macrocyclization reagent (e.g., 2-methyl-6-nitrobenzoic anhydride (Shiina's reagent) or 2,4,6-trichlorobenzoyl chloride (Yamaguchi's reagent)).

In certain embodiments, the conditions used to join a compound of Formula (C-1) with a compound of Formula (J-1) comprise a transition metal (e.g., nickel or chromium). In certain embodiments, the coupling reaction is catalytic in transition metal (e.g., 2-40 mol %). In certain embodiments, the coupling reaction is stoichiometric in transition metal (e.g., 1-3 equivalents). In certain embodiments, the coupling comprises a ligand or ligated transition metal complex (e.g., see Scheme 4). In certain embodiments, following the reductive coupling of a compound of Formula (C-1) and a compound of (J-1), the synthetic route comprises an intramolecular furan cyclization reaction. In certain embodiments, the furan cyclization reaction conditions comprise displacement of a leaving group with an intermediate oxy- Scheme S3.

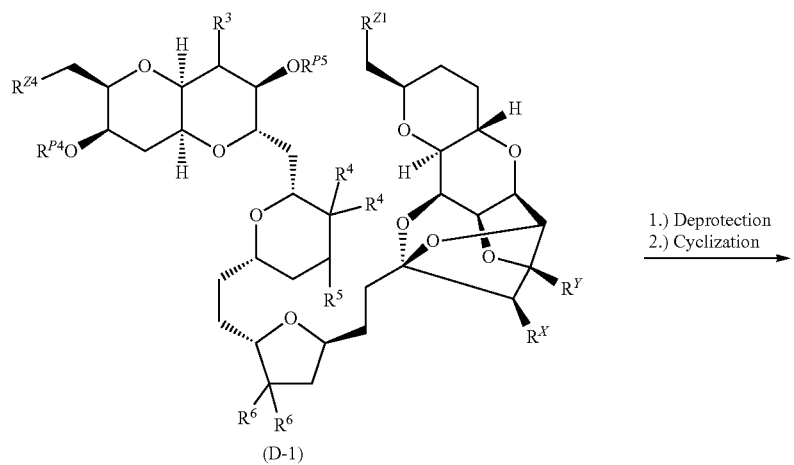

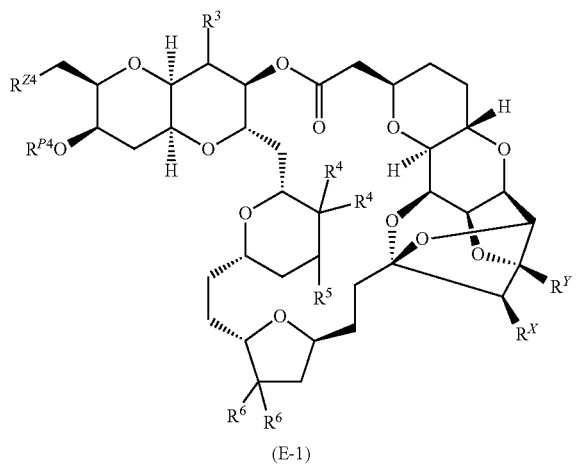

In certain embodiments, preparation of a compound of Formula (D-1) or salt thereof comprises joining an intermediate compound of Formula (C-1) or salt thereof and an intermediate of Formula (J-1) or salt thereof (see Scheme S4). Compounds of Formula (C-1) are joined with a compound of Formula (J-1) under reductive coupling conditions.

anion generated using a base (e.g., an amide or silazide base such as LDA or LiHMDS). In certain embodiments, the furan cyclization reaction conditions comprise displacement of a halide with a hydroxyl group using one or more silver salts (e.g., $Ag_2O$, AgOTf). In certain embodiments, $R^{Z3}$ is bromine and $R^{Z2}$ is chlorine.

Scheme S4.

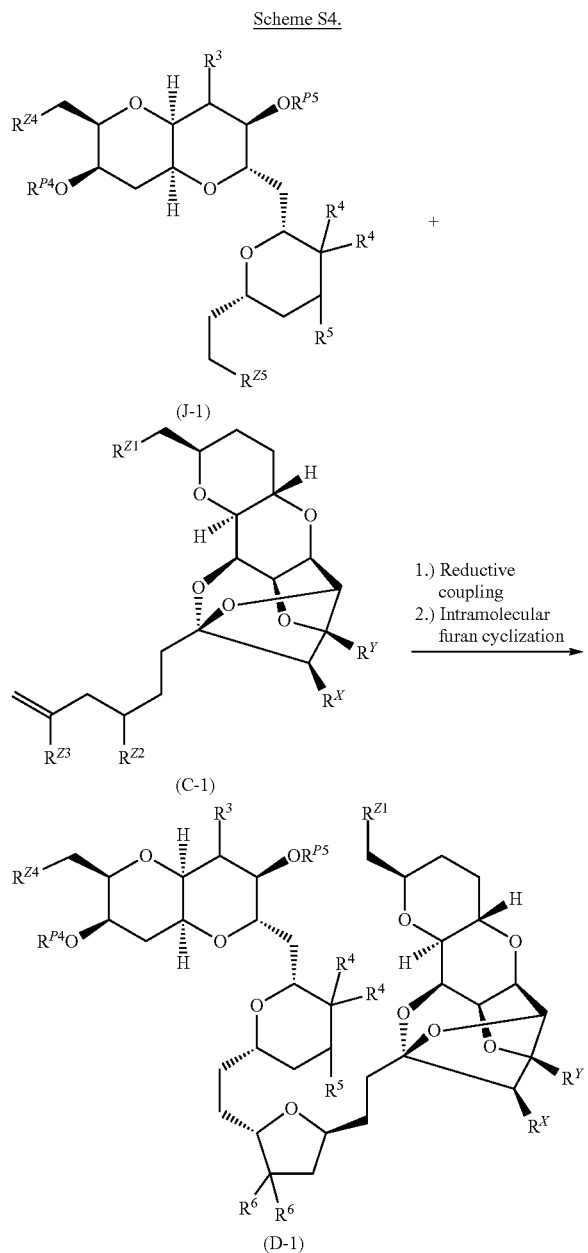

(J-1)

(C-1)

(D-1)

Scheme S5.

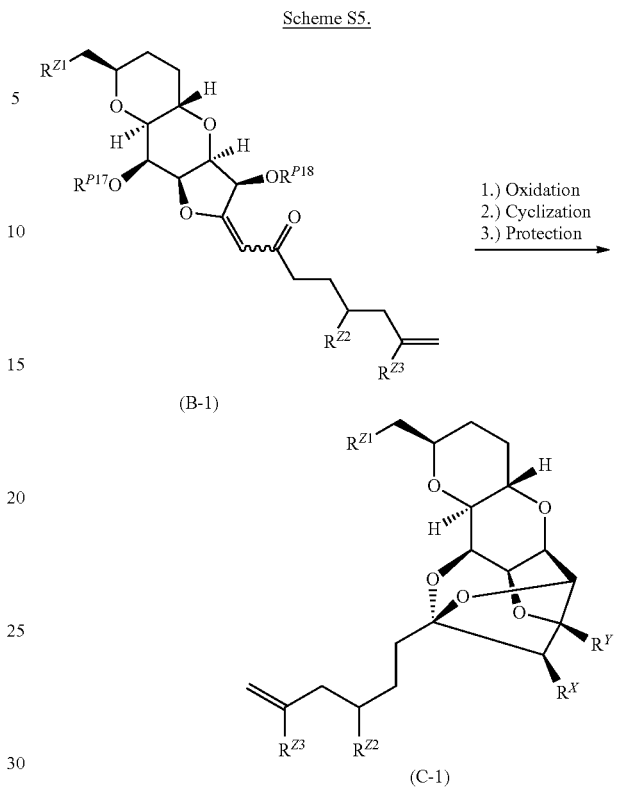

(B-1)

1.) Oxidation
2.) Cyclization
3.) Protection (C-1)

In certain embodiments, preparation of a compound of Formula (C-1) or a salt thereof comprises cyclizing an intermediate compound of Formula (B-1) or salt thereof (see Scheme S5). In certain embodiments, the cyclization reaction conditions comprise an intermediate epoxidation or oxidation reaction. In certain embodiments, the epoxidation or oxidation reaction comprises an organic oxidant (e.g., dimethyldioxirane or t-butyl hydroperoxide). In certain embodiments, the cyclization conditions comprise an acid. In certain embodiments, the cyclization conditions comprise a Brønsted acid (i.e., a source of H+). In certain embodiments, the cyclization conditions comprise an organic acid (e.g., camphorsulfonic acid). In certain embodiments, wherein $R^X$ and or $R^Y$ of a compound of (D-1) are hydroxyl groups, one or both groups are optionally protected. In certain embodiments, both $R^X$ and $R^Y$ are protected as an acetal or ketal protecting group (e.g., an acetonide or ap-methoxyphenyl group).

In certain embodiments, preparation of a compound of Formula (B-1) or salt thereof comprises joining an intermediate compound of Formula (A-1) or salt thereof and an intermediate aldehyde or salt thereof (see Scheme S6). Compounds of Formula (A-1) and the aldehyde are joined under reductive coupling conditions. In certain embodiments, the conditions used to join a compound of Formula (A-1) with the aldehyde comprise a transition metal (e.g., nickel or chromium). In certain embodiments, the coupling reaction is catalytic in transition metal (e.g., 2-40 mol %). In certain embodiments, the coupling reaction is stoichiometric in transition metal (e.g., 1-3 equivalents). In certain embodiments, the coupling comprises a ligand or ligated transition metal complex (e.g., see Scheme 4). In certain embodiments, following the reductive coupling of a compound of Formula (A-1) and the aldehyde, the synthetic route comprises an oxidation step. In certain embodiments, the oxidation is carried out under mild and selective conditions (e.g., Dess-Martin periodinane, $SO_3$•pyridine, or Swern oxidation). In certain embodiments, following the oxidation reaction, when $R^{P18}$ and/or $R^{P19}$ is a protecting group, the synthetic route comprises a selective deprotection step. In certain embodiments, when $R^{P18}$ and/or $R^{P19}$ is a silyl protecting group (e.g., t-butyldimethylsilyl), selective deprotection of $R^{P18}$ and/or $R^{P19}$ comprises a mild source of fluoride (e.g., TBAF, HF•pyridine). In certain embodiments, following the optional deprotection reaction, the synthetic route comprises an intramolecular furan cyclization reaction. In certain embodiments, the cyclization reaction comprises a conjugate addition reaction proceeding through an oxyanion intermediate. In certain embodiments, the deprotection and conjugate addition reactions occur in a single step. In certain embodiments, the cyclization conditions comprise an acid or a base. In certain embodiments, a compound of Formula (B-1) is formed as a single (E)-alkene stereoisomer. In certain embodiments, a mixture of (E)- and (Z)-alkene stereoisomers is formed (e.g., a 1:1, 2:1, 5:1, >5:1, 1:2, 1:5, or >1:5 ratio of (E)- to (Z)-isomers).

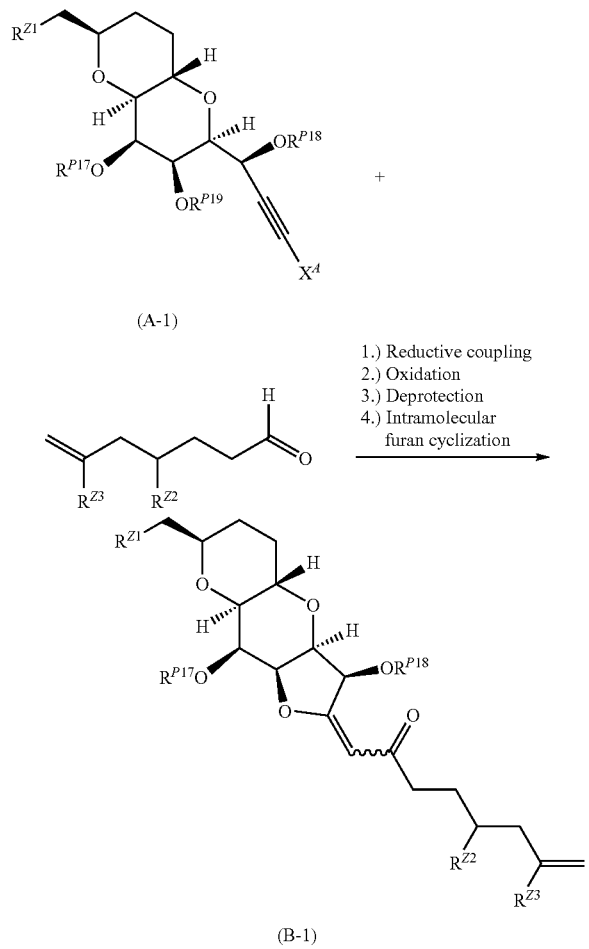

In certain embodiments, preparation of compounds of Formula (II) or norhalichondrin A or pharmaceutically acceptable salts thereof comprises cyclizing an intermediate compound of Formula (G-1) or salt thereof (see Scheme S7). In certain embodiments, when a compound of Formula (G-1) is protected (e.g., with silyl or benzylic protecting groups), the synthetic route comprises a deprotection step prior to cyclization. In certain embodiments, deprotection of a compound of Formula (G-1) comprises a source of fluoride (e.g., TBAF, HF•pyridine). In certain embodiments, deprotection of a compound of Formula (G-1) comprises a hydrogenolysis (e.g., a palladium or nickel catalyst and $H_2$) or oxidation (e.g., DDQ) step. In certain embodiments, the cyclization conditions comprise an acid. In certain embodiments, the cyclization conditions comprise a Brønsted acid (i.e., a source of H+). In certain embodiments, the cyclization conditions comprise an organic acid (e.g., PPTS). In certain embodiments, the cyclization conditions provide a compound of Formula (II) or norhalichondrin A as a single diastereomer. In certain embodiments, the cyclization conditions provide a diastereomeric mixture that is enriched in one of two epimeric C38 ketals. In certain embodiments, the synthetic route comprises an equilibration step to enrich a compound of Formula (II) or norhalichondrin A in one of two epimeric C38 ketals. In certain embodiments, the equilibration step enriches a compound of Formula (II) or norhalichondrin A (n the (R)-epimer. In certain embodiments, the equilibration step enriches a compound of Formula (II) or norhalichondrin A in the (R)-epimer in a range of 2:1, 3:1, 4:1, 5:1, or >5:1. In certain embodiments, the equilibration step enriches a compound of Formula (II) or norhalichondrin A in the (S)-epimer. In certain embodiments, the equilibration step enriches a compound of Formula (II) or norhalichondrin A in the (S)-epimer in a range of 2:1, 3:1, 4:1, 5:1, 10:1, or >10:1. In certain embodiments, the equilibration step comprises a Lewis acid. In certain embodiments, the equilibration step comprises a silyl Lewis acid (e.g., a silicon tetrahalide or and organosilicon halide or triflate). In certain embodiments, the equilibration step comprises trimethylsilyl triflate. In certain embodiments, the equilibration step comprises a solvent. In certain embodiments, the equilibration step comprises a halogenated (e.g., dichloromethane) or ethereal (e.g., diethylether) solvent. In certain embodiments, when $R^7$ is not hydrogen, the synthetic route comprises a hydrolysis step comprising a base (e.g., lithium, sodium, or potassium hydroxide).

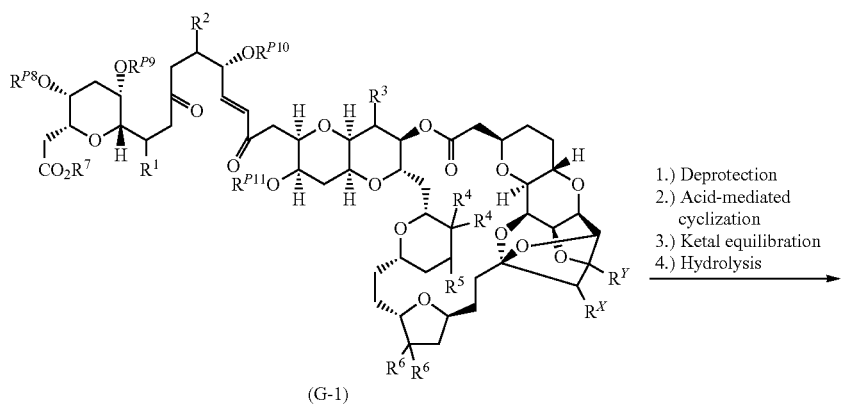

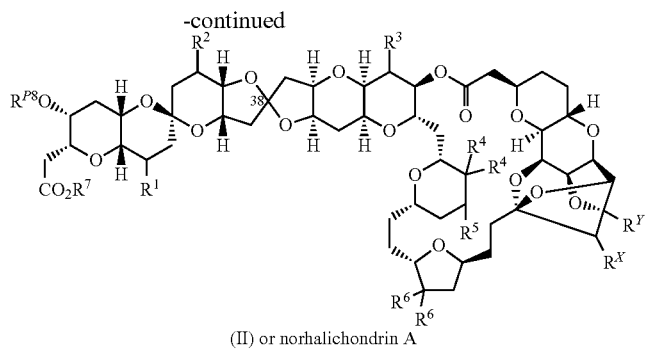

(II) or norhalichondrin A

In certain embodiments, preparation of a compound of Formula (G-1) or salt thereof comprises joining an intermediate compound of Formula (E-1) or salt thereof and an intermediate of Formula (K-1) or salt thereof (see Scheme S8). In certain embodiments, when $R^{Z4}$ is —$CH_2OR^{Z4a}$ and $R^{Z4a}$ is a protecting group, the synthetic route comprises a deprotection step. In certain embodiments, when $R^{Z4a}$ is a silyl protecting group (e.g., t-butyldimethylsilyl), selective deprotection of $R^{Z4a}$ comprises a mild source of fluoride (e.g., TBAF, HF•pyridine). In certain embodiments, when $R^{Z4}$ is —$CH_2OH$, the synthetic route comprises an oxidation step. In certain embodiments, $R^{Z4}$ is oxidized into an aldehyde (—CHO) under mild and selective conditions (e.g., Dess-Martin periodinane, $SO_3$•pyridine, or Swern oxidation). Compounds of Formula (E-1) are joined with a compound of Formula (K-1) under reductive coupling conditions. In certain embodiments, the conditions used to join a compound of Formula (E-1) with a compound of Formula (K-1) comprise a transition metal (e.g., nickel or chromium). In certain embodiments, the coupling reaction is catalytic in transition metal (e.g., 2-40 mol %). In certain embodiments, the coupling reaction is stoichiometric in transition metal (e.g., 1-3 equivalents). In certain embodiments, the coupling comprises a ligand or ligated transition metal complex (e.g., see Scheme 4). The reaction used to join a compound of Formula (E-1) and Formula (K-1) provides an intermediate hydroxy group that must be oxidized to provide a compound of Formula (G-1). In certain embodiments, the oxidation is carried out under mild and selective conditions (e.g., Dess-Martin periodinane, $SO_3$•pyridine, or Swern oxidation).

Scheme S8.

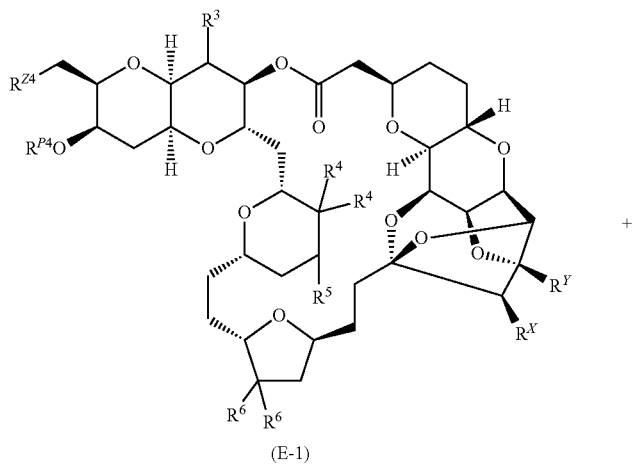

(E-1)

+

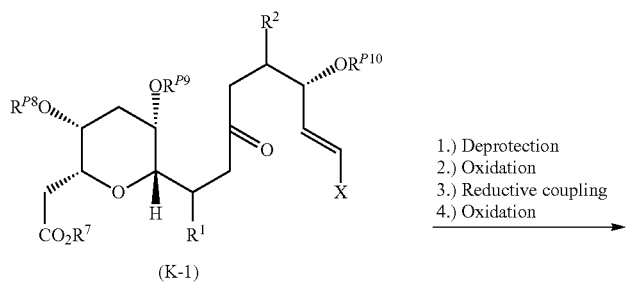

(K-1)

1.) Deprotection
2.) Oxidation
3.) Reductive coupling
4.) Oxidation

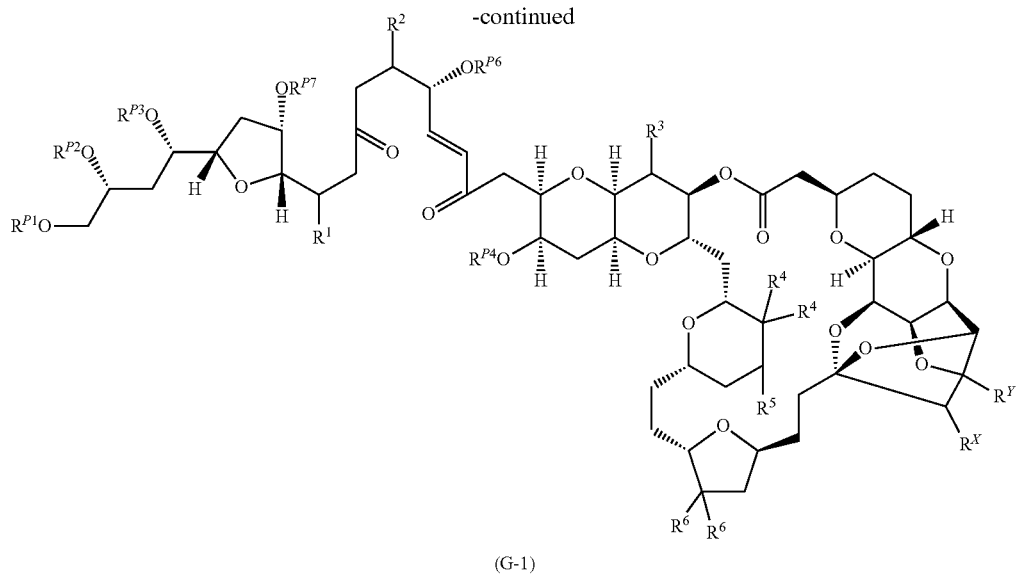

(G-1)

In certain embodiments, preparation of compounds of Formula (III) or homohalichondrin A or pharmaceutically acceptable salts thereof comprises cyclizing an intermediate compound of Formula (H-1) or salt thereof (see Scheme S9). In certain embodiments, when a compound of Formula (H-1) is protected (e.g., with silyl or benzylic protecting groups), the synthetic route comprises a deprotection step prior to cyclization. In certain embodiments, deprotection of a compound of Formula (G-1) comprises a source of fluoride (e.g., TBAF, HF·pyridine). In certain embodiments, deprotection of a compound of Formula (H-1) comprises a hydrogenolysis (e.g., a palladium or nickel catalyst and 112) or oxidation (e.g., DDQ) step. In certain embodiments, the cyclization conditions comprise an acid. In certain embodiments, the cyclization conditions comprise a Brønsted acid (i.e., a source of H+). In certain embodiments, the cyclization conditions comprise an organic acid (e.g., PPTS). In certain embodiments, the cyclization conditions provide a compound of Formula (III) or homohalichondrin A as a single diastereomer. In certain embodiments, the cyclization conditions provide a diastereomeric mixture that is enriched in one of two epimeric C38 ketals. In certain embodiments, the synthetic route comprises an equilibration step to enrich a compound of Formula (III) or homohalichondrin A in one of two epimeric C38 ketals. In certain embodiments, the equilibration step enriches a compound of Formula (III) or homohalichondrin A in the (R)-epimer. In certain embodiments, the equilibration step enriches a compound of Formula (III) or homohalichondrin A in the (R)-epimer in a range of 2:1, 3:1, 4:1, 5:1, or >5:1. In certain embodiments, the equilibration step enriches a compound of Formula (III) or homohalichondrin A in the (S)-epimer. In certain embodiments, the equilibration step enriches a compound of Formula (III) or homohalichondrin A in the (S)-epimer in a range of 2:1, 3:1, 4:1, 5:1, 10:1, or >10:1. In certain embodiments, the equilibration step comprises a Lewis acid. In certain embodiments, the equilibration step comprises a silyl Lewis acid (e.g., a silicon tetrahalide or and organosilicon halide or triflate). In certain embodiments, the equilibration step comprises trimethylsilyl triflate. In certain embodiments, the equilibration step comprises a solvent. In certain embodiments, the equilibration step comprises a halogenated (e.g., dichloromethane) or ethereal (e.g., diethylether) solvent.

Scheme S9.

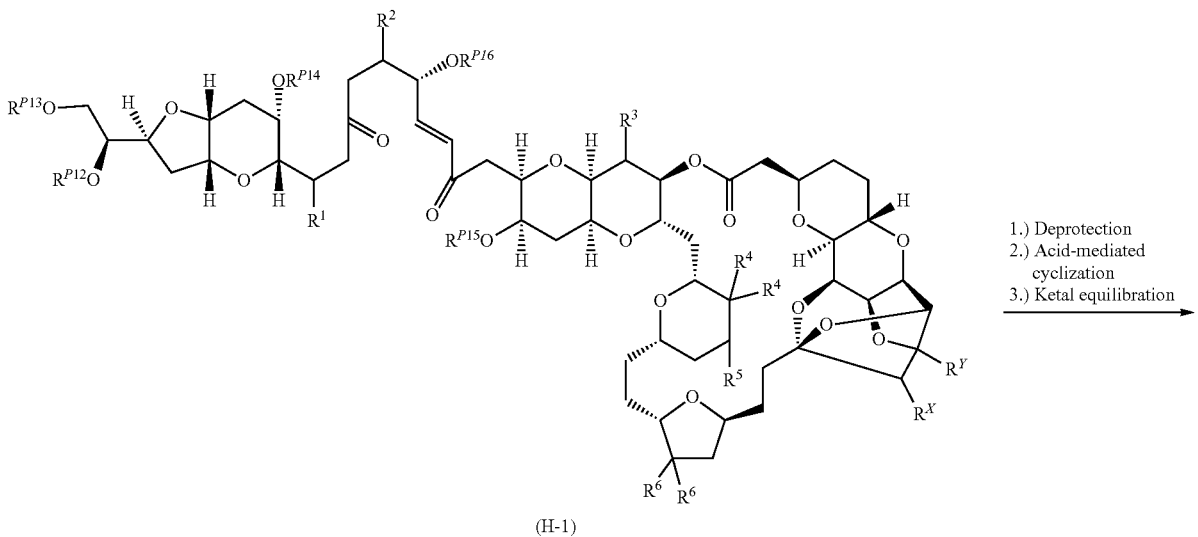

(H-1)

1.) Deprotection
2.) Acid-mediated cyclization
3.) Ketal equilibration

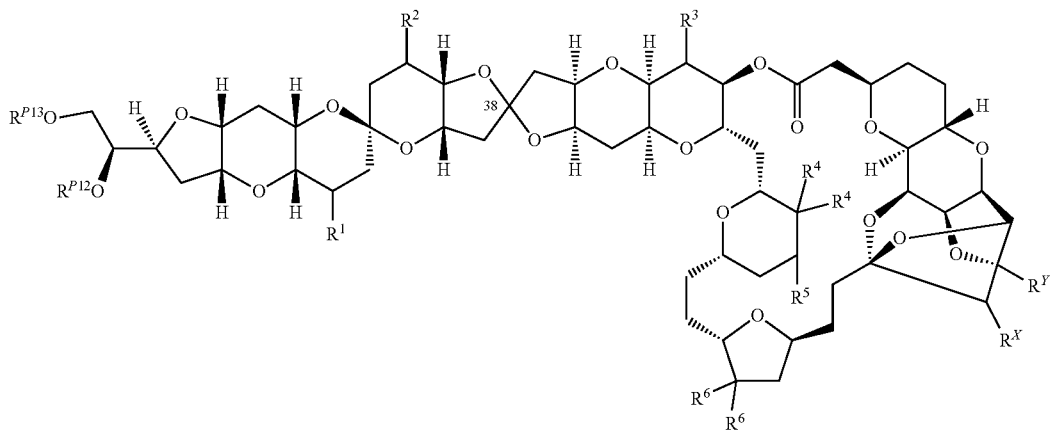

(III) or homohalichondrin A

In certain embodiments, preparation of a compound of Formula (H-1) or salt thereof comprises joining an intermediate compound of Formula (E-1) or salt thereof and an intermediate of Formula (L-1) or salt thereof (see Scheme S10). In certain embodiments, when $R^{Z4}$ is —$CH_2OR^{Z4a}$ and $R^{Z4a}$ is a protecting group, the synthetic route comprises a deprotection step. In certain embodiments, when $R^{Z4a}$ is a silyl protecting group (e.g., t-butyldimethylsilyl), selective deprotection of $R^{Z4a}$ comprises a mild source of fluoride (e.g., TBAF, HF•pyridine). In certain embodiments, when $R^{Z4}$ is —$CH_2OH$, the synthetic route comprises an oxidation step. In certain embodiments, $R^{Z4}$ is oxidized into an aldehyde (—CHO) under mild and selective conditions (e.g., Dess-Martin periodinane, $SO_3$•pyridine, or Swern oxidation). Compounds of Formula (E-1) are joined with a compound of Formula (L-1) under reductive coupling conditions. In certain embodiments, the conditions used to join a compound of Formula (E-1) with a compound of Formula (L-1) comprise a transition metal (e.g., nickel or chromium). In certain embodiments, the coupling reaction is catalytic in transition metal (e.g., 2-40 mol %). In certain embodiments, the coupling reaction is stoichiometric in transition metal (e.g., 2-3 equivalents). In certain embodiments, the coupling comprises a ligand or ligated transition metal complex (e.g., see Scheme 4). The reaction used to join a compound of Formula (E-1) and Formula (L-1) provides an intermediate hydroxy group that must be oxidized to provide a compound of Formula (H-1). In certain embodiments, the oxidation is carried out under mild and selective conditions (e.g., Dess-Martin periodinane, $SO_3$•pyridine, or Swern oxidation).

Scheme S10.

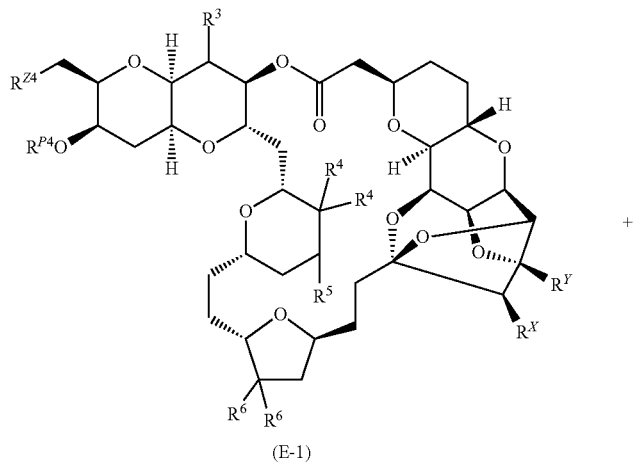

(E-1)

+

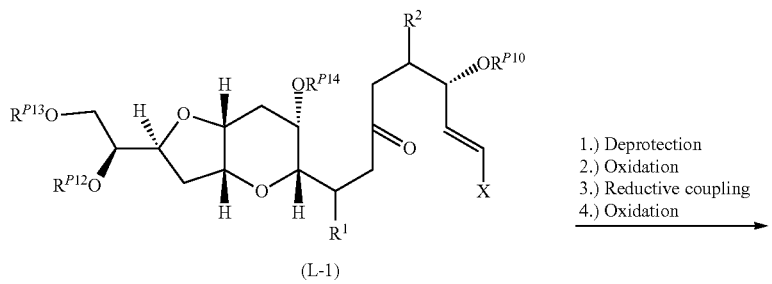

(L-1)

1.) Deprotection
2.) Oxidation
3.) Reductive coupling
4.) Oxidation

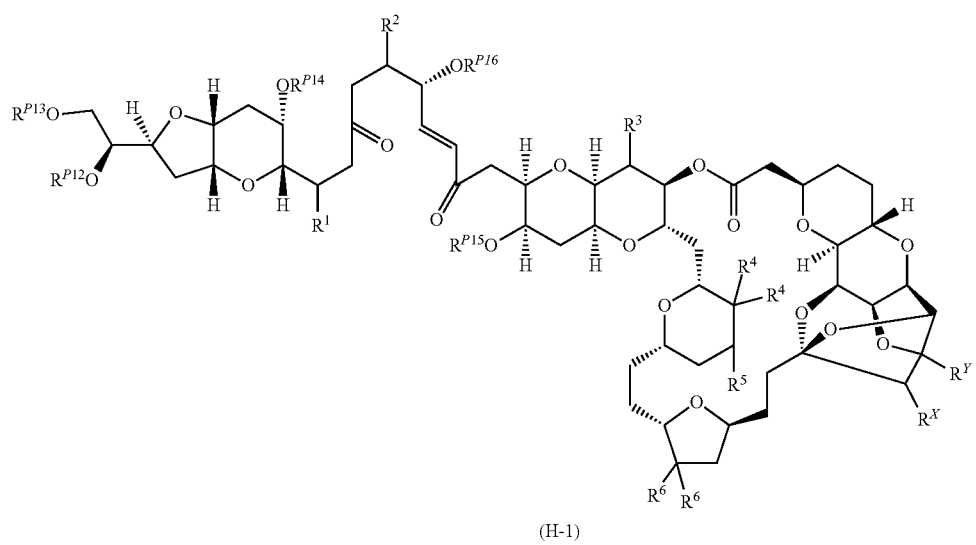

(H-1)

EXAMPLES

In order that the invention described herein may be more fully understood, the following Examples are set forth. The synthetic and biological examples described in this Application are offered to illustrate the compounds, pharmaceutical compositions, and methods provided herein and are not to be construed in any way as limiting their scope.

Example 1. Synthesis of the Compounds

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

General Procedures and Methods

NMR spectra were recorded on a Varian Inova 600 MHz, 500 MHz, or 400 MHz spectrometer. Chemical shifts are reported in parts per million (ppm). For $^1$H NMR spectra (CDCl$_3$, C$_6$D$_6$, and/or CD$_3$OD), the residual solvent peak was used as the internal reference (7.26 ppm in CDCl$_3$; 7.16 ppm in C$_6$D$_6$; 3.31 ppm in CD$_3$OD), while the central solvent peak as the reference (128.0 ppm in C$_6$D$_6$; 49.0 ppm in CD$_3$OD) for $^{13}$C NMR spectra. Optical rotations were measured at 20° C. using a Perkin-Elmer 241 polarimeter. IR spectra were recorded on a Bruker Alpha FT-IR spectrometer. Analytical and semi-preparative thin layer chromatography (TLC) was performed with E. Merck pre-coated TLC plates, silica gel 60 F$_{254}$, layer thickness 0.25 and 1.00 mm, respectively. TLC plates were visualized by staining with p-anisaldehyde or phosphomolybdic acid stain. Flash chromatography separations were performed on E. Merck Kieselgel 60 (230-400) mesh silica gel. High performance liquid chromatography (HPLC) was carried out with Waters 1525 on a UV spectrophotometric detector (254 nm, Waters 2489) to which a 21.2×250 nm size column (Zobrax SIL) packed with silica gel (7.0 μm) was attached. All moisture sensitive reactions were conducted under an inert atmosphere. Reaction vessels were oven-dried and allowed to cool under vacuum (1 mmHg). Reagents and solvents were commercial grade and were used as supplied, unless otherwise noted.

For the synthesis of E-9 and Z-9 from 8 and the synthesis of β-10 from E-9, please refer to Yamamoto, A; Ueda, A.; Brémond, P.; Tiseni, P. S.; Kishi, Y. *J. Am. Chem. Soc.* 2012, 134, 893.

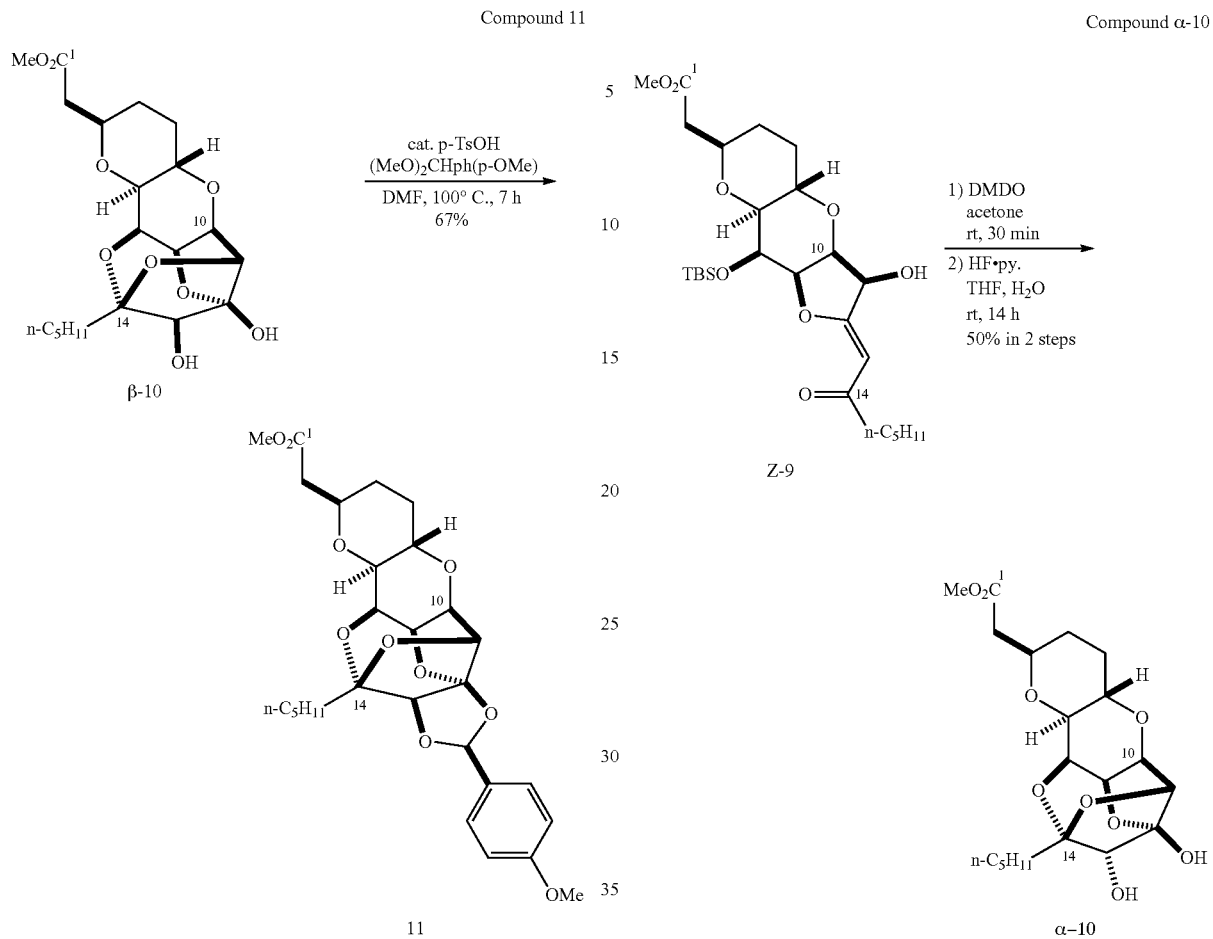

To diol (7.3 mg, 18 µmol) and p-anisaldehyde dimethyl acetal (30 µL, 0.18 mmol) in DMF (0.35 mL) was added camphorsulfonic acid (CSA, 0.2 mg, 0.9 µmol) at room temperature and the reaction mixture was heated at 100° C. for 7 h. After cooling to room temperature, the reaction mixture was quenched with sat. NaHCO$_3$ aq. and extracted with Et$_2$O three times. The combined organic extracts were washed with water, dried over Na$_2$SO$_4$, and concentrated under vacuum. The crude product was purified by preparative TLC (40% EtOAc in hexanes) to yield acetal 11 (6.2 mg, 67%) as a white solid.

11: $^1$H NMR (600 MHz, C$_6$D$_6$) δ: 7.35 (2H, d, J=8.8 Hz, ArH), 6.70 (1H, d, J=8.8 Hz, ArH), 6.13 (1H, s, ArCH), 4.57-4.55 (1H, m, H-8), 4.53 (ddd, J=10.0, 10.0, 4.7 Hz, H-6), 4.41 (1H, dd, J=5.3, 1.8 Hz, H-11), 4.16 (1H, s, H-13), 4.06 (1H, dd, J=6.5, 5.3 Hz, H-10), 3.80-3.73 (2H, m, H-9, 3), 3.30 (3H, s, CO$_2$CH$_3$), 3.21 (3H, s, ArOCH$_3$), 2.54 (1H, d, J=10.0 Hz, H-7), 2.53 (1H, dd, J=16.1, 7.6 Hz, H-2a), 2.26-2.18 (1H, m, H-15a), 2.11 (1H, dd, J=16.1, 5.0 Hz, H-2b), 2.11-2.06 (1H, m, H-15b), 2.05-1.99 (1H, m, H-5a), 1.86-1.76 (2H, m, H-16a,16b), 1.40-1.34 (1H, m, H-4a), 1.32-1.15 (5H, m, H-4b, 5b, 17a, 17b, 18a, 18b), 0.84 (3H, t, J=7.0 Hz, CH$_2$CH$_3$). $^{13}$C NMR (100 MHz, C$_6$D$_6$) δ: 171.0, 161.4, 128.8 (2C), 128.6, 118.8, 114.1 (2C), 109.8, 109.0, 89.8, 83.6, 79.0, 76.2, 74.7, 74.3, 74.0, 68.3, 54.7, 51.0, 40.5, 34.8, 32.1, 30.7, 30.4, 23.5, 23.0, 14.1. HRMS (ESI) m/z: [M+H]$^+$ calcd for C$_{28}$H$_{37}$O$_{10}$, 533.2381; found, 533.2381.

To a solution of Z-enone Z-9 (2.0 mg, 3.9 µmol) in acetone (0.20 mL) was added freshly prepared dimethyldioxirane$^{17}$ (DMDO, 0.08 M in acetone, 98 µL, 7.8 µmol) solution and stirred at room temperature for 30 min. The reaction mixture was evaporated by a stream of nitrogen gas. The above crude material was dissolved in THF (0.20 mL) and HF•pyridine complex (70% HF content, 2.0 µL, 78 µmol) was added to the reaction at room temperature. After stirring for 3 h at room temperature, wet CH$_2$Cl$_2$ (0.20 mL) was added to the reaction mixture, which was further stirred for 11 h at room temperature. The reaction mixture was quenched with sat. NaHCO$_3$ aq. and extracted with EtOAc four times. The combined organic layers were dried over Na$_2$SO$_4$, filtered, and concentrated under vacuum. The residue was purified by preparative TLC (EtOAc/hexanes=2:1, developed twice) to give α-10 (0.8 mg, 50% overall yield from Z-9) exclusively.

α-10: $^1$H NMR (600 MHz, CDCl$_3$) δ: 4.58 (1H, dd, J=4.4, 2.2 Hz), 4.41 (1H, dd, J=5.3, 4.0 Hz), 4.40 (1H, d, J=5.3 Hz), 4.33 (1H, dd, J=4.4, 4.0 Hz), 4.32 (1H, ddd, J=10.3, 9.2, 5.0 Hz), 3.88 (1H, d, J=12.4 Hz), 3.86-3.82 (1H, m), 3.67 (3H, s), 3.34 (1H, br s), 2.90 (1H, dd, J=9.8, 2.2 Hz), 2.65 (1H, dd, J=16.1, 6.7 Hz), 2.57 (1H, d, J=12.3 Hz), 2.39 (1H, dd, J=16.1, 6.2 Hz), 2.15-2.08 (1H, m), 1.95-1.87 (1H, m), 1.86-1.79 (1H, m), 1.68-1.58 (2H, m), 1.52-1.23 (7H, m), 0.91 (3H, t, J=7.0 Hz). HRMS (ESI) nm/z: [M+Na]$^+$ calcd for C$_{20}$H$_{30}$O$_9$Na, 437.1782; found, 437.1796.

NOE Experiment of p-Anisylidene Acetal 6a:

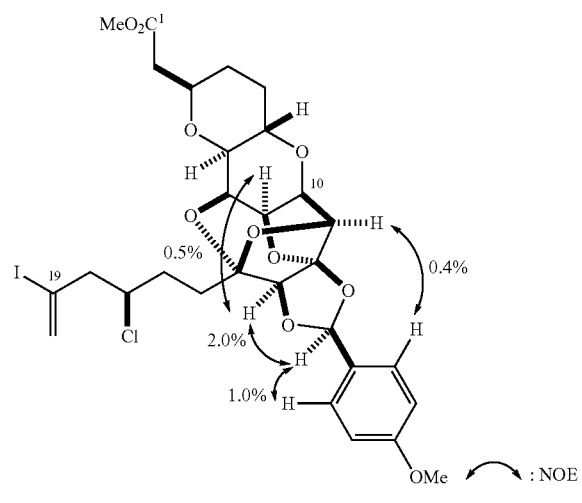

To a solution of alcohol S-1[18] (653 mg, 2.38 mmol, >99% ee) in $CH_2Cl_2$ (16 mL) was added solid $NaHCO_3$ (1.00 g, 11.9 mmol) and Dess-Martin periodinane (1.51 g, 3.57 mmol) in one portion at room temperature and stirred for 1.5 h at the same temperature. The solution was quenched with 10 wt. % $Na_2S_2O_3$ aq. and sat. $NaHCO_3$ aq. and stirred vigorously for 30 min. The aqueous phase was extracted with $CH_2Cl_2$ three times and the combined organic phases were dried over $Na_2SO_4$. The crude material was purified by short column chromatography on silica gel (5% EtOAc in hexanes) to give aldehyde 13a (590 mg, 91%) as colorless oil. This material was immediately used for the next step without further purification.

13a: $^1$H NMR (600 MHz, $C_6D_6$) δ: 9.13 (1H, s, CHO), 5.73-5.62 (1H, m, C19=CHH), 5.55 (1H, d, J=1.5 Hz, C19=CHH), 3.89 (1H, dddd, J=9.3, 8.5, 5.3, 3.4 Hz, H-17), 2.28 (1H, ddd, J=14.6, 8.5, 1.0 Hz, H-18a), 2.22 (1H, dd, J=14.6, 5.3 Hz, H-18b), 1.97 (1H, ddd, J=18.5, 8.8, 5.3 Hz, H-15a), 1.82 (1H, ddd, J=18.5, 8.8, 6.4 Hz, H-a5b), 1.62 (1H, dddd, J=14.7, 8.8, 6.4, 3.4 Hz, H-16a), 1.42 (1H, dddd, J=14.7, 9.3, 8.8, 5.3 Hz, H-16b).

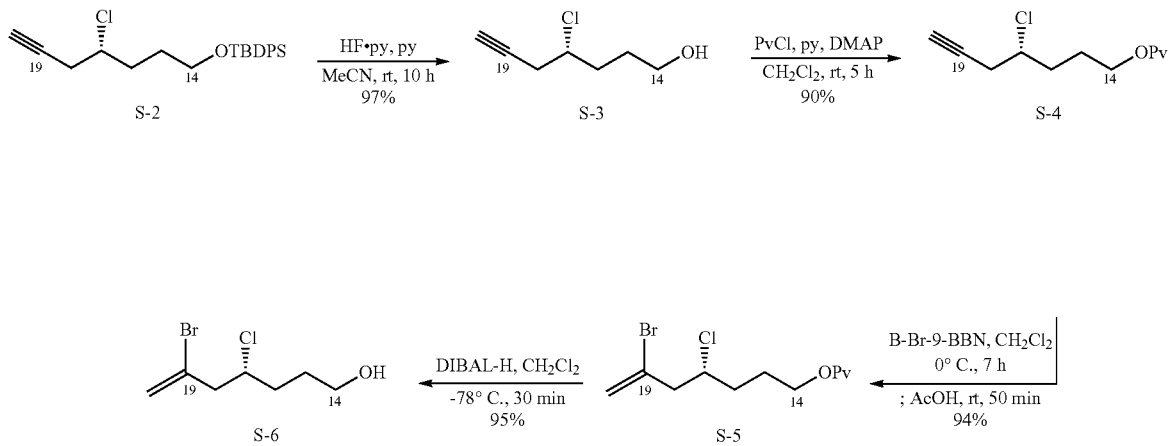

Compound S-6

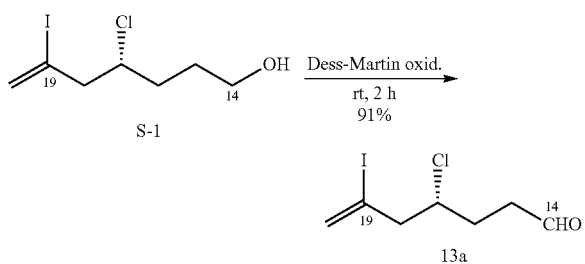

Compound 13a

To a stirred solution of TBDPS-ether S-2[18] (3.10 g, 8.05 mmol, >99% ee) and pyridine (3.25 mL, 40.3 mmol) in MeCN (40 mL) was added HF•pyridine complex (70% HF content, 1.46 mL, 56.4 mmol) at 0° C.[19] After stirring for 10 h at room temperature, the reaction mixture was carefully quenched with sat. $NaHCO_3$ aq and solid $NaHCO_3$ at 0° C. The aqueous phase was extracted with EtOAc three times and the combined organic phases were washed with 1 M HCl aq and brine, dried over $Na_2SO_4$, and concentrated under reduced pressure. The residue was purified by flash column chromatography on silica gel (eluent: 10% then 40% EtOAc in hexanes) to give alcohol S-3 (1.13 g, 97%) as a colorless oil.

To a solution of alcohol S-3 (1.13 g, 7.74 mmol) in $CH_2Cl_2$ (26 mL) at 0° C. were added pyridine (1.25 mL, 15.5 mmol), pivaloyl chloride (1.42 mL, 11.6 mmol), and 4-dimethylaminopyridine (94.4 mg, 0.774 mmol) and the reaction was stirred for 5 h at room temperature. After cooling to 0° C., the reaction mixture was added MeOH (0.7 mL) and stirred for 5 min at 0° C. The resultant mixture was carefully quenched with 1 M HCl aq. at 0° C. and the aqueous layer was extracted with $CH_2Cl_2$ once. The combined organic layers were washed with brine, dried over $Na_2SO_4$, and concentrated under vacuum. Purification of the residue by flash column chromatography on silica gel (eluent: 5% EtOAc in hexanes) afforded pivaloyl ester S-4 (1.60 g, 90%) as a colorless oil.

To a solution of alkyne S-4 (800 mg, 3.48 mmol) in $CH_2Cl_2$ (13.9 mL) was dropped B-bromo-9-BBN[20] solution (1 M in $CH_2Cl_2$, 10.4 mL, 10.4 mmol) at 0° C. and stirred for 7 h at the same temperature prior to the addition of AcOH (1.19 mL, 20.9 mmol). After stirring at room temperature for 50 min, the reaction was cooled to 0° C. and carefully added 3 M NaOH aq. (8.35 mL, 25.1 mmol) and $H_2O_2$ solution (30% in $H_2O$, 11.8 mL, 104 mmol), and further stirred for 10 min at 0° C. The reaction mixture was quenched with 10 wt. % $Na_2S_2O_3$ aq. The aqueous phase was extracted with $CH_2Cl_2$ three times and the combined organic extracts were washed with 10 wt. % $Na_2S_2O_3$ and sat. $NaHCO_3$ aq. and dried over sodium sulfate, and concentrated under vacuum. The residue was purified by flash column chromatography on silica gel eluted with 1% $Et_2O$ in hexanes to give bromoalkene S-5 (1.02 g, 94%) as colorless oil.

To a solution of bromoalkene S-5 (1.02 g, 3.28 mmol) in $CH_2Cl_2$ (33 mL) at −78° C. was added DIBAL-H solution (1 M in toluene, 6.56 mL, 6.56 mmol) and stirred for 30 min at the same temperature. The reaction mixture was carefully quenched by adding $Na_2SO_4 \cdot 10H_2O$. The resultant white suspension was filtered through a pad of Celite (1 cm) and the filter cake was washed with $CH_2Cl_2$. After removal of the solvent, the residue was purified by flash column chromatography on silica gel (10% then 20% EtOAc in hexanes) to provide alcohol S-6 (704 mg, 95%) as colorless oil.

S-6: $[\alpha]^{20}_D$ +4.6 (c 0.57, $CHCl_3$). $^1H$ NMR (500 MHz, $C_6D_6$) δ: 5.29 (1H, d, J=2.0 Hz, C19=CHH), 5.26 (1H, ddd, J=2.0, 2.0, 1.0 Hz, C19=CHH), 4.08 (1H, dddd, J=9.0, 8.3, 4.9, 3.4 Hz, H-17), 3.17 (2H, td, J=5.9, 5.4 Hz, H-14), 2.44 (1H, dd, J=14.6, 8.3 Hz, H-18a), 2.35 (1H, dd, J=14.6, 4.9 Hz, H-18b), 1.58-1.45 (2H, m), 1.45-1.34 (1H, m), 1.35-1.25 (1H, m), 0.38 (1H, t, J=5.4 Hz, OH). $^{13}C$ NMR (125 MHz, $C_6D_6$) δ: 129.9, 120.0, 61.8, 60.1, 50.1, 34.1, 29.6. HRMS (ESI) m/z: $[M+Na]^+$ calcd for $C_7H_{12}OBrClNa$, 248.9652; found, 248.9653.

Compound S-7

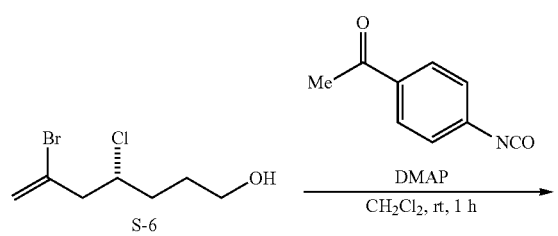

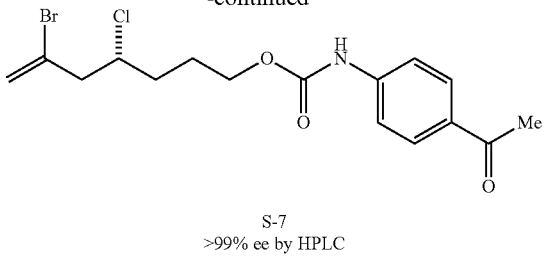

S-7
>99% ee by HPLC

To a solution of alcohol S-6 (2.2 mg, 9.7 μmol) in $CH_2Cl_2$ (0.10 mL) were added 4-acetylphenyl isocyanate (1.9 mg, 11.6 μmol) and 4-dimethylaminopyridine (0.2 mg, 2 μmol) at room temperature. The reaction mixture was stirred for 1 h at the same temperature prior to quenching with sat. $NaHCO_3$ aq. The aqueous phase was extracted with EtOAc twice and the combined organic phases were dried ($Na_2SO_4$) and concentrated in vacuo. The residue was purified by preparative TLC (30% EtOAc in hexanes) to give urethane S-7 (3.2 mg, 86%) as a white solid. Racemic sample of S-7 was also prepared from racemic alcohol of compound 8 in footnote reference 3 via chlorination of secondary alcohol followed by above 5 step protocol. The optical purity of urethane S-7 was determined as >99% ee by HPLC analysis (Chart S1). HPLC Condition. Column: chiralpak OJ-H; solvent system: hexanes/i-propanol/diethylamine=85%/15%/0.1%; flow rate 1.0 mL/min; detector=UV at 277 nm; retention time: 40.4 and 37.0 min for (R)- and (S)-enantiomers, respectively.

The optical purity of alcohol S-6 was determined as >99% ee by HPLC analysis (OJ-H chiral column) of its 4-acetylphenylurethane derivative S-7 prepared from S-6.

Compound 13b

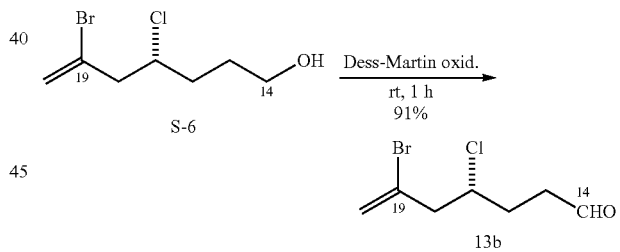

To a solution of alcohol S-6 (701 mg, 3.09 mmol) in $CH_2Cl_2$ (31 mL) were added $NaHCO_3$ (2.60 g, 30.9 mmol) and Dess-Martin periodinane (1.97 g, 4.64 mmol) at room temperature and stirred for 1 h at room temperature. The reaction mixture was quenched with 10 wt. % $Na_2S_2O_3$ and sat. $NaHCO_3$ aq. and vigorously stirred for 30 min. The aqueous phase was extracted with $CH_2Cl_2$ three times and the combined organic phases were washed with 10 wt. % $Na_2S_2O_3$ and sat. $NaHCO_3$ aq. and then dried over sodium sulfate. After removal of the solvent, the crude material was purified by flash chromatography on short silica gel column (5% EtOAc in hexanes) to give aldehyde 13b (635 mg, 91%) as colorless oil. This material was immediately used for the next step without further purification.

13b: $^1H$ NMR (500 MHz, $C_6D_6$) δ: 9.12 (1H, s, CHO), 5.33-5.24 (1H, m, C19=CHH), 5.24-5.18 (1H, m, C19=CHH), 3.92 (1H, dddd, J=9.2, 8.3, 5.4, 3.4 Hz, H-17), 2.33 (1H, dd, J=14.6, 8.3 Hz, H-18a), 2.23 (1H, dd, J=14.6, 5.4 Hz, H-18b), 1.97 (1H, ddd, J=18.6, 8.8, 5.4 Hz, H-15a), 1.81 (1H, ddd, J=18.6, 8.8, 6.3 Hz, H-15b), 1.62 (1H, dddd, J=14.6, 8.8, 6.3, 3.4 Hz, H-16a), 1.41 (1H, dddd, J=14.6, 9.2, 8.8, 5.4 Hz, H-16b).

Compound 14a

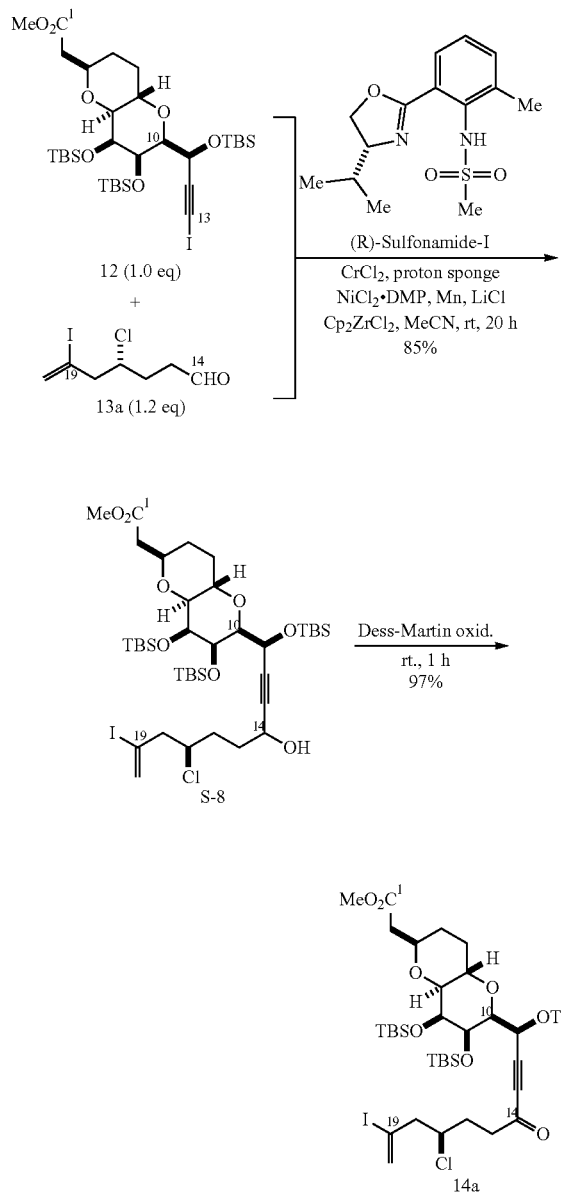

12 (1.0 eq)
+
13a (1.2 eq)

(R)-Sulfonamide-I
CrCl$_2$, proton sponge
NiCl$_2$·DMP, Mn, LiCl
Cp$_2$ZrCl$_2$, MeCN, rt, 20 h
85%

Dess-Martin oxid.
rt., 1 h
97%

S-8

14a

To a mixture of CrCl$_2$ (41.6 mg, 0.338 mmol), (R)-sulfonamide ligand I[21] (116 mg, 0.372 mmol), and proton sponge (79.6 mg, 0.372 mmol) in a glove box was added MeCN (4.2 mL) and stirred for 1 h at room temperature. In a separate flask, iodide 125 (1.30 g, 1.69 mmol), aldehyde 13a (552 mg, 2.03 mmol), NiCl$_2$.2,9-dimethyl-1,10-phenanthroline complex (NiCl$_2$.DMP, 0.055 mg, 0.00017 mmol, doped in LiCl), LiCl (143 mg, 3.38 mmol), Mn (186 mg, 3.38 mmol), Cp$_2$ZrCl$_2$ (493 mg, 1.69 mmol) were mixed together and the Cr-complex solution was transferred to the flask. Additional NiCl$_2$.DMP (0.055 mg each, 0.00017 mmol) was added after 4 and 8 h and the reaction was further stirred for 12 h at room temperature. The reaction was removed from the glove box and diluted with EtOAc. Florisil was added and the suspension was stirred vigorously for 30 min. The resultant suspension was filtered through short pad of silica gel (1 cm, EtOAc) and concentrated. The crude material was purified by flash chromatography on silica gel (5% then 15% EtOAc in hexanes) to give alcohol S-8 (1.32 g, 85%).

To a solution of propargylic alcohol S-8 (1.32 g, 1.44 mmol) in CH$_2$Cl$_2$ (28 mL) were added NaHCO$_3$ (1.21 g, 14.4 mmol) and Dess-Martin periodinane (916 mg, 2.16 mmol) at room temperature and the reaction mixture was stirred for 1 h at room temperature. The reaction was quenched with 10 wt. % Na$_2$S$_2$O$_3$ aq. and sat. NaHCO$_3$ aq. and vigorously stirred for 30 min. The aqueous phase was extracted with CH$_2$Cl$_2$ three times and the combined organic phases were dried over Na$_2$SO$_4$ and concentrated under vacuum. The residue was purified by flash column chromatography on silica gel (5% EtOAc in hexanes) to provide ynone 14a (1.28 g, 97%) as colorless oil.

14a: $[\alpha]^{20}_D$ −33.8 (c 1.0, CHCl$_3$). $^1$H NMR (600 MHz, C$_6$D$_6$) δ: 5.72 (1H, d, J=2.9 Hz, H-11), 5.70 (1H, ddd, J=1.5, 1.2, 1.0 Hz, C19=CHH), 5.55 (1H, d, J=1.5 Hz, C19=CHH), 4.42 (1H, ddd, J=9.9, 9.4, 4.8 Hz, H-6), 4.22 (1H, dd, J=6.6, 2.9 Hz, H-10), 4.16 (1H, dd, J=2.2, 2.1 Hz, H-8), 4.00 (1H, dddd, J=9.8, 8.2, 5.3, 3.2 Hz, H-17), 3.88 (1H, dd, J=6.6, 2.2 Hz, H-9), 3.85-3.76 (1H, m, H-3), 3.36 (3H, s, OCH$_3$), 2.90 (1H, dd, J=9.4, 2.1 Hz, H-7), 2.75 (1H, ddd, J=17.9, 8.8, 5.3 Hz, H-15a), 2.59 (1H, ddd, J=17.9, 8.8, 6.4 Hz, H-15b), 2.48 (1H, dd, J=15.2, 8.2 Hz, H-2a), 2.33 (1H, ddd, J=14.6, 8.2, 1.0 Hz, H-18a), 2.29 (1H, ddd, J=14.6, 5.3, 1.2 Hz, H-18b), 2.29-2.23 (1H, m, H-5a), 2.13 (1H, dd, J=15.2, 5.0 Hz, H-2b), 1.90 (1H, dddd, J=14.7, 8.8, 6.4, 3.2 Hz, H-16a), 1.66 (1H, dddd, J=14.7, 9.8, 8.8, 5.3 Hz, H-16b), 1.51-1.37 (3H, m, H-4a, 4b, 5b), 1.13 (9H, s, SiC(CH$_3$)$_3$), 1.06 (9H, s, SiC(CH$_3$)$_3$), 0.90 (9H, s, SiC(CH$_3$)$_3$), 0.44 (3H, s, SiCH$_3$), 0.32 (3H, s, SiCH$_3$), 0.32 (3H, s, SiCH$_3$), 0.27 (3H, s, SiCH$_3$), 0.05 (6H, s, 2×SiCH$_3$). $^{13}$C NMR (125 MHz, C$_6$D$_6$) δ: 184.5, 170.9, 128.9, 105.9, 92.4, 86.8, 82.2, 79.3, 74.6, 73.0, 70.1, 65.2, 64.0, 60.3, 53.4, 51.1, 42.2, 40.8, 31.0, 30.9, 29.3, 26.6 (3C), 26.4 (3C), 26.3 (3C), 19.1, 18.9, 18.4, −3.2, −3.6, −3.8, −4.4, −4.46, −4.51. HRMS (ESI) m/z: [M+H]$^+$ calcd for C$_{39}$H$_{71}$ClIO$_8$Si$_3$, 913.3184; found, 913.3212.

Compounds E-15a and Z-15a

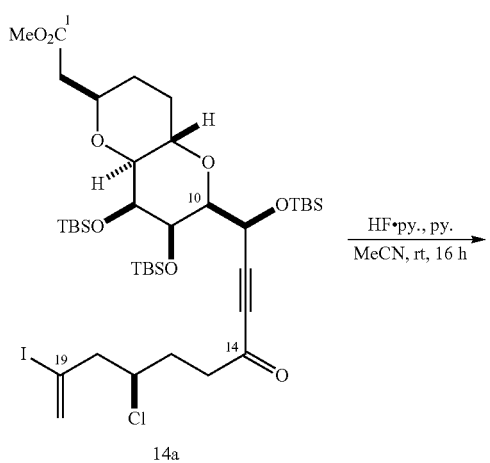

14a

HF·py., py.
MeCN, rt, 16 h

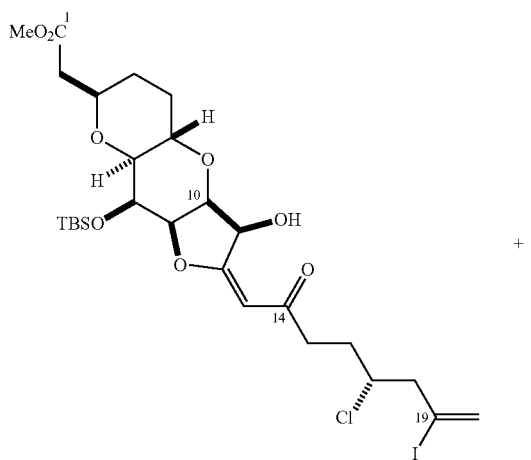

E-15a
62%

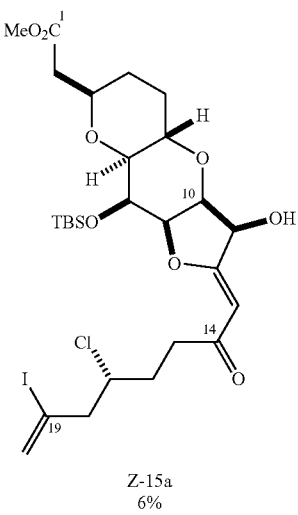

Z-15a
6%

To a 0° C. solution of ynone 14a (513 mg, 0.561 mmol) in pyridine (4.53 mL, 56.1 mmol) and MeCN (11.2 mL) in a plastic vial was added HF•pyridine complex (70% HF content, 1.45 mL, 56.1 mmol) and stirred at room temperature for 16 h. The reaction was cooled to 0° C. and carefully neutralized with sat. NaHCO$_3$ aq. and solid NaHCO$_3$. The mixture was extracted with EtOAc four times, dried over Na$_2$SO$_4$, and concentrated under reduced pressure. H NMR of the crude material showed 10:1 ratio of E-15a and Z-5a. The crude material was purified by flash column chromatography on silica gel eluted with 10%, 17.5% (for E-15a), and then 30% (for Z-15a) EtOAc in hexanes to afford E-15a (238 mg, 62%) and Z-15a (23.0 mg, 6%). Since these E- and Z-compounds are in equilibrium, purified material E-15a was immediately used for the next step without further purification.

E-15a: $[\alpha]^{20}_D$ −125.3 (c 0.12, CHCl$_3$). $^1$H NMR (600 MHz, C$_6$D$_6$) δ: 5.75 (1H, d, J=0.8 Hz, H-13), 5.73 (1H, ddd, J=1.5, 1.2, 0.9 Hz, C19=CHH), 5.57 (1H, d, J=1.5 Hz, C19=CHH), 5.10 (1H, ddd, J=7.9, 7.3, 0.8 Hz, H-11), 4.86 (1H, d, J=7.3 Hz, C11-OH), 4.30 (1H, ddd, J=10.5, 9.8, 4.8 Hz, H-6), 4.08 (1H, dddd, J=9.8, 7.6, 5.9, 3.2 Hz, H-17), 3.91 (1H, dd, J=4.7, 1.6 Hz, H-8), 3.85 (1H, dd, J=8.5, 7.9 Hz, H-10), 3.78 (1H, dd, J=8.5, 4.7 Hz, H-9), 3.68 (1H, dddd, J=10.9, 8.8, 4.3, 1.9 Hz, H-3), 3.39 (3H, s, OCH$_3$), 2.54 (1H, dd, J=9.8, 1.6 Hz, H-7), 2.53 (1H, ddd, J=17.1, 8.5, 5.3 Hz, H-15a), 2.42-2.34 (3H, m, H-15b, 18a, 18b), 2.33 (1H, dd, J=15.5, 8.8 Hz, H-2a), 2.04-1.96 (3H, m, H-2b, 5a, 16a), 1.73 (1H, dddd, J=14.6, 9.8, 8.5, 5.3 Hz, H-16b), 1.27-1.15 (2H, m, H-4a, 5b), 1.02 (9H, s, SiC(CH$_3$)$_3$), 0.98-0.91 (1H, m, H-4b), 0.19 (3H, s, SiCH$_3$), 0.16 (3H, s, SiCH$_3$). $^{13}$C NMR (125 MHz, C$_6$D$_6$) δ: 198.0, 176.5, 170.9, 128.8, 106.3, 102.3, 77.4, 77.1, 74.7, 71.1, 69.7, 67.7, 66.0, 60.9, 53.6, 51.1, 40.5, 40.2, 31.9, 30.1, 29.9, 26.0 (3C), 18.7, −4.4, −4.6. HRMS (ESI) m/z: [M+H]$^+$ calcd for C$_{27}$H$_{43}$ClIO$_8$Si, 685.1455; found, 685.1455.

Compounds 16 and 6a

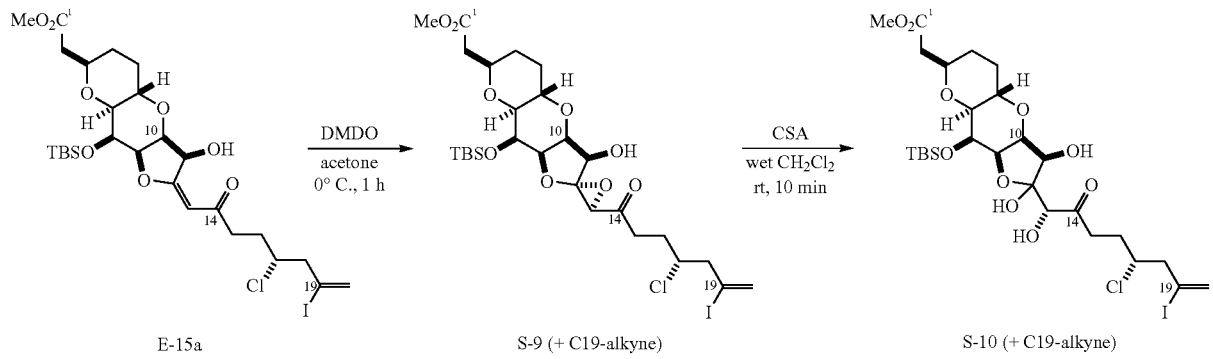

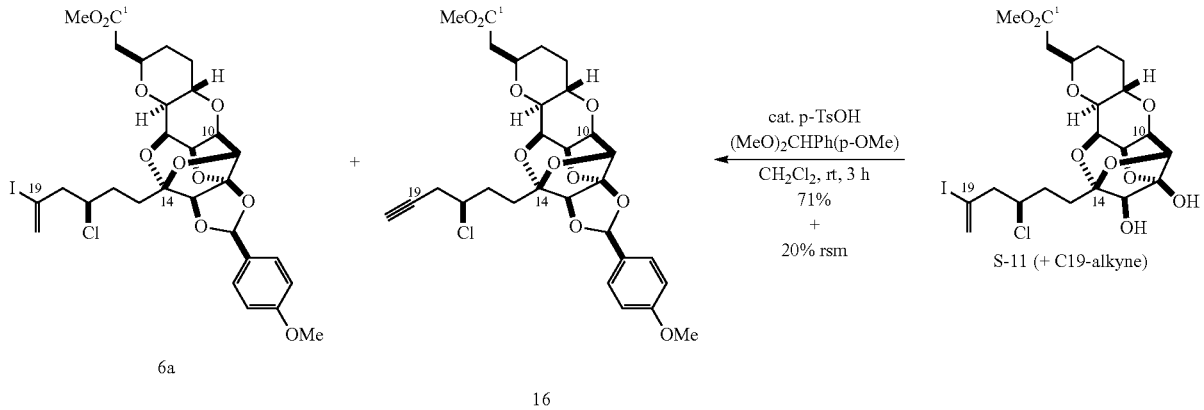

To a solution of enone E-15a (238 mg, 0.347 mmol) in acetone (11 mL) at 0° C. was dropped DMDO solution (0.08 M in acetone, 8.7 mL, 0.69 mmol) over 30 min. The reaction was further stirred for 30 min at 0° C. and the solvent was removed by a stream of nitrogen to give crude epoxide S-9.

The residue S-9 was dissolved in $CH_2Cl_2$ (6.9 mL) and added CSA in wet $CH_2Cl_2$ solution (1 mg/mL, 0.35 mL) at room temperature.

After evaporation of the solvent, the obtained triol S-10 was dissolved in MeCN (6.9 mL) and added HF·pyridine (70% HF content, 0.90 mL, 35 mmol) at room temperature. The reaction mixture was stirred for 2 h at room temperature and then carefully quenched with sat. $NaHCO_3$ aq. and solid $NaHCO_3$ at 0° C. The mixture was extracted with EtOAc four times and the combined organic phases were dried over $Na_2SO_4$ and concentrated under vacuum. Purification of the crude material by flash column chromatography on silica gel (40% then 60% EtOAc in hexanes) gave polycyclic ketal S-11 (128 mg, 63%) as white foam.

To a solution of diol S-11 in $CH_2Cl_2$ (20 mL) were added p-anisaldehyde dimethyl acetal (0.348 mL, 2.05 mmol) and p-TsOH·$H_2O$ (1.5 mg, 8.2 μmol) at room temperature. The pale violet solution was stirred for 3 h at room temperature and quenched with $Et_3N$ (0.1 μL, turned to colorless clear solution) and sat. $NaHCO_3$ aq. The aqueous phase was extracted with EtOAc three times and the combined organic phases were dried over $Na_2SO_4$ and concentrated under vacuum. The residue was purified by flash column chromatography on silica gel ($CH_2Cl_2$ to remove excess dimethyl acetal, 30% EtOAc in hexanes to collect desired product, then 60% EtOAc in hexanes to recover starting material) to provide a mixture of anisylidene acetal 6a and 16 (204 mg, 71%, 2:1) along with recovery of starting material S-11 (47.5 mg, 20% rsm). These iodoolefin 6a and terminal acetylene 16 was separated by HPLC under the following conditions; column: Zobrax SIL, flow rate: 5 mL/min, eluent: 30% EtOAc in hexanes: retention time, 41.3 min for 6a and 48.0 min for 16.

6a: $[\alpha]^{20}_D$ −50.6 (c 1.00, $CHCl_3$). $^1$H NMR (600 MHz, $C_6D_6$) δ: 7.34 (2H, d, J=8.8 Hz, ArH), 6.70 (2H, d, J=8.8 Hz, ArH), 6.11 (1H, s, ArCH), 5.77 (1H, d, J=1.2 Hz, C19=CHH), 5.62 (1H, d, J=0.9 Hz, C19=CHH), 4.49 (1H, dd, J=3.4, 1.2 Hz, H-8), 4.41-4.35 (1H, m, H-6), 4.37 (1H, dd, J=5.3, 1.2 Hz, H-11), 4.16 (1H, dddd, J=9.4, 8.5, 5.0, 3.5 Hz, H-17), 4.05 (1H, s, H-13), 4.02 (1H, dd, J=6.4, 5.3 Hz, H-10), 3.75 (1H, ddd, J=6.4, 3.4, 1.2 Hz, H-9), 3.74-3.69 (1H, m, H-3), 3.32 (3H, s, $CO_2CH_3$), 3.22 (3H, s, ArOCH$_3$), 2.57-2.48 (3H, m, H-2a, 7, 18a), 2.48-2.44 (1H, m, H-15a), 2.44 (1H, dd, J=15.2, 8.5 Hz, H-18b), 2.24 (1H, dddd, J=13.5, 9.4, 6.7, 4.1 Hz, H-16a), 2.15 (1H, dd, J=15.8, 5.0 Hz, H-2b), 2.19-2.11 (1H, m, H-16b), 2.07 (1H, ddd, J=13.2, 11.4, 4.1 Hz. H-15b), 2.04-1.98 (1H, m, H-5a), 1.38-1.32 (1H, m, H-4a), 1.30-1.16 (2H, m, H-4b, 5b). $^{13}$C NMR (125 MHz, $C_6D_6$) δ: 170.9, 161.4, 128.7 (3C), 128.4, 118.7, 114.1 (2C), 109.2, 109.0, 106.7, 89.7, 83.7, 78.7, 76.2, 74.7, 74.2, 73.9, 68.3, 61.1, 54.7, 53.2, 51.1, 40.5, 31.7, 31.4, 30.6, 30.4. HRMS (ESI) m/z: [M+H]$^+$ calcd for $C_{29}H_{35}ClIO_{10}$, 705.0958; found, 705.0954.

16: $^1$H NMR (600 MHz, $C_6D_6$) δ: 7.36-1.29 (2H, m, ArR), 6.73-6.66 (2H, m, ArH), 6.09 (1H, s, ArCH), 4.46 (1H, dd, J=3.5, 1.5 Hz, H-8), 4.37 (1H, ddd, J=10.0, 10.0, 4.7 Hz, H-6), 4.34 (1H, dd, J=5.3, 1.5 Hz, H-11), 4.02 (1H, s, H-13), 4.01-3.94 (2H, m, H-10, 17), 3.77-3.73 (1H, m, H-3), 3.72 (1H, ddd, J=6.4, 3.5, 1.5 Hz, H-9), 3.31 (3H, s, $CO_2CH_3$), 3.22 (3H, s, ArOCH$_3$), 2.55 (1H, dd, J=15.8, 7.9 Hz, H-2a), 2.50-2.42 (4H, m, H-7, 15a, 16a, 18a), 2.39 (1H, ddd, J=17.0, 6.4, 2.6 Hz, 11-16b), 2.16 (1H, dd, J=15.8, 4.7 Hz, H-2b), 2.15-2.07 (2H, m, 11-15b, 18b), 2.02-1.96 (1H, m, H-5a), 1.90 (1H, t, J=2.6 Hz, C≡CH), 1.39-1.33 (1H, m, H-4a), 1.29-1.22 (2H, m, H-4b, 5b). $^{13}$C NMR (100 MHz, $C_6D_6$) δ: 171.0, 161.4, 128.7 (2C), 128.4, 118.7, 114.1 (2C), 109.10, 109.07, 89.8, 83.7, 80.1, 78.7, 76.2, 74.6, 74.1, 73.9, 71.7, 68.3, 59.9, 54.7, 51.1, 40.6, 31.5, 31.4, 30.6, 30.3, 28.8. HRMS (ESI) m/z: [M+Na]$^+$ calcd for $C_{29}H_{33}ClO_{10}Na$, 599.1654; found, 599.1665.

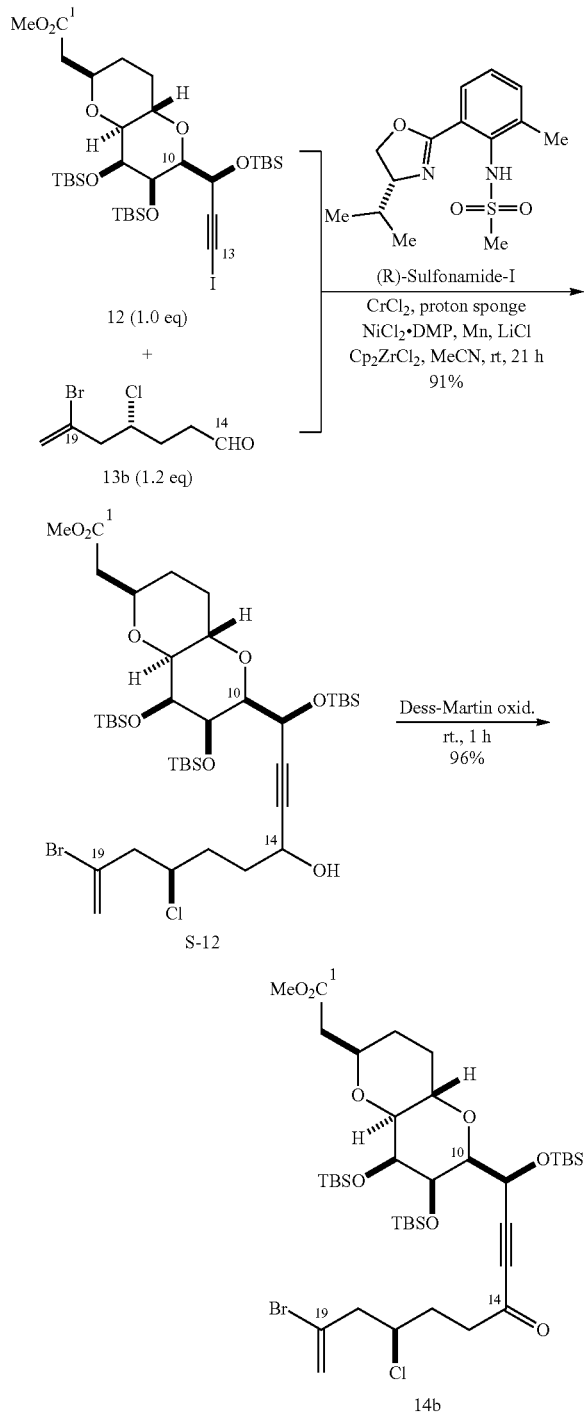

Compound 14b

To a mixture of CrCl$_2$ (47.0 mg, 0.382 mmol), (R)-sulfonamide ligand I (131 mg, 0.420 mmol), and proton sponge (89.9 mg, 0.420 mmol) in a glove box was added MeCN (4.8 mL) and stirred for 1 h at room temperature. In a separate flask, iodide 12 (1.47 g, 1.91 mmol), aldehyde 13b (518 mg, 2.29 mmol), NiCl$_2$·2,9-diethyl-1,10-phenanthroline complex (NiCl$_2$-DEP, 0.070 mg, 0.00019 mmol, doped in LiCi), LiCl (162 mg, 3.82 mmol), Mn (210 mg, 3.82 mmol), Cp$_2$ZrCl$_2$ (558 mg, 1.91 mmol) were mixed together and the Cr-complex solution was transferred to the flask. Additional NiCl$_2$-DEP (0.070 mg each, 0.00019 mmol) was added after 7 and 19 h and the reaction was further stirred for 2 h at room temperature. The reaction was removed from the glove box and diluted with EtOAc. Florisil was added and the suspension was stirred vigorously for 30 min. The resultant suspension was filtered through short pad of silica gel (1 cm, EtOAc) and concentrated. The crude material was purified by flash chromatography on silica gel (5% then 15% EtOAc in hexanes) to give alcohol S-12 (1.51 g, 91%).

To a solution of propargylic alcohol S-12 (1.51 g, 1.74 mmol) in CH$_2$Cl$_2$ (35 mL) were added NaHCO$_3$ (1.46 g, 17.4 mmol) and Dess-Martin periodinane (1.11 g, 2.61 mmol) at room temperature and the reaction mixture was stirred for 1 h at room temperature. The reaction was quenched with 10 wt. % Na$_2$S$_2$O$_3$ aq. and sat. NaHCO$_3$ aq. and vigorously stirred for 30 min. The aqueous phase was extracted with CH$_2$Cl$_2$ three times and the combined organic phases were dried over Na$_2$SO$_4$ and concentrated under vacuum. The residue was purified by flash column chromatography on silica gel (5% EtOAc in hexanes) to provide ynone 14b (1.44 g, 96%) as colorless oil.

14b: [α]$^{20}_D$ −31.8 (c 0.50, CHCl$_3$). $^1$H NMR (600 MHz, C$_6$D$_6$) δ: 5.72 (1H, d, J=2.9 Hz, H-11), 5.27 (1H, d, J=1.8 Hz, C19=CHH), 5.24 (1H, ddd, J=1.8, 1.1, 0.7 Hz, C19=CHH), 4.41 (1H, ddd, J=9.9, 9.5, 4.8 Hz, H-6), 4.21 (1H, dd, J=6.6, 2.9 Hz, H-10), 4.16 (1H, dd, J=2.2, 2.1 Hz, H-8), 4.03 (1H, dddd, J=9.8, 8.5, 5.2, 3.2 Hz, H-17), 3.88 (1H, dd, J=6.6, 2.2 Hz, H-9), 3.84-3.77 (1H, m, H-3), 3.36 (3H, s, OCH$_3$), 2.90 (1H, dd, J=9.5, 2.1 Hz, H-7), 2.75 (1H, ddd, J=17.9, 8.8, 5.0 Hz, H-15a), 2.59 (1H, ddd, J=17.9, 8.8, 6.4 Hz, H-15b), 2.48 (1H, dd, J=15.2, 8.5 Hz, H-2a), 2.38 (1H, ddd, J=14.9, 8.5, 0.7 Hz, H-18a), 2.30 (1H, ddd, J=14.9, 5.2, 1.1 Hz, H-18b), 2.28-2.24 (1H, m, H-5a), 2.12 (1H, dd, J=15.2, 4.7 Hz, H-2b), 1.90 (1H, dddd, J=14.8, 8.8, 6.4, 3.2 Hz, H-16a), 1.65 (1H, dddd, J=14.8, 9.8, 8.8, 5.0 Hz, H-16b), 1.52-1.38 (3H, m, H-4a, 4b, 5b), 1.13 (9H, s, SiC(CH$_3$)$_3$), 1.06 (9H, s, SiC(CH$_3$)$_3$), 0.90 (9H, s, SiC(CH$_3$)$_3$), 0.43 (3H, s, SiCH$_3$), 0.32 (3H, s, SiCH$_3$), 0.32 (3H, s, SiCH$_3$), 0.27 (3H, s, SiCH$_3$), 0.05 (6H, s, 2×SiCH$_3$). $^{13}$C NMR (125 MHz, C$_6$D$_6$) δ: 184.5, 170.9, 129.3, 120.1, 92.4, 86.8, 82.2, 79.3, 74.6, 73.0, 70.9, 65.2, 64.0, 59.1, 51.1, 50.0, 42.2, 40.8, 31.1, 30.9, 29.2, 26.6 (3C), 26.4 (3C), 26.3 (3C), 19.1, 18.9, 18.4, −3.2, −3.6, −3.8, −4.3, −4.4, −4.5. HRMS (ESI) m/z: [M+Na]$^+$ calcd for C$_{39}$H$_{70}$BrClO$_8$Si$_3$Na, 887.3143; found, 887.3113.

Compounds E-15b and Z-15b

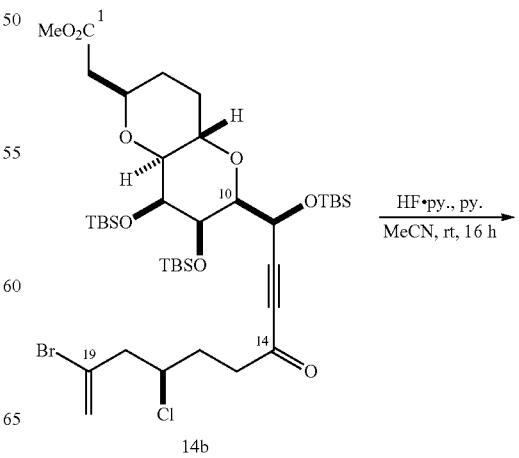

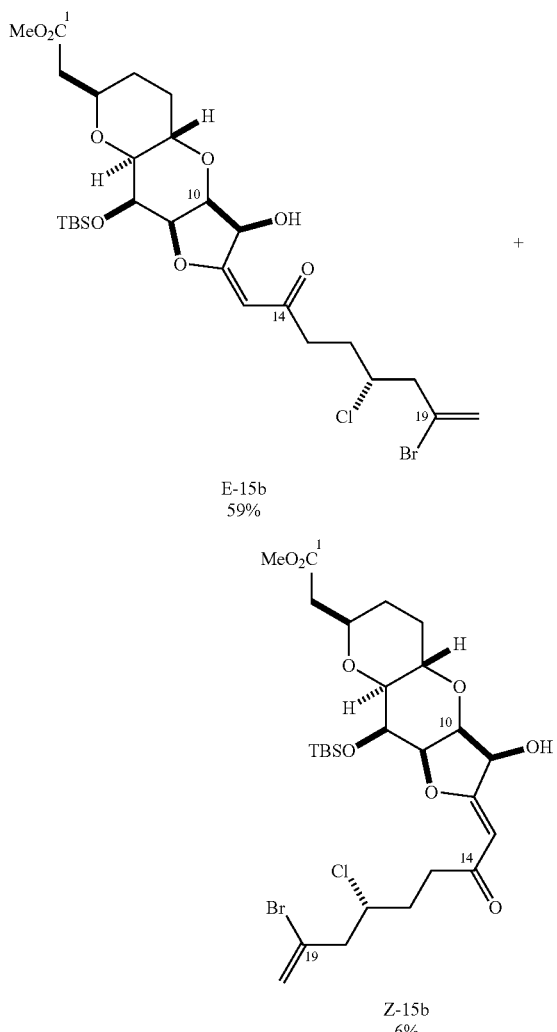

E-15b
59%

Z-15b
6%

To a 0° C. solution of ynone 14b (1.34 g, 1.55 mmol) in pyridine (12.5 mL, 155 mmol) and MeCN (31 mL) in a plastic vial was added HF•pyridine complex (70% HF content, 4.03 mL, 155 mmol) and stirred for 16 h at room temperature. The reaction was cooled to 0° C. and carefully neutralized with sat. NaHCO$_3$ aq. and solid NaHCO$_3$. The mixture was extracted with EtOAc four times, dried over Na$_2$SO$_4$, and concentrated under reduced pressure. $^1$H NMR of the crude material showed 10:1 ratio of E-15b and Z-15b. The crude material was purified by flash column chromatography on silica gel eluted with 10%, 17.5% (for E-15b), and then 30% (for Z-15b) EtOAc in hexanes to afford E-15b (581 mg, 59%) and Z-15b (59.1 mg, 6%). Since these two compounds are in equilibrium, purified material, E-15b was immediately used for the next step without further purification.

E-15b: [α]$^{20}_D$ −135.2 (c 0.63, CHCl$_3$). $^1$H NMR (600 MHz, C$_6$D$_6$) δ: 5.75 (1H, d, J=1.2 Hz, H-13), 5.29 (1H, d, J=1.8 Hz, C19=CHH), 5.28 (1H, ddd, J=1.8, 1.2, 0.7 Hz, C19=CHH), 5.10 (1H, ddd, J=7.6, 7.4, 1.2 Hz, H-11), 4.85 (1H, d, J=7.6 Hz, C11-OH), 4.29 (1H, ddd, J=10.3, 10.0, 4.7 Hz, H-6), 4.12 (1H, dddd, J=9.8, 8.2, 5.3, 3.5 Hz, H-17), 3.91 (1H, dd, J=4.7, 1.8 Hz, H-8), 3.85 (1H, dd, J=8.6, 7.4 Hz, H-10), 3.77 (1H, dd, J=8.6, 4.7 Hz, H-9), 3.68 (1H, dddd, J=11.1, 8.8, 4.2, 2.1 Hz, H-3), 3.39 (3H, s, OCH$_3$), 2.54 (1H, dd, J=10.0, 1.8 Hz, H-7), 2.54 (1H, ddd, J=17.0, 8.2, 5.3 Hz, H-15a), 2.44 (1H, ddd, J=14.6, 8.2, 0.7 Hz, H-18a), 2.37 (1H, ddd, J=14.6, 5.3, 1.2 Hz, H-18b), 2.37 (1H, ddd, J=17.0, 8.2, 6.0 Hz, H-15b), 2.33 (1H, dd, J=15.2, 8.8 Hz, H-2a), 2.04-1.97 (3H, m, H-2b, 5a, 16a), 1.73 (1H, dddd, J=14.6, 9.8, 8.2, 5.3 Hz, H-16b), 1.27-1.15 (2H, m, H-4a, 5b), 1.01 (9H, s, SiC(CH$_3$)$_3$), 0.98-0.90 (1H, m, H-4b), 0.18 (3H, s, SiCH$_3$), 0.15 (3H, s, SiCH$_3$). $^{13}$C NMR (125 MHz, C$_6$D$_6$) δ: 197.9, 176.4, 170.9, 129.7, 120.0, 102.3, 77.3, 77.0, 74.7, 71.2, 69.6, 67.7, 66.0, 59.8, 51.1, 50.1, 40.5, 40.2, 32.1, 30.1, 29.9, 26.0 (3C), 18.7, −4.4, −4.6. HRMS (ESI) m/z: [M+H]$^+$ calcd for C$_{27}$H$_{43}$BrClO$_8$Si, 637.1594; found, 637.1564.

Compound S-15

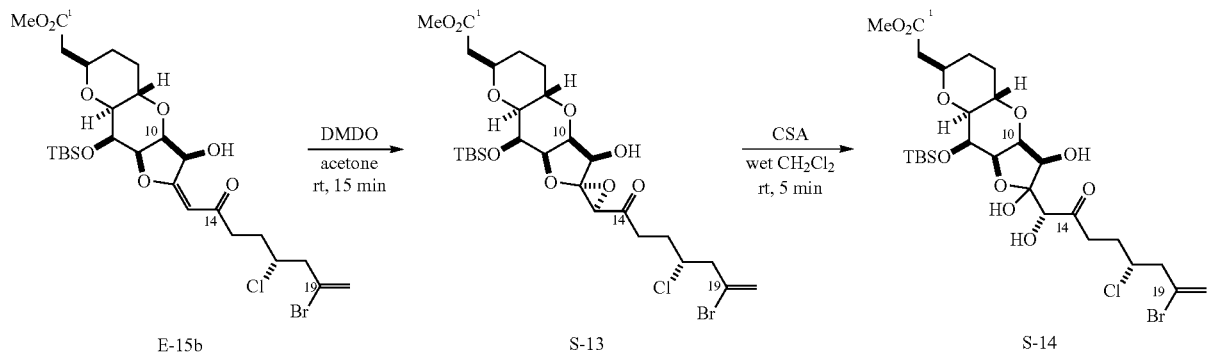

HF•py.
MeCN, rt, 3 h
92% in 3 steps

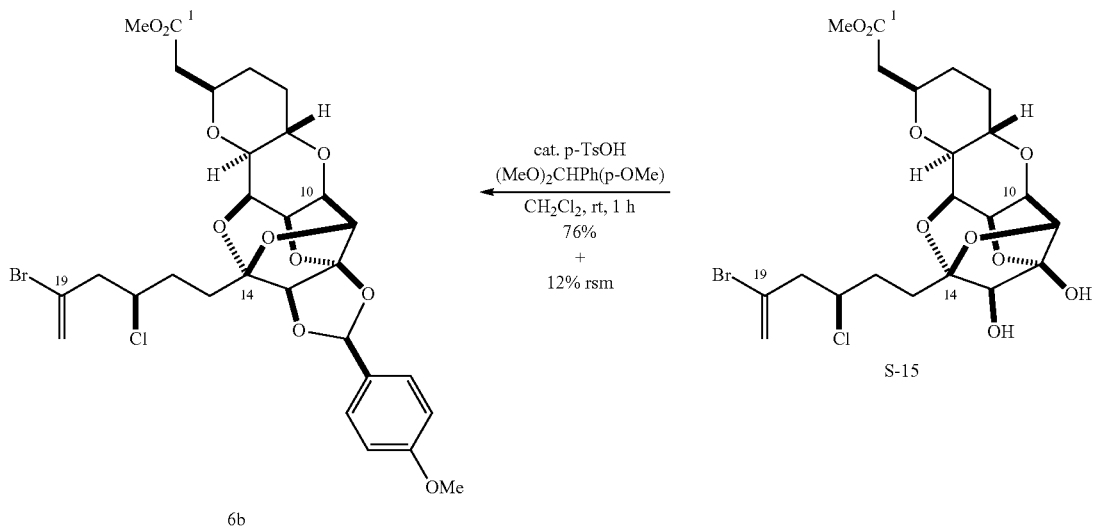

To an acetone (18 mL) solution of E-15b (581 mg, 0.911 mmol) in a plastic vial was added DMDO solution (0.08 M in acetone, 22.8 mL, 1.82 mmol) in one portion at room temperature. After stirring for 15 min at room temperature, the reaction mixture was concentrated by a stream of nitrogen in a fume hood to give epoxide S-13.

The crude material S-13 was dissolved in $CH_2Cl_2$ (9.0 mL) and treated with CSA in wet $CH_2Cl_2$ solution (1 mg/mL, 2.0 mL) at room temperature. After stirring for 5 min at room-temperature, the solvent was removed to afford triol S-14.

The crude product S-14 was dissolved in MeCN (18 mL) and HF•pyridine (70% HF content, 2.37 mL, 91.1 mmol) was added to the solution at room temperature. The reaction mixture was stirred for 3 h at room temperature and then carefully quenched with sat. $NaHCO_3$ aq. and solid $NaHCO_3$ at 0° C. The mixture was extracted with EtOAc four times and the combined organic phases were dried over $Na_2SO_4$ and concentrated under vacuum. Purification of the residue by flash column chromatography on silica gel (40% then 80% EtOAc in hexanes) gave polycyclic ketal S-15 (450 mg, 92% in 3 steps) as a pale yellow amorphous.

To a solution of diol S-15 (450 mg, 0.835 mmol) in $CH_2Cl_2$ (84 mL) were added p-anisaldehyde dimethyl acetal (0.71 mL, 4.18 mmol) and p-TsOH (3.2 mg, 16.7 μmol) at room temperature. The mixture was stirred for 1 h at room temperature and during that time the reaction color turned to clear pink. The reaction was quenched with triethylamine (0.1 mL, pink color disappeared) and sat. $NaHCO_3$ aq. The organic phase was separated and the aqueous phase was extracted with EtOAc three times. Combined organic phases were dried over $Na_2SO_4$ and concentrated under vacuum. The crude material was purified by flash column chromatography on silica gel ($CH_2Cl_2$ to remove excess reagent, 20%, 30% for desired product, 40%, then 60% for starting material) to afford acetal 6b (416 mg, 76%) as a white solid along with recovery of starting material S-15 (53.0 mg, 12% rsm).

6b: Mp 128-130° C. $[\alpha]^{20}_D$ −48.4 (c 0.50, $CHCl_3$). $^1H$ NMR (600 MHz, $C_6D_6$) δ: 7.33 (2H, d, J=8.8 Hz, ArH), 6.70 (2H, d, J=8.8 Hz, ArH), 6.11 (1H, s, ArCH), 5.34 (1H, d, J=1.8 Hz, C19=CHH), 5.32-5.30 (1H, m, C19=CHH), 4.48 (1H, dd, J=3.4, 1.5 Hz, H-8), 4.42-4.35 (1H, m, H-6), 4.36 (1H, dd, J=5.4, 1.3 Hz, H-11), 4.18 (1H, dddd, J=9.1, 7.3, 5.1, 5.1 Hz, H-17), 4.05 (1H, s, H-13), 4.02 (1H, dd, J=6.5, 5.4 Hz, H-10), 3.74 (1H, ddd, J=6.5, 3.4, 1.3 Hz, H-9), 3.74-3.69 (1H, m, H-3), 3.31 (3H, s, $CO_2CH_3$), 3.21 (3H, s, ArOCH$_3$), 2.57-2.44 (5H, m, H-2a, 7, 15a, 18a, 18b), 2.25 (1H, dddd, J=13.8, 9.1, 6.9, 4.1 Hz, H-16a), 2.15 (1H, dd, J=15.8, 5.0 Hz, H-2b), 2.16-2.10 (1H, m, H-16b), 2.07 (1H, ddd, J=13.5, 11.4, 4.1 Hz, H-15b), 2.04-1.99 (1H, m, H-5a), 1.37-1.32 (1H, m, H-4a), 1.30-1.17 (2H, m, H-4b, 5b). $^{13}C$ NMR (125 MHz, $C_6D_6$) δ: 170.9, 161.4, 129.9, 128.8 (2C), 128.4, 120.0, 118.7, 114.2 (2C), 109.1, 108.9, 89.7, 83.7, 78.7, 76.2, 74.6, 74.1, 73.8, 68.3, 60.1, 54.8, 51.2, 49.7, 40.4, 31.7, 31.5, 30.6, 30.3. HRMS (ESI) m/z: [M+H]$^+$ calcd for $C_{29}H_{35}BrClO_{10}$, 657.1097; found, 657.1115.

The precursor of aldehyde 7, alcohol S-16, was synthesized via two different routes as described in Scheme 8.

Scheme 8.
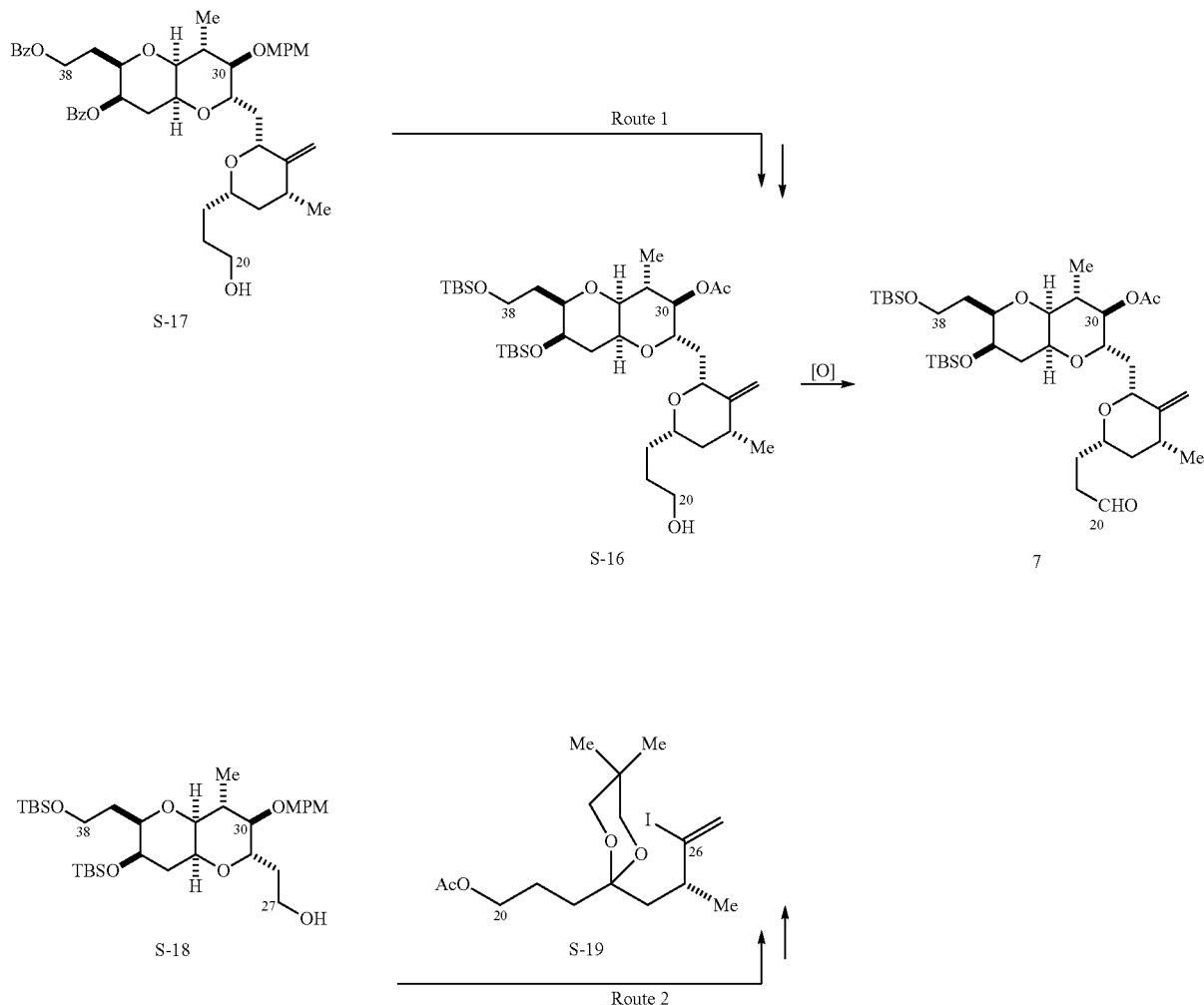
Compound S-16
Route 1,
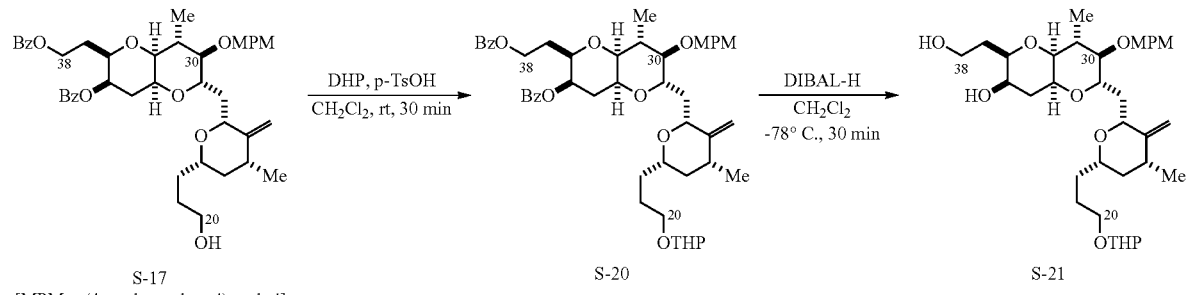

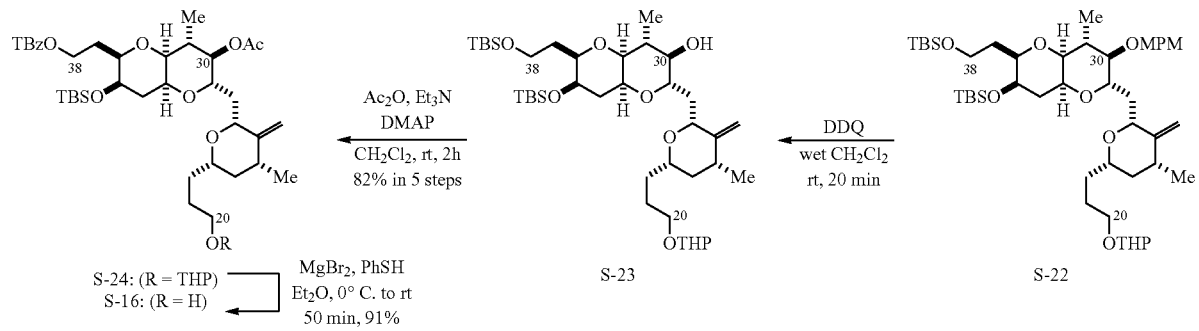

To a solution of alcohol S-17[22] (959 mg, 1.29 mmol) in $CH_2Cl_2$ (13 mL) were added 3,4-dihydro-2H-pyran (DHP, 0.353 mL, 3.87 mmol) and p-TsOH·$H_2O$ (16 mg, 0.064 mmol) at room temperature and stirred for 30 min. The reaction mixture was quenched with sat. $NaHCO_3$ aq., extracted with $CH_2Cl_2$ three times, and dried over $Na_2SO_4$. Removal of the solvent gave crude material S-20, which was used for the next step without further purification.

To a solution of dibenzoate S-20 in $CH_2Cl_2$ at −78° C. was added DIBAL-H solution (1 M in toluene, 5.16 mL, 5.16 mmol) and stirred for 30 min at the same temperature. The reaction was carefully quenched with $Na_2SO_4$—$H_2O$ and warmed up to room temperature. The $CH_2Cl_2$ solution was directly passed through a short plug of silica gel (15 g, 2 cm), which was first washed with 20%, 30%, and 40%, EtOAc in hexanes (80, 80, and 40 mL, respectively), and the desired material was eluted with 0% and 10% MeOH in EtOAc (30 and 250 mL, respectively). The solvent was removed in vacuo to afford the diol S-21 as a colorless oil.

This material was used for the next step without further purification. To a mixture of diol S-21 and 2,6-lutidine (0.900 mL, 7.74 mmol) in $CH_2Cl_2$ (13 mL) was dropped TBSOTf (0.888 mL, 3.87 mmol) at −78° C. and stirred for 1 h at the same temperature. The reaction mixture was quenched with sat. $NaHCO_3$ aq. and then warmed to room temperature. The aqueous phase was extracted with EtOAc three times and the combined organic phases were washed with 1 M HCl and sat. $NaHCO_3$ aq., dried over $Na_2SO_4$, and concentrated under reduced pressure to give S-22.

To a solution of crude MPM-ether S-22 in wet $CH_2Cl_2$ (26 mL) was added 2,3-dichloro-5,6-dicyano-p-benzoquinone (DDQ, 586 mg, 2.58 mmol) in one portion at room temperature and the resultant dark brown solution was vigorously stirred for 20 min at room temperature. The reaction mixture was quenched with 10 wt. % $Na_2S_2O_3$ aq. and sat. $NaHCO_3$ aq., extracted with $CH_2Cl_2$ twice, and dried over $Na_2SO_4$. The solution was passed through a short silica gel column (25 g, 3 cm), which was washed first with $CH_2Cl_2$ (100 mL) to remove p-anisaldehyde and then eluted with $Et_2O$—$CH_2Cl_2$ (1:1, 400 mL). After concentration under vacuum, alcohol S-23 was obtained as pale yellow oil, which was used for the next step without further purification.

To a mixture of alcohol S-23 and triethylamine (1.79 mL, 12.9 mmol) in $CH_2Cl_2$ (13 mL) were added $Ac_2O$ (0.609 mL, 6.45 mmol) and DMAP (47.2 mg, 0.387 mmol) at room temperature and stirred for 2 h at room temperature. The reaction mixture was quenched with sat. $NaHCO_3$ aq. and the aqueous phase was extracted with $CH_2Cl_2$ three times. The combined organic phases were washed with brine, dried over $Na_2SO_4$, and concentrated under vacuum. Purification of the crude material by flash column chromatography on silica gel (3% then 5% EtOAc in hexanes) afforded acetate S-24 (815 mg, 82% in 5 steps) as colorless syrup.

To a solution of THP-ether S-24 (1.03 g, 1.34 mmol) in $Et_2O$ (134 mL) at 0° C. were added thiophenol (freshly distilled, 0.687 mL, 6.70 mmol) and $MgBr_2$[8] (4.93 g, 26.8 mmol) in one portion and the resultant white suspension was gradually warmed to room temperature over 50 min with vigorous stirring (reaction was carefully monitored by TLC to minimize C38 primary TBS-ether deprotection). The reaction mixture was cooled to 0° C., quenched with sat. $NaHCO_3$ aq., and vigorously stirred for 30 min at room temperature. The aqueous phase was extracted with EtOAc three times. Combined organic phases were washed with brine, dried over $MgSO_4$, and concentrated under vacuum. The crude residue was purified by flash column chromatography on silica gel (5% for phenyl 2-tetrahydropyranyl sulfide, 10% for starting material, then 20% EtOAc in hexanes for desired product) to give alcohol S-16 (830 mg, 91%) as a colorless syrup along with recovery of starting material S-24 (23.5 mg, 2% rsm).

S-16: $[\alpha]^{20}_D$ −7.7 (c 0.12, $CHCl_3$). $^1$H NMR (600 MHz, $C_6D_6$) δ: 5.04 (1H, dd, J=8.6, 6.7 Hz, H-30), 5.02 (1H, s, C26=CHH), 4.84 (1H, d, J=1.2 Hz, C26=CHH), 4.45 (1H, ddd, J=8.6, 5.9, 5.0 Hz, H-29), 4.19 (1H, dd, J=7.0, 5.4 Hz, H-27), 3.89 (1H, ddd, J=9.9, 9.6, 4.5 Hz, H-38a), 3.74 (1H, ddd, J=9.9, 5.5, 4.5 Hz, H-38b), 3.68-3.57 (3H, m, H-20a, 20b, 33), 3.51-3.45 (1H, m, H-23), 3.45-3.40 (2H, m, H-35, 36), 3.17 (1H, dd, J=4.6, 3.2 Hz, H-32), 2.33 (1H, ddd, J=14.4, 5.4, 5.0 Hz, H-28a), 2.20 (qdd, J=7.3, 6.7, 4.6 Hz, H-31), 2.17 (1H, ddd, J=14.4, 7.0, 5.9 Hz, H-28b), 2.13-2.00 (4H, m, 20-OH, H-25, 34a, 37a), 1.79-1.68 (2H, m, H-21a, 37b), 1.67 (3H, s, $COCH_3$), 1.66-1.60 (1H, m, H-21b), 1.60-1.53 (1H, m, H-22a), 1.50-1.42 (2H, m, H-22b, 34b), 1.37 (1H, ddd, J=12.6, 4.1, 2.1 Hz, H-24a), 1.22 (3H, d, J=7.3 Hz, C31-$CH_3$), 1.10-1.04 (1H, m, H-24b), 1.01 (18H, s, 2×SiC($CH_3$)$_3$), 0.96 (3H, d, J=6.4 Hz, C25-$CH_3$), 0.11 (3H, s, Si$CH_3$), 0.11 (3H, s, Si$CH_3$), 0.10 (3H, s, Si$CH_3$), 0.04 (3H, s, Si$CH_3$). $^{13}$C NMR (125 MHz, $C_6D_6$) δ: 170.4, 151.9, 104.0, 78.7, 77.5, 75.1, 75.0, 74.8, 70.7, 67.3, 64.7, 62.6, 59.7, 43.2, 39.2, 36.3, 35.6, 35.5, 34.0, 32.6, 29.5, 26.1 (6C), 20.7, 18.5, 18.4, 18.1, 16.6, −4.1, −4.9, −5.2, −5.4. IR (film): 3446, 1742 cm$^{-1}$. HRMS (ESI) m/z: [M+H]$^+$ calcd for $C_{36}H_{69}O_8Si_2$, 685.4525; found, 685.4505.

Compound 7

Route 1,

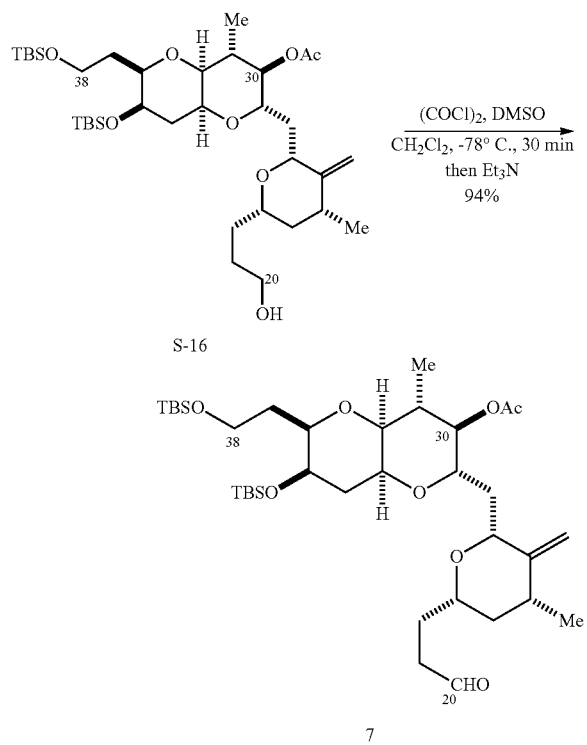

To a solution of oxalyl chloride (74.2 μL, 0.876 mmol) in CH$_2$Cl$_2$ (4.0 mL) at −78° C. was dropped dimethylsulfoxide (124 μL, 1.75 mmol) solution in CH$_2$Cl$_2$ (0.3 mL) over 5 min. The reaction mixture was stirred for 15 min at −78° C. A solution of alcohol S-16 (400 mg, 0.584) in CH$_2$Cl$_2$ (1.5 mL) was added to the reaction at −78° C. over 5 min. The reaction mixture was stirred for 30 min at −78° C. and was added triethylamine (406 μL, 2.92 mmol) at −78° C. After stirring for 10 min at −78° C., the reaction mixture was quenched with sat. NH$_4$Cl aq. The aqueous phase was extracted with CH$_2$Cl$_2$ three times and combined organic phases were dried over Na$_2$SO$_4$ and the solvent was removed in vacuo. The residue was purified by flash column chromatography on silica gel eluted with 8% EtOAc in hexanes to give aldehyde 7 (374 mg, 94%) as a colorless oil. The aldehyde 7 was used for the next step without further purification.

7: $^1$H NMR (600 MHz, C$_6$D$_6$) δ: 9.56 (1H, dd, J=1.5, 1.5 Hz, CHO), 4.99 (1H, br s, C26-CHH), 4.96 (1H, dd, J=8.3, 7.5 Hz, H-30), 4.82 (1H, d, J=1.2 Hz, 26-CHH), 4.38 (1H, ddd, J=8.3, 5.6, 5.6 Hz, H-29), 4.08 (1H, dd, J=6.2, 6.2 Hz, H-27), 3.90 (1H, ddd, J=9.9, 9.6, 4.5 Hz, H-38a), 3.75 (1H, ddd, J=9.9, 5.5, 4.2 Hz, H-38b), 3.59 (1H, ddd, J=4.5, 4.1, 3.7 Hz, H-33), 3.49-3.42 (2H, m, H-35, 36), 3.41-3.34 (1H, m, H-23), 3.18 (1H, dd, J=4.8, 3.7 Hz, H-32), 2.33-2.24 (3H, m, H-21a, 21b, 28a), 2.21 (1H, ddd, J=7.2, 7.2, 5.0 Hz, H-31), 2.15 (1H, ddd, J=14.4, 6.4, 5.6 Hz, H-28b), 2.09-2.00 (3H, m, H-25, 34a, 37a), 1.76-1.71 (1H, m, H-37b), 1.69 (3H, s, COCH$_3$), 1.62-1.56 (2H, m, H-22a, 2b), 1.48 (1H, ddd, J=14.4, 4.5, 4.5 Hz, H-34b), 1.30 (1H, ddd, J=12.5, 4.2, 2.1 Hz, H-24a), 1.21 (3H, d, J=7.3 Hz, C31-CH), 1.02 (9H, s, SiC(CH$_3$)$_3$), 1.01 (9H, s, SiC(CH$_3$)$_3$), 0.93 (3H, d, J=6.4 Hz, C25-CH$_3$), 0.94-0.89 (1H, m, H-24b), 0.11 (3H, s, SiCH$_3$), 0.11 (6H, s, 2×SiCH$_3$), 0.04 (3H, s, SiCH$_3$).

Route 2,

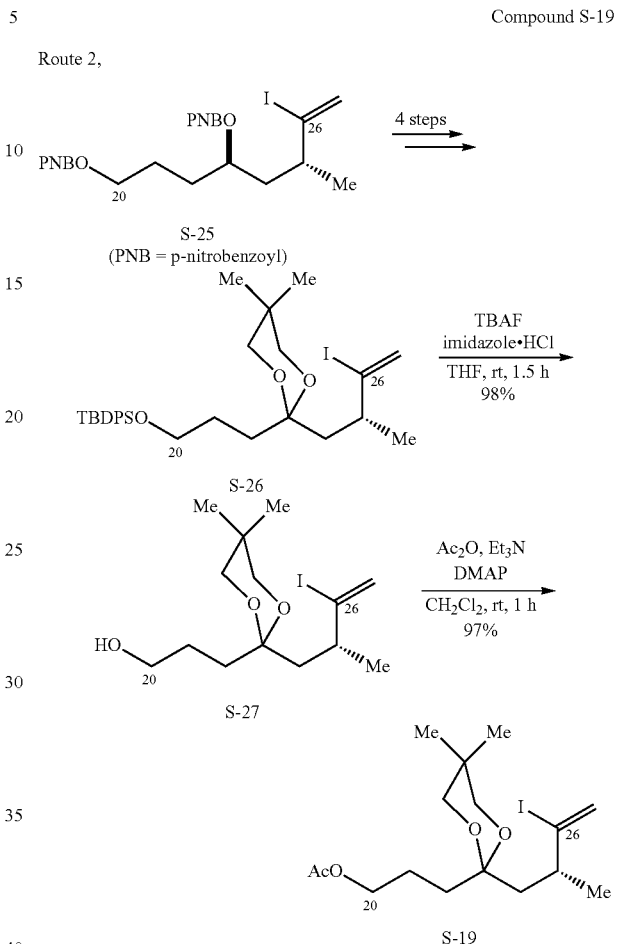

The ketal S-19 was prepared from previously reported compound S-25 (ee: >99%)[24] by the following 4 step sequences. 1) K$_2$CO$_3$, MeOH-THF (1:1), rt, 16 h, 97%. 2) TBDPSCl, Et$_3$N, DMAP, CH$_2$Cl$_2$, rt, 36 h. 3) (COCl)$_2$, DMSO, CH$_2$Cl$_2$, −78° C. then Et$_3$N, −78° C. to rt, 30 min, 91% in 2 steps. 4) CSA, 2,2-dimethyl-1,3-propanediol, benzene, reflux, 12 h, 94%.

To TBDPS ether S-26 (2.37 g, 3.91 mmol) in THF (26 mL) were added imidazole hydrochloride (122 mg, 1.17 mmol) and TBAF solution (1 M in THF, 5.86 mL, 5.86 mmol) at room temperature and the reaction was stirred for 1.5 h at room temperature. Solvent was removed to approximately one third by volume and water was added to the mixture. The aqueous phase was extracted with EtOAc three times and the combined organic phases were dried over Na$_2$SO$_4$ and concentrated under reduced pressure. The crude residue was purified by flash column chromatography on silica gel (3% then 20% EtOAc in hexanes containing 1% of Et$_3$N) to give alcohol S-27 (1.42 g, 98%) as a pale yellow oil.

To alcohol S-27 (1.42 g, 3.86 mmol) in CH$_2$Cl$_2$ (26 mL) were added Et$_3$N (2.15 mL, 15.4 mmol), acetic anhydride (0.729 mL, 7.72 mmol), and 4-dimethylaminopyridine (47 mg, 0.386 mmol) at 0° C. The reaction was stirred for 1 h at room temperature, added MeOH at 0° C., and further stirred for 5 min at room temperature. Sat. NaHCO$_3$ aq. was added to the reaction and the aqueous phase was extracted with CH$_2$Cl$_2$ three times. Combined organic phases were dried over Na$_2$SO$_4$ and evaporated. The crude product was purified by flash column chromatography on silica gel (3% EtOAc in hexanes) to provide acetate S-19 (1.53 g, 97%) as a pale yellow oil.

S-19: [α]$^{20}_D$ −12.8 (c 1.03, CHCl$_3$). $^1$H NMR (500 MHz, C$_6$D$_6$) δ: 5.90 (1H, d, J=1.0 Hz, C=CHH), 5.56 (1H, d, J=1.5 Hz, C=CHH), 4.03 (2H, t, J=6.3 Hz, H-20a,b), 3.35-3.19 (4H, m, OCH$_2$CMe$_2$), 2.30-2.18 (1H, m, H-25), 1.97 (1H, dd, J=14.6, 5.4 Hz, H-24a), 1.83-1.62 (5H, m, 5H), 1.69 (3H, s, COCH$_3$), 1.09 (3H, d, J=6.8 Hz, C25-CH$_3$), 0.72 (s, 3H, CCH$_3$CH$_3$), 0.72 (33, s, CCH$_3$CH$_3$). $^{13}$C NMR (125 MHz, C$_6$D$_6$) δ: 170.1, 124.9, 123.7, 99.8, 70.2, 70.0, 64.6, 41.9, 40.5, 31.2, 29.4, 23.34, 23.28, 22.8, 22.7, 20.5. IR (film): 1736 cm$^{-1}$. HRMS (ESI) m/z: [M+Na]$^+$ calcd for C$_{16}$H$_{27}$IO$_4$Na, 433.0846; found, 433.0866.

mL, 2.89 mmol), and 4-dimethylaminopyridine (8.8 mg, 0.072 mmol) at room temperature. The reaction mixture was stirred at the same temperature for 12 h and was quenched by adding sat. NaHCO$_3$ aq. The aqueous layer was extracted with CH$_2$Cl$_2$ three times and the combined organic layers were dried over Na$_2$SO$_4$ and concentrated in vacuo. The residue was purified by flash column chromatography on silica gel (eluent: 1% then 5% EtOAc in hexanes) to give acetate S-30 (409 mg, 91% in 3 steps) as a pale yellow oil.

To a stirred solution of (1-ethoxy)ethyl ether S-30 (409 mg, 0.661 mmol) in Et$_2$O (22 mL) at 0° C. was added magnesium bromide (365 mg, 1.98 mmol) in one portion The resultant white suspension was gradually warmed to room temperature over 35 min. The reaction mixture was cooled again to 0° C. and was quenched with sat. NaHCO$_3$ aq. and stirred vigorously for 30 min at room temperature. The aqueous layer was extracted with EtOAc three times

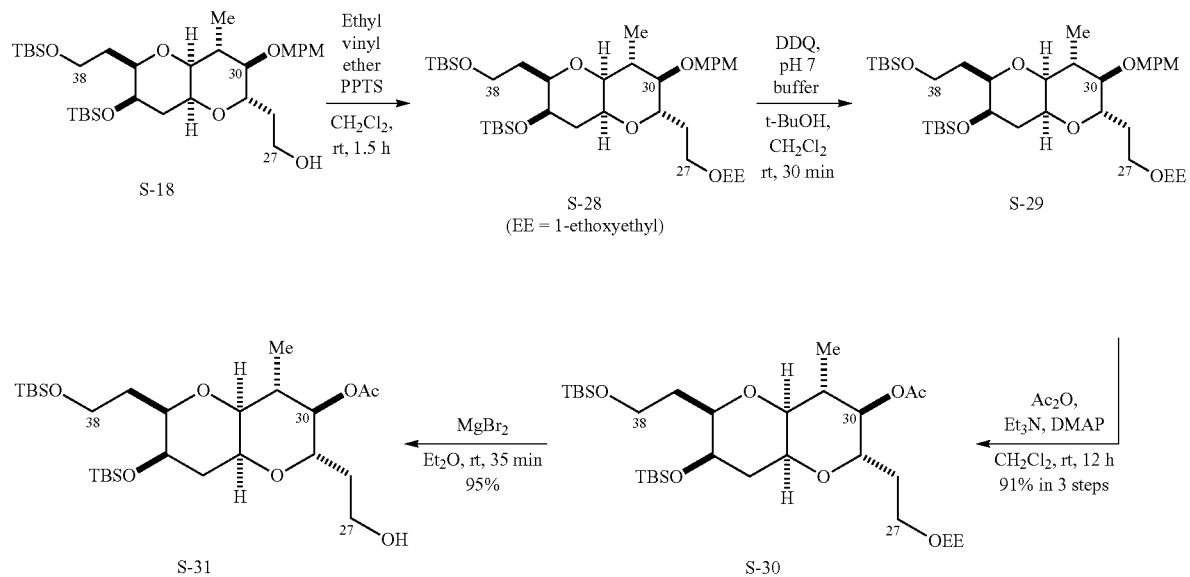

Route 2, Compound S-31

To alcohol S-18[25] (452 mg, 0.723 mmol) in CH$_2$Cl$_2$ (7.2 mL) were added ethyl vinyl ether (0.207 mL, 2.17 mmol) and pyridinium p-toluenesulfonate (9.1 mg, 36.2 μmol) at room temperature. The reaction mixture was stirred for 1.5 h at room temperature and then quenched with sat. NaHCO$_3$ aq. The aqueous layer was extracted with CH$_2$Cl$_2$ three times and the combined organic layers were dried over Na$_2$SO$_4$ and evaporated. The obtained crude material S-28 was used for the next step without further purification.

To a solution of MPM ether S-28 in CH$_2$Cl$_2$ (14 mL), t-BuOH (0.29 mL), and pH 7 phosphate buffer (1.4 mL) was added 2,3-dichloro-5,6-dicyano-p-benzoquinone (328 mg, 1.45 mmol) in one portion at room temperature and the resultant dark brown suspension was vigorously stirred for 30 min at room temperature. The reaction mixture was quenched with sat. NaHCO$_3$ aq. and further stirred for 10 min at room temperature. After partitioning into two layers, aqueous layer was extracted twice with CH$_2$Cl$_2$. The combined organic phases were dried over Na$_2$SO$_4$ and concentrated under reduced pressure to give crude product S-29, which was used for the next step without further purification.

To alcohol S-29 in CH$_2$Cl$_2$ (7.2 mL) were added triethylamine (0.603 mL, 4.34 mmol), acetic anhydride (0.273 and the combined organics were washed with brine, dried over Na$_2$SO$_4$, and concentrated under reduced pressure. The reside was purified by flash column chromatography on silica gel eluted with 10% EtOAc in hexanes to furnish alcohol S-31 (342 mg, 95%) as a colorless oil.

S-31: [α]$^{20}_D$ +2.8 (c 0.80, CHCl$_3$). $^1$H NMR (500 MHz, C$_6$D$_6$) δ: 4.76 (1H, dd, J=9.0, 8.1 Hz, H-30), 4.17 (1H, ddd, J=9.0, 6.8, 4.9 Hz, H-29), 3.87 (1H, ddd, J=9.8, 9.8, 4.4 Hz, H-38a), 3.84-3.79 (1H, m, H-27a), 3.79-3.72 (1H, m, H-27b), 3.70 (1H, ddd, J=9.8, 5.6, 4.2 Hz, H-38b), 3.46-3.33 (3H, m, H-33, 35, 36), 3.09 (1H, dd, J=4.9, 3.4 Hz, H-32), 2.29 (1H, br s, OH), 2.12 (dqd, J=8.1, 7.3, 4.9 Hz, H-31), 2.00 (dddd, J=14.1, 9.7, 4.2, 4.2 Hz, H-37a), 1.92 (1H, ddd, J=14.3, 4.2, 4.2 Hz, H-34a), 1.78-1.71 (2H, m, H-28a, 28b), 1.70-1.64 (1H, m, H-37b), 1.63 (3H, s, COCH$_3$), 1.38 (ddd, J=14.5, 4.5, 4.5 Hz, H, 34b), 1.09 (3H, d, J=7.3 Hz, C31-CH$_3$), 1.01 (9H, s, SiC(CH$_3$)$_3$), 1.00 (9H, s, SiC(CH$_3$)$_3$), 0.10 (3H, s, SiCH$_3$), 0.09 (3H, s, SiCH$_3$), 0.09 (3H, s, SiCH$_3$), 0.03 (3H, s, SiCH$_3$). $^{13}$C NMR (125 MHz, C$_6$D$_6$) δ: 170.0, 78.8, 74.8, 74.5, 73.2, 67.3, 65.0, 60.4, 59.7, 39.1, 35.6, 35.4, 34.4, 26.19 (3C), 26.16 (3C), 20.5, 18.6, 18.5, 16.5, −4.0, −4.9, −5.1, −5.3. IR (film): 3474, 1741 cm$^{-1}$. HRMS (ESI) m/z: [M+Na]$^+$ calcd for C$_{27}$H$_{54}$O$_7$Si$_2$Na, 569.3300; found, 569.3312.

Route 2, Compound S-32

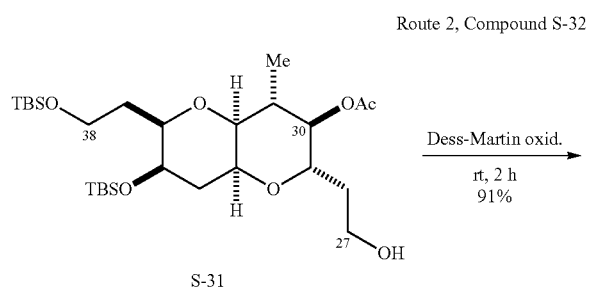

To alcohol S-31 (526 mg, 0.962 mmol) in CH$_2$Cl$_2$ (9.6 mL) were added NaHCO$_3$ (808 mg, 9.62 mmol) and Dess-Martin periodinane (612 mg, 1.44 mmol) at room temperature. The resultant suspension was stirred for 1 h at the same temperature. The reaction mixture was quenched with 10 wt % Na$_2$SO$_3$ aq and sat. NaHCO$_3$ aq and vigorously stirred for another 30 min at room temperature. The aqueous layer was extracted with CH$_2$Cl$_2$ three times. The combined organic layers were dried over Na$_2$SO$_4$ and concentrated under vacuum. The residue was purified by flash column chromatography on silica gel (eluent: 5% EtOAc in hexanes) to give aldehyde S-32 (475 mg, 91%) as a white amorphous.

S-32: $[\alpha]^{20}_D$ −24.0 (c 1.02, CH$_2$Cl$_2$). $^1$H NMR (600 MHz, C$_6$D$_6$) δ: 9.68 (1H, dd, J=2.9, 2.3 Hz, CHO), 4.65 (1H, dd, J=9.4, 7.2 Hz, H-30), 4.58 (1H, ddd, J=9.4, 6.5, 5.9 Hz, H-29), 3.85 (1H, ddd, J=9.7, 9.4, 4.1 Hz, H-38a), 3.68 (1H, ddd, J=9.7, 5.9, 4.1 Hz, H-38b), 3.44 (1H, ddd, J=4.1, 3.5, 3.5 Hz, H-33), 3.40 (1H, ddd, J=9.4, 2.9, 1.8 Hz, H-36), 3.35 (1H, ddd, J=4.1, 3.8, 1.8 Hz, H-35), 3.10 (1H, dd, J=4.1, 3.5 Hz, H-32), 2.46 (1H, ddd, J=15.8, 6.5, 2.3 Hz, H-28a), 2.35 (1H, ddd, J=15.8, 5.9, 2.9 Hz, H-28b), 2.10 (1H, dqd, J=7.2, 7.0, 4.1 Hz, H-31), 1.99 (1H, dddd, J=14.1, 9.4, 4.1, 4.1 Hz, H-37a), 1.95 (1H, ddd, J=14.7, 3.8, 3.5 Hz, H-34a), 1.64 (1H, dddd, J=14.1, 9.4, 5.9, 2.9 Hz, H-37b), 1.61 (3H, s, COCH$_3$), 1.31 (1H, ddd, J=14.7, 4.3, 4.1 Hz, H-34b), 1.05 (3H, d, J=7.0 Hz, C31-CH$_3$), 1.00 (9H, s, SiC(CH$_3$)$_3$), 0.96 (9H, s, SiC(CH$_3$)$_3$), 0.09 (3H, s, SiCH$_3$), 0.08 (3H, s, SiCH$_3$), 0.04 (3H, s, SiCH$_3$), 0.00 (3H, s, SiCH$_3$). $^{13}$C NMR (125 MHz, C$_6$D$_6$) δ: 199.1, 169.9, 78.9, 75.5, 75.2, 68.3, 67.2, 65.1, 59.6, 47.5, 39.5, 35.63, 35.62, 26.15 (3C), 26.12 (30, 20.4, 18.6, 18.5, 16.8, −4.0, −4.9, −5.1, −5.3. IR (film): 1741, 1734 cm$^{-1}$. HRMS (ESI) m/z: [M+NH$_4$]$^+$ calcd for C$_{27}$H$_{56}$NO$_7$Si$_2$, 562.3590; found, 562.3565.

Route 2, Compound S-33

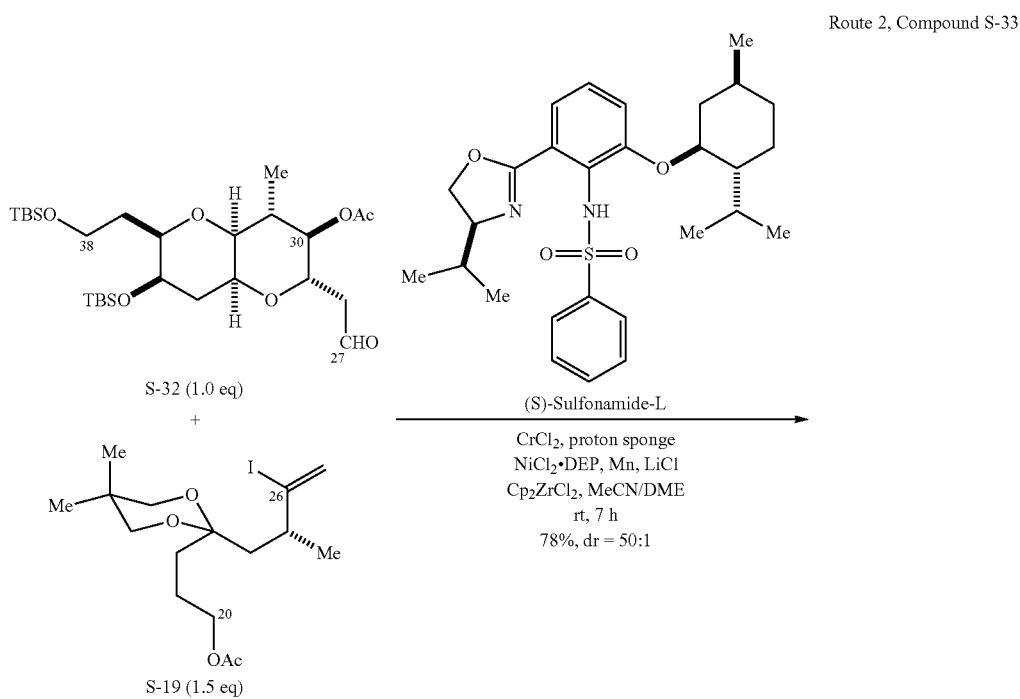

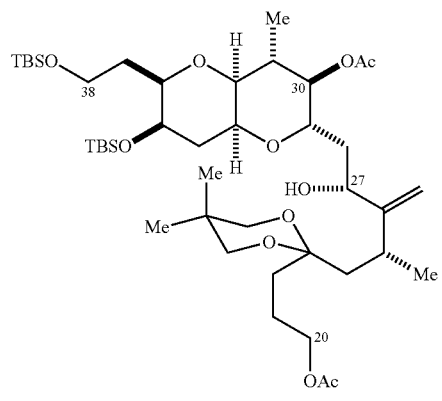

S-33

To a mixture of CrCl$_2$ (10.7 mg, 87.2 µmol), (S)-sulfonamide ligand L (47.9 mg, 95.9 µmol), and proton sponge (20.5 mg, 95.9 µmol) in a glove box was added MeCN (1.65 mL) and the resultant suspension was stirred for 1 h at room temperature. In a separate flask, iodide S-19 (536 mg, 1.31 mmol), aldehyde S-32 (475 mg, 0.872 mmol), NiCl$_2$.DEP (6.4 mg, 17.4 µmol), LiCl (73.9 mg, 1.74 mmol), Mn (95.5 mg, 1.74 mmol), Cp$_2$ZrCl$_2$ (255 mg, 0.872 mmol), 1,2-dimethoxyethane (0.55 mL) were mixed together and the Cr-complex solution was transferred to the flask. Additional NiCl$_2$.DEP (6.4 mg each, 17.4 µmol) was added after 3 and 6 h and the reaction was further stirred for 1 h at room temperature. The reaction was removed from the glove box and diluted with EtOAc. Florisil was added and the suspension was stirred vigorously for 30 min. The resultant suspension was filtered through short pad of silica gel (1 cm, EtOAc) and concentrated. The crude material was purified by flash chromatography on silica gel (5% then 15% EtOAc in hexanes) to give alcohol S-33 (563 mg, 78%, dr: 50:1 based on integration ratio of $^1$H NMR) as a colorless oil.

S-33: $[\alpha]^{20}_D$ −10.1 (c 0.98, CH$_2$Cl$_2$). $^1$H NMR (600 MHz, C$_6$D$_6$) δ: 5.44 (1H, s, C26=CHH), 5.03 (1H, s, C26=CHH), 4.79 (1H, dd, J=8.8, 8.8 Hz, H-30), 4.56 (1H, dd, J=8.2, 2.9 Hz, H-27), 4.16 (1H, ddd, J=8.8, 8.5, 3.5 Hz, H-29), 4.12-4.03 (2H, m, H-20a, 20b), 3.86 (1H, ddd, J=10.5, 8.8, 4.4 Hz, H-38a), 3.74 (1H, br s, OH), 3.70 (1H, ddd, J=10.5, 5.9, 4.1 Hz, H-38b), 3.46 (1H, ddd, J=4.7, 4.1, 3.5 Hz, H-33), 3.40 (1H, ddd, J=9.4, 2.9, 1.8 Hz, H-36), 3.39-3.35 (2H, m, H-36, OCHHC(CH$_3$)$_2$), 3.34 (1H, d, J=11.7 Hz, OCHHC(CH$_3$)$_2$), 3.30 (1H, d, J=11.7 Hz, OCHHC(CH$_3$)$_2$), 3.28 (1H, d, J=11.7 Hz, OCHHC(CH$_3$)$_2$), 3.08 (1H, dd, J=5.3, 3.5 Hz, H-32), 2.69 (dqd, J=7.0, 7.0, 4.7 Hz, H-25), 2.14 (1H, dqd, J=8.8, 7.0, 5.3 Hz, H-31), 2.05 (1H, dd, J=14.7, 4.7 Hz, H-24a), 2.03-1.91 (4H, m, H-28a, 28b, 34a, 37a), 1.87 (1H, dd, J=14.7, 7.0 Hz, H-24b), 1.85-1.74 (4H, m, H-21a, 21b, 22a, 22b), 1.73 (3H, s, COCH$_3$), 1.70 (3H, s, COCH$_3$), 1.66 (1H, dddd, J=14.1, 8.8, 5.9, 2.9 Hz, H-37b), 1.46 (1H, ddd, J=14.7, 4.7, 4.7 Hz, H-34b), 1.35 (3H, d, J=7.0 Hz, C25-CH$_3$), 1.09 (3H, d, J=7.0 Hz, C31-CH$_3$), 1.02 (9H, s, SiC(CH$_3$)$_3$), 1.00 (9H, s, SiC(CH$_3$)$_3$), 0.79 (3H, s, C(CH$_3$)$_3$), 0.75 (3H, s, C(CH$_3$)$_3$), 0.11 (3H, s, SiCH$_3$), 0.10 (3H, s, SiCH$_3$), 0.09 (3H, s, SiCH$_3$), 0.03 (3H, s, SiCH$_3$). $^{13}$C NMR (125 MHz, C$_6$D$_6$) δ: 170.2, 170.0, 159.2, 107.9, 100.4, 78.7, 75.3, 74.6 (2C), 74.4, 70.1 (2C), 67.2, 64.9, 64.7, 59.7, 41.9, 38.7, 38.5, 35.6, 35.2, 31.0, 30.9, 29.5, 26.22 (3C), 26.17 (3C), 23.4, 23.0, 22.8, 22.7, 20.6, 20.5, 18.6, 18.5, 16.3, −3.9, −4.9, −5.1, −5.3. IR (film): 3500, 1740 cm$^{-1}$. HRMS (ESI) m/z: [M+Na]$^+$ calcd for C$_{43}$H$_{80}$O$_{11}$Si$_2$Na, 851.5131; found, 851.5145.

Route 2, Compound S-34

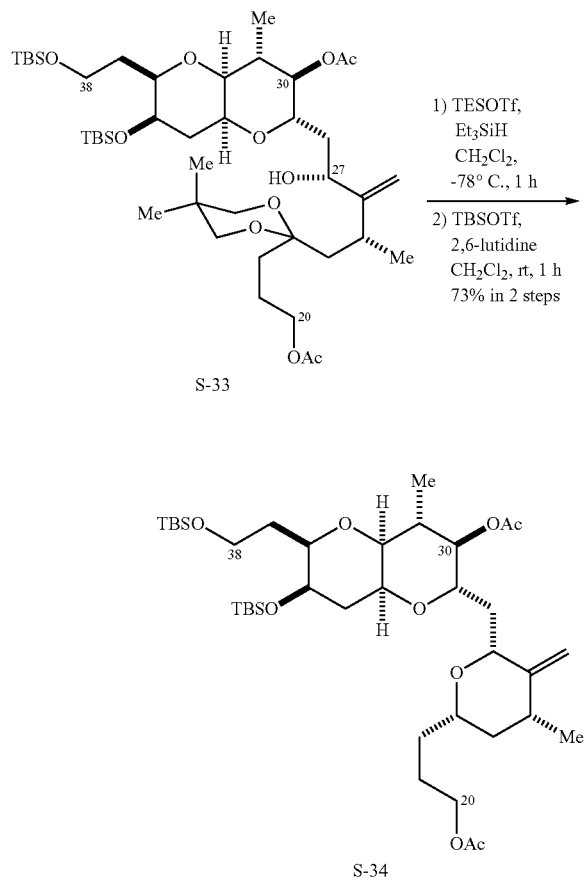

S-33

1) TESOTf, Et₃SiH CH₂Cl₂, −78° C., 1 h
2) TBSOTf, 2,6-lutidine CH₂Cl₂, rt, 1 h
73% in 2 steps

S-34

1.71 (3H, s, COCH₃), 1.70-1.64 (2H, m, H-21b, 37b), 1.54 (1H, dddd, J=9.8, 8.3, 4.9, 2.4 Hz, H-22a), 1.48 (1H, ddd, J=14.3, 4.6, 4.4 Hz, H-34b), 1.41-1.34 (2H, m, H-21b, 24a), 1.21 (3H, d, J=6.8 Hz, C31-CH₃), 1.07-1.03 (1H, m, H-24b), 1.02 (9H, s, SiC(CH₃)₃), 1.02 (9H, s, SiC(CH₃)₃), 0.96 (3H, d, J=6.8 Hz, C31-CH₃), 0.11 (3H, s, 2×SiCH₃), 0.11 (3H, s, SiCH₃), 0.04 (3H, s, SiCH₃). ¹³C NMR (125 MHz, C₆D₆) δ: 170.1, 170.0, 152.0, 104.1, 78.8, 77.0, 75.3, 75.1, 74.8, 71.1, 67.4, 64.9, 64.5, 59.8, 43.3, 39.3, 36.4, 35.59, 35.55, 34.5, 32.5, 26.2 (6C), 25.4, 20.7, 20.6, 18.6, 18.5, 18.2, 16.7, −4.0, −4.8, −5.1, −5.3. IR (film): 1738 cm⁻¹. HRMS (ESI) m/z: [M+NH₄]⁺ calcd for C₃₈H₇₄NO₉Si₂, 744.4897; found, 744.4892.

Route 2, Compound S-16

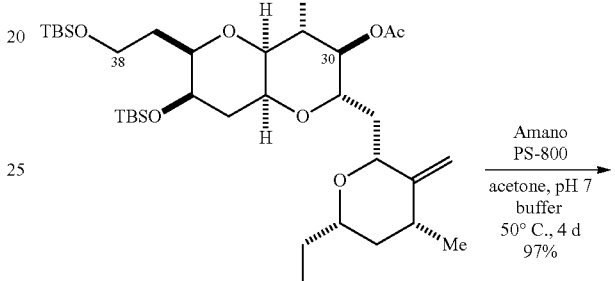

S-34

Amano PS-800
acetone, pH 7 buffer
50° C., 4 d
97%

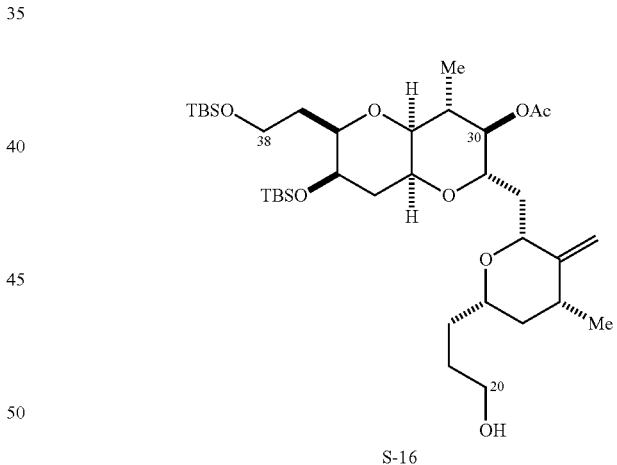

S-16

To ketal S-33 (563 mg, 0.679 mmol) in CH₂Cl₂ (6.8 mL) were added triethylsilane (1.08 mL, 6.79 mmol) and TES-OTf (0.460 mL, 2.04 mmol) at −78° C. and the reaction mixture was stirred for 1 h at the same temperature. The reaction mixture was quenched with triethylamine (1 mL) and sat. NaHCO₃ aq. The aqueous layer was extracted with CH₂Cl₂ three times and the combined organic layers were dried over Na₂SO₄ and evaporated.

The crude material was co-evaporated with benzene, dissolved in CH₂Cl₂ (6.8 mL), then 2,6-lutidine (0.632 mL, 5.43 mmol) and TBSOTf (0.934 mL, 4.07 mmol) were added to the reaction mixture at 0° C. The reaction mixture was stirred for 1 h at room temperature and quenched with 0.5 M NaHSO₄ aq. The aqueous layer was extracted with CH₂Cl₂ and the combined organic layers were washed with brine, dried over Na₂SO₄, and concentrated under reduced pressure. Purification of the crude by flash column chromatography on silica gel eluted with 5% EtOAc in hexanes yielded TBS-ether S-34 (361 mg, 73% in 2 steps) as a pale yellow oil.

S-34: [α]²⁰_D+5.7 (c 0.95, CHCl₃). ¹H NMR (500 MHz, C₆D₆) δ: 5.02 (1H, br s, C26=CHH), 4.99 (1H, dd, J=7.3, 8.3 Hz, 1H), 4.84 (d, J=1.5 Hz, C26=CHH), 4.40 (1H, ddd, J=8.4, 5.6, 5.6 Hz, H-29), 4.17-4.10 (3H, m, H-20a, 20b, 27), 3.90 (1H, ddd, J=9.9, 9.5, 4.4 Hz, H-38a), 3.74 (1H, ddd, J=9.9, 5.7, 4.4 Hz, H-38b), 3.59 (1H, ddd, J=4.9, 4.4, 4.4 Hz, H-33), 3.49-3.40 (3H, m, H-23, 35, 36), 3.18 (1H, dd, J=4.9, 3.4 Hz, H-32), 2.32 (1H, ddd, J=14.2, 5.6, 5.4 Hz, H-28a), 2.26-2.15 (2H, m, H-28b, 31), 2.14-2.00 (3H, m, H-25, 34a, 37a), 1.88-1.77 (1H, m, H-21a), 1.75-1.73 (3H, s, COCH₃), To a solution of acetate S-34 (191 mg, 0.263 mmol) in acetone (5.3 mL)/pH 7 phosphate buffer (0.53 mL) was added Amano lipase PS-800 (19 mg) at room temperature. The resultant suspension was heated at 50° C. for four days. The reaction mixture was cooled to room temperature and filtered through a pad of Celite. After removal of acetone, the residue was added sat. NaHCO₃ aq and was extracted with EtOAc three times. Combined organic phases were dried over Na₂SO₄ and concentrated under vacuum. The crude product was purified by flash column chromatography on silica gel eluted with 20% EtOAc in hexanes to give alcohol S-16 (175 mg, 97%, colorless oil), which was identical with S-16 prepared from S-17 via Route 1.

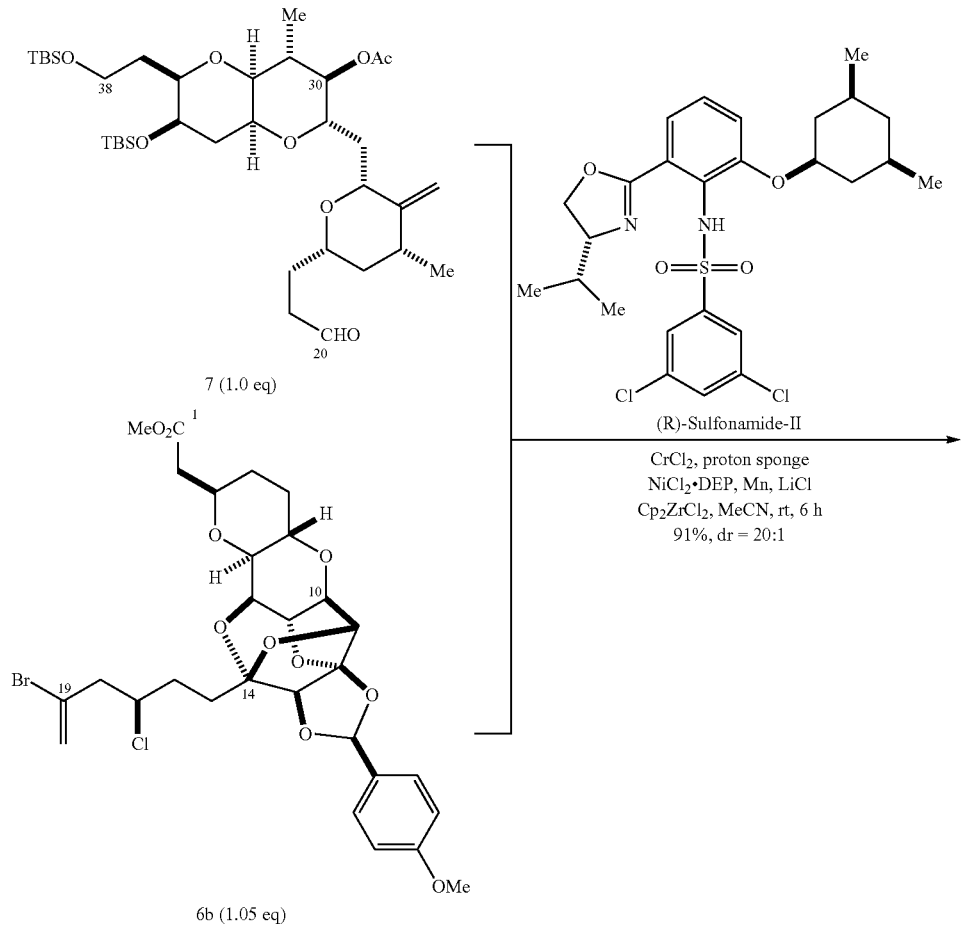
Compound 17
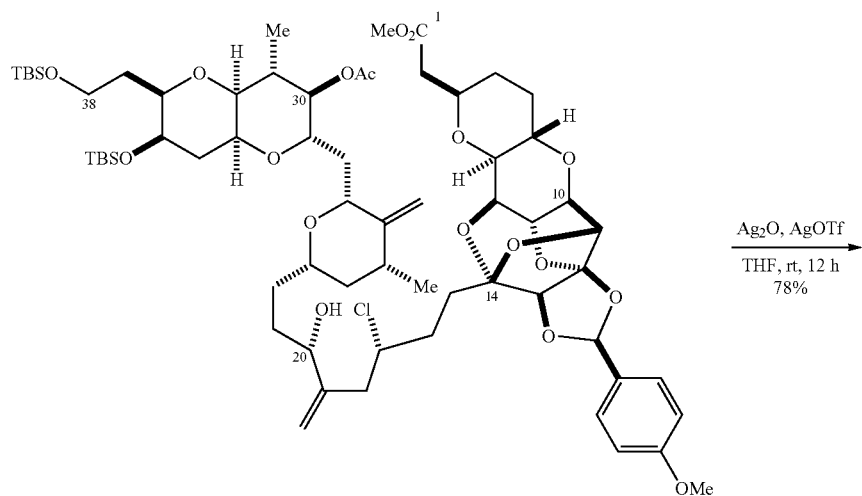

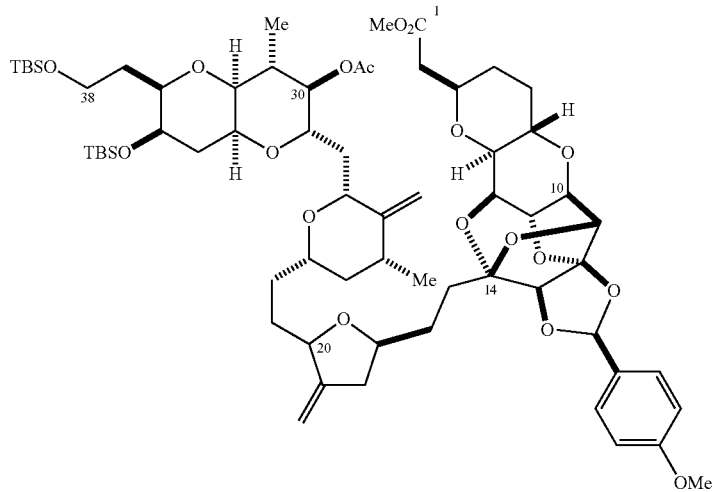

17

To a mixture of CrCl₂ (21.4 mg, 0.174 mmol), (R)-sulfonamide ligand II (103 mg, 0.191 mmol), and proton sponge (40.9 mg, 0.191 mmol) in a glove box was added MeCN (1.1 mL) and stirred for 1 h at room temperature. In a separate flask, aldehyde 7 (297 mg, 0.435 mmol), bromide 6b (171 mg, 0.261 mmol), NiCl₂.DEP (3.2 mg, 8.7 µmol), LiCl (73.8 mg, 1.74 mmol), Mn (95.5 mg, 1.74 mmol), Cp₂ZrCl₂ (152 mg, 0.522 mmol) were mixed together and the above Cr-complex solution was transferred to the flask. Additional NiCl₂.DEP (3.2 mg each, 8.7 µmol, four times) and bromide 6b (86 mg each, 0.13 mmol, twice) were added after 2, 3, 4, and 5 h and 2 and 4 h, respectively. In total, the reaction mixture was stirred for 6 h at room temperature. The reaction was removed from the glove box and diluted with EtOAc (2.2 mL). Florisil was added and the suspension was stirred vigorously for 30 min. The resultant suspension was filtered through a short pad of silica gel (1 cm, EtOAc) and concentrated. The crude material was purified by flash chromatography on silica gel (0%, 10%, then 20% Et₂O in CH₂Cl₂) to give alcohol S-35 (499 mg, 91%, dr=20:1) as a white foam.

To a THF (8.0 mL) solution of allyl alcohol S-35 (499 mg, 0.395 mmol) in a flask covered with aluminum foil were added silver(I) oxide (229 mg, 0.988 mmol) and silver trifluoromethanesulfonate (253 mg, 0.988 mmol) at room temperature and the resultant black suspension was stirred for 12 h at room temperature. The reaction was quenched with triethylamine (0.5 mL), diluted with EtOAc, and filtered through a pad of Celite (1.5 cm). After removal of the solvent, the residue was purified by flash column chromatography on silica gel (20% then 30% EtOAc in hexanes) to give cyclized product 17 (378 mg, 78%) as a white foam. Note: transformation of S-35 to 17 is also achieved with use of other bases such as SrCO₃ and CaCO₃.

17: $[\alpha]^{20}_D$ −40.4 (c 0.11, CHCl₃). $^1$H NMR (600 MHz, C₆D₆) δ: 7.34 (2H, d, J=8.8 Hz, ArH), 6.69 (2H, d, J=8.8 Hz, ArH), 6.10 (1H, s, ArCH), 5.00 (1H, br s, C19=CHH), 4.98 (1H, dd, J=7.9, 7.9 Hz, H-30), 4.96-4.95 (1H, m, C26=CHH), 4.95-4.93 (1H, m, C19=CHH), 4.83 (1H, d, J=1.2 Hz, C26-CHH), 4.57-4.54 (1H, m, H-20), 4.53 (1H, dd, J=3.5, 1.5 Hz, H-8), 4.50 (1H, ddd, J=10.0, 9.7, 4.4 Hz, H-6), 4.38 (1H, dd, J=5.3, 1.2 Hz, H-11), 4.38-4.34 (1H, m, H-29), 4.15 (1H, dd, J=6.2, 6.2 Hz, H-27), 4.11 (1H, s, H-13), 4.07-4.03 (1H, m, H-17), 4.04 (1H, dd, J=6.5, 5.3 Hz, H-10), 3.89 (ddd, J=9.5, 9.5, 4.4 Hz, H-38a), 3.76 (1H, ddd, J=6.5, 3.6, 1.2 Hz, H-9), 3.76-3.71 (2H, m, H-3, 38b), 3.60-3.53 (2H, m, H-23, 33), 3.47-3.41 (2H, m, H-35, 36), 3.35 (3H, s, CO₂CH₃), 3.23 (3H, s, ArOCH₃), 3.15 (1H, dd, J=5.0, 3.5 Hz, H-32), 2.57 (1H, dd, J=15.8, 7.6 Hz, H-2a), 2.53 (1H, dd, J=9.7, 1.5 Hz, H-7), 2.51-2.46 (1H, m, H-18a), 2.41-2.34 (1H, m, H-15a), 2.30 (1H, ddd, J=14.3, 6.2, 5.0 Hz, H-28a), 2.27-2.08 (7H, m, H-2b, 15b, 16a, 18b, 25, 28b, 31), 2.08-1.99 (3H, m, H-5a, 34a, 37a), 1.94-1.80 (3H, m, H-16b, 21a, 22a), 1.79-1.72 (2H, m, H-21b, 37b), 1.71 (3H, s, OCOCH₃), 1.66-1.58 (1H, m, H-22b), 1.51-1.43 (2H, m, H-24a, 34b), 1.43-1.35 (1H, m, H-4a), 1.31-1.22 (2H, m, H-4b, 5b), 1.19 (3H, d, J=7.0 Hz, C31-CH₃), 1.13-1.05 (1H, m, H-24b), 1.01 (18H, s, 2×SiC(CH₃)₃), 0.96 (3H, d, J=6.4 Hz, C25-CH₃), 0.11 (3H, s, SiCH₃), 0.10 (3H, s, SiCH₃), 0.10 (3H, s, SiCH₃), 0.04 (3H, s, SiCH₃). $^{13}$C NMR (125 MHz, C₆D₆) δ: 171.0, 170.0, 161.3, 152.8, 152.3, 128.8 (2C), 128.3, 118.8, 114.1 (2C), 109.5, 109.0, 104.6, 103.9, 89.8, 83.6, 79.5, 78.8, 78.7, 77.5, 77.1, 76.2, 75.2, 75.1, 74.8, 74.6, 74.2, 73.9, 71.4, 68.3, 67.4, 64.8, 59.8, 54.8, 51.1, 43.4, 40.5, 39.1, 39.0, 36.4, 35.5, 35.4, 34.6, 32.1, 31.7, 31.2, 30.6, 30.3, 29.3, 26.2 (3C), 26.1 (3C), 20.7, 18.6, 18.5, 18.2, 16.6, −4.0, −4.8, −5.1, −5.3. HRMS (ESI) m/z: [M+Na]⁺ calcd for C₆₅H₁₀₀O₁₈Si₂Na, 1247.6340; found, 1247.6308.

Compound S-35

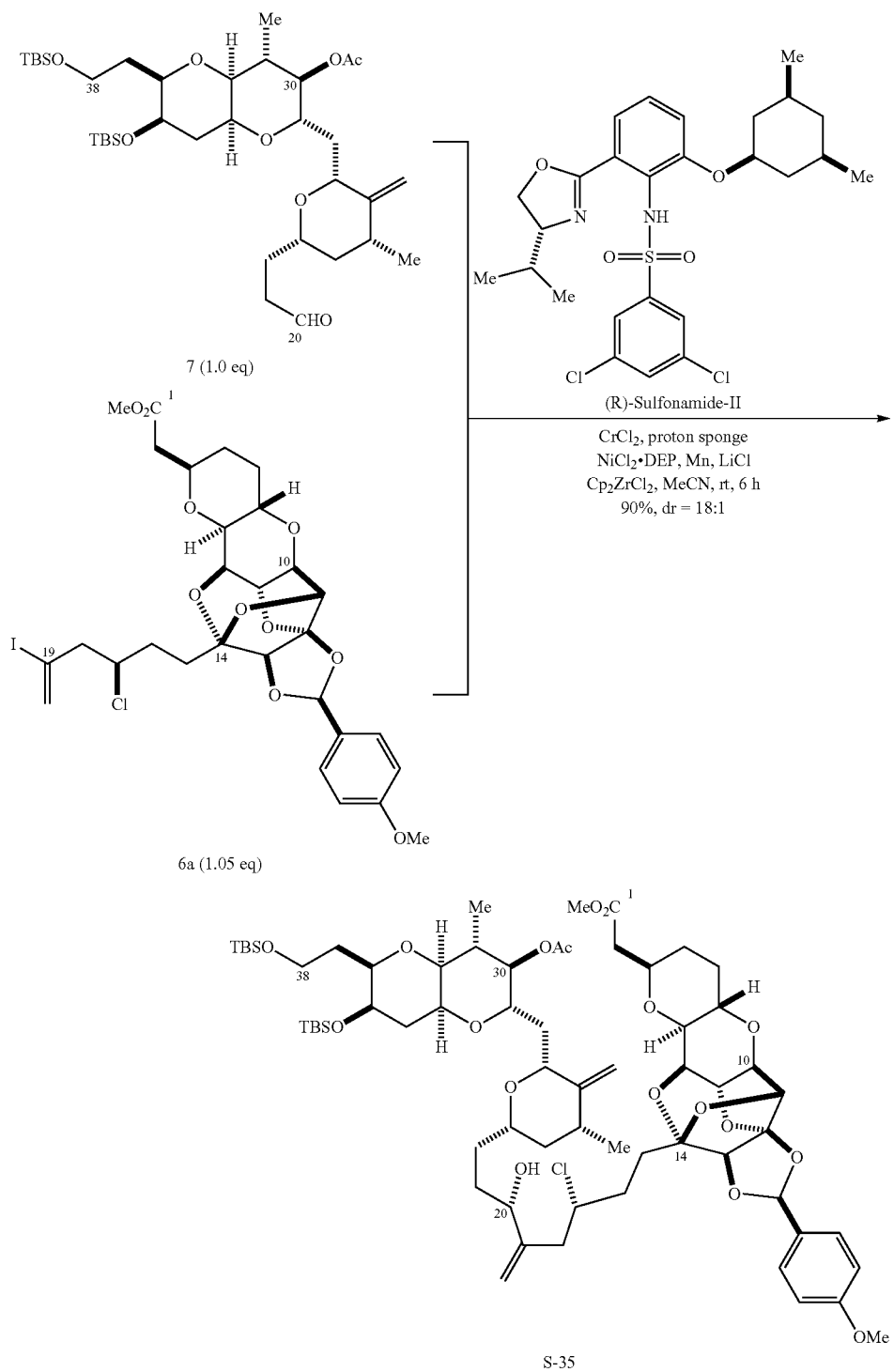

To a mixture of CrCl$_2$ (0.96 mg, 7.8 μmol), (R)-sulfonamide ligand II (4.7 mg, 8.6 μmol), and proton sponge (1.9 mg, 8.6 μmol) in a glove box was added MeCN (0.10 mL) and stirred for 1 h at room temperature. In a separate flask, aldehyde 7 (26.7 mg, 39.1 μmol), iodide 6a (29.0 mg, 41.0 μmol), NiCl$_2$.DEP (0.14 mg, 0.39 μmol, doped in LiCl), LiCl (6.6 mg, 0.156 mmol), Mn (8.6 mg, 0.156 mmol), Cp$_2$ZrCl$_2$ (13.7 mg, 46.9 μmol) were mixed together and the above Cr-complex solution was transferred to the flask. Additional NiCl$_2$.DEP (0.14 mg each, 0.39 μmol, twice, doped in LiCl) and was added after 2 and 4 h, respectively. In total, the reaction mixture was stirred for 6 h at room temperature. The reaction mixture was removed from the glove box and diluted with EtOAc. Florisil was added and the suspension was vigorously stirred for 30 min. The resultant suspension was filtered through a short pad of silica gel (1 cm, EtOAc) and concentrated in vacuo. The crude material was purified by flash chromatography on silica gel (0%, 10%, then 20% Et$_2$O in CH$_2$Cl$_2$) to give alcohol S-35 (44.4 mg, 90%, dr=18:1, white foam), which was identical with S-35 obtained by coupling of aldehyde 7 and bromide 6b.
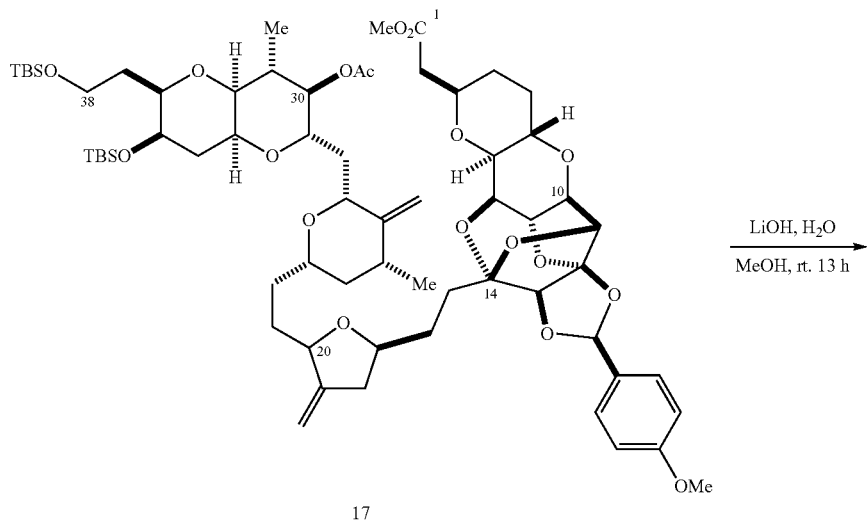
Compound 18
17
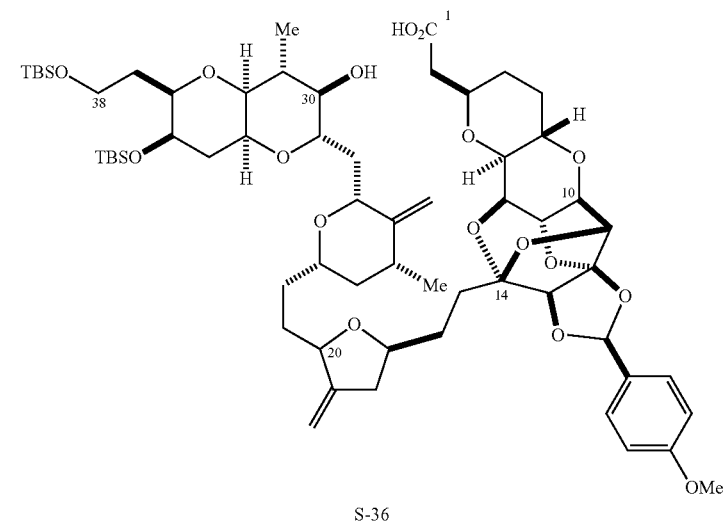
S-36
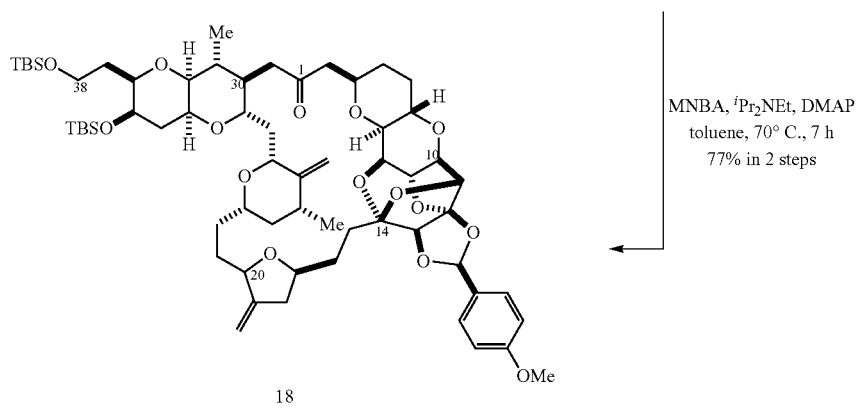
18

To a solution of ester 17 (93.3 mg, 76.1 μmol) in MeOH (2.3 mL) and water (0.23 mL) at room temperature was added LiOH (91.3 mg, 3.80 mmol) and the reaction was stirred for 13 h at room temperature. The resultant suspension was cooled to 0° C. and acidified with 0.5 M HCl aq. then extracted with EtOAc four times: Combined organic phases were washed with brine, dried over $Na_2SO_4$, and concentrated under vacuum to give seco-acid S-36.

To a solution of 2-methyl-6-nitrobenzoic anhydride (MNBA, 157 mg, 0.457 mmol) and 4,4-dimethylaminopyridine (111 mg, 0.913 mmol) in toluene (35 mL) at 70° C. were dropped a solution of the seco-acid S-36 and N,N-diisopropylethylamine (79.5 μL, 0.457 mmol) in toluene (15 mL) over 6 h by using syringe pump. After completion of the addition, the solution was further stirred for 1 h at 70° C. The reaction mixture was cooled to 0° C. and then sat. $NaHCO_3$ aq was added and separated. The aqueous phase was extracted with EtOAc three times and combined organic phases were dried over $Na_2SO_4$ and evaporated. The residue was purified by flash column chromatography on silica gel (10% EtOAc in hexanes) to give macrolactone 18 (67.8 mg, 77% in 2 steps) as a white foam. Note: macrolactonization of S-36 to 18 is also achieved with use of the Yamaguchi protocol (see Yamaguchi et ah, *J. Am. Chem. Soc.,* 1992, 114, 3162).

18: $[\alpha]^{20}{}_D$ −43.5 (c 1.17, $CHCl_3$). $^1$H NMR (600 MHz, $C_6D_6$) δ: 7.36 (2H, d, J=8.8 Hz, ArH), 6.73 (2H, d, J=8.8 Hz, ArH), 6.09 (1H, s, ArCH), 5.14 (1H, br s, C19=CHH), 5.06 (1H, br s, C19=CHH), 4.97 (1H, br s, C26=CHH), 4.86 (1H, dd, J=7.6, 5.9 Hz, H-30), 4.84-4.78 (1H, m, H-29), 4.81 (1H, br s, C26=CHH), 4.66 (1H, br d, J=10.0 Hz, H-20), 4.50 (1H, ddd, J=10.5, 9.7, 4.2 Hz, H-6), 4.42 (1H, dd, J=3.1, 1.6 Hz, H-8), 4.38 (1H, dd, J=5.1, 1.3 Hz, H-11), 4.07 (1H, s, H-13), 4.05-3.93 (4H, m, H-3, 10, 17, 38a), 3.86-3.79 (2H, m, H-27, 38b); 3.77-3.69 (2H, m, H-9, 23), 3.56-3.46 (3H, m, H-33, 35, 36), 3.22 (3H, s, $OCH_3$), 3.19 (1H, dd, J=5.0, 3.5 Hz, H-32), 2.78 (1H, dd, J=16.7, 7.6 Hz, H-2a), 2.65 (1H, dddd, J=15.8, 7.6, 4.7, 2.6 Hz, H-18a), 2.52 (1H, dd, J=9.4, 1.5 Hz, H-7), 2.41-2.23 (6H, m, H-2b, 15a, 15b, 16a, 28a, 31), 2.20-2.05 (6H, m, H-18b, 21a, 25, 28b, 34a, 37a), 2.05-1.99 (1H, m, H-5a), 1.94 (1H, dddd, J=14.4, 11.4, 3.2, 2.7 Hz, H-22a), 1.89-1.82 (1H, m, H-22b), 1.79 (1H, dddd, J=14.1, 8.8, 5.3, 3.2 Hz, H-37b), 1.72 (1H, dddd, J=13.8, 10.3, 5.3, 3.2 Hz, H-21b), 1.58-1.48 (3H, m, H-16b, 24a, 34b), 1.48-1.41 (1H, m, H-4a), 1.39-1.26 (2H, m, H-4b, 5b), 1.23 (3H, d, J=7.3 Hz, C31-$CH_3$), 1.15-1.07 (1H, m, H-24b), 1.05 (3H, d, J=6.7 Hz, C25-$CH_3$), 1.04 (9H, s, $SiC(CH_3)_3$), 1.02 (9H, s, $SiC(CH_3)_3$), 0.15 (3H, s, $SiCH_3$), 0.14 (6H, s, 2×$SiCH_3$), 0.09 (3H, s, $SiCH_3$). $^{13}$C NMR (100 MHz, $C_6D_6$) δ: 171.1, 161.4, 152.9, 152.7, 128.7 (2C), 128.2, 119.0, 114.1 (2C), 109.3, 109.0, 104.8, 103.8, 90.2, 83.8, 78.3, 78.2, 77.9, 76.0, 76.0, 75.7, 74.9, 74.8, 74.2, 74.0, 73.8, 73.7, 70.1, 68.3, 67.2, 64.6, 59.9, 54.8, 44.0, 41.3, 39.6, 39.3, 38.6, 36.4, 35.9, 35.7, 32.3, 31.0, 30.9, 30.2 (2C), 27.6, 26.3 (3C), 26.2 (3C), 18.6, 18.5, 18.2, 16.7, −4.0, −4.7, −5.0, −5.2. HRMS (ESI) m/z: $[M+H]^+$ calcd for $C_{62}H_{95}O_{16}Si_2$, 1151.6153; found, 1151.6197.

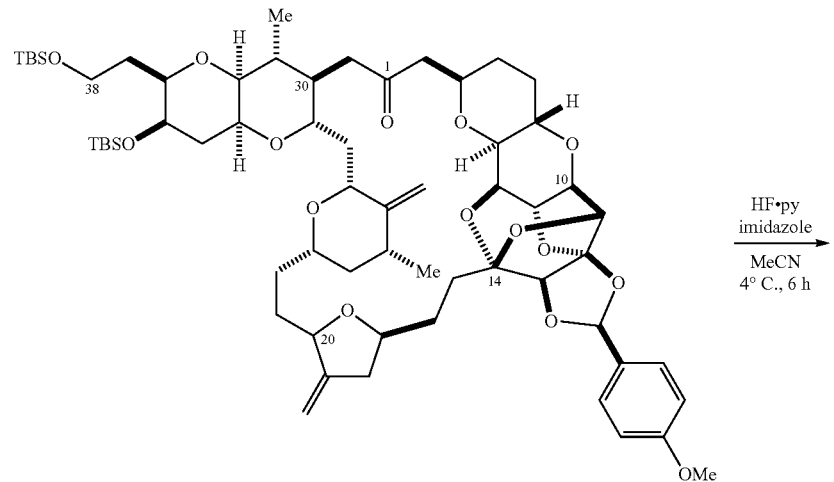

Compound 19

18

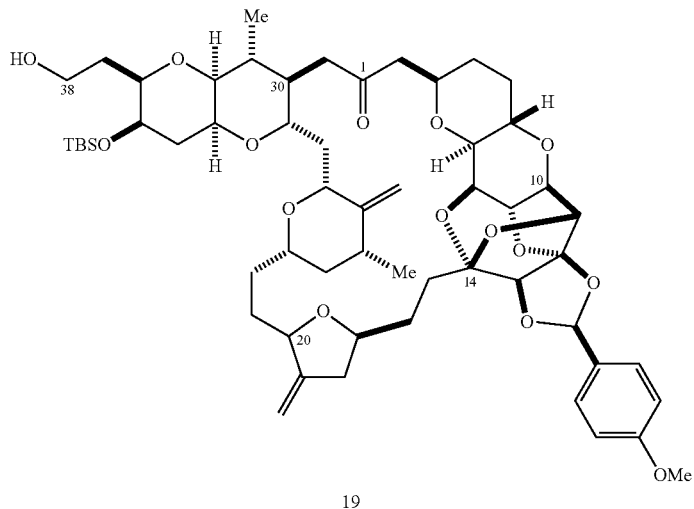

19

To TBS-ether 18 (238 mg, 0.207 mmol) and imidazole (56.3 mg, 0.828 mmol) in MeCN (2.1 mL) was added HF·pyridine complex (70% HF content, 21.5 μL, 0.828 mmol) at 0° C. and the reaction mixture was kept in a refrigerator (4° C.) for 6 h. The reaction mixture was quenched with sat. NaHCO₃ aq. at 0° C. and stirred for 10 min. The aqueous layer was extracted with EtOAc/hexanes (4:1) four times and the combined organic phases were dried over Na₂SO₄ and evaporated. The crude was purified by flash column chromatography on silica gel (40% EtOAc in hexanes) to give alcohol 19 (197 mg, 92%) as a colorless oil, contaminated with a small amount of imidazole (ca. 5%), which was effectively removed at the next oxidation step.

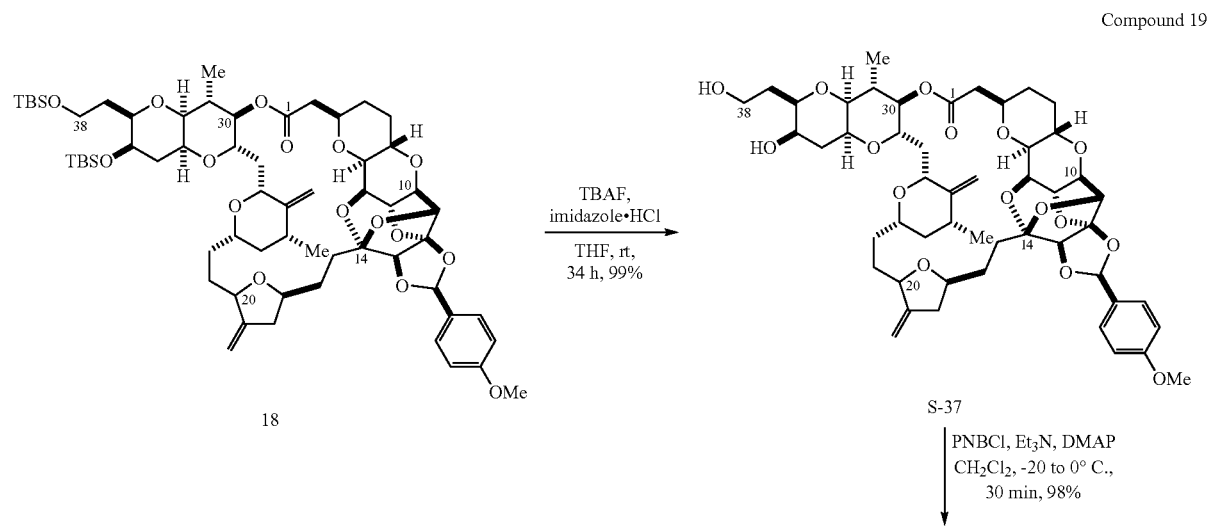

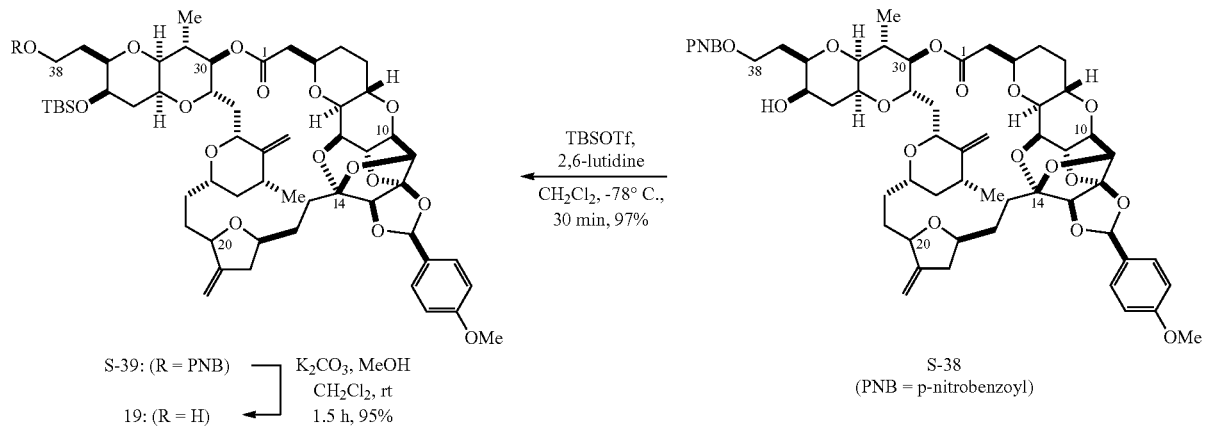

To a solution of bis-TBS ether 18 (267 mg, 0.232 mmol) in THF (7.7 mL) was added TBAF solution (0.95 M in THF, buffered with 0.5 eq of imidazole-hydrochloride, 0.98 mL, 0.928 mmol) at room temperature. After stirring for 34 h at room temperature, solvent was removed by a stream of nitrogen gas and redissolved in EtOAc and water. The aqueous layer was extracted with EtOAc four times and the combined organic layer was dried over $Na_2SO_4$. After removal of the solvent, the residue was purified by flash column chromatography on silica gel (40% EtOAc in hexanes then EtOAc) to give diol S-37 (213 mg, 99%) as a white semisolid.

S-37: $[\alpha]^{20}_D$ –104.8 (c 0.10, $CHCl_3$). $^1$H NMR (600 MHz, $C_6D_6$) δ: 7.34 (2H, d, J=8.8 Hz, 2×ArH), 6.71 (2H, d, J=8.8 Hz, 2×ArH), 6.06 (1H, s, ArCH), 5.31 (1H, br s, C19=CHH), 5.16 (1H, br s, C19=CHH), 4.75 (1H, br s, C26=CHH), 4.74 (1H, br s, C26=CHH), 4.70 (1H, br d, J=10.5 Hz, H-30), 4.66-4.61 (2H, m, H-20, 29), 4.47 (1H, dd, J=3.5, 2.1 Hz, H-8), 4.36 (1H, dd, J=5.1, 1.3 Hz, H-11), 4.37-4.31 (1H, m, H-6), 4.11 (1H, s, H-13), 4.07-4.01 (1H, m, H-17), 3.97 (1H, dd, J=6.5, 5.1 Hz, H-10), 3.92-3.84 (4H, m, H-3, 27, 38a, 38b), 3.71-3.66 (1H, m, H-23), 3.63 (1H, ddd, J=6.5, 3.5, 1.3 Hz, H-9), 3.37-3.32 (1H, m, H-35), 3.29 (1H, br s, H-33), 3.24 (1H, br d, J=11.1 Hz, C35-OH), 3.22 (3H, s, $OCH_3$), 3.18-3.14 (1H, m, H-36), 3.09 (1H, br s, C38-OH), 2.76 (1H, dd, J=17.2, 10.5 Hz, H-2a), 2.77-2.73 (1H, m, H-32), 2.67 (1H, dd, J=17.3, 2.3 Hz, H-2b), 2.61 (1H, dddd, J=15.2, 7.6, 4.7, 2.6 Hz, H-18a), 2.57-2.51 (2H, m, H-15a, 31), 2.49 (1H, dd, J=9.4, 2.1 Hz, H-7), 2.38-2.30 (2H, m, H-16a, 37a), 2.29-2.22 (2H, m, H-15b, 28a), 2.10-1.88 (6H, m, H-5&, 18b, 21a, 22a, 28b, 34a), 1.81-1.73 (1H, m, H-25), 1.66 (1H, dddd, J=14.9, 4.7, 4.5, 3.8 Hz, H-37b), 1.60-1.49 (3H, m, H-16b, 21b, 22b), 1.46 (1H, ddd, J=12.6, 4.4, 1.8 Hz, H-24a), 1.30-1.25 (1H, m, H-4a), 1.24-1.15 (3H, m, H-4b, 5b, 34b), 1.05-0.98 (1H, m, H-24b), 0.96 (3H, d, J=6.4 Hz, C25-$CH_3$), 0.87 (3H, d, J=7.9 Hz, C31-$CH_3$). $^{13}$C NMR (125 MHz, $C_6D_6$) δ: 170.6, 161.3, 153.1, 152.4, 128.7, 128.6 (2C), 118.9, 114.1 (2C), 109.0, 108.9, 105.0, 103.4, 90.4, 84.0, 80.6, 78.1, 77.5, 76.3, 75.8, 75.2, 75.1, 74.7, 73.74, 73.72, 73.6, 73.32 73.1, 68.5, 66.7, 62.5, 60.7, 54.7, 43.9, 40.8, 38.7, 36.2, 35.6, 35.2, 35.0, 34.7, 32.6, 31.6, 31.1, 31.0, 30.5, 27.8, 17.9, 16.4. HRMS (ESI) m/z: [M+H]$^+$ calcd for $C_{50}H_{67}O_{16}$, 945.4243; found, 945.4274.

To a stirred solution of diol S-37 (213 mg, 0.231 mmol, azeotropically dried with benzene prior to use) in $CH_2Cl_2$ (7.7 mL) and triethylamine (0.77 mL) at –20° C. were added p-nitrobenzoyl chloride (128 mg, 0.693 mmol) and 4,4-dimethylaminopyridine (8.5 mg, 69.3 μmol) and the reaction mixture was gradually warmed to 0° C. over 30 min. The reaction was quenched with MeOH (0.2 mL) at 0° C. and the resultant mixture was further stirred for 15 min at room temperature. The reaction was diluted with $Et_2O$ (8 mL) to precipitate white solid and the reaction flask was sonicated for five seconds. After filtration through a Celite pad (1 cm) and evaporation of the solvent, the crude material was purified by flash column chromatography on silica gel (30% then 40% EtOAc in hexanes) to give p-nitrobenzoate S-38 (242 mg, 98%) as a pale yellow amorphous. The obtained product was co-evaporated with benzene before starting next step.

To a mixture of alcohol S-38 (242 mg, 0.226 mmol) and 2,6-lutidine (158 μL, 1.35 mmol) in $CH_2Cl_2$ (7.5 mL) was dropped TBSOTf (0.155 mL, 0.678 mmol) at –78° C. and the reaction mixture was stirred for 30 min at the same temperature prior to the addition of sat. $NaHCO_3$ aq. The aqueous phase was extracted with $CH_2Cl_2$ twice and combined organic phases were dried over $Na_2SO_4$, concentrated under reduced pressure, and connected to high vacuum pump to remove remaining 2,6-lutidine. The obtained residue was purified by flash column chromatography on silica gel (10% then 20% EtOAc in hexanes) to give TBS ether S-39 (259 mg, 97%) as a pale yellow amorphous.

To a solution of p-nitrobenzoate S-39 (39.8 mg, 33.6 μmol) in $CH_2Cl_2$ (0.55 mL) and MeOH (1.1 mL) was added $K_2CO_3$ (4.6 mg, 34 μmol) at room temperature and the resultant suspension was stirred for 1.5 h at the same temperature. The reaction was quenched with silica gel powder (0.3 g), diluted with $Et_2O$ (5 mL), and then passed through a pad of silica gel (0.5 cm), which was washed with $Et_2O$ (60 mL). After removal of the solvent, the crude residue was purified by preparative TLC (50% EtOAc in hexanes) to give alcohol 19 (33.0 mg, 95%) as a white semisolid.

19: $[\alpha]^{20}_D$ −50.0 (c 0.45, CHCl$_3$). $^1$H NMR (600 MHz, C$_6$D$_6$) δ: 7.36 (2H, d, J=8.8 Hz, 2×ArH), 6.73 (2H, d, J=8.8 Hz, 2×ArH), 6.09 (1H, s, ArCH), 5.35 (1H, br s, C19=CHH), 5.16-5.12 (1H, m, C19=CHH), 4.94 (1H, br s, C26=CHH), 4.85 (1H, ddd, J=10.3, 7.3, 2.9 Hz, H-29), 4.81 (1H, dd, J=7.3, 3.5 Hz, H-30), 4.79 (1H, br s, C26=CHH), 4.68 (1H, d, J=9.4 Hz, H-20), 4.51 (1H, ddd, J=10.8, 9.7, 4.4 Hz, H-6), 4.41 (1H, dd, J=3.7, 1.3 Hz, H-8), 4.37 (1H, dd, J=5.3, 1.2 Hz, H-11), 4.08 (1H, s, H-13), 4.06-4.03 (1H, m, H-17), 4.02 (1H, dd, J=6.5, 5.3 Hz, H-10), 4.01-3.97 (1H, m, H-3), 3.92-3.86 (1H, m, H-38a), 3.83 (1H, ddd, J=10.3, 8.5, 3.5 Hz, H-38b), 3.78 (1H, d, J=11.4 Hz, H-27), 3.76-3.72 (1H, m, H-23), 3.71 (1H, ddd, J=6.5, 3.7, 1.2 Hz, H-9), 3.48 (ddd, J=3.5, 3.5, 3.1 Hz, H-33), 3.33 (1H, ddd, J=4.0, 3.4, 2.1 Hz, H-35), 3.23 (3H, s, OCH$_3$), 3.20 (1H, ddd, J=9.7, 3.4, 2.1 Hz, H-36), 3.03 (1H, dd, J=4.2, 3.1 Hz, H-32), 2.79 (1H, dd, J=16.8, 8.3 Hz, H-2a), 2.73 (1H, br s, C38-OH), 2.66 (1H, dddd, J=15.5, 7.3, 4.7, 2.1 Hz, H-18a), 2.55 (1H, dd, J=9.7, 1.3 Hz, H-7), 2.48 (1H, dd, J=16.8, 3.5 Hz, H-2b), 2.39-2.25 (4H, m, H-15a, 15b, 16a, 28a), 2.23-2.11 (4H, m, H-21a, 25, 31, 37a), 2.11-2.01 (4H, m, H-5a, 18b, 28b, 34a), 2.00-1.95 (1H, m, H-22a), 1.91-1.85 (1H, m, H-22b), 1.84-1.78 (1H, m, H-21b), 1.61 (1H, ddd, J=12.3, 4.4, 2.1 Hz, H-24a), 1.53 (1H, dddd, J=13.5, 10.3, 6.4, 3.5 Hz, H-16b), 1.47 (1H, dddd, J=14.6, 6.2, 3.5, 3.2 Hz, H-37b), 1.43-1.33 (3H, m, H-4a, 4b, 34b), 1.31-1.24 (1H, m, H-5b), 1.17-1.12 (1H, m, H-24b), 1.11 (3H, d, J=7.3 Hz, C31-CH$_3$), 1.05 (3H, d, J=6.4 Hz, C25-CH$_3$), 1.02 (9H, s, SiC(CH$_3$)$_3$), 0.13 (3H, s, SiCH$_3$), 0.10 (3H, s, SiCH$_3$). $^{13}$C NMR (125 MHz, C$_6$D$_6$) δ: 171.3, 161.4, 152.9, 152.2, 128.7 (2C), 128.6, 119.0, 114.1 (2C), 109.4, 109.0, 105.4, 103.7, 90.3, 83.8, 79.2, 78.4, 77.4, 77.2, 76.2, 75.8, 75.7, 75.1, 74.2, 74.1, 74.0, 73.8, 69.9, 68.3, 66.8, 64.0, 61.2, 54.7, 44.3, 41.1, 39.3, 39.2, 39.1, 36.4, 35.9, 34.8, 32.4, 31.2, 30.8, 30.3, 30.1, 27.5, 26.4 (3C), 18.7, 18.2, 16.4, −4.2, −4.6. HRMS (ESI) m/z: [M+H]$^+$ calcd for C$_{56}$H$_{81}$O$_{16}$Si, 1037.5288; found, 1037.5239.

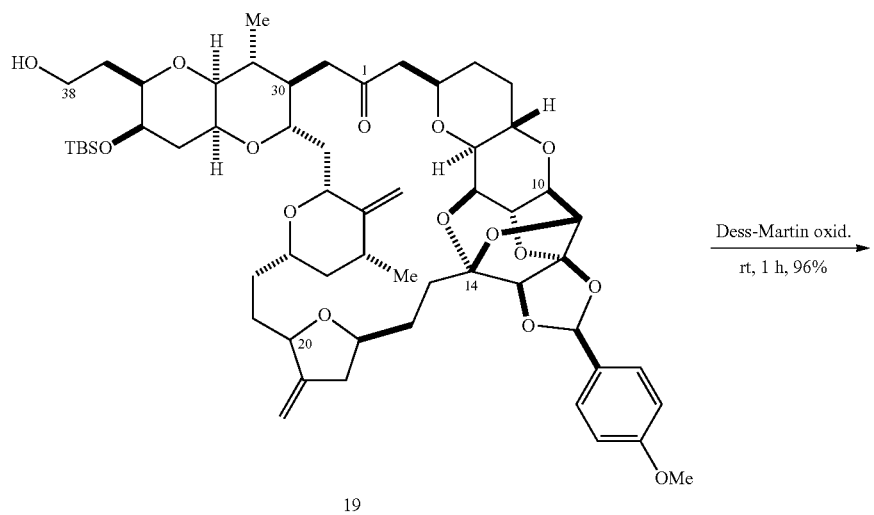

19

Dess-Martin oxid.
rt, 1 h, 96%

Compound S-40

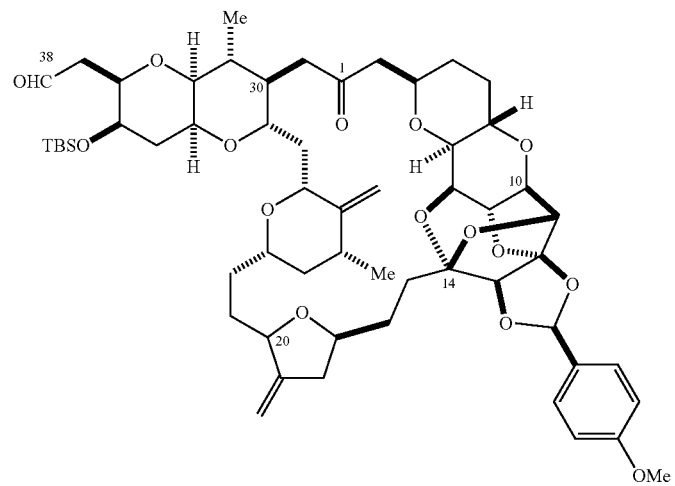

S-40

To a solution of alcohol 19 (33.0 mg, 31.8 μmol) in CH$_2$Cl$_2$ (1.1 mL) were added NaHCO$_3$ (26.7 mg, 0.318 mmol) and Dess-Martin periodinane (27.0 mg, 63.6 μmol) at room temperature and the reaction mixture was stirred for 1 h at the same temperature. The reaction was quenched by adding 10 wt % Na$_2$S$_2$O$_3$ aq. and sat. NaHCO$_3$ aq. and then vigoursly stirred for 30 min at room temperature. The aqueous phase was extracted with CH$_2$Cl$_2$ three times and combined organic phases were dried over sodium sulfate. After evaporation of the solvent, the crude material was purified by flash chromatography on silica gel short plug (20% then 30% EtOAc in hexanes) to give aldehyde S-40 (31.8 mg, 96%) as a white semisolid.

S-40: $^1$H NMR (600 MHz, C$_6$D$_6$) δ: 9.72 (1H, dd, J=1.6, 1.6 Hz, 070), 7.36 (2H, d, J=8.8 Hz, 2×ArH), 6.73 (2H, d, J=8.8 Hz, 2×ArH), 6.08 (1H, s, ArCH), 5.17 (1H, br s, C19=CHH), 5.10-5.06 (1H, m, C19=CHH), 4.93 (1H, br s, C26=CHH), 4.82'.79 (1H, m, C26=CHH), 4.78 (1H, dd, J=7.0, 5.3 Hz, H-30), 4.75 (1H, ddd, J=7.5, 7.0, 2.6 Hz, H-29), 4.66 (1H, d, J=10.5 Hz, H-20), 4.49 (1H, ddd, J=10.5, 9.5, 4.4 Hz, H-6), 4.42 (1H, dd, J=3.4, 1.6 Hz, H-8), 4.38 (1H, dd, J=5.3, 1.4 Hz, H-11), 4.07 (1H, s, H-13), 4.04-4.01 (1H, m, H-17), 4.01 (1H, dd, J=6.4, 5.3 Hz, H-10), 3.97-3.91 (1H, m, H-3), 3.77 (1H, d, J=11.1 Hz, H-27), 3.74-3.71 (1H, m, H-23), 3.71 (1H, ddd, J=6.4, 3.4, 1.3 Hz, H-9), 3.52 (1H, ddd, J=7.1, 4.9, 2.3 Hz, H-36), 3.44 (1H, ddd, J=5.0, 4.0, 3.5 Hz, H-33), 3.42 (1H, ddd, J=4.5, 4.0, 2.3 Hz, H-35), 3.22 (3H, s, OCH$_3$), 3.03 (1H, dd, J=4.7, 3.5 Hz, H-32), 2.77 (1H, dd, J=16.7, 7.9 Hz, H-2a), 2.68-2.60 (2H, m, H-18a, 37a), 2.52 (1H, dd, J=9.5, 1.6 Hz, H-7), 2.39-2.23 (7H, m, H-2b, 15a, 15b, 16a, 28a, 31, 37b), 2.17 (1H, dddd, J=13.8, 11.4, 3.4, 2.8 Hz, H-21a), 2.12-1.99 (5H, m, H-5a, 18b, 25, 28b, 34a), 1.95 (1H, dddd, J=14.4, 11.4, 3.2, 2.8 Hz, H-22a), 1.83 (1H, dddd, J=14.4, 8.8, 5.3, 3.4 Hz, H-22b), 1.73 (1H, dddd, J=13.8, 10.5, 5.3, 3.2 Hz, H-21b), 1.58-1.47 (2H, m, H-16b, 24a), 1.47-1.40 (2H, m, H-4a, 34b), 1.36-1.23 (2H, m, H-4b, 5b), 1.16 (3H, d, J=7.3 Hz, C31-CH$_3$), 1.12-1.05 (1H, m, H-24b), 1.03 (3H, d, J=6.4 Hz, C25-CH$_3$), 0.97 (9H, s, SiC(CH$_3$)$_3$), 0.08 (3H, s, SiCH$_3$), 0.04 (3H, s, SiCH$_3$). HRMS (ESI) m/z: [M+H]$^+$ calcd for C$_{56}$H$_{79}$O$_{16}$Si, 1035.5132; found, 1035.5097.

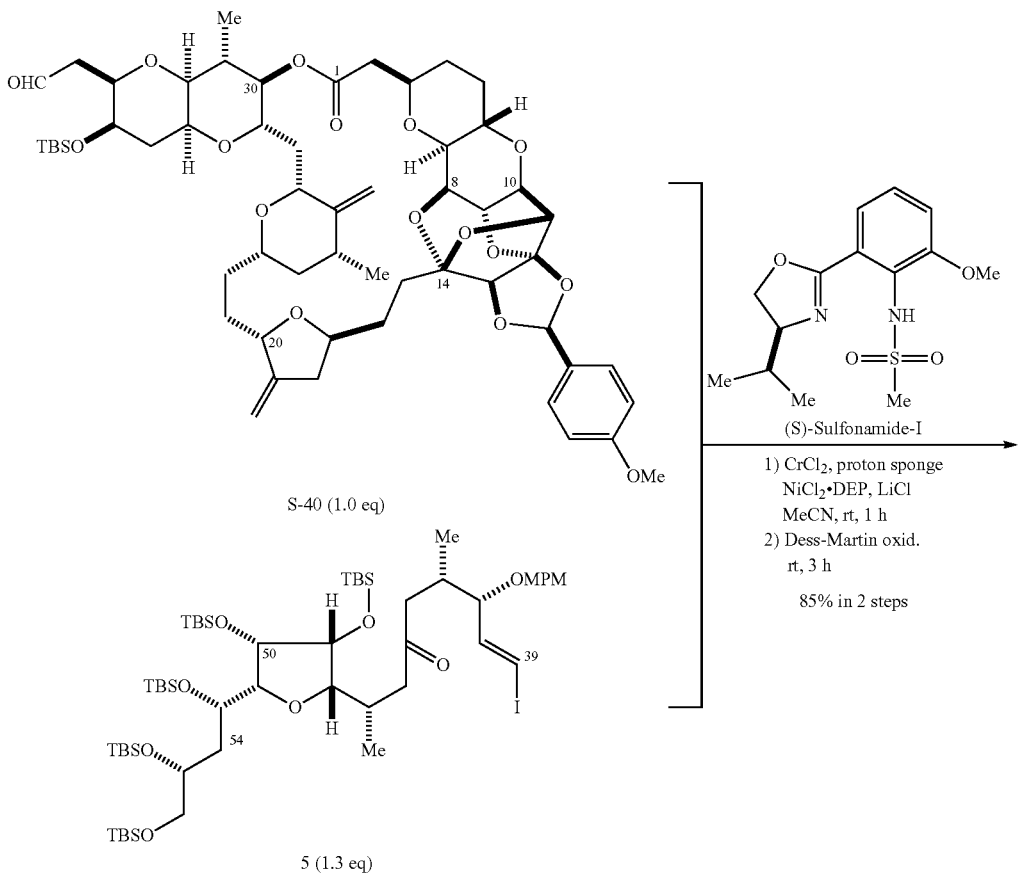

Compound 20

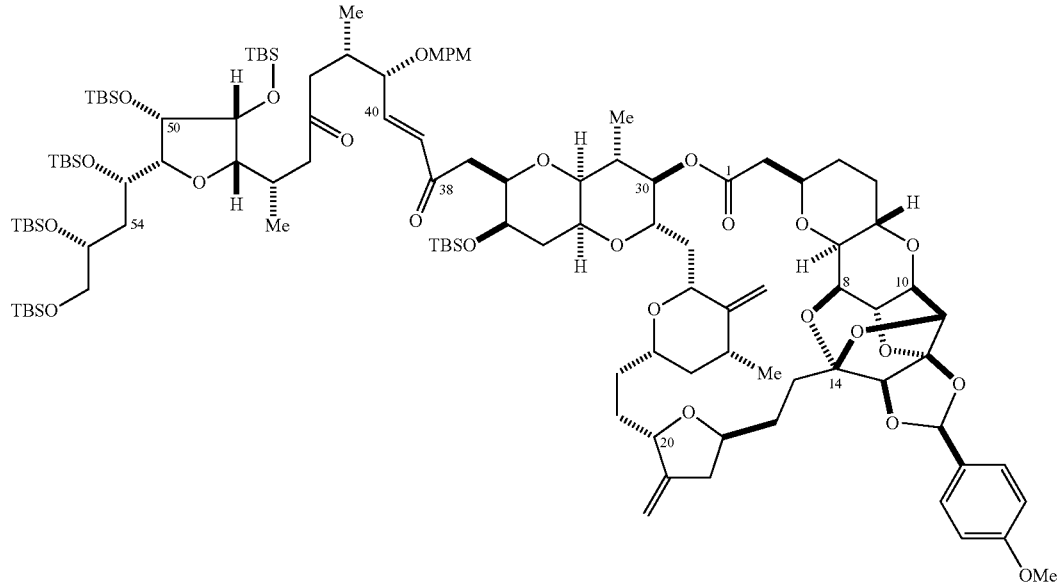

20

To a mixture of CrCl$_2$ (95.3 mg, 0.775 mmol), (S)-sulfonamide ligand I (266 mg, 0.853 mmol), and proton sponge (182 mg, 0.853 mmol) in a glove box was added MeCN (7.8 mL) and stirred for 1 h at room temperature. In a separate flask, aldehyde S-40 (160 mg, 155 μmol), iodoolefin 5[26] (214 mg, 202 μmol), NiCl$_2$.DEP (0.28 mg, 0.78 μmol, doped in LiCl), LiCl (26.3 mg, 0.620 mmol), were mixed together and the Cr-complex solution was transferred to the flask. Additional NiCl$_2$.DEP (0.28 mg each, 0.78 μmol, doped in LiCl) was added after 15, 30, and 45 min and the reaction was further stirred for 30 min at room temperature. The reaction mixture was removed from the glove box and diluted with EtOAc (8 mL) and potassium serinate[27] (1 M aq., 8 mL) and the mixture was vigorously stirred for 30 min. The resultant mixture was extracted with EtOAc/hexanes (1:1) three times, dried over sodium sulfate, and concentrated. The crude material was purified by flash column chromatography on silica gel (15% then 25% EtOAc in hexanes) to give allyl alcohol.

To a solution of the above allyl alcohol in CH$_2$Cl$_2$ (7.8 mL) were added NaHCO$_3$ (130 mg, 1.55 mmol) and Dess-Martin periodinane (197 mg, 465 μmol) at room temperature and the reaction mixture was stirred for 1.5 h at room temperature. Additional Dess-Martin periodinane (197 mg, 465 μmol) and NaHCO$_3$ (130 mg, 1.55 mmol) was added to the reaction, which was stirred for further 1.5 h. The reaction was quenched with 10 wt. % Na$_2$S$_2$O$_3$ aq. and sat. NaHCO$_3$ aq. and vigorously stirred for 30 min. The aqueous phase was extracted with CH$_2$Cl$_2$ three times and the combined organic phases were dried over Na$_2$SO$_4$ and concentrated under vacuum. The residue was purified by flash column chromatography on silica gel (30% EtOAc in hexanes) to give enone 20 (259 mg, 85% in 2 steps) as a colorless oil.

20: $[\alpha]^{20}_D$ −41.5 (c 0.17, CHCl$_3$). $^1$H NMR (600 MHz, C$_6$D$_6$) δ: 7.35 (2H, d, J=8.8 Hz, 2×CHArH), 7.25 (2H, d, J=8.5 Hz, 2×CH$_2$ArH), 6.85 (2H, d, J=8.5 Hz, 2×CH$_2$ArH), 6.79 (1H, dd, J=16.1, 6.7 Hz, H-40), 6.73 (2H, d, J=8.8 Hz, 2×CHArH), 6.40 (1H, dd, J=16.1, 0.9 Hz, H-39), 6.07 (1H, s, ArCH), 5.19 (1H, br s, C19=CHH), 5.10-5.04 (1H, m, C19=CHH), 4.95 (1H, br s, C26=CHH), 4.80 (1H, br s, C26=CHH), 4.84-4.77 (2H, m, H-29, 30), 4.67 (1H, br d, J=10.3 Hz, H-20), 4.48 (1H, d, J=11.4 Hz, ArCHH), 4.52-4.45 (1H, m, H-6), 4.41 (1H, dd, J=3.8, 1.5 Hz, H-8), 4.36 (1H, dd, J=5.3, 1.2 Hz, H-11), 4.30-4.24 (1H, m, H-53), 4.19 (1H, d, J=11.4 Hz, ArCHH), 4.06 (1H, s, H-13), 4.05-3.97 (4H, m, H-10, 17, 36, 51), 3.96-3.89 (3H, m, H-3, 35, 48), 3.81 (1H, dd, J=10.3, 3.5 Hz, H-54a), 3.80 (1H, br d, J=11.7 Hz, H-27), 3.83-3.75 (1H, m, H-50), 3.72 (1H, ddd, J=6.7, 3.8, 1.2 Hz, H-9), 3.69 (1H, dd, J=10.3, 6.2 Hz, H-54b), 3.74-3.67 (1H, m, H-23), 3.65 (1H, ddd, J=6.7, 6.0, 0.9 Hz, H-41), 3.48 (1H, ddd, J=4.4, 4.4, 3.4 Hz, H-33), 3.35 (3H, s, CH$_2$ArOCH$_3$), 3.23 (3H, s, CHArOCH$_3$), 3.17 (1H, dd, J=4.5, 3.4 Hz, H-32), 3.16 (1H, dd, J=17.9, 7.3 Hz, H-37a), 3.10 (1H, dd, J=8.5, 3.8 Hz, H-47), 3.03 (1H, dd, J=17.9, 5.6 Hz, H-37b), 3.02 (1H, dd, J=16.5, 2.5 Hz, H-45a), 2.78 (1H, dd, J=16.8, 7.8 Hz, H-2a), 2.75-2.65 (2H, m, H-18a, 46), 2.61 (1H, dd, J=17.0, 4.1 Hz, H-43a), 2.53 (1H, dd, J=9.4, 1.5 Hz, H-7), 2.57-2.50 (1H, m, H-42), 2.39 (1H, dd, J=16.8, 4.2 Hz, H-2b), 2.36-2.24 (7H, m, H-15a, 15b, 16a, 28a, 31, 43b, 45b), 2.24-2.18 (1H, m, H-21a), 2.15-2.07 (4H, m, H-18b, 25, 28b, 34a), 2.04-1.96 (2H, m, H-5a, 52a), 1.96-1.88 (2H, m, H-22a, 49a), 1.84-1.69 (3H, m, H-21b, 22b, 52b), 1.63-1.56 (2H, m, H-34b, 49b), 1.56-1.51 (1H, m, H-16b), 1.51-1.44 (2H, m, H-4a, 24a), 1.36-1.24 (2H, m, H-4b, 5b), 1.21 (3H, d, J=7.3 Hz, C31-CH$_3$), 1.15-1.11 (1H, m, H-24b), 1.09 (9H, s, SiC(CH$_3$)$_3$), 1.07 (9H, s, SiC(CH₃)₃), 1.04 (3H, d, J=7.9 Hz, C25-CH₃), 1.02 (9H, s, SiC(CH₃)₃), 1.02 (9H, s, SiC(CH₃)₃), 0.98 (3H, d, J=6.7 Hz, C46-CH₃), 0.97 (9H, s, SiC(CH₃)₃), 0.97 (3H, d, J=6.7 Hz, C42-CH₃), 0.29 (3H, s, SiCH₃), 0.28 (3H, s, SiCH₃), 0.27 (3H, s, SiCH₃), 0.26 (3H, s, SiCH₃), 0.16 (3H, s, SiCH₃), 0.14 (3H, s, SiCH₃), 0.14 (3H, s, SiCH₃), 0.11 (3H, s, SiCH₃), 0.03 (3H, s, SiCH₃), 0.02 (3H, s, SiCH₃). $^{13}$C NMR (125 MHz, C₆D₆) δ: 207.9, 197.1, 171.0, 161.4, 159.8, 152.9 (2C), 144.9, 132.5, 130.6, 129.7 (2C), 128.8 (2C), 128.6, 119.0, 114.1 (2C), 114.0 (2C), 109.3, 109.0, 105.0, 103.8, 90.2, 87.3, 83.8, 82.1, 81.2, 78.3, 78.1, 77.7, 76.1, 76.0, 75.7, 75.1, 74.7, 74.2, 73.9, 73.8, 73.6, 72.9, 72.0, 71.3, 70.9, 70.4, 68.4, 68.0, 66.1, 64.4, 54.7 (2C), 47.7, 45.9, 44.0, 42.6, 41.3, 39.4, 39.3, 39.0, 38.7, 38.4, 36.3, 35.3, 33.7, 32.3, 31.2, 30.9, 30.3, 30.2, 28.8, 27.7, 26.37 (3C), 26.32 (3C), 26.28 (3C), 26.26 (3C), 26.0 (3C), 18.6, 18.6, 18.5, 18.4, 18.2, 18.1, 17.1, 16.7, 16.6, −3.6, −3.8, −3.9, −4.0, −4.2, −4.3, −4.6, −5.0, −5.1, −5.2. HRMS (ESI) m/z: [M+NH₄]⁺ calcd for $C_{106}H_{176}NO_{24}Si_5$, 1987.1423; found, 1987.1422.
Halichondrin A
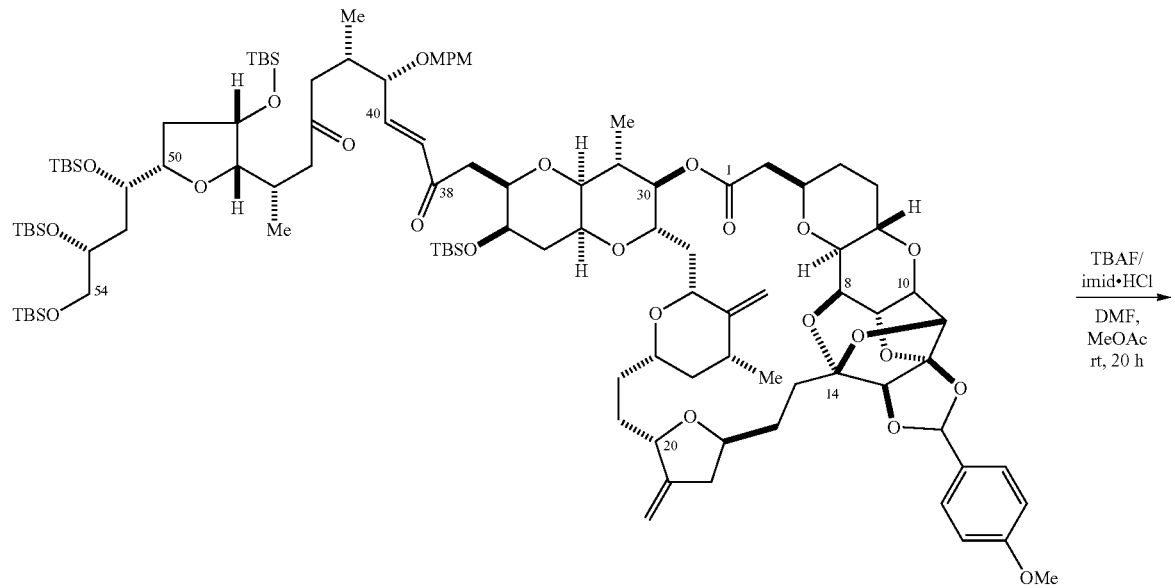
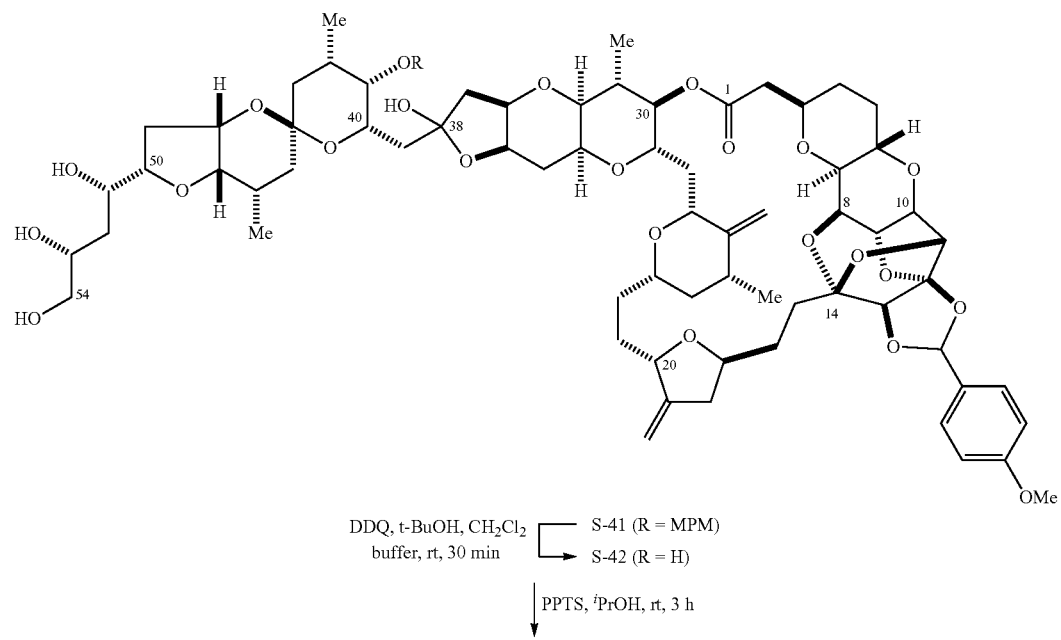

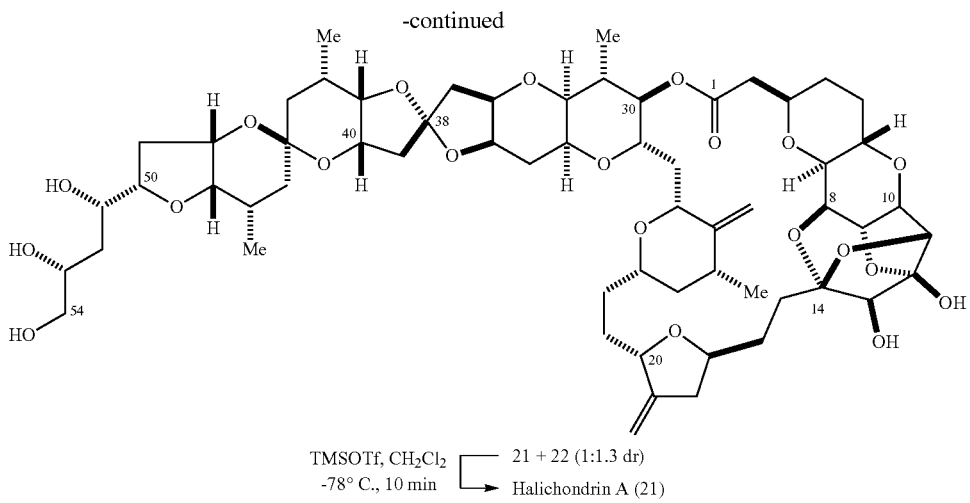

TMSOTf, CH₂Cl₂
−78° C., 10 min
→ 21 + 22 (1:1.3 dr)
→ Halichondrin A (21)

To a solution of enone 20 (20.6 mg, 10.4 mol) in DMF (1.0 mL) and MeOAc (0.10 mL) was added TBAF solution (55 μL, 0.52 μmol, Aldrich, 0.95 M in THF bufferized with 0.5 equiv. of imidazole hydrochloride) and TBAF solution (55 μL, 0.52 μmol, TCI, product number T1125, 0.95 M in THF bufferized with 0.5 equiv. of imidazole hydrochloride) at room temperature. After stirring for 20 h at the same temperature, the solvent was evaporated by stream of nitrogen gas. The residue was passed through silica gel pad twice (2 cm, eluent: 5% MeOH in EtOAc) to remove TBAF residue. After removal of the solvent, the crude product S-41 was used for the next step without further purification.

The MPM ether S-41 was dissolved in CH₂Cl₂ (2.0 mL), t-BuOH (40 μL), and pH 7.0 phosphate buffer (0.20 mL), and DDQ (23.6 mg, 104 μmol) were added to the solution at room temperature. The reaction mixture was vigorously stirred for 30 min at room temperature then quenched with sat. NaHCO₃ aq. and further stirred for 5 min. The aqueous layer was extracted with CH₂Cl₂ six times and the combined organic layers were dried over Na₂SO₄ and concentrated under vacuum. The residue was passed through silica gel and washed with CH₂Cl₂ to remove p-anisaldehyde then with EtOAc, 5% MeOH in EtOAc. After removal of the solvent, co-evaporated with benzene, and dried under high vacuum, the crude product S-42 was used for the next step without further purification.

The hemiacetal S-42 was dissolved in i-PrOH (2.0 mL, freshly distilled from sodium twice) and pyridinium p-toluenesulfonate (26.1 mg, 104 μmol) was added to the solution at room temperature. After stirring for 3 h at room temperature, the reaction mixture was quenched with triethylamine (50 μL), diluted with EtOAc, and passed through plug of silica gel (bottom, 1 cm)/amino silica gel (top, 1 cm), which was washed with 20% MeOH in EtOAc. The obtained solution was concentrated under reduced pressure, and the residue was passed through silica gel eluted with CH₂Cl₂ to remove p-anisaldehyde then with 20% MeOH in EtOAc. After removal of the solvent, the crude ¹H NMR shows the diastereomeric ratio at C38 position is 1:1.3 (21:22). The obtained crude mixture of 21 and 22 was co-evaporated with benzene and further dried under high vacuum.

To a solution of acetal in CH₂Cl₂ (5.0 mL) was dropped TMSOTf (100 μL) at −78° C. and the reaction mixture was stirred for 10 min at the same temperature. The reaction mixture was quickly poured into a solution of sat. NaHCO₃ aq. (25 mL) in a separate flask at 0° C. with vigorous stirring (rare earth extra power stir bar and Yazawa magnetic stirrer, model KF-82 were used). The resultant solution was stirred for 1 h at 0° C. The aqueous layer was extracted with CH₂Cl₂ six times and the combined organic layers were dried over Na₂SO₄ and concentrated under vacuum. The crude ¹H NMR shows the diastereomeric ratio at C38 position is >10:1 (21:22). The crude material was purified by preparative TLC (0.5 mm thickness, 10×20 cm, EtOAc/CH₂Cl₂/MeOH=5:5:1, developed three times) to furnish halichondrin A (4.6 mg, 39% in 4 steps) as a white amorphous.

21: $[\alpha]^{20}_D$ −69.2 (c 0.41, MeOH). ¹H NMR (600 MHz, ¹²CD₃OD) δ: 5.08 (1H, d, J=1.8 Hz, C19=CHH), 5.03 (1H, d, J=1.8 Hz, C19=CHH), 4.88 (1H, br s, C26=CHH), 4.81, (1H, d, J=1.2 Hz, C26=CHH), 4.62 (1H, dd, J=7.3, 4.4 Hz, H-30), 4.45 (1H, d, J=11.2 Hz, H-20), 4.37 (1H, dd, J=4.7, 2.9 Hz, H-8), 4.32 (1H, ddd, J=10.0, 10.0, 4.1 Hz, H-6), 4.32-4.28 (2H, m, H-9, 11), 4.25 (1H, ddd, J=11.2, 4.4, 2.1 Hz, H-29), 4.20 (1H, dd, J=3.2, 2.1 Hz, H-10), 4.14-4.07 (4H, m, H-17, 35, 36, 48), 4.05 (1H, ddd, J=2.3, 2.3, 2.3 Hz, H-40), 3.99 (1H, ddd, J=9.5, 4.8, 4.1 Hz, H-50), 3.91-3.84 (3H, m, H-3, 33, 53), 3.78 (1H, ddd, J=8.8, 4.8, 4.4 Hz, H-51), 3.75-3.70 (1H, m, H-23), 3.69 (1H, dd, J=2.3, 2.3 Hz, H-41), 3.61 (1H, d, J=11.7 Hz, H-27), 3.56 (1H, dd, J=2.3, 1.8 Hz, H-47), 3.53 (1H, s, H-13), 3.53 (1H, dd, J=11.2, 4.7, Hz, H-54a), 3.47 (1H, dd, J=11.2, 6.5 Hz, H-54b), 3.22 (1H, dd, J=6.5, 4.7 Hz, H-32), 2.94 (1H, dd, J=10.0, 2.3 Hz, H-7), 2.82 (1H, dddd, J=15.8, 7.6, 4.7, 2.9 Hz, H-18a), 2.57 (1H, dd, J=17.9, 9.7 Hz, H-2a), 2.45 (1H, dd, J=17.9, 1.8 Hz, H-2b), 2.40 (1H, dd, J=13.2, 6.2 Hz), 2.36-2.24 (6H, m), 2.20-2.13 (1H, m), 2.10-1.97 (4H, m), 1.92-1.79 (4H, m), 1.78-1.67 (4H, m), 1.60 (1H, ddd, J=14.2, 8.4, 8.4 Hz, H-52b), 1.56-1.42 (4H, m), 1.42-1.28 (5H, m), 1.10 (3H, d, J=6.5 Hz, C25-CH₃), 1.06 (3H, d, J=7.6 Hz, C31-CH₃), 1.02 (3H, d, J=7.0 Hz, C46-CH₃), 1.04-0.98 (1H, m, H-24b), 0.97 (3H, d, J=7.0 Hz, C42-CH₃). ¹³C NMR (125 MHz, ¹²CD₃OD) δ:172.8, 153.3, 153.1, 114.8, 113.3, 112.9, 105.7, 104.8, 98.4, 85.5, 82.3, 81.3, 81.2, 80.7, 79.0, 78.0 (2C), 77.6, 77.4, 76.3, 76.0, 75.8, 75.5, 75.2, 75.1 (2C), 73.8, 73.7, 73.3, 73.1, 73.0, 71.6, 69.6, 67.2, 65.6, 45.6, 45.9), 44.9, 41.1, 39.8, 37.93, 37.90, 37.8, 37.51, 37.47, 37.2, 36.2, 33.0, 31.8, 31.34, 31.31, 30.85, 30.82, 28.4, 27.11, 27.07, 18.4, 18.3, 18.1, 15.9. HRMS (ESI) m/z. [M+H]⁺ calcd for C₆₀H₈₇O₂₁, 1143.5734; found, 1143.5701.

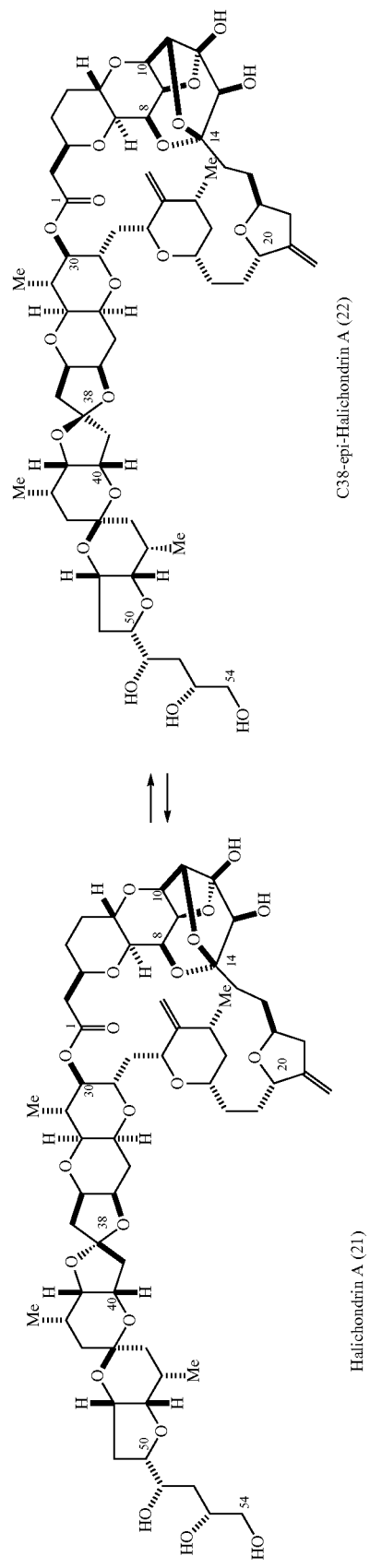

To a solution of halichondrin A (21) or its C38-epimer (22) (ca. 0.05 mg) in solvent (0.30 mL) was treated with acid (ca. 100 eq) at room temperature or at −78° C. The reaction was done at room temperature and monitored by TLC until 21 and 22 were in equilibrium. For the reaction operated at −78° C., the reaction mixture was stirred for 10 min at −78° C. then quenched with sat. NaHCO$_3$ aq. with vigorous stirring without dry-ice/acetone bath. The ratio of 21 and 22 were estimated by $^1$H NMR (600 MHz, C$_6$D$_6$) and/or HPTLC (EtOAc/CH$_2$Cl$_2$/MeOH=5:5:1, R$_f$=0.28 for 21, R$_f$=0.33 for 22).

Under the same conditions, equilibration of halichondrins B (1) and C (S-46), as well as norhalichondrin A methyl ester (S-43), was also studied, thereby showing their equilibration behavior to be identical with that of halichondrin A.

For illustration of the ratio estimation by NMR, $^1$H NMR spectra of halichondrin A (21) and its C38-epimer (22), norhalichondrin methyl ester (S-43) and its C38-epimer (S-44), halichondrin B (1) and its C38-epimer (S-45), and halichondrin C (S-46) and its C38-epimer (S-47) are shown in FIGS. 4 and 5. In all the series, the C19-proton resonances were found to be useful for estimating the ratio, cf., broken lines in red for the natural series vs. broken lines in blue for the C38-epi series.

C38-epi-Halichondrin A (22): $^1$H NMR (600 MHz, CD$_3$OD): see NMR chart in Table 1. HRMS (ESI) m/z: [M+NH$_4$]$^+$ calcd for C$_{60}$H$_{90}$NO$_{21}$, 1160.0000; found, 1160.6039.

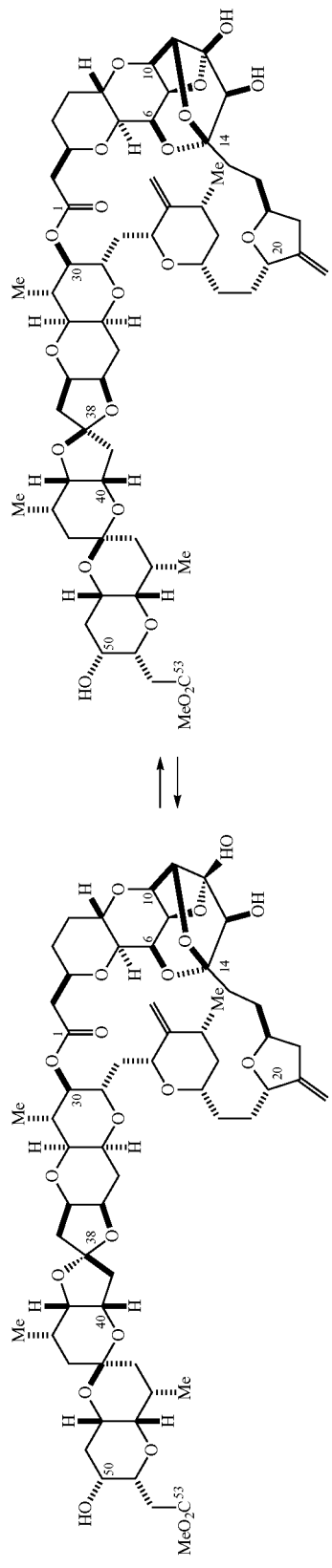

Norhalichondrin A methyl ester (S-43): $^1$H NMR (600 MHz, CD$_3$OD): see NMR chart in Table 1. HRMS (ESI) m/z: [M+Na]$^+$ calcd for C$_{60}$H$_{84}$O$_{21}$Na, 1163.5397; found, 1163.5366. C38-epi-Norhalichondrin A methyl ester (S-44): $^1$H NMR (600 MHz, CD$_3$OD): see NMR chart in Table 1. HRMS (ESI) m/z: [M+Na]$^+$ calcd for C$_{60}$H$_{84}$O$_{21}$Na, 1163.5397; found, 1163.5357.

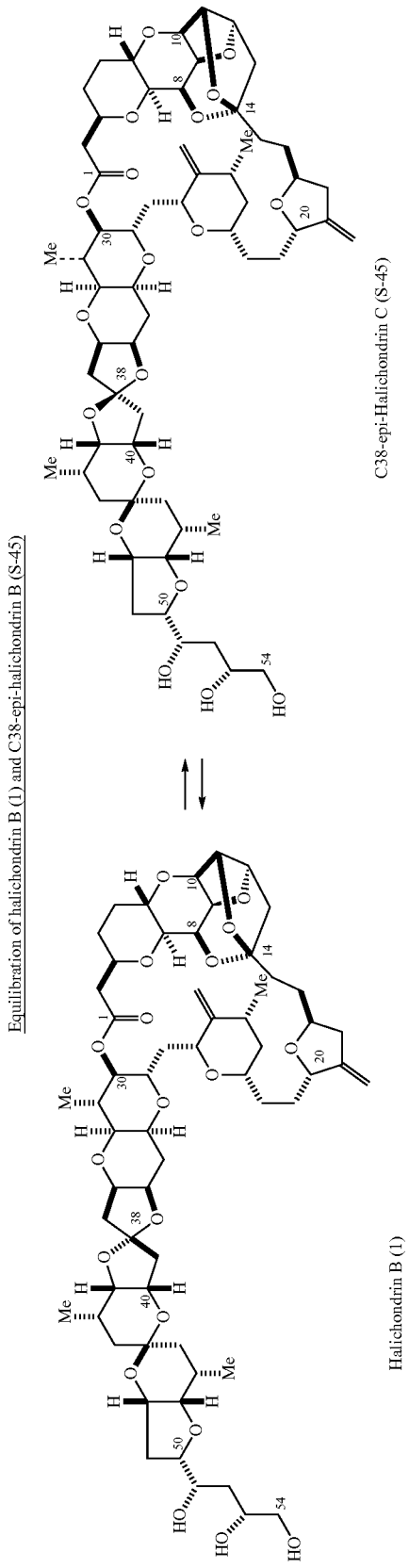

Halichondrin B (1): see reference.[16] C38-epi-Halichondrin B (S-45): $^1$H NMR (600 MHz, CD$_3$OD): see NMR chart in Table 1. HRMS (ESI) m/z: [M+H]$^+$ calcd for C$_{60}$H$_{87}$O$_{19}$, 1111.5836; found, 1111.5805.

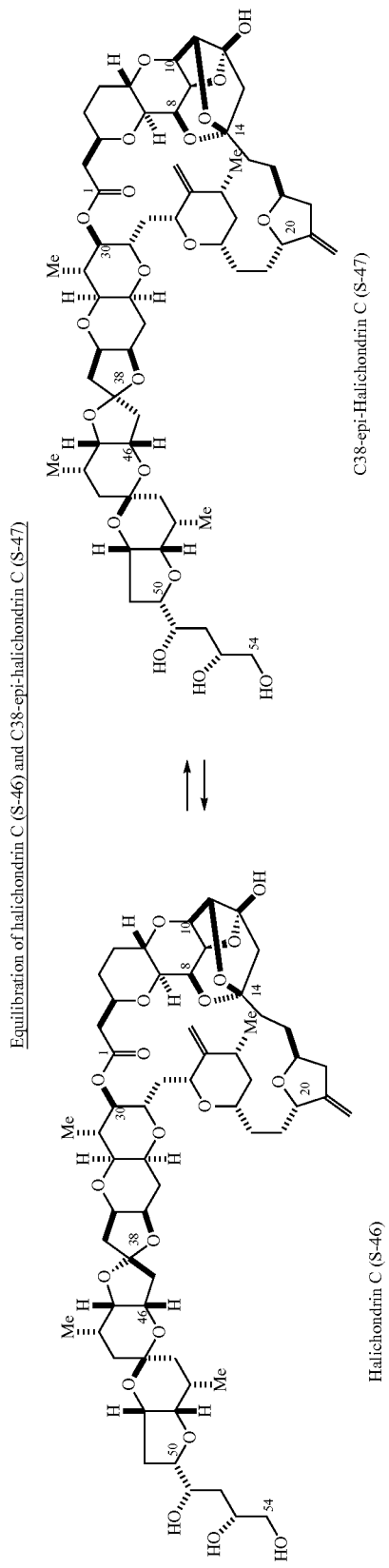

Halichondrin C (S-46): see reference.[5] C38-epi-Halichondrin C (S-47): $^1$H NMR (600 MHz, CD$_3$OD): see NMR chart in Table 1. HRMS (ESI) m/z: [M+Na]$^+$ calcd for C$_{60}$H$_{86}$O$_{20}$Na 1149.5605; found, 1149.5644.

0.29 µmol, doped in LiCl), LiCl (5.0 mg, 0.12 mmol), were mixed together and the Cr-complex solution was transferred to the flask. Additional NiCl$_2$.DEP (0.10 mg, 0.29 µmol) was added after 30 min and the reaction was further stirred for 30

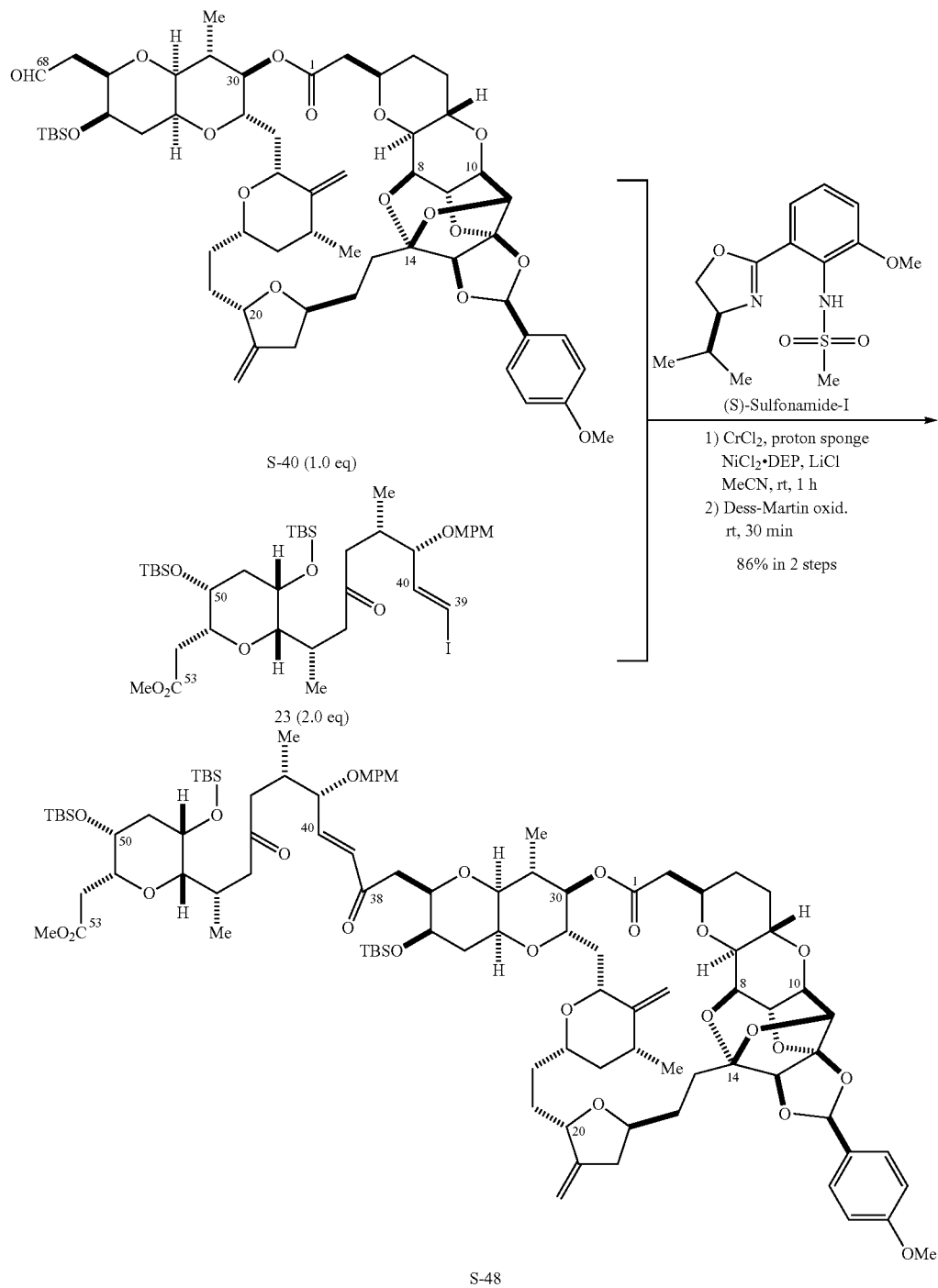

Compound S-48

To a mixture of CrCl$_2$ (18.1 mg, 0.147 mmol), (S)-sulfonamide ligand I (50.5 mg, 0.162 mmol), and proton sponge (34.6 mg, 0.162 mmol) in a glove box was added MeCN (1.5 mL) and stirred for 1 h at room temperature. In a separate flask, aldehyde S-40 (30.5 mg, 29.4 µmol), iodoolefin 23[28] (49.0 mg, 58.8 µmol), NiCl$_2$-DEP (0.10 mg, min at room temperature. The reaction was removed from the glove box and diluted with EtOAc (1.5 mL) and potassium serinate (1 M aq., 1.5 mL) and the mixture was stirred vigorously for 30 min. The resultant mixture was extracted with EtOAc five times, dried over sodium sulfate, and concentrated. The crude material was purified by flash column chromatography on silica gel (20%, 30%, then 40% EtOAc in hexanes) to give allyl alcohol.

To a solution of the above allyl alcohol in $CH_2Cl_2$ (1.5 mL) were added $NaHCO_3$ (24.7 mg, 0.294 mmol) and Dess-Martin periodinane (24.9 mg, 58.8 μmol) at room temperature and the reaction mixture was stirred for 30 min at room temperature. Additional Dess-Martin periodinane (12.5 mg, 29.4 μmol) was added and the reaction was stirred for further 30 min. The reaction was quenched with 10 wt. % $Na_2S_2O_3$ aq. and sat. $NaHCO_3$ aq. and vigorously stirred for 30 min. The aqueous phase was extracted with $CH_2Cl_2$ three times and the combined organic phases were dried over $Na_2SO_4$ and concentrated under vacuum. The residue was purified by preparative TLC (40% EtOAc in hexanes) to provide enone S-48 (43.7 mg, 86% in 2 steps) as colorless oil.

S-48: M.p. 81-83° C. $[α]^{20}_D$ −54.1 (c 0.13, $CHCl_3$). $^1H$ NMR (600 MHz, $C_6D_6$) δ: 7.36 (2H, d, J=8.8 Hz, 2×CHArH), 7.27 (2H, d, J=8.5 Hz, 2×$CH_2$ArH), 6.86 (2H, d, J=8.5 Hz, 2×$CH_2$ArH), 6.80 (1H, dd, J=16.1, 6.4 Hz, H-40), 6.73 (2H, d, J=8.8 Hz, 2×CHArH), 6.41 (1H, dd, J=16.1, 1.0 Hz, H-39), 6.08 (1H, s, ArCH), 5.20 (1H, br s, C19=CHH), 5.11-5.06 (1H, m, C19=CHH), 4.95 (1H, br s, C26=CHH), 4.80 (1H, br s, C26=CHH), 4.85-4.78 (2H, m, H-29, 30), 4.68 (1H, br d, J=10.3 Hz, H-20), 4.53-4.47 (1H, m, H-6), 4.48 (d, J=11.1 Hz, ArCHH), 4.42 (1H, dd, J=3.7, 1.5 Hz, H-8), 4.37 (1H, dd, J=5.3, 1.2 Hz, H-11), 4.21 (1H, d, J=11.1 Hz, ArCHH), 4.07 (1H, s, H-13), 4.06-3.93 (4H, m, H-3, 10, 17, 36), 3.93-3.89 (1H, m, H-35), 3.81 (11H, br d, J=11.7 Hz, H-27), 3.78 (1H, ddd, J=8.5, 4.8, 2.1 Hz, H-51), 3.72 (1H, ddd, J=6.5, 3.7, 1.2 Hz, H-9), 3.75-3.69 (1H, m, H-23), 3.67 (1H, ddd, J=6.4, 5.9, 1.0 Hz, H-41), 3.61 (1H, ddd, J=4.2, 2.5, 1.8 Hz, H-48), 3.49 (2H, m, H-33, 50), 3.48 (3H, s, $CO_2CH_3$), 3.35 (3H, s, $CH_2ArOCH_3$), 3.23 (3H, s, $CHArOCH_3$), 3.16 (1H, dd, J=17.9, 7.3 Hz, H-37a), 3.17 (1H, dd, J=4.8, 3.4 Hz, H-32), 3.04 (1H, dd, J=17.9, 5.3 Hz, H-37b), 2.93 (1H, dd, J=16.8, 3.4 Hz, H-45a), 2.87 (1H, dd, J=16.1, 8.5 Hz, H-52a), 2.85 (1H, dd, J=8.8, 1.8 Hz, H-47), 2.78 (1H, dd, J=17.0, 7.8 Hz, H-2a), 2.74 (1H, ddddd, J=15.5, 7.3, 2.6, 2.2, 2.2 Hz, H-18a), 2.66 (1H, ddqd, J=9.1, 8.8, 6.7, 3.4 Hz, H-46), 2.58-2.50 (3H, m, H-7, 42, 43a), 2.48 (1H, dd, J=16.1, 4.8 Hz, H-52b), 2.40 (1H, dd, J=17.0, 4.4 Hz, H-2b), 2.37-2.17 (8H, m, H-15a, 15b, 16a, 21a, 28a, 31, 43b, 45b), 2.16-2.07 (4H, m, H-18b, 25, 28b, 34a), 2.05-2.00 (1H, m, H-5a), 1.99-1.92 (1H, m, H-22a), 1.87 (1H, ddd, J=14.7, 2.6, 2.5 Hz, H-49a), 1.85-1.79 (1H, m, H-22b), 1.73 (1H, dddd, J=13.5, 10.3, 5.0, 3.2 Hz, H-21b), 1.61 (ddd, J=14.6, 4.7, 4.7 Hz, H-34b), 1.58-1.52 (11H, m, H-16b), 1.52-1.44 (3H, m, H-4a, 24a, 49b), 1.37-1.27 (2H, m, H-4b, 5b), 1.22 (3H, d, J=7.3 Hz, $C31-CH_3$), 1.12-1.06 (1H, m, H-24b), 1.04 (3H, d, J=6.2 Hz, $C25-CH_3$), 1.04 (9H, s, $SiC(CH_3)_3$), 1.03 (9H, s, $SiC(CH_3)_3$), 0.97 (9H, s, $SiC(CH_3)_3$), 0.93 (3H, d, J=6.7 Hz, $C46-CH_3$), 0.92 (3H, d, J=6.7 Hz, $C42-CH_3$), 0.16 (3H, s, $SiCH_3$), 0.13 (3H, s, $SiCH_3$), 0.12 (3H, s, $SiCH_3$), 0.07 (3H, s, $SiCH_3$), 0.05 (3H, s, $SiCH_3$), −0.05 (3H, s, $SiCH_3$). $^{13}C$ NMR (125 MHz, $C_6D_6$) δ: 208.4, 197.1, 171.8, 171.1, 161.4, 159.8, 152.9 (2C), 144.9, 132.5, 130.7, 129.7 (2C), 128.8 (2C), 128.7, 119.0, 114.1 (2C), 114.0 (2C), 109.3, 109.0, 105.0, 103.8, 90.3, 84.6, 83.8, 82.1, 78.3, 78.2, 78.0, 77.8, 76.1, 76.0, 75.7, 75.1, 74.7, 74.2, 74.0, 73.8, 73.7, 71.2, 70.3, 68.4, 66.2, 65.9, 64.7, 64.5, 54.8, 54.7, 51.1, 46.7, 45.7, 44.0, 42.7, 41.3, 39.4, 39.3, 38.9, 38.5, 37.1, 36.4, 35.4, 33.7, 32.3, 31.2, 30.9, 30.3, 30.2, 29.9, 27.7, 36.5 (3C), 26.4 (3C), 26.3 (3C), 18.6, 18.5, 18.4, 18.2, 16.9, 16.5, 16.4, −2.6, −3.6, −4.0, −4.5, −5.0, −5.1. HRMS (ESI) m/z: $[M+Na]^+$ calcd for $C_{94}H_{142}O_{24}Si_3Na$, 1761.9091; found, 1761.9086.

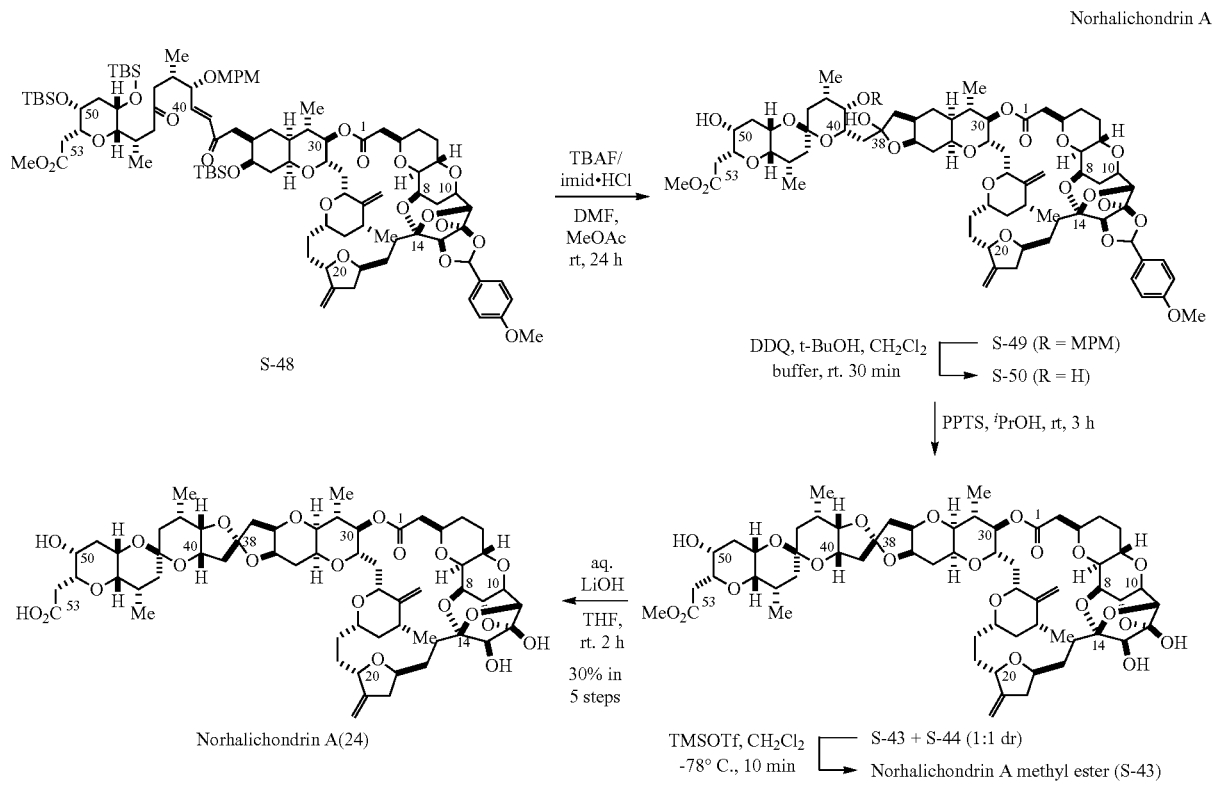

To a solution of enone S-48 (18.4 mg, 10.5 μmol) in DMF (1.1 mL) and MeOAc (0.11 mL) was added TBAF solution (55 μL, 0.52 μmol, Aldrich, 0.95 M in THF bufferized with 0.5 equiv. of imidazole hydrochloride) and TBAF solution (55 μL, 0.52 μmol, TCI, product number T1125, 0.95 M in THF bufferized with 0.5 equiv. of imidazole hydrochloride) at room temperature. After stirring for 24 h at the same temperature, the solvent was evaporated by stream of nitrogen gas. The residue was passed through silica gel pad twice (2 cm, eluent: 5% MeOH in EtOAc) to remove TBAF residue. After removal of the solvent, the crude product S-49 was used for the next step without further purification.

The MPM ether S-49 was dissolved in $CH_2Cl_2$ (2.1 mL), t-BuOH (42 μL), and pH 7.0 phosphate buffer (0.21 mL), and DDQ (23.8 mg, 105 μmol) was added to the solution at room temperature. The reaction mixture was vigorously stirred for 30 min at room temperature then quenched with sat. $NaHCO_3$ aq. and further stirred for 5 min. The aqueous layer was extracted with $CH_2Cl_2$ six times and the combined organic layers were dried over $Na_2SO_4$ and concentrated under vacuum. The residue was passed through silica gel and washed with $CH_2Cl_2$ to remove p-anisaldehyde then with EtOAc, 5% MeOH in EtOAc. After removal of the solvent, co-evaporated with benzene, and dried under high vacuum, the crude product S-50 was used for the next step without further purification.

The hemiacetal S-50 was dissolved in i-PrOH (2.1 mL, freshly distilled from sodium twice) and pyridinium p-toluenesulfonate (26 mg, 105 μmol) was added to the solution at room temperature. After stirring for 3 h at the same temperature, the reaction mixture was quenched with triethylamine (50 μL), diluted with EtOAc, and passed through plug of silica gel (bottom, 1 cm)/amino silica gel (top, 1 cm), which was washed with 20% MeOH in EtOAc. The obtained solution was concentrated under reduced pressure, and the residue was passed through silica gel eluted with $CH_2Cl_2$ to remove p-anisaldehyde then with 20% MeOH in EtOAc. After removal of the solvent, the crude $^1$H NMR shows the diastereomeric ratio at C38 position is 1:1 (S-43:S-44). The obtained crude mixture of S-43 and S-44 was co-evaporated with benzene and further dried under high vacuum.

To a solution of above acetal in $CH_2Cl_2$ (5.0 mL) was dropped TMSOTf (100 μL) at −78° C. and the reaction mixture was stirred for 10 min at the same temperature. The reaction mixture was quickly poured into a solution of sat. $NaHCO_3$ aq. (25 mL) in a separate flask at 0° C. with vigorous stirring (rare earth extra power stir bar and Yazawa magnetic stirrer, model KF-82 were used). The resultant solution was stirred for 1 h at 0° C. The aqueous layer was extracted with $CH_2Cl_2$ six times and the combined organic layers were dried over $Na_2SO_4$ and concentrated under vacuum. The crude $^1$H NMR shows the diastereomeric ratio at C38 position is >10:1 (S-43:S-44). The crude material was purified by preparative TLC (0.5 mm thickness, 10×20 cm, EtOAc/$CH_2Cl_2$/MeOH=5:5:1, developed three times) to furnish norhalichondrin A methyl ester S-43 as a white amorphous.

To methyl ester S-43 in THF (1.8 mL) was added LiOH solution (1 M aq., 0.30 mL) at room temperature and the reaction mixture was stirred for 2 h at the same temperature. The reaction mixture was diluted with water (0.9 mL) and THF was removed by a stream of nitrogen gas. After cooling to 0° C., the reaction mixture was quenched with 1 M HCl aq (0.3 mL) and extracted with EtOAc five times. The combined organic phases were dried over $Na_2SO_4$ and concentrated under reduced pressure. The crude was purified by preparative TLC (EtOAc/$CH_2Cl_2$/MeOH=5:5:1, developed three times) to give product, which was further purified by polystyrene column (TSK G3000S, loaded with 50% EtOH/$H_2O$) eluted with 0%, 25%, 50% EtOH/$H_2O$ to give norhalichondrin A (24, 3.5 mg, 30% in 5 steps) as a white amorphous.

24: $^1$H NMR (600 MHz, $^{12}CD_3OD$) δ: 5.06 (1H, d, J=1.5 Hz, C19=CHH), 5.02 (d, J=1.8 Hz, C19=CHH), 4.86 (1H, m, C26=CHH), 4.81 (1H, d, J=1.2 Hz, C26=CHH), 4.62 (1H, dd, J=7.3, 4.7 Hz, H-30), 4.44 (1H, d, J=11.1 Hz, H-20), 4.39-4.35 (1H, m, H-8), 4.35-4.29 (3H, m, H-6, 9, 11), 4.24 (1H, ddd, J=11.2, 4.3, 2.1 Hz, H-29), 4.20 (1H, dd, J=3.2, 2.3 Hz, H-10), 4.16-4.05 (3H, m, H-17, 35, 36), 4.00-3.96 (1H, m, H-40), 3.92-3.85 (2H, m, H-3, 33), 3.81-3.75 (2H, m, H-48, 51), 3.74-3.67 (2H, m, H-23, 41), 3.65-3.59 (2H, m, H-27, 50), 3.53 (1H, s, H-13), 3.33-3.28 (1H, m, H-47), 3.21 (1H, dd, J=6.4, 4.7 Hz, H-32), 2.93 (1H, dd, J=9.8, 2.2 Hz, H-7), 2.83 (1H, ddd, J=16.0, 8.1, 2.1 Hz, H-18a), 2.58 (1H, dd, J=17.6, 9.7 Hz, H-2a), 2.48 (2H, d, J=6.7 Hz, H-52a, 52b), 2.45 (1H, dd, J=17.6, 2.1 Hz, H-2b), 2.39 (1H, dd, J=13.2, 6.2 Hz, H-37a), 2.37-2.23 (6H, m, H-18b), 2.20-2.12 (2H, m), 2.10-1.97 (6H, m), 1.94 (1H, ddd, J=14.9, 3.1, 3.1 Hz, H-49b), 1.91-1.79 (2H, m), 1.76-1.66 (3H, m), 1.63-1.45 (3H, m), 1.43-1.31 (5H, m), 1.10 (3H, d, J=6.4 Hz, C25-$CH_3$), 1.06 (3H, d, J=7.0 Hz, C31-$CH_3$), 1.04-1.00 (1H, m, H-24b), 0.98 (3H, d, J=6.4 Hz, C42-$CH_3$), 0.96 (3H, d, J=6.7 Hz, C46-$CH_3$). $^{13}$C NMR (125 MHz, $^{12}CD_3OD$) δ: 172.8 (2C), 153.3, 153.1, 114.8, 113.3, 112.9, 105.7, 104.8, 98.5, 85.5, 82.3, 80.6, 79.0, 77.9 (3C), 77.6, 77.36, 77.27, 76.3, 76.0, 75.8, 75.5, 75.2, 75.0 (2C), 73.78, 73.74, 72.6, 69.6, 68.14, 68.11, 65.6, 45.5, 44.9 (2C), 41.1, 39.8, 38.3, 38.1, 37.8, 37.5, 37.1, 35.8, 32.9, 31.8, 31.32, 31.29, 30.8 (3C), 30.1, 28.4, 27.3, 18.4, 18.1, 17.4, 15.8. HRMS (ESI) m/z: [M+$NH_4$]$^+$ calcd for $C_{59}H_{86}NO_{21}$, 1144.5687; found, 1144.5646.

TABLE 3

NMR chemical shifts of natural and synthetic norhalichondrin A (24, in $CD_3OD$)[29]

| | $^1$H NMR (δ in ppm) | | | $^{13}$C NMR (δ in ppm) | |
| --- | --- | --- | --- | --- | --- |
| | Natural | Synthetic | | Natural | Synthetic |
| H2 | 2.44 | 2.45 | C1 | 172.8 | 172.8 |
| H2 | 2.58 | 2.58 | C2 | 41.1 | 41.1 |
| H3 | 3.89 | 3.88 | C3 | 75.1 | 75.0 |
| H6 | 4.32 | 4.32 | C6 | 69.6 | 69.6 |
| H7 | 2.93 | 2.93 | C7 | 79.0 | 77.9 |
| H8 | 4.37 | 4.37 | C8 | 75.8 | 75.8 |
| H9 | 4.31 | 4.31 | C9 | 73.8 | 73.7 |
| H10 | 4.21 | 4.20 | C10 | 85.5 | 85.5 |
| H11 | 4.31 | 4.31 | C11 | 75.5 | 75.5 |
| H13 | 3.53 | 3.53 | C12 | 113.4 | 113.3 |
| H17 | 4.09 | 4.10 | C13 | 82.4 | 82.3 |
| H18 | 2.32 | 2.33 | C14 | 112.9 | 112.9 |
| H18 | 2.82 | 2.83 | C17 | 76.3 | 76.3 |
| C19=$CH_2$ | 5.02 | 5.02 | C18 | 39.8 | 39.8 |
| C19=$CH_2$ | 5.06 | 5.06 | C19 | 153.2 | 153.1 |
| H20 | 4.44 | 4.44 | C19=$CH_2$ | 105.8 | 105.7 |
| H23 | 3.72 | 3.72 | C20 | 76.0 | 76.0 |
| C25—Me | 1.09 | 1.10 | C23 | 75.3 | 75.2 |
| C26=$CH_2$ | 4.81 | 4.81 | C25 | 37.2 | 37.1 |
| C26=$CH_2$ | 4.86 | 4.86 | C25—Me | 18.4 | 18.4 |
| H27 | 3.61 | 3.62 | C26 | 153.2 | 153.2 |
| H29 | 4.24 | 4.24 | C26=$CH_2$ | 104.8 | 104.8 |
| H30 | 4.61 | 4.62 | C27 | 75.1 | 75.0 |
| C31—Me | 1.06 | 1.06 | C29 | 73.8 | 73.7 |
| H32 | 3.22 | 3.21 | C30 | 77.3 | 77.4 |
| H33 | 3.87 | 3.88 | C31 | 37.5 | 37.5 |
| H35 | 4.11 | 4.10 | C31—Me | 15.9 | 15.8 |
| H36 | 4.09 | 4.10 | C32 | 77.9 | 77.9 |
| H40 | 3.98 | 3.98 | C33 | 65.6 | 65.6 |

TABLE 3-continued

NMR chemical shifts of natural and synthetic norhalichondrin A (24, in $CD_3OD$)[29]

| | $^1$H NMR (δ in ppm) | | | $^{13}$C NMR (δ in ppm) | |
|---|---|---|---|---|---|
| | Natural | Synthetic | | Natural | Synthetic |
| H41 | 3.69 | 3.70 | C35 | 77.6 | 77.6 |
| C42—Me | 0.97 | 0.98 | C36 | 78.0 | 77.9 |
| C46—Me | 0.96 | 0.96 | C37 | 45.6 | 45.5 |
| H47 | 3.30 | 3.30 | C38 | 114.9 | 114.8 |
| H48 | 3.77 | 3.78 | C39 | 44.9 | 44.9 |
| H49 | 1.94 | 1.94 | C40 | 72.7 | 72.6 |
| H49 | 2.09 | 2.10 | C41 | 80.7 | 80.6 |
| H50 | 3.61 | 3.62 | C42 | 27.3 | 27.3 |
| H51 | 3.78 | 3.78 | C42—Me | 18.1 | 18.1 |
| H52 | 2.47 | 2.48 | C44 | 98.5 | 98.5 |
| H52 | 2.47 | 2.48 | C46 | 30.1 | 30.1 |
| | | | C46—Me | 17.5 | 17.4 |
| | | | C47 | 77.2 | 77.2 |
| | | | C48 | 68.2 | 68.1 |
| | | | C50 | 68.1 | 68.1 |
| | | | C51 | 79.1 | 79.0 |
| | | | C53 | 172.8 | 172.8 |

REFERENCES AND NOTES

1. For reviews on Cr-mediated carbon-carbon bond-forming reactions, see: (a) Saccomano, N. A. in *Comprehensive Organic Synthesis*; Trost, B. M., Fleming, I., Eds.; Pergamon: Oxford, 1991; Vol. 1, p 173. (b) Fürstner, A. *Chem. Rev.* 1999, 99, 991. (c) Wessjohann, L. A.; Scheid, G. *Synthesis*, 1999, 1. (d) Takai, K.; Nozaki, H. *Proc. Japan Acad. Ser. B* 2000, 76, 123. (e) Hargaden, G. C.; Guiry, P. J. *Adv. Synth. Catal.* 2007, 349, 2407.

2. (a) Guo, H.; Dong, C.-G.; Kim, D.-S.; Urabe, D.; Wang, J.; Kim, J. T.; Liu, X.; Sasaki, T.; Kishi, Y. *J. Am. Chem. Soc.* 2009, 131, 15387. (b) Kim, D.-S.; Dong, C.-G.; Kim, J. T.; Guo, H.; Huang, J.; Tiseni, P. S.; Kishi, Y. *J. Am. Chem. Soc.* 2009, 131, 15636. (c) Dong, C.-G.; Henderson, J. A.; Kaburagi, Y.; Sasaki, T.; Kim, D.-S.; Kim, J. T.; Urabe, D.; Guo, H.; Kishi, Y. *J. Am. Chem. Soc.* 2009, 131, 15642. (d) Liu, X.; Henderson, J. A.; Sasaki, T.; Kishi, Y. *J. Am. Chem. Soc.* 2009, 131, 16678 and references cited therein.

3. Buszek, K. R.; Fang, F. G.; Forsyth, C. J.; Jung, S. H.; Kishi, Y.; Scola, P. M.; Yoon, S. K. *Tetrahedron Lett.* 1992, 33, 1553.

4. In the previous synthesis of halichondrins B and C, the $C_8$-$C_{14}$ polycycle was built after the macrolactonization.

5. Yamamoto, A.; Ueda, A.; Brémond, P.; Tiseni, P. S.; Kishi, Y. *J. Am. Chem. Soc.* 2012, 134, 893 and references cited therein.

6. Anisylidene formation of β-10 gave a single stereoisomer, whose stereochemistry was assigned, based on the NOE experiments done on 6a.

7. For example, see: (a) Aicher, T. D.; Kishi, Y. *Tetrahedron Lett.* 1987, 28, 3463. (b) Usanov, D. L.; Yamamoto, H. *J. Am. Chem. Soc.* 2011, 133, 1286.

8. For possibly relevant examples, see: (a) Mahadevan, A.; Fuchs, P. L. *J. Am. Chem. Soc.* 1995, 117, 3272. (b) Knapp, S.; Naughton, A. B. J.; Murali Dhar, T. G. *Tetrahedron Lett.* 1992, 33, 1025.

9. Reich, H. J.; Peake, S. L. *J. Am. Chem. Soc.* 1978, 100, 4888.

10. Kang, B.; Mowat, J.; Pinter, T.; Britton, R. *Org. Lett.* 2009, 11, 1717.

11. Shiina, I.; Kubota, M.; Ibuka, R. *Tetrahedron Lett.* 2002, 43, 7535.

12. For recent examples, see for example: (a) Phillips, S. T.; Shair, M. D. *J. Am. Chem. Soc.* 2007, 129, 6589; Fortner, K. C.; Kato, D.; Tanaka, Y.; Shair, M. D. *J. Am. Chem. Soc.* 2010, 132, 275. (b) Ravindar, K.; Reddy, M. S.; Lindqvist, L.; Pelletier, J.; Deslongchamps, P. *Org. Lett.* 2010, 12, 4420. (c) Tlais, S. F.; Dudley, G. B. *Org. Lett.* 2010, 12, 4698.

13. TMSOTf was most effective to induce the equilibration. Other Lewis acids, including TBSOTf and $BF_3 \cdot Et_2O$, were also found to be effective.

14. Solvent tested included: (a) no-oxygen containing solvents: toluene and dichloroethane; (b) oxygen-containing solvents; THF and $H_2O$.

15. Fang, F. G.; Kishi, Y.; Matelich, M. C.; Scola, P. M. *Tetrahedron Lett.* 1992, 33, 1557.

16. Aicher, T. D.; Buszek, K. R.; Fang, F. G.; Forsyth, C. J.; Jung, S. H.; Kishi, Y.; Matelich, M. C.; Scola, P. M.; Spero, D. M.; Yoon, S. K. *J. Am. Chem. Soc.* 1992, 114, 3162.

17. Freshly prepared according to the literature: (a) Murray, R. W.; Singh, M. *Org. Synth.* 1997, 74, 91; 1998, Coll. Vol. 9, 288. (b) Cerrè, C.; Hofmann, A. F.; Schteingart, C. D. *Tetrahedron*, 1997, 53, 435.

18. Liu, S.; Kim, J. T.; Dong, C.-G.; Kishi, Y. *Org. Lett.* 2009, 11, 4520.

19. Standard TBAF-mediated TBDPS deprotection resulted in partial elimination of chloride to give trans-enyne by-product.

20. Hara, S.; Dojo, H.; Takinami, S.; Suzuki, A. *Tetrahedron Lett.* 1983, 24, 731.

21. (a) Choi, H.; Demeke, D.; Kang, F.-A.; Kishi, Y.; Nakajima, K.; Nowak, P.; Wan, Z.-K.; Xie, C. *Pure Appl. Chem.* 2003, 75, 1. (b) Guo, H.; Dong, C.-G.; Kim, D.-S.; Urabe, D.; Wang, J.; Kim, J. T.; Liu, X.; Sasaki, T.; Kishi, Y. *J. Am. Chem. Soc.* 2009, 131, 15387.

22. Dong, C.-G.; Henderson, J. A.; Kaburagi, Y.; Sasaki, T.; Kim, D.-S.; Kim, J. T.; Urabe, D.; Guo, H.; Kishi, Y. *J. Am. Chem. Soc.* 2009, 131, 15642.

23. Kim, S.; Park, J. H. *Tetrahedron Lett.* 1987, 28, 439.

24. Shan, M.; Kishi, Y. *Org. Lett.* 2012, 14, 660.

25. (a) Chen, C.-L.; Namba, K.; Kishi, Y. *Org. Lett.* 2009, 11, 409. (b) Aicher, T. D.; Buszek, K. R.; Fang, F. G.; Forsyth, C. J.; Jung, S. H.; Kishi, Y.; Scola, P. M. *Tetrahedron Lett.* 1992, 33, 1549.

26. 5 was synthesized by the method reported in: Buszek, K. R.; Fang, F. G.; Forsyth, C. J; Jung, S. H.; Kishi, Y.; Scola, P. M.; Yoon, S. K. *Tetrahedron Lett.* 1992, 33, 1553.

27. Stamos, D. P.; Sheng, X. C.; Chen, S. S.; Kishi, Y. *Tetrahedron Lett.* 1997, 38, 6355.

28. 23 was synthesized by the method reported in: (a) Fang, F. G.; Kishi, Y.; Matelich, M. C.; Scola, P. M. *Tetrahedron Lett.* 1992, 33, 1557. (b) Chen, C.-L.; Namba, K.; Kishi, Y. *Org. Lett.* 2009, 11, 409.

29. Uemura, D.; Takahashi, K.; Yamamoto, T.; Katayama, C.; Tanaka, J.; Okumura, Y. Hirata, Y. *J. Am. Chem. Soc.* 1985, 107, 4796.

OTHER EMBODIMENTS

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed is ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of treating liver cancer in a subject, the method comprising administering to the subject a therapeutically effective amount of a compound of Formula (III):

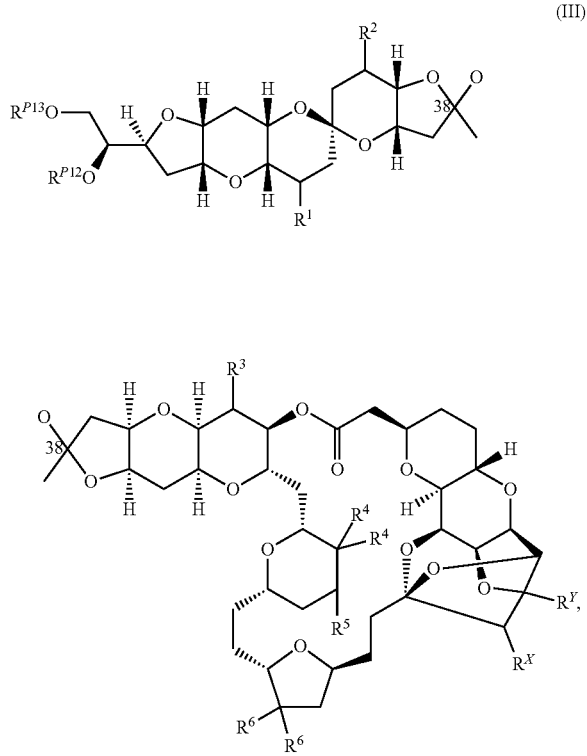

or a pharmaceutically acceptable salt or stereoisomer thereof, wherein:

$R^{P12}$ and $R^{P13}$ are each independently hydrogen, substituted or unsubstituted alkyl, or an oxygen protecting group;

$R^1$, $R^2$, $R^3$, and $R^5$ are each independently hydrogen, halogen, or substituted or unsubstituted alkyl;

each instance of $R^4$ is independently hydrogen, halogen, or substituted or unsubstituted alkyl, or two $R^4$ groups are taken together to form a

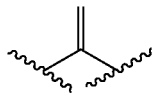 [SMILES: *C(*)=C]

group;

each instance of $R^6$ is independently hydrogen, halogen, or substituted or unsubstituted alkyl, or two $R^6$ groups are taken together to form a

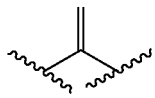 [SMILES: *C(*)=C]

group;

$R^X$ is —$OR^{X1}$, wherein $R^{X1}$ is hydrogen, substituted or unsubstituted alkyl, or an oxygen protecting group; and $R^Y$ is —$OR^{Y1}$, wherein $R^{Y1}$ is hydrogen, substituted or unsubstituted alkyl, or an oxygen protecting group;

wherein $R^X$ and $R^Y$ can be taken together with their intervening atoms to form a substituted or unsubstituted heterocyclic ring.

2. The method of claim 1, wherein $R^1$ is substituted or unsubstituted $C_{1-6}$ alkyl.

3. The method of claim 1, wherein $R^2$ is substituted or unsubstituted $C_{1-6}$ alkyl.

4. The method of claim 1, wherein $R^3$ is substituted or unsubstituted $C_{1-6}$ alkyl.

5. The method of claim 1, wherein $R^5$ is substituted or unsubstituted $C_{1-6}$ alkyl.

6. The method of claim 1, wherein $R^1$, $R^2$, $R^3$, and $R^5$ are each substituted or unsubstituted $C_{1-6}$ alkyl.

7. The method of claim 1, wherein $R^1$, $R^2$, $R^3$, and $R^5$ are each methyl.

8. The method of claim 1, wherein the two $R^4$ groups are taken together to form:

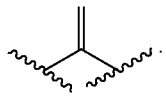 [SMILES: *C(*)=C]

9. The method of claim 1, wherein the two $R^6$ groups are taken together to form:

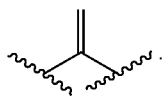 [SMILES: *C(*)=C]

10. The method of claim 1, wherein $R^{P12}$ is hydrogen.
11. The method of claim 1, wherein $R^{P13}$ is hydrogen.
12. The method of claim 1, wherein $R^{P12}$ and $R^{P13}$ are each hydrogen.
13. The method of claim 1, wherein $R^{X1}$ is hydrogen.
14. The method of claim 1, wherein $R^{Y1}$ is hydrogen.
15. The method of claim 1, wherein $R^{X1}$ and $R^{Y1}$ are each hydrogen.
16. The method of claim 1, wherein the compound is homohalichondrin A:

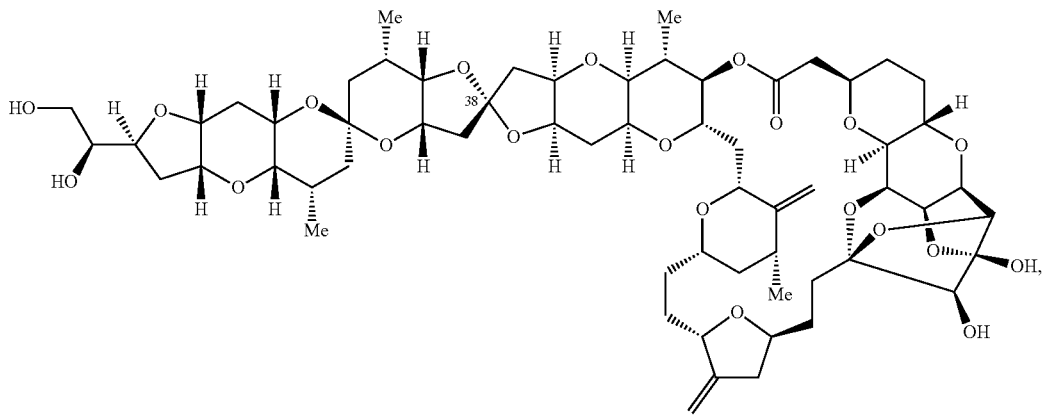

(homohalichondrin A)

or a pharmaceutically acceptable salt or stereoisomer thereof.

17. The method of claim 16, wherein the compound is homohalichondrin A, or a pharmaceutically acceptable salt thereof.

18. The method of claim 1, wherein the subject is a human.

19. The method of claim 1, wherein the liver cancer is hepatocellular cancer (HCC) or malignant hepatoma.

20. The method of claim 1 further comprising administering to the subject one or more additional anti-cancer agents.

21. The method of claim 1, wherein the compound is a compound of Formula (III), or a pharmaceutically acceptable salt thereof.

* * * * *